United States Patent
Heim et al.

(10) Patent No.: US 10,155,021 B2
(45) Date of Patent: *Dec. 18, 2018

(54) ANTIMICROBIAL 4-OXOQUINOLIZINES

(71) Applicant: Emergent Product Development Gaithersburg Inc., Reinach Gaithersburg, MD (US)

(72) Inventors: Jutta Heim, Ramlinsburg (CH); Peter Schneider, Bottmingen/BL (CH); Patrick Roussel, Mulhouse (FR); Daniel Milligan, San Francisco, CA (US); Christian Bartels, Allschwil/BL (CH); Glenn Dale, Basel (CH)

(73) Assignee: Emergent Product Development Gaithersburg Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/191,067

(22) Filed: Jun. 23, 2016

(65) Prior Publication Data

US 2017/0106045 A1  Apr. 20, 2017
US 2017/0232060 A9  Aug. 17, 2017

Related U.S. Application Data

(63) Continuation of application No. 13/823,187, filed as application No. PCT/EP2012/051563 on Jan. 31, 2012, now Pat. No. 9,403,818.

(Continued)

(51) Int. Cl.
*A61K 31/4375* (2006.01)
*A61K 38/12* (2006.01)
(Continued)

(52) U.S. Cl.
CPC .......... *A61K 38/12* (2013.01); *A61K 31/4375* (2013.01); *A61K 31/444* (2013.01);
(Continued)

(58) Field of Classification Search
CPC . C07D 455/00; C07D 221/04; A61K 31/4375
See application file for complete search history.

(56) References Cited

U.S. PATENT DOCUMENTS

| | | | |
|---|---|---|---|
| 4,623,650 | A | 11/1986 | Gilligan et al. |
| 5,789,591 | A | 8/1998 | Chu et al. |

(Continued)

FOREIGN PATENT DOCUMENTS

| | | |
|---|---|---|
| EP | 0 308 019 A2 | 3/1989 |
| EP | 1 227 096 B1 | 9/2004 |

(Continued)

OTHER PUBLICATIONS

International Preliminary Report on Patentability from International Application No. PCT/EP2012/051563 dated May 21, 2013.

(Continued)

*Primary Examiner* — Jeffrey E. Russel
(74) *Attorney, Agent, or Firm* — Sterne, Kessler, Goldstein & Fox P.L.L.C.

(57) ABSTRACT

This invention provides novel 4-oxoquinolizine compounds and their uses for a series of broad-spectrum antibiotics having no cross-resistance to existing or emerging classes of antibiotics. In addition the novel 4-oxoquinolizine compounds are useful against CDC Category A and B pathogens. The invention also provides pharmaceutical compositions comprising certain 4-oxoquinolizines in combination with subinhibitory concentrations of polymyxin B against clinical isolates which are resistant to quinolones, carbapenems and other antimicrobial agents.

14 Claims, 10 Drawing Sheets

Related U.S. Application Data

(60) Provisional application No. 61/438,543, filed on Feb. 1, 2011.

(51) Int. Cl.
| | |
|---|---|
| *A61K 31/444* | (2006.01) |
| *A61K 31/4545* | (2006.01) |
| *A61K 31/4709* | (2006.01) |
| *A61K 31/496* | (2006.01) |
| *A61K 31/506* | (2006.01) |
| *C07D 455/02* | (2006.01) |

(52) U.S. Cl.
CPC ...... *A61K 31/4545* (2013.01); *A61K 31/4709* (2013.01); *A61K 31/496* (2013.01); *A61K 31/506* (2013.01); *C07D 455/02* (2013.01); *Y02A 50/402* (2018.01); *Y02A 50/475* (2018.01); *Y02A 50/478* (2018.01); *Y02A 50/479* (2018.01); *Y02A 50/481* (2018.01)

(56) References Cited

U.S. PATENT DOCUMENTS

| | | | | |
|---|---|---|---|---|
| 5,977,133 | A | 11/1999 | Fung et al. | |
| 6,525,066 | B2 | 2/2003 | Fukumoto et al. | |
| 6,881,731 | B1* | 4/2005 | Shanbrom | A61K 9/0014 514/183 |
| 7,223,773 | B2* | 5/2007 | Fukumoto | A61K 31/4375 514/306 |
| 8,962,842 | B2* | 2/2015 | Roussel | A61K 31/4375 546/138 |
| 9,403,818 | B2* | 8/2016 | Heim | A61K 31/506 |
| 2009/0181101 | A1* | 7/2009 | Rademacher | A61K 41/0052 424/499 |
| 2010/0028334 | A1 | 2/2010 | Cottarel et al. | |
| 2013/0245035 | A1* | 9/2013 | Roussel | A61K 31/4375 514/253.04 |

FOREIGN PATENT DOCUMENTS

| | | |
|---|---|---|
| EP | 1 437 354 B1 | 8/2008 |
| JP | 2002308876 | 10/2002 |
| JP | 2003012670 | 1/2003 |
| JP | 2003261566 | 9/2003 |
| WO | 1995/010519 A1 | 4/1995 |
| WO | 1999/07696 A1 | 2/1999 |
| WO | 2002/048143 A2 | 6/2002 |

OTHER PUBLICATIONS

Alder et al., "Efficacies of ABT-719 and related 2-pyridones, members of a new class of antibacterial agents, against experimental bacterial infections," Antimicrobial Agents and Chemotherapy 39(4): 971-75 (1995).
Fung & Shen "The 2-pyridone antibacterial agents: 8-position modifications," Current Pharmaceutical Design 5(7): 515-43 (1999).
Kuhnz & Gieschen "Predicting the oral bioavailability of 19-nortestosterone progestins in vivo from their metabolic stability in human liver microsomal preparations in vitro," Drug Metabolism and Disposition 26(11):1120-27 (1998).
Ma et al., "Synthesis and antimicrobial activity of 4H-4-oxoquinolizine derivatives: Consequences of structural modification at the C-8 position," Journal of Medicinal Chemistry 42(20):4202-13 (1999).
Database CA, Chemical Abstracts Service, Columbus, Ohio, US; XP002672416, STN Database Accession No. 2003:734778. Oya et al., "Preparation of 4-oxo-4H-quinolizine-3-carboxylic acid derivatives as antibacterial agents," Sep. 19, 2003.
Database CA, Chemical Abstracts Service, Columbus, Ohio, US; XP002672417, Database Accession No. 405141-67-5. Oya et al., "Preparation of 4-oxo-4H-quinolizine-3-carboxylic acid derivatives as antibacterial agents," Apr. 12, 2002.
Database CA, Chemical Abstracts Service, Columbus, Ohio, US; XP002672418, Database Accession No. 405141-68-6. Oya et al., "Preparation of 4-oxo-4H-quinolizine-3-carboxylic acid derivatives as antibacterial agents," Apr. 12, 2002.
Database CA, Chemical Abstracts Service, Columbus, Ohio, US; XP002672419, STN Database Accession No. 2003:36453, Fukumoto et al., "Preparation of 1-cyclopropyl 8 heterocyclyl-4-oxo-4H-quinolizine-3-carboxylic acid derivatives as antibacterial agents," Jan. 30, 2003.
Database CA, Chemical Abstracts Service, Columbus, Ohio, US; XP002672420, Database Accession No. 483370-57-6, Fukumoto et al., "Preparation of 1-cyclopropyl 8 heterocyclyl-4-oxo-4H-quinolizine-3-carboxylic acid derivatives as antibacterial agents," Jan. 30, 2003.
Database CA, Chemical Abstracts Service, Columbus, Ohio, US; XP002672421, Database Accession No. 483370-55-4, Fukumoto et al., "Preparation of 1-cyclopropyl 8 heterocyclyl-4-oxo-4H-quinolizine-3-carboxylic acid derivatives as antibacterial agents," Jan. 30, 2003.
Database CA, Chemical Abstracts Service, Columbus, Ohio, US; XP002672422, Database Accession No. 483370-53-2, Fukumoto et al., "Preparation of 1-cyclopropyl 8 heterocyclyl-4-oxo-4H-quinolizine-3-carboxylic acid derivatives as antibacterial agents," Jan. 30, 2003.
Database CA, Chemical Abstracts Service, Columbus, Ohio, US; XP002672423, STN Database Accession No. 2002:802427, Fukumoto et al., "4-Oxoquinolizines, their preparation, and antibacterial agents containing them," Oct. 23, 2002.
Database CA, Chemical Abstracts Service, Columbus, Ohio, US; XP002672424, Database Accession No. 472957-91-8, Fukumoto et al., "4-Oxoquinolizines, their preparation, and antibacterial agents containing them," Nov. 11, 2002.
Database CA, Chemical Abstracts Service, Columbus, Ohio, US; XP002672425, Database Accession No. 472957-94-1, Fukumoto et al., "4-Oxoquinolizines, their preparation, and antibacterial agents containing them," Nov. 11, 2002.
Database CA, Chemical Abstracts Service, Columbus, Ohio, US; XP002672426, Database Accession No. 472957-95-2, Fukumoto et al., "4-Oxoquinolizines, their preparation, and antibacterial agents containing them," Nov. 11, 2002.
International Search Report and Written Opinion from International Application No. PCT/EP2012/051563 dated Apr. 11, 2012.
"The Merck Index", 2001, Merck & Co., Inc., Whitehouse Station, N.J. XP002672427, pp. 1359-1360.
Li, Q., et al., "Synthesis and Structure-Activity Relationships of 2-Pyridones: A Novel Series of Potent DNA Gyrase Inhibitors as Antibacterial Agents," J. Med. Chem. 39:3070-3088, American Chemical Society, United States (1996).

* cited by examiner

Scaffold A

Scaffold B

Scaffold C

Scaffold D

Scaffold D

ANTIMICROBIAL 4-OXOQUINOLIZINES

CROSS-REFERENCE TO RELATED APPLICATIONS

This application is a continuation of U.S. application Ser. No. 13/823,187, filed Jun. 3, 2013, now U.S. Pat. No. 9,403,818 B2, which is a national stage application under 35 U.S.C. § 371 of International Application No. PCT/EP2012/51563, filed Jan. 31, 2012, which claims the benefit of U.S. Provisional Application No. 61/438,543, filed Feb. 1, 2011.

FIELD OF THE INVENTION

This invention encompasses novel 2-pyridone compounds and their pharmaceutical compositions. In particular the invention relates to novel 4-oxoquinolizine compounds and their pharmaceutical compositions. In certain embodiments, the invention is directed to 4-oxoquinolizines in combination with subinhibitory concentrations of polymyxin B.

BACKGROUND OF THE INVENTION

Description of Related Art

Second generation quinolones such as Ciprofloxacin are widely accepted for the treatment of bacterial infections of the respiratory and urinary tracts, skin and soft tissues. They have good pharmacokinetic profiles, potent activities against a wide range of Gram-positive and Gram-negative pathogens, and are widely used in both hospital and community settings. However, increasing frequency of bacterial resistance to quinolones has led to an urgent need for new analogs to overcome antibiotic resistance.

2-pyridones have the potential to exhibit a new mechanism of action with broad-spectrum antibacterial activity and favorable drug-like properties to become the first 2-pyridone members in such clinical use. 2-pyridones are distantly related to quinolones, but with a different heterocyclic nucleus and different electronic distribution over the molecule leading to significant changes in chemical reactivity.

In 1994, Abbott reported that 2-pyridone analogs were efficacious against certain quinolone resistant microorganisms (34th Interscience Conference on Antimicrobial Agents and Chemotherapy (ICAAC, paper F41), 1994; U.S. Pat. No. 5,789,591), specifically ABT-719, a 4-oxo-quinolizine (also described herein as compound 10)

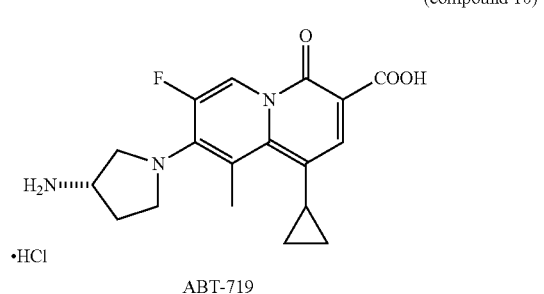

(compound 10)

ABT-719 possessing potent antibacterial activity against both Gram-positive and Gram-negative pathogens. More recently, Sato disclosed a family of 4-oxo-quinolizines on a 2-pyridone scaffold (U.S. Pat. No. 6,525,066; U.S. Pat. No. 7,223,773) exhibiting strong antibacterial activity against Gram-positive and Gram-negative and anaerobic bacteria.

There is a continuing need for antimicrobial compounds that have potent activity against many pathogens particularly multiresistant ones.

SUMMARY OF THE INVENTION

Provided herein are 2-pyridone compounds and their uses as antimicrobial agents Preferably the 2-pyridone compounds of the invention are 4-oxoquinolizine compounds.

In one aspect the invention provides pharmaceutical compositions comprising a Polymyxin and a 4-oxoquinolizine compound represented by formula (II)

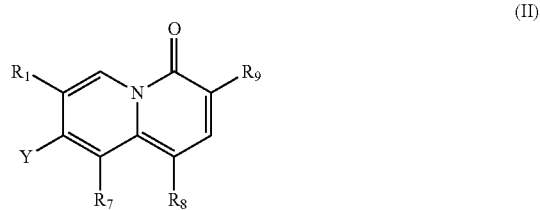

(II)

wherein $R_1$ is hydrogen, halogen, cyano, $C_{1-8}$ alkyl, $C_{1-8}$ haloalkyl, —$OR^X$, —$N(R^X)_2$, —$C(O)R^X$, —$C(O)OR^X$, or —$C(O)N(R^X)_2$, wherein each $R^X$ is independently hydrogen, $C_{1-8}$ alkyl, or $C_{1-8}$haloalkyl; and $R_7$ is hydrogen, halogen, cyano, $C_{1-8}$ alkyl, $C_{1-8}$ alkoxyl, $C_{1-8}$ haloalkyl, heterocyclyl, —$OR^{11}$, —$N(R^{11})_2$, or —$C(O)N(R^{11})_2$, wherein each $R^{11}$ is independently hydrogen, $C_{1-8}$ alkyl, or $C_{1-8}$ haloalkyl; and $R_8$ is a $C_{1-8}$ alkyl, $C_{1-8}$ haloalkyl, $C_{3-8}$cycloalkyl, or heteroaryl, wherein the cycloalkyl and heteroaryl are optionally substituted with one to five groups that are each independently halogen, $C_{1-8}$ alkyl, —$OR^{21}$, —$N(R^{21})_2$, or —$C(O)OR^{21}$, wherein each $R^{21}$ is independently hydrogen or $C_{1-8}$ alkyl; and $R_9$ is $(CH_2)_n$—COOH or $(CH_2)_n$—COO—$R_{10}$, wherein n is a integer in the range of 0 to 3 and $R_{10}$ is hydrogen or a carboxyl protecting group; and Y is heterocyclyl, aryl, or heteroaryl, each optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$, wherein $R^Y$ is nitro, cyano, —$OR^{Y1}$, —$SR^{Y1}$, —$N(R^{Y1})_2$, —$C(O)R^{Y1}$, —$C(O)OR^{Y1}$, —$C(O)N(R^{Y1})_2$, —$OC(O)R^{Y1}$, —$OC(O)OR^{Y1}$, —$OC(O)N(R^{Y1})_2$, —$N(R^{Y1})C(O)R^{Y1}$, —$N(R^{Y1})C(O)OR^{Y1}$, —$N(R^{Y1})C(O)N(R^{Y1})_2$, —$S(O)_2R^{Y1}$, —$S(O)_2OR^{Y1}$, —$S(O)_2N(R^{Y1})_2$, —$OS(O)_2R^{Y1}$, —$OS(O)_2OR^{Y1}$, —$OS(O)_2N(R^{Y1})_2$, —$N(R^{Y1})S(O)_2R^{Y1}$, —$N(R^{Y1})S(O)_2OR^{Y1}$, or —$N(R^{Y1})S(O)_2N(R^{Y1})_2$, wherein each $R^{Y1}$ is independently hydrogen, $C_{1-8}$ alkyl, or $C_{1-8}$ haloalkyl.

Said polymyxin may be any of the polymyxins described herein below in the section "Polymyxin" and said 4-oxoquinolizine compound may be any of the 4-oxoquinolizine compounds described herein below in the sections "4-oxoquinolizines" and "Particular 4-oxoquinolizines".

The invention also provides said pharmaceutical compositions for use in the treatment of a bacterial infection, which for example may be any of the bacterial infections described herein below in the section "Bacterial infection".

In a further aspect, the invention provides 2-pyridone compounds represented by formula (I), or a pharmaceutically acceptable salt thereof:

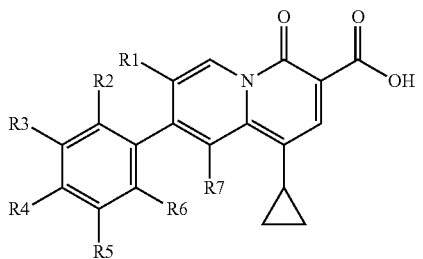
(I)

wherein $R_1$ and $R_2$ are independently hydrogen or fluorine, $R_3$ and $R_5$ are independently hydrogen, fluorine or chlorine, $R_4$ is —$NH_2$ or —$CH_2NH_2$, $R_6$ is H or F, and $R_7$ is H, $CF_3$, $CONH_2$, $CH_3$, $OCH_3$, or —CN.

In certain embodiments, 2-pyridone compounds are provided having the structure of one of compounds 1, 2, 3, 4, 5, 6 and 17, as shown herein.

In another aspect of the invention antimicrobial agents and pharmaceutical compositions thereof comprising a 2-pyridone compound are provided.

In another aspect, the invention provides for pharmaceutical compositions comprising a 2-pyridone compound in combination with polymyxin B, wherein the polymyxin B is present in a subinhibitory concentration.

In another aspect, the invention provides for the use of pharmaceutical compositions comprising the instant 2-pyridone compounds as antimicrobials.

Uses of the pharmaceutical compositions are provided herein against one of: *Burkholderia pseudomallei, Bacillus anthracis, Yersinia pestis, Francisella tularensis,* and *Brucella abortus, Klebsiella, Pseudomonas, Acinetobacter, Staphylococcus aureus* MRSA, *S. epidermidis, Streptococcus aureus, Streptococcus pneumonia, Enterococcus faecalis, Enterococcus faecium, B. pseudomallei, Pseudomonas aeruginosa, Burkholderia thailandensi, Acinetobacter baumannii,* or *Acinetobacter, Escherichia coli,* and *Klebsiella*.

In a further aspect the invention provides kit-of-parts comprising a polymyxin, which may be any of the polymyxins described herein below in the section "Polymyxin" and a 4-oxoquinolizine compound, which may be any of the 4-oxoquinolizine compounds described herein below in the sections "4-oxoquinolizines" and "Particular 4-oxoquinolizines".

In another aspect the invention provides 4-oxoquinolizine compounds represented by formula (I), or a pharmaceutically acceptable salt thereof:

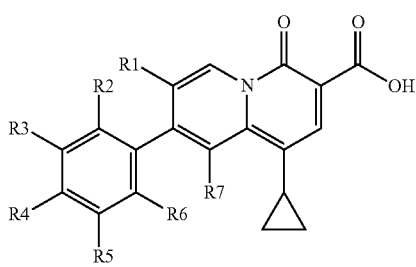
(I)

wherein
R1 is hydrogen or fluorine; and
R3 is fluorine, —$(CH_2)_n$—$NH_2$ or $C_{1-3}$-alkyl, wherein n is an integer in the range of 0 to 2; and
R4 is —$(CH_2)_n$—$NH_2$, —NH—$(CH2)_n$—$CH_3$ or $C_{1-3}$-alkyl, wherein n is an integer in the range of 0 to 2; and
R5 is hydrogen or $C_{1-3}$ alkyl; and
R2 and R6 are hydrogen; and
R7 is $C_{1-3}$ alkyl or $C_{1-3}$ alkoxy
with the proviso that when R3 is fluorine and R4 is amine, then R1 is fluorine.

In a still further aspect the invention provides 4-oxoquinolizine compounds of formula (I) or a pharmaceutically acceptable salt thereof, wherein
R1 is as defined herein below in relation to formula III; and
R2, R3, R4, R5 and R6 each independently are hydrogen, hydroxyl, —$(CH_2)_n$—NH—(C═O)—$(CH_2)_m$—$CH_3$, —(C═O)—$C_{1-8}$ alkyl, —(C═O)—$C_{1-8}$ haloalkyl, halogen, —$(CH_2)_n$—$NH_2$, —NH—$(CH_2)_n$—$CH_3$, $C_{1-8}$-alkyl or $C_{1-8}$ alkoxy, wherein n and m each independently is an integer in the range of 0 to 3 and wherein at least one of R2, R3, R4, R5 or R6 is hydroxyl, —$(CH_2)_n$—NH—(C═O)—$(CH_2)_n$—$CH_3$ or —(C═O)—$C_{1-8}$ haloalkyl; and
R7 is as defined herein below in relation to formula III.

In yet another aspect the invention provides 4-oxoquinolizine compounds of formula (V) or a pharmaceutically acceptable salt thereof,

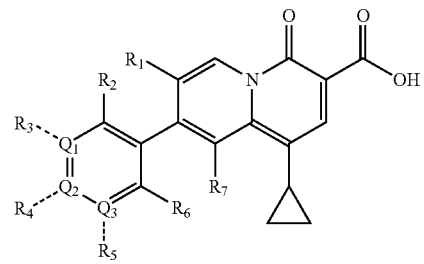

wherein $R_1$ is hydrogen or fluorine; and
$R_2$, $R_3$, $R_4$ and $R_5$ each individually are selected from the group consisting of hydrogen, $(CH_2)_n$-hydroxyl, fluorine, $C_{1-3}$ alkyl, —$(CH_2)_n$—$NH_2$, —NH—$(CH_2)_n$—$CH_3$ and a 5 to 6 membered heterocyclic ring, wherein n is an integer in the range of 0 to 2; and
$R_6$ is hydrogen and
$R_7$ is $C_{1-3}$ alkyl or $C_{1-3}$ alkoxy; and
$Q_1$, $Q_2$ and $Q_3$ each individually are C or N, wherein at least one of $Q_1$, $Q_2$ and $Q_3$ is N and at least one of $Q_1$, $Q_2$ and $Q_3$ is C, and wherein if $Q_1$ is N, then $R_3$ is not present, and if $Q_2$ is N, then $R_4$ is not present and if $Q_3$ is N, then $R_5$ is not present
with the provisos that
if $Q_1$ is N and $Q_2$ and $Q_3$ are C, then at least one of $R_2$, $R_4$ and $R_5$ is not hydrogen; and
if $Q_1$ is N and $Q_2$ and $Q_3$ are C and $R_4$ is —$NH_2$, then $R_1$ is fluorine and/or $R_7$ is methoxy; and
if $Q_3$ is N and $Q_2$ and $Q_1$ are C, then at least one of $R_2$, $R_3$ and $R_4$ is not hydrogen; and
if $Q_3$ is N and $Q_2$ and $Q_1$ are C and $R_4$ is —$NH_2$, then $R_1$ is fluorine and/or $R_7$ is methoxy.

In another aspect the invention provides 4-oxoquinolizine compounds of formula (IIIa) or pharmaceutically acceptable salts thereof, wherein R₁ is as defined herein below in relation to compounds of formula III; and Y is a heterobicyclic ring system optionally substituted with one or more substituents selected from the group consisting of oxo, —$(CH_2)_n$—$NH_2$, —NH—$(CH_2)_n$—$CH_3$, —$(CH_2)_n$—OH, $C_{1-8}$ alkyl, $C_{1-8}$ alkoxy, $C_{3-8}$-cycloalkyl and halogen, wherein n is an integer in the range of 0 to 3; and R₇ is as defined herein below in relation to compounds of formula III.

In an even further aspect the invention relates to 4-oxoquinolizine compounds of formula (IIIa) or pharmaceutically acceptable salts thereof, wherein R₁ is as defined herein below in relation to compounds of formula III; and Y is selected from the group consisting of pyrazolyl and tetrahydropyrinidyl optionally substituted with one or more substituents selected from the group consisting of oxo, —$(CH_2)_n$—$NH_2$, —NH—$(CH_2)_n$—$CH_3$, —$(CH_2)_n$—OH, $C_{1-8}$ alkyl, $C_{1-8}$ alkoxy, $C_{3-8}$-cycloalkyl and halogen, wherein n is an integer in the range of 0 to 3; and R₇ is as defined herein below in relation to compounds of formula III.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings.

Figure 1:
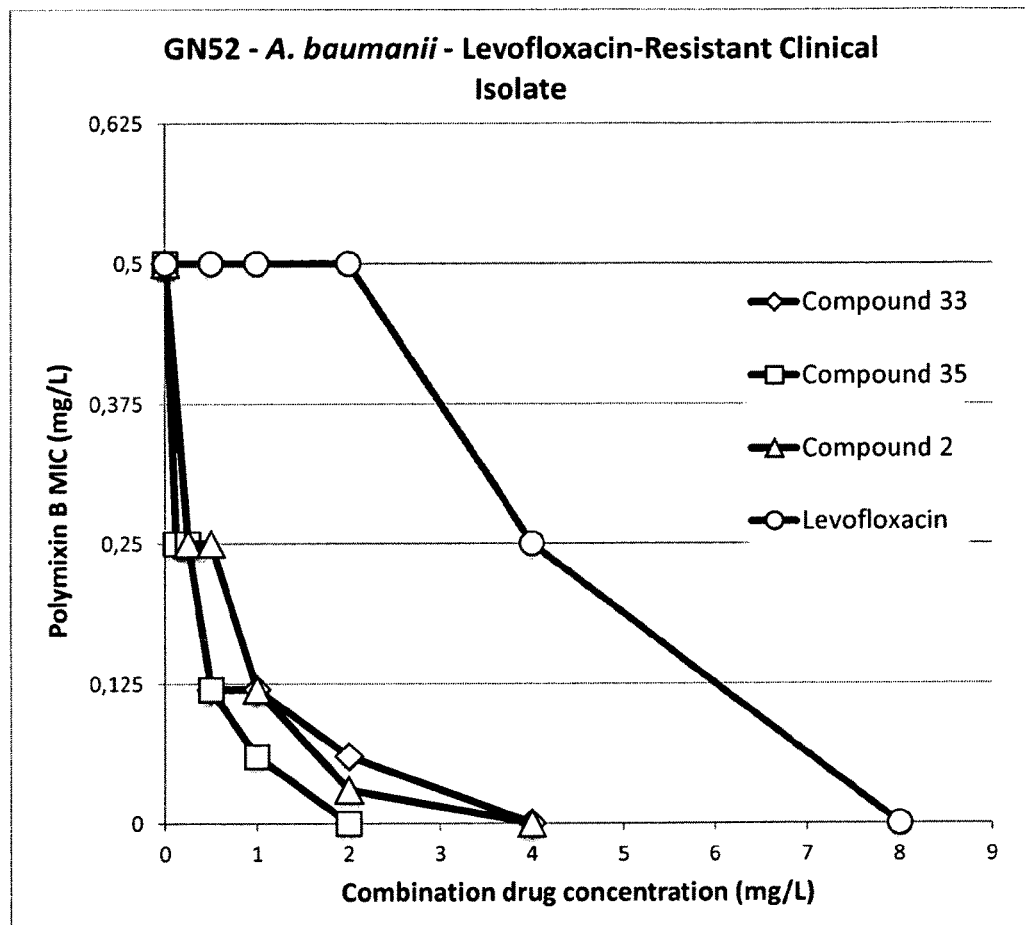
FIG. 1 shows the Isobologram related to the synergy of the antibacterial activity of compounds 2, 33 and 35 with Polymyxin B on the *Acinetobacter* GN52 strain.

Elements in the figures are illustrated for simplicity and clarity and have not necessarily been drawn to scale. For example, the dimensions of some of the elements in the figures can be exaggerated relative to other elements to help improve understanding of the embodiment(s) of the present invention.

DETAILED DESCRIPTION OF THE INVENTION

Definitions

Specific compounds are named herein as Compound followed by a number, i.e. Compound n, wherein n is an integer. This refers to the compounds as named and numbered in Table 1 herein below.

The term "alkyl" as used herein refers to a saturated, straight or branched hydrocarbon chain. The hydrocarbon chain preferably contains of from one to eight carbon atoms ($C_{1-8}$ alkyl), such preferably from one to six carbon atoms ($C_{1-6}$ alkyl), more preferred of from one to five carbon atoms ($C_{1-5}$-alkyl), including methyl, ethyl, propyl, isopropyl, butyl, isobutyl, secondary butyl, tertiary butyl, pentyl, isopentyl, neopentyl and tertiary pentyl. In a preferred embodiment alkyl represents a $C_{1-4}$-alkyl group, which may in particular include methyl, ethyl, propyl, isopropyl, butyl, isobutyl, secondary butyl, and tertiary butyl.

The term "aryl" as used herein refers to an aromatic ring or aromatic ring system substituent. Aryl may for example be phenyl or naphthyl.

The term "cycloalkyl" as used herein refers to a cyclic alkyl group, preferably containing of from three to eight carbon atoms ($C_{3-8}$-cycloalkyl), including cyclopropyl, cyclobutyl, cyclopentyl, cyclohexyl, cycloheptyl and cyclooctyl, more preferably 3 carbon atoms (cyclopropyl).

The term "haloalkyl" as used herein refers to an alkyl group as defined herein, which alkyl group is substituted one or more times with one or more halogen.

The term "heteroaryl" refers to an aryl, wherein one or more ring carbons have been exchanged for a heteroatom. The heteroatom is in general selected from the group consisting of N, S and O. The heteroaryl preferably contains 1 to 3 heteroatoms.

The term "heterocyclyl" as used herein refers to a monocyclic group or a multicyclic group holding one or more heteroatoms in its ring structure. Preferably heterocyclyl refers to monocyclic or bicyclic groups. Preferred heteroatoms include nitrogen (N), oxygen (O) and sulphur (S). Examples of 5-membered monocyclic heterocyclic groups include pyrrolidinyl, pyrrolyl, 3H-pyrrolyl, oxolanyl, furanyl, thiolanyl, thiophenyl, pyrazolyl, pyrazolidinyl, imidazolyl, imidazolidinyl, 1,2-oxazolyl, 1,3-oxazolyl, 1,2-thiazolyl, 1,3-thiazolyl, and 1,2,5-oxadiazolyl. Examples of 6-membered monocyclic heterocyclic groups include piperidinyl, pyridinyl, oxanyl, 2-H-pyranyl, 4-H-pyranyl, thianyl, 2H-thiopyranyl, pyridazinyl, 1,2-diazinanyl, pyrimidinyl, 1,3-diazinanyl, pyrazinyl, piperazinyl, 1,4-dioxinyl, 1,4-dioxanyl, 1,4-oxazinyl, morpholinyl, thiomorpholinyl and 1,4-oxathianyl.

The term "bicyclic heteroaryl" as used herein refers to a bicyclic aromatic ring system substituent derived by fusion of two monocyclic groups, where at least one of said two monocyclic groups holds one or more heteroatoms in its ring structure. Preferred heteroatoms include nitrogen (N), oxygen (O) and sulphur (S). Examples of bicyclic heterocyclic group includes 1H-indolyl, decahydroquinolinyl, octahydrocyclopenta[b]pyrrolyl, 4H-chromenyl, 2,3-dihydro-1-benzofuranyl, 2H-1,3-benzodioxolyl, 1H-1,3-benzodiazolyl and 1,3-benzothiazolyl.

The term "halogen" as used herein refers to a substituent selected from the group consisting of —Cl, —F, —Br and —I.

The term "oxo" as used herein refers to =O.

4-Oxoquinolizine Compounds

The instant invention provides novel 2-pyridones having potency, breadth of antimicrobial activity, lack of cross-resistance to existing drugs, safety, and/or efficacy in animal models for Category A & B CDC pathogens including the particularly problematic bacteria residing inside mammalian host cells. The preferred 2-pyridone compounds of the invention are 4-oxoquinolizine compounds. The disclosed 2-pyridone compounds have substituted 2-pyridone scaffolds and preferably the 2-pyridone compounds contain a substituted 4-oxoquinolizine scaffold. They target the well validated IIA bacterial topoisomerases, e.g. DNA gyrase and topoisomerase IV, thereby inhibiting a broad spectrum of Gram-positive as well as Gram-negative bacteria—importantly, those resistant to quinolones and topoisomerase inhibitors, such as for example piperidinylalkylquinolines. By synthesis and profiling in vitro and in vivo, the presently disclosed series of 4-oxoquinolizine antibiotics have been found to be broad-spectrum and very potent against CDC pathogens, including *Burkholderia pseudomallei, Bacillus anthracis, Yersinia pestis, Francisella tularensis*, and *Brucella abortus* in MIC90 ranges of low nanograms per milliliter. Similar MICs are obtained against important nosocomial pathogens, among them quinolone-resistant *Klebsiella, Pseudomonas, Acinetobacter* and *Staphylococcus aureus* MRSA. Furthermore, we have found that 4-oxoquinolizines are equally effective against a surrogate *Burkholderia* strain replicating inside mammalian host cells.

2-pyridones are distantly related to quinolones, but with a different heterocyclic nucleus and different electronic distribution over the molecule leading to significant changes in chemical reactivity. Exhibiting a possibly new mechanism of action against a well-validated bacterial target, with favorable drug-like properties, the instant 2-pyridones are likely to become the first 2-pyridone members in such clinical use. In particular, the 2-pyridones may be 4-oxoquinolizine compounds.

It is one aspect of the present invention to provide pharmaceutical compositions comprising 2-pyridone compounds in combination with polymyxin. Said 2-pyridone compound is preferably a 4-oxoquinolizine compound and said Polymyxin is preferably present in a subinhibitory concentration and is preferably Polymyxin B as described herein elsewhere.

The 2-pyridone compound according to the present invention may be any compound having a 2-pyridone skeleton as a partial structure. In a preferred embodiment the 2-pyridone compound is a 4-oxoquinolizine compound, i.e. a compound comprising a 4-oxoquinolizine skeleton structure.

Thus, in a preferred embodiment of the invention the present invention relates to pharmaceutical compositions comprising a 4-oxoquinolizine compound and polymyxin, wherein said polymyxin preferably is present in subinhibitory concentrations.

The 4-oxoquinolizine compound is preferably a compound of the formula (II):

(II)

or a pharmaceutically acceptable salt thereof, wherein $R_1$ is hydrogen, halogen, cyano, $C_{1-8}$ alkyl, $C_{1-8}$ haloalkyl, —$OR^X$, —$N(R^X)_2$, —$C(O)R^X$, —$C(O)OR^X$ or —$C(O)N(R^X)_2$, wherein each $R^X$ is independently hydrogen, $C_{1-8}$ alkyl, or $C_{1-8}$ haloalkyl; and $R_7$ is hydrogen, halogen, cyano, $C_{1-8}$ alkyl, $C_{1-8}$ alkoxyl, $C_{1-8}$ haloalkyl, heterocyclyl, —$OR^{11}$, —$N(R^{11})_2$, or —$C(O)N(R^{11})_2$, wherein each $R^{11}$ is independently hydrogen, $C_{1-8}$ alkyl, or $C_{1-8}$ haloalkyl; and $R_8$ is a $C_{1-8}$ alkyl, $C_{1-8}$ haloalkyl, $C_{3-8}$ cycloalkyl, or heteroaryl, wherein the cycloalkyl and heteroaryl are optionally substituted with one to five groups that are each independently halogen, $C_{1-8}$ alkyl, —$OR^{21}$, —$N(R^{21})_2$, or —$C(O)OR^{21}$, wherein each $R^{21}$ is independently hydrogen or $C_{1-8}$ alkyl; and $R_9$ is $(CH_2)_n$—COOH or $(CH_2)_n$—COO—$R_{10}$, wherein n is a integer in the range of 0 to 3 and $R_{10}$ is hydrogen or a carboxyl protecting group; and Y is heterocyclyl, aryl, or heteroaryl, each optionally substituted by one to five groups that are each independently halogen, $C_{1-8}$ alkyl, $C_{1-8}$ haloalkyl, $C_{3-8}$ cycloalkyl, heterocyclyl, aryl, heteroaryl, $C_{3-8}$ cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$, wherein $R^Y$ is nitro, cyano, —$OR^{\gamma 1}$, —$SR^{\gamma 1}$, —$N(R^{\gamma 1})_2$, —$C(O)R^{\gamma 1}$, —$C(O)OR^{\gamma 1}$, —$C(O)N(R^{\gamma 1})_2$, —$OC(O)R^{\gamma 1}$, —$OC(O)OR^{\gamma 1}$, —$OC(O)N(R^{\gamma 1})_2$, —$N(R^{\gamma 1})C(O)R^{\gamma 1}$, —$N(R^{\gamma 1})C(O)OR^{\gamma 1}$, —$N(R^{\gamma 1})C(O)N(R^{\gamma 1})_2$, —$S(O)_2R^{\gamma 1}$, —$S(O)_2OR^{\gamma 1}$, —$S(O)_2N(R^{\gamma 1})_2$, —$OS(O)_2R^{\gamma 1}$, —$OS(O)_2OR^{\gamma 1}$, —$OS(O)_2N(R^{\gamma 1})_2$, —$N(R^{\gamma 1})S(O)_2R^{\gamma 1}$, —$N(R^{\gamma 1})S(O)_2OR^{\gamma 1}$, or —$N(R^{\gamma 1})S(O)_2N(R^{\gamma 1})_2$, wherein each $R^{\gamma 1}$ is independently hydrogen, $C_{1-8}$ alkyl, or $C_{1-8}$ haloalkyl.

In relation to compounds of formula (II) it is preferred that $R_9$ is $(CH_2)_n$—COOH, and more preferably $R_9$ is —COOH.

More preferably the 4-oxoquinolizine compound is a compound of formula (III):

(III)

or a pharmaceutically acceptable salt thereof, wherein $R_1$ is hydrogen, halogen, cyano, C18 alkyl, $C_{1-8}$ haloalkyl, —$OR^X$, —$N(R^X)_2$, —$C(O)R^X$, —$C(O)OR^X$ or —$C(O)$ $N(R^X)_2$, wherein each $R^X$ is independently hydrogen, $C_{1-8}$ alkyl, or $C_{1-8}$haloalkyl; and $R_7$ is hydrogen, halogen, cyano, $C_{1-8}$ alkyl, $C_{1-8}$ alkoxyl, $C_{1-8}$ haloalkyl, heterocyclyl, —$OR^{11}$, —$N(R^{11})_2$, or —$C(O)N(R^{11})_2$, wherein each $R^{11}$ is independently hydrogen, $C_{1-8}$ alkyl, or $C_{1-8}$ haloalkyl;

$R_8$ is a $C_{1-8}$ alkyl, $C_{1-8}$ haloalkyl, $C_{3-8}$cycloalkyl, or heteroaryl, wherein the cycloalkyl and heteroaryl are optionally substituted with one to five groups that are each independently halogen, $C_{1-8}$ alkyl, —$OR^{21}$, —$N(R^{21})_2$, or —$C(O)OR^{21}$, wherein each $R^{21}$ is independently hydrogen or $C_{1-8}$ alkyl;

Y is heterocyclyl, aryl, or heteroaryl, each optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl$(C_{1-8})$ alkyl, heterocyclyl$(C_{1-8})$alkyl, aryl$(C_{1-8})$alkyl, heteroaryl$(C_{1-8})$alkyl, —$R^Y$, or —$C_{1-8}$ alkyl-$R^Y$, wherein $R^Y$ is nitro, cyano, —$OR^{Y1}$, —$SR^{Y1}$, —$N(R^{Y1})_2$, —$C(O)R^{Y1}$, —$C(O)OR^{Y1}$, —$C(O)N(R^{Y1})_2$, —$OC(O)R^{Y1}$, —$OC(O)OR^{Y1}$, —$OC(O)N(R^{Y1})_2$, —$N(R^{Y1})C(O)R^{Y1}$, —$N(R^{Y1})C(O)OR^{Y1}$, —$N(R^{Y1})C(O)N(R^{Y1})_2$, —$S(O)_2R^{Y1}$, —$S(O)_2OR^{Y1}$, —$S(O)_2N(R^{Y1})_2$, —$OS(O)_2R^{Y1}$, —$OS(O)_2R^{Y1}$, —$OS(O)_2N(R^{Y1})_2$, —$N(R^{Y1})S(O)_2R^{Y1}$, —$N(R^{Y1})S(O)_2OR^{Y1}$, or —$N(R^{Y1})S(O)_2N(R^{Y1})_2$, wherein each $R^{Y1}$ is independently hydrogen, $C_{1-8}$ alkyl, or $C_{1-8}$ haloalkyl.

In one embodiment of the invention the 4-oxoquinolizine compound is a compound of formula IIIa:

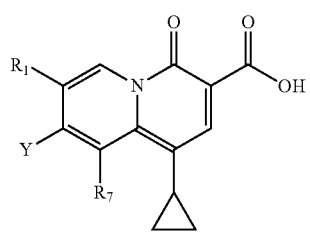

(IIIa)

or a pharmaceutically acceptable salt thereof, wherein the $R_1$, $R_7$ and Y are as defined herein above in relation to compounds of formula (III).

In another embodiment of the invention the 4-oxoquinolizine compound is a compound of formula IIIb:

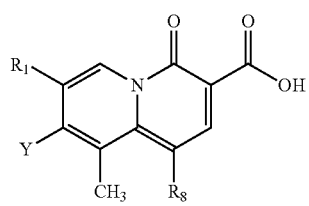

(IIIb)

or a pharmaceutically acceptable salt thereof, wherein the $R_1$, $R_8$ and Y are as defined herein above in relation to compounds of formula (III).

In another embodiment of the invention the 4-oxoquinolizine compound is a compound of formula IIIc:

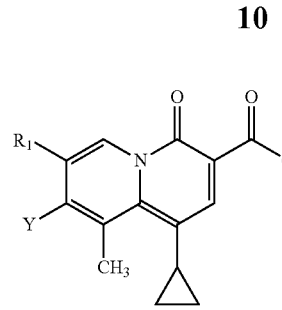

(IIIc)

or a pharmaceutically acceptable salt thereof, wherein the $R_1$ and Y are as defined herein above in relation to compounds of formula (III).

In relation to compounds according to formula (II). (III) and (IIIa) the $R_7$ may preferably be as described in the following paragraph:

In one preferred embodiment $R_7$ is hydrogen, halogen, or $C_{1-8}$ alkyl, and more preferably $R_7$ is hydrogen or $C_{1-8}$ alkyl, yet more preferably $R_7$ is hydrogen or $C_{1-5}$ alkyl, yet more preferably $R_7$ is hydrogen or $C_{1-2}$ alkyl, yet more preferably $R_7$ is hydrogen or methyl. In another embodiment, $R_7$ is halogen or $C_{1-8}$ alkyl. In another embodiment, $R_7$ is $C_{1-8}$ alkyl, preferably $R_7$ is $C_{1-5}$ alkyl, yet more preferably $R_7$ is $C_{1-2}$ alkyl, yet more preferably $R_7$ is methyl. In another embodiment, $R_7$ is halogen. In another embodiment $R_7$ is $C_{1-8}$ haloalkyl, —$OR^{11}$, or —$C(O)N(R^{11})_2$. In another embodiment $R_7$ is trifluoromethyl, methoxy, or —$C(O)NH_2$.

In relation to compounds of formula (II), (III), (IIIa), (IIIb) and (IIIc), then $R_7$ may be as described herein above and $R_1$ may preferably be as described in the following paragraph: In one preferred embodiment $R_1$ may be hydrogen or halogen. Thus in one very preferred embodiment $R_1$ is hydrogen. In another preferred embodiment $R_1$ is halogen, and more preferably $R_1$ may be fluorine. In another embodiment, $R_1$ is hydrogen, halogen, $C_{1-8}$ alkyl, $C_{1-8}$ alkoxy, amino, $C_{1-8}$ alkylamino, or di($C_{1-8}$ alkyl)amino, preferably $R_1$ may be $C_{1-8}$ alkyl, more preferably $C_{1-5}$ alkyl, even more preferably $C_{1-2}$ alkyl, yet more preferably methyl. In another embodiment, $R_1$ is —$OR^X$, —$N(R^X)_2$, —$C(O)R^X$, —$C(O)OR^X$, or —$C(O)N(R^X)_2$. In another embodiment, $R_1$ is —$OR^X$ or —$N(R^X)_2$. In another embodiment, $R_1$ is —$C(O)R^X$, —$C(O)OR^X$ or —$C(O)N(R^X)_2$. In another embodiment, $R_1$ is $C_{1-8}$haloalkyl (e.g., trifluoromethyl).

In particular preferred embodiments of the invention the compounds of formula (II), (III) and (IIIa) have $R_7$ and $R_1$ selected from one of the following combinations:

(a) $R_7$ is hydrogen, halogen, or $C_{1-8}$ alkyl; and $R_1$ is hydrogen or halogen.
(b) $R_7$ is hydrogen, halogen, or $C_{1-8}$ alkyl; and $R_1$ is hydrogen.
(c) $R_7$ is hydrogen, halogen, or $C_{1-8}$ alkyl; and $R_1$ is halogen.
(d) $R_7R^1$ is hydrogen, halogen, or $C_{1-8}$ alkyl; and $R_1$ is fluoro.
(e) $R_7$ is hydrogen or $C_{1-8}$ alkyl; and $R_1$ is hydrogen or halogen.
(f) $R_7$ is hydrogen or $C_{1-8}$ alkyl; and $R_1$ is hydrogen.
(g) $R_7$ is hydrogen or $C_{1-8}$ alkyl; and $R_1$ is halogen.
(h) $R_7$ is hydrogen or $C_{1-8}$ alkyl; and $R_1$ is fluoro.
(i) $R_7$ is hydrogen or methyl; and $R_1$ is hydrogen or halogen.
(j) $R_7$ is hydrogen or methyl; and $R_1$ is hydrogen.
(k) $R_7$ is hydrogen or methyl; and $R_1$ is halogen.
(l) $R_7$ is hydrogen or methyl; and $R_1$ is fluoro.

(m) $R_7$ is halogen or $C_{1-8}$ alkyl; and $R_1$ is hydrogen or halogen.
(n) $R_7$ is halogen or $C_{1-8}$ alkyl; and $R_1$ is hydrogen.
(o) $R_7$ is halogen or $C_{1-8}$ alkyl; and $R_1$ is halogen.
(p) $R_7$ is halogen or $C_{1-8}$ alkyl; and $R_1$ is fluoro.
(q) $R_7$ is $C_{1-8}$ alkyl; and $R_1$ is hydrogen or halogen.
(r) $R_7$ is $C_{1-8}$ alkyl; and $R_1$ is hydrogen.
(s) $R_7$ is $C_{1-8}$ alkyl; and $R_1$ is halogen.
(t) $R_7$ is $C_{1-8}$ alkyl; and $R_1$ is fluoro.

In relation to compounds of formula (II), (III), (IIIa), (IIIb) and (IIIc), then $R_1$ and $R_7$ may preferably be as described herein above and Y may preferably be as described in the following paragraphs 1) to 19):

1) In one embodiment Y is aryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, $C(O)R^{Y1}$, or —$C_{1-8}$ alkyl-$R^Y$.
2) In another embodiment Y is phenyl substituted with one group which is halogen, cyano, —$OR^{Y1}$, —$SR^{Y1}$, —$N(R^{Y1})_2$, $C_{1-8}$ alkyl, —$C_{1-8}$ alkyl-$N(R^{Y1})_2$, or —$C_{1-8}$ alkyl-$OR^{Y1}$, and optionally substituted by one to two groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$.
3) In another embodiment Y is phenyl substituted with one group which is cyano, —$OR^{Y1}$, —$N(R^{Y1})_2$, $C_{1-8}$ alkyl, or —$C_{1-8}$ alkyl-$N(R^{Y1})_2$, and optionally substituted by one to two groups that are each independently halogen, $C_{1-8}$ alkyl, —$R^Y$, or —$C_{1-8}$ alkyl-$R^Y$.
4) In another embodiment Y is phenyl substituted with one group which is —$N(R^{Y1})_2$ or —$C_{1-8}$ alkyl-$N(R^{Y1})_2$, and optionally substituted by one to two groups that are each independently halogen, $C_{1-8}$ alkyl, —$R^Y$, or —$C_{1-8}$ alkyl-$R^Y$.
5) In another embodiment Y is phenyl substituted with one group which is —$NH_2$ or —$C_{1-8}$ alkyl-$NH_2$, and optionally substituted by one to two groups that are each independently halogen, $C_{1-8}$ alkyl, —$R^Y$, or —$C_{1-8}$ alkyl-$R^Y$.
6) In another embodiment Y is phenyl substituted with one group which is —$NH_2$ or —$CH_2NH_2$, and optionally substituted by one to two groups that are each independently halogen, $C_{1-8}$ alkyl, —$R^Y$, or —$C_{1-8}$ alkyl-$R^Y$.
7) In another embodiment Y is phenyl substituted with one group which is —$NH_2$ or —$CH_2NH_2$, and substituted by one to two groups that are each independently halogen, $C_{1-8}$ alkyl, —$R^Y$, or —$C_{1-8}$ alkyl-$R^Y$.
8) In another embodiment Y is heteroaryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$.
9) In another embodiment Y is a 5-membered or 6-membered heteroaryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$) alkyl, aryl($C_{1-8}$)alkyl, heteroaryl($C_{1-8}$)alkyl, —$R^Y$, or —$C_{1-8}$ alkyl-$R^Y$.
10) In another embodiment Y is a 5-membered or 6-membered heteroaryl substituted with one group which is —$N(R^{Y1})_2$ or —$C_{1-8}$ alkyl-$N(R^{Y1})_2$, and optionally substituted by one to two groups that are each independently halogen, $C_{1-8}$ alkyl, —$R^Y$, or —$C_{1-8}$ alkyl-$R^Y$.
11) In another embodiment Y is pyrazolyl.
12) In another embodiment Y is pyridyl, furyl, or thienyl each optionally substituted with one group which is —$N(R^{Y1})_2$ or —$C_{1-8}$ alkyl-$N(R^{Y1})_2$, and each optionally substituted by one to two groups that are each independently halogen, $C_{1-8}$ alkyl, —$R^Y$, or —$C_{1-8}$ alkyl-$R^Y$.
13) In another embodiment Y is pyridyl, furyl, or thienyl each optionally substituted with one group which is —$NH_2$ or —$CH_2NH_2$, and each optionally substituted by one to two groups that are each independently halogen, $C_{1-8}$ alkyl, —$R^Y$, or —$C_{1-8}$ alkyl-$R^Y$.
14) In another embodiment Y is pyridyl, tetrahydropyridinyl or pyrimidinyl optionally substituted with one group, which is halogen, $C_{1-8}$ alkyl or $R^Y$.
15) In another embodiment Y is a bicyclic heteroaryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$) alkyl, heteroaryl($C_{1-8}$)alkyl, —$R^Y$, or —$C_{1-8}$ alkyl-$R^Y$.
16) In another embodiment Y is a benzofuranyl, benzothienyl, indolyl, indazolyl, benzimidazolyl, benzoxazolyl, benzoisoxazolyl, benzothiazolyl, benzoisothiazolyl, or benzotriazolyl, each optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$.
17) In another embodiment Y is indazolyl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl ($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$.
18) In another embodiment Y is indazolyl.
19) In another embodiment Y is indolinyl or pyrrolopyridinyl optionally substituted with oxo.

In one preferred embodiment of the invention, then Y in relation to compounds of formula (II), (III), (IIIa), (IIIb) and (IIIc) is phenyl or pyridyl substituted with —$(CH_2)_n$—$NH_2$ or —$(CH_2)_n$—$NH$—$(CH_2)_m$—$CH_3$, wherein n and m independently are integers in the range of 0 to 3, wherein said phenyl or said pyridyl optionally may be substituted with one or two additional substituents selected from the group consisting of halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl ($C_{1-8}$)alkyl, —$R^Y$, or —$C_{1-8}$ alkyl-$R^Y$, wherein $R^Y$ is nitro, cyano, —$OR^{Y1}$, —$SR^{Y1}$, —$N(R^{Y1})_2$, —$C(O)R^{Y1}$, —$C(O)OR^{Y1}$, —$C(O)N(R^{Y1})_2$, —$OC(O)R^{Y1}$, —$OC(O)OR^{Y1}$, —$OC(O)N(R^{Y1})_2$, —$N(R^{Y1})C(O)R^{Y1}$, —$N(R^{Y1})C(O)OR^{Y1}$, —$N(R^{Y1})C(O)N(R^{Y1})_2$, —$S(O)_2R^{Y1}$, —$S(O)_2OR^{Y1}$, —$S(O)_2N(R^{Y1})_2$, —$OS(O)_2R^{Y1'}$, —$OS(O)_2OR^{Y1}$, —$OS(O)_2N(R^{Y1})_2$, —$N(R^{Y1})S(O)_2R^{Y1'}$, —$N(R^{Y1})S(O)_2OR^{Y1}$, or —$N(R^{Y1})S(O)_2N(R^{Y1})_2$, wherein each $R^{Y1}$ is independently hydrogen, $C_{1-8}$ alkyl, or $C_{1-8}$ haloalkyl.

In this embodiment it is preferred that Y in relation to compounds of formula (II), (III), (IIIa), (IIIb) and (IIIc) is phenyl substituted with —$(CH_2)_n$—$NH_2$ or —$(CH_2)_n$—$NH$—$(CH_2)_m$—$CH_3$, wherein n and m independently are integers in the range of 0 to 1, wherein said phenyl may optionally be substituted with one or two additional substituents selected from the group consisting of halogen, $C_{1-8}$ alkyl, $C_{1-8}$ haloalkyl, nitro, cyano and hydroxyl.

In relation to compounds of formula (II), (III) and (IIIb), then $R_1$, $R_7$ and Y are preferably as described herein above and $R_8$ may preferably be as described in the following paragraph: In a preferred embodiment $R_8$ is a $C_{1-8}$ alkyl, $C_{1-8}$ haloalkyl, or $C_{3-8}$cycloalkyl. In another embodiment $R_8$ is a $C_{1-8}$ alkyl (e.g., methyl). In another embodiment $R_8$ is a $C_{1-8}$ haloalkyl (e.g., trifluoromethyl). In a very preferred embodiment $R_8$ is $C_{3-8}$cycloalkyl (e.g., cyclopropyl, cyclobutyl, cyclopentyl, or cyclohexyl), and more preferably cyclopropyl or cyclobutyl, yet more preferably cyclopropyl. In one embodiment $R_8$ is $C_{3-8}$cycloalkyl optionally substituted by one or two groups that are each independently halogen or $C_{1-8}$ alkyl (e.g., fluoro or methyl). In another embodiment $R_8$ is heteroaryl, wherein the heteroaryl is optionally substituted with one to five groups that are each independently halogen, $C_{1-8}$ alkyl, $-OR^{21}$, $-N(R^{21})_2$, or $-C(O)OR^{21}$, wherein each $R^{21}$ is independently hydrogen or $C_{1-8}$ alkyl.

In one embodiment of the invention the 4-oxoquinolizine compound is a compound of the formula (IV):

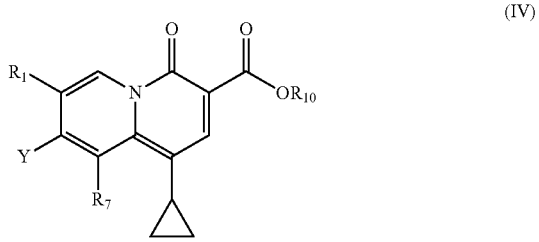

(IV)

or a pharmaceutically acceptable salt thereof, wherein $R_1$ is hydrogen or a halogen; and $R_7$ is hydrogen, halogen, a lower alkyl, a lower alkoxyl or a hydroxyl; and $R_{10}$ is hydrogen or a carboxyl protecting group; and Y is a phenyl or an aromatic group selected from the group consisting of 5 membered or 6-membered heterocyclic groups each optionally substituted with a group selected from the group consisting of lower alkyl, lower alkoxy, nitro, cyano, amino, acyl, carbamoyl, ureido, halogen, hydroxyl and carboxyl.

In particular, the 4-oxoquinolizine compound may be any of the 4-oxoquinolizine compounds described in US patent application US2004/0229903, the content of which is hereby incorporated by reference. More particular, the 4-oxoquinolizine compounds may be selected from the group of compounds described in Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122 and 123 of US2004/0229903.

In a preferred embodiment of the invention the 4-oxoquinolizine compound is selected from the group of compounds mentioned in Table 1 herein below.

TABLE 1

Examples of 4-oxoquinolizines compounds

| Compounds | Structure | Name |
|---|---|---|
| Compound 1 | ![structure] | 8-(3-fluoro-4-amino-phenyl)-1-cyclopropyl-9-methyl-4-oxo-quinolizine-3-carboxylic acid |
| Compound 2 | ![structure] | 8-(3,6-difluoro-4-amino-phenyl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 3 | 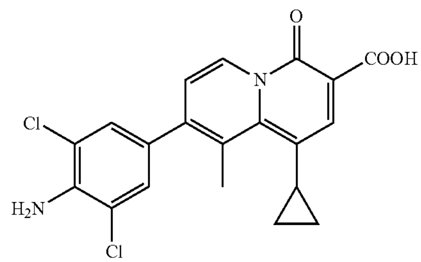 [SMILES: Cc1c(-c2cc(Cl)c(N)c(Cl)c2)ccn2c(=O)c(C(=O)O)cc(C3CC3)c12] | 8-(3,5-dichloro-4-amino-phenyl)-1-cyclopropyl-9-methyl-4-oxo-quinolizine-3-carboxylic acid |
| Compound 4 | 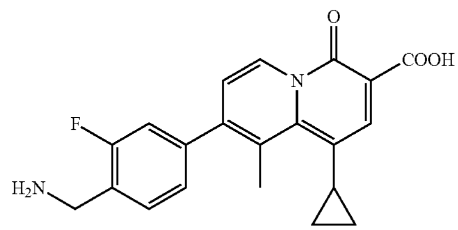 [SMILES: Cc1c(-c2ccc(CN)c(F)c2)ccn2c(=O)c(C(=O)O)cc(C3CC3)c12] | 8-(3-fluoro-4-aminomethyl-phenyl)-1-cyclopropyl-9-methyl-4-oxo-quinolizine-3-carboxylic acid |
| Compound 5 | 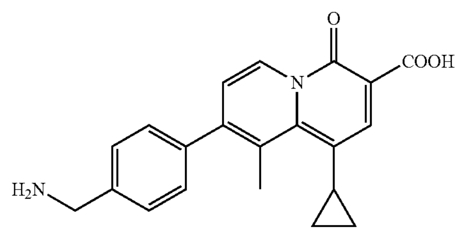 [SMILES: Cc1c(-c2ccc(CN)cc2)ccn2c(=O)c(C(=O)O)cc(C3CC3)c12] | 8-(4-aminomethyl-phenyl)-1-cyclopropyl-9-methyl-4-oxo-quinolizine-3-carboxylic acid |
| Compound 6 | 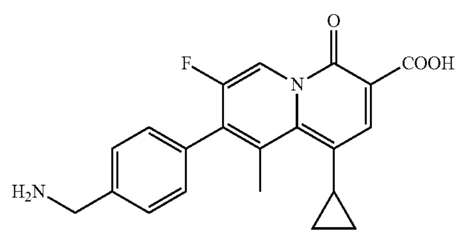 [SMILES: Cc1c(-c2ccc(CN)cc2)c(F)cn2c(=O)c(C(=O)O)cc(C3CC3)c12] | 8-(4-aminomethyl-phenyl)-1-cyclopropyl-7-fluoro-9-methyl-4-oxo-quinolizine-3-carboxylic acid |
| Compound 7 | 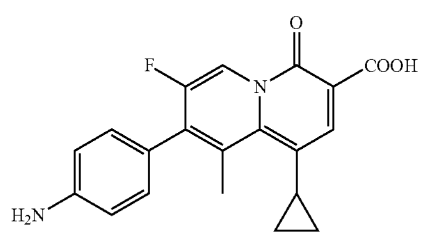 | 8-(4-amino-phenyl)-1-cyclopropyl-7-fluoro-9-methyl-4-oxo-quinolizine-3-carboxylic acid |
| Compound 8 | 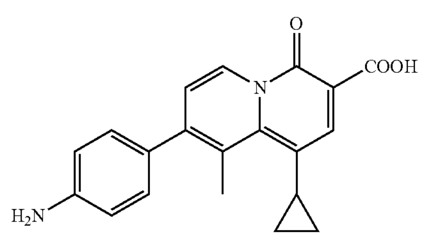 | 8-(4-amino-phenyl)-1-cyclopropyl-9-methyl-4-oxo-quinolizine-3-carboxylic acid |

TABLE 1-continued

Examples of 4-oxoquinolizines compounds

| Compounds | Structure | Name |
| --- | --- | --- |
| Compound 9 | 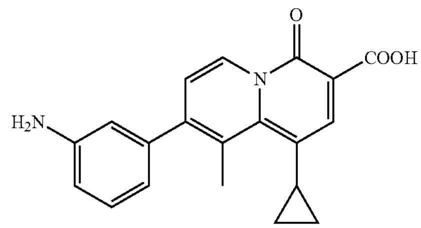 [SMILES: Cc1c(-c2cccc(N)c2)ccn2c(=O)c(C(=O)O)cc(C3CC3)c12] | 8-(3-amino-phenyl)-1-cyclopropyl-9-methyl-4-oxo-quinolizine-3-carboxylic acid |
| Compound 10 | 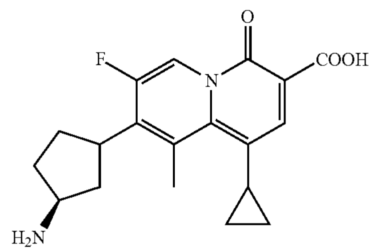 [SMILES: Cc1c(C2CC[C@H](N)C2)c(F)cn2c(=O)c(C(=O)O)cc(C3CC3)c12] | 8-[(3S)-3-aminocyclopentyl]-1-cyclopropyl-7-fluoro-9-methyl-4-oxo-quinolizine-3-carboxylic acid |
| Compound 11 | 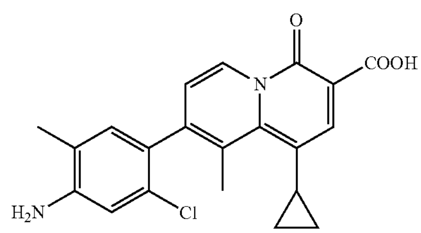 [SMILES: Cc1cc(-c2ccn3c(=O)c(C(=O)O)cc(C4CC4)c3c2C)c(Cl)cc1N] | 8-(2-chloro-4-amino-5-methyl-phenyl)-1-cyclopropyl-9-methyl-4-oxo-quinolizine-3-carboxylic acid |
| Compound 12 | 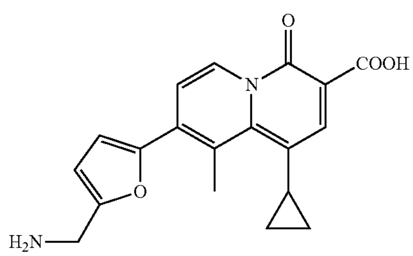 | 8-[5-aminomethyl)-2-furyl]-1-cyclopropyl-9-methyl-4-oxo-quinolizine-3-carboxylic acid |
| Compound 13 | 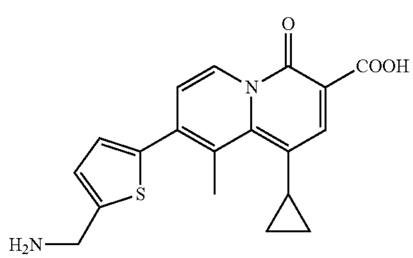 | 8-[5-aminomethyl)-2-thienyl]-1-cyclopropyl-9-methyl-4-oxo-quinolizine-3-carboxylic acid |
| Compound 14 | 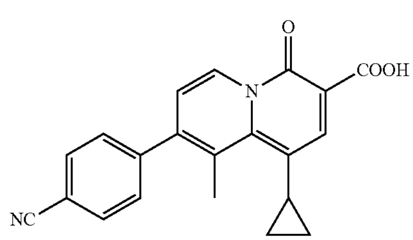 [SMILES: Cc1c(-c2ccc(C#N)cc2)ccn2c(=O)c(C(=O)O)cc(C3CC3)c12] | 8-(4-cyanophenyl)-1-cyclopropyl-9-methyl-4-oxo-quinolizine-3-carboxylic acid |

TABLE 1-continued

Examples of 4-oxoquinolizines compounds

| Compounds | Structure | Name |
| --- | --- | --- |
| Compound 15 | 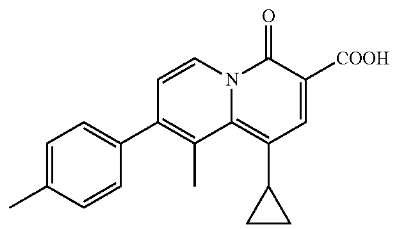 [SMILES: Cc1ccc(-c2ccn3c(=O)c(C(=O)O)cc(C4CC4)c3c2C)cc1] | 8-(p-tolyl)-1-cyclopropyl-9-methyl-4-oxo-quinolizine-3-carboxylic acid |
| Compound 16 | 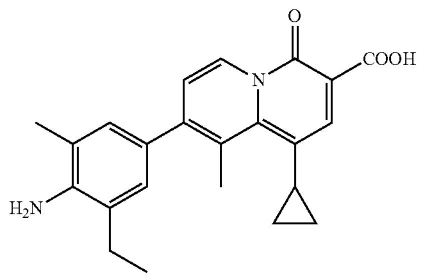 [SMILES: CCc1cc(-c2ccn3c(=O)c(C(=O)O)cc(C4CC4)c3c2C)cc(C)c1N] | 8-(4-amino-3-ethyl-5-methyl-phenyl)-1-cyclopropyl-9-methyl-4-oxo-quinolizine-3-carboxylic acid |
| Compound 17 | 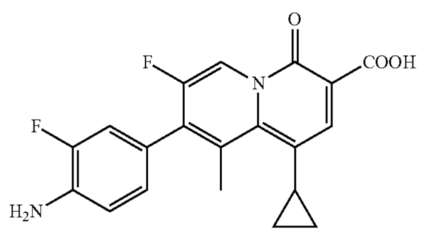 [SMILES: Cc1c(-c2ccc(N)c(F)c2)c(F)cn2c(=O)c(C(=O)O)cc(C3CC3)c12] | 8-(3-fluoro-4-amino-phenyl)-1-cyclopropyl-7-fluoro-9-methyl-4-oxo-quinolizine-3-carboxylic acid |
| Compound 18 | 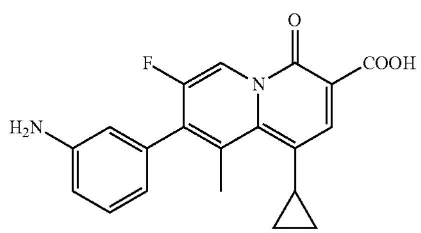 [SMILES: Cc1c(-c2cccc(N)c2)c(F)cn2c(=O)c(C(=O)O)cc(C3CC3)c12] | 8-(3-amino-phenyl)-1-cyclopropyl-7-fluoro-9-methyl-4-oxo-quinolizine-3-carboxylic acid |
| Compound 19 | 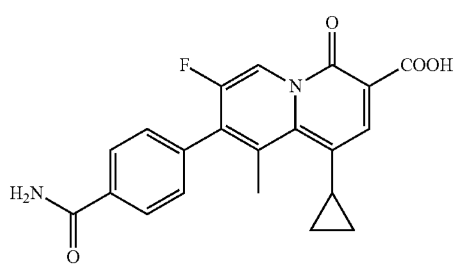 [SMILES: Cc1c(-c2ccc(C(N)=O)cc2)c(F)cn2c(=O)c(C(=O)O)cc(C3CC3)c12] | 8-(4-carbamoyl-phenyl)-1-cyclopropyl-7-fluoro-9-methyl-4-oxo-quinolizine-3-carboxylic acid |
| Compound 20 | 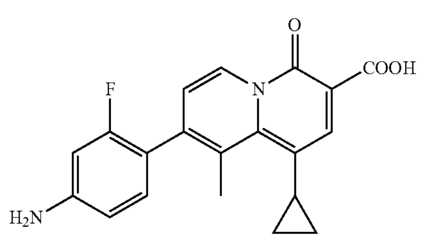 [SMILES: Cc1c(-c2ccc(N)cc2F)ccn2c(=O)c(C(=O)O)cc(C3CC3)c12] | 8-(2-fluoro-4-amino-phenyl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 21 | 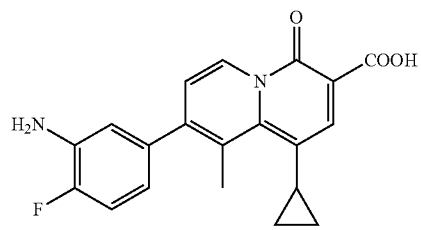 [SMILES: Cc1c(-c2ccc(F)c(N)c2)ccn2c(=O)c(C(=O)O)cc(C3CC3)c12] | 8-(3-amino-4-fluoro-phenyl)-1-cyclopropyl-9-methyl-4-oxo-quinolizine-3-carboxylic acid |
| Compound 22 | 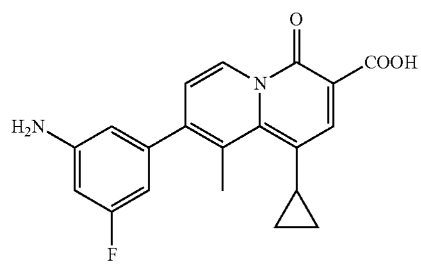 [SMILES: Cc1c(-c2cc(N)cc(F)c2)ccn2c(=O)c(C(=O)O)cc(C3CC3)c12] | 8-(3-amino-5-fluoro-phenyl)-1-cyclopropyl-9-methyl-4-oxo-quinolizine-3-carboxylic acid |
| Compound 23 | 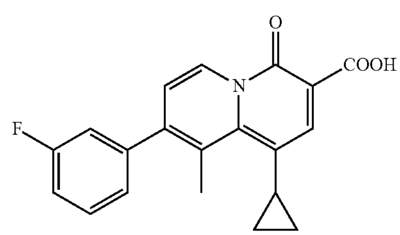 | 8-(3-fluoro-phenyl)-1-cyclopropyl-9-methyl-4-oxo-quinolizine-3-carboxylic acid |
| Compound 24 | 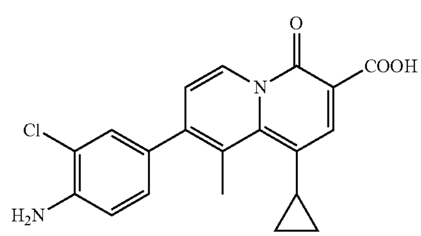 [SMILES: Cc1c(-c2ccc(N)c(Cl)c2)ccn2c(=O)c(C(=O)O)cc(C3CC3)c12] | 8-(3-chloro-4-amino-phenyl)-1-cyclopropyl-9-methyl-4-oxo-quinolizine-3-carboxylic acid |
| Compound 25 | 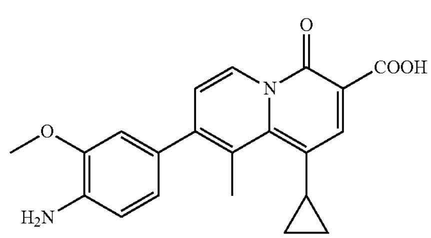 | 8-(3-methoxy-4-amino-phenyl)-1-cyclopropyl-9-methyl-4-oxo-quinolizine-3-carboxylic acid |
| Compound 26 | 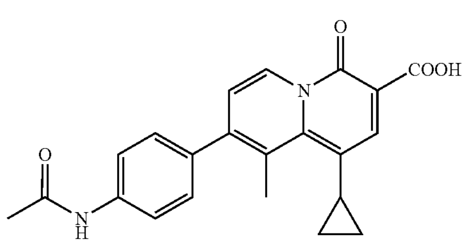 [SMILES: CC(=O)Nc1ccc(-c2ccn3c(=O)c(C(=O)O)cc(C4CC4)c3c2C)cc1] | 8-(4-acetamido-phenyl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 27 | 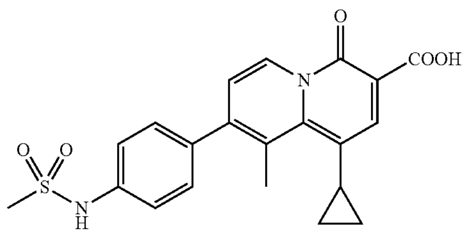 [SMILES: Cc1c(-c2ccc(NS(C)(=O)=O)cc2)ccn2c(=O)c(C(=O)O)cc(C3CC3)c12] | 8-(4-sulfonamido-phenyl)-1-cyclopropyl-9-methyl-4-oxo-quinolizine-3-carboxylic acid |
| Compound 28 | 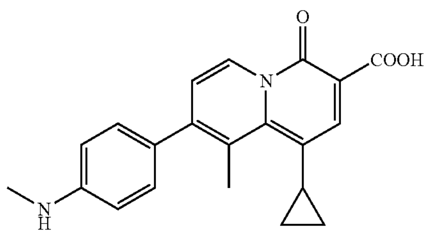 [SMILES: CNc1ccc(-c2ccn3c(=O)c(C(=O)O)cc(C4CC4)c3c2C)cc1] | 8-(4-methylamino-phenyl)-1-cyclopropyl-9-methyl-4-oxo-quinolizine-3-carboxylic acid |
| Compound 29 | 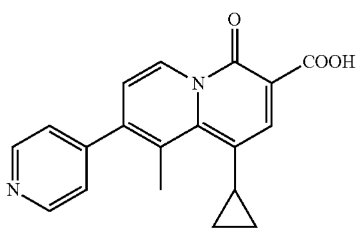 [SMILES: Cc1c(-c2ccncc2)ccn2c(=O)c(C(=O)O)cc(C3CC3)c12] | 8-(4-pyridyl)-1-cyclopropyl-9-methyl-4-oxo-quinolizine-3-carboxylic acid |
| Compound 30 | 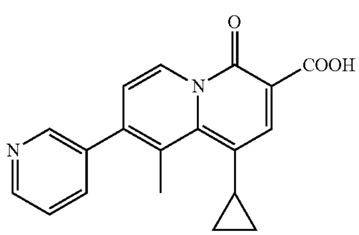 [SMILES: Cc1c(-c2cccnc2)ccn2c(=O)c(C(=O)O)cc(C3CC3)c12] | 8-(3-pyridyl)-1-cyclopropyl-9-methyl-4-oxo-quinolizine-3-carboxylic acid |
| Compound 31 | 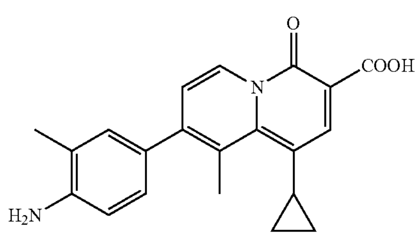 | 8-(3-methyl-4-amino-phenyl)-1-cyclopropyl-9-methyl-4-oxo-quinolizine-3-carboxylic acid |
| Compound 32 | 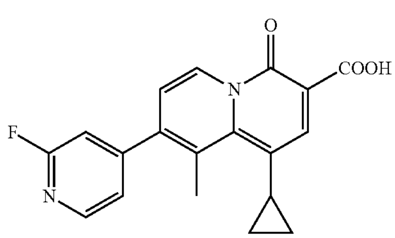 [SMILES: Cc1c(-c2ccnc(F)c2)ccn2c(=O)c(C(=O)O)cc(C3CC3)c12] | 8-(2-fluoro-4-pyridyl)-1-cyclopropyl-9-methyl-4-oxo-quinolizine-3-carboxylic acid |

TABLE 1-continued

Examples of 4-oxoquinolizines compounds

| Compounds | Structure | Name |
| --- | --- | --- |
| Compound 33 | 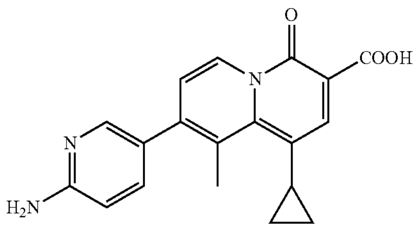 [SMILES: Cc1c(-c2ccc(N)nc2)ccn2c(=O)c(C(=O)O)cc(C3CC3)c12] | 8-(6-amino-3-pyridyl)-1-cyclopropyl-9-methyl-4-oxo-quinolizine-3-carboxylic acid |
| Compound 34 | 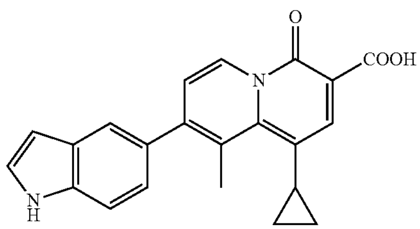 [SMILES: Cc1c(-c2ccc3[nH]ccc3c2)ccn2c(=O)c(C(=O)O)cc(C3CC3)c12] | 8-(1H-indol-5-yl)-1-cyclopropyl-9-methyl-4-oxo-quinolizine-3-carboxylic acid |
| Compound 35 | 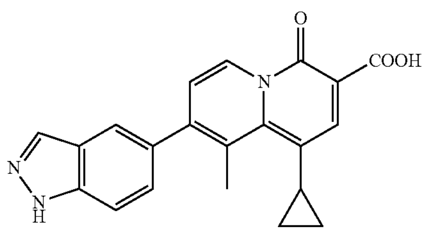 [SMILES: Cc1c(-c2ccc3[nH]ncc3c2)ccn2c(=O)c(C(=O)O)cc(C3CC3)c12] | 8-(1H-indazol-5-yl)-1-cyclopropyl-9-methyl-4-oxo-quinolizine-3-carboxylic acid |
| Compound 36 | 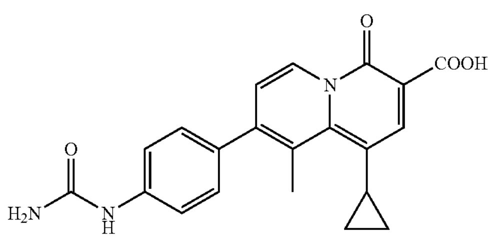 [SMILES: Cc1c(-c2ccc(NC(N)=O)cc2)ccn2c(=O)c(C(=O)O)cc(C3CC3)c12] | 8-(4-ureido-phenyl)-1-cyclopropyl-9-methyl-4-oxo-quinolizine-3-carboxylic acid |
| Compound 37 | 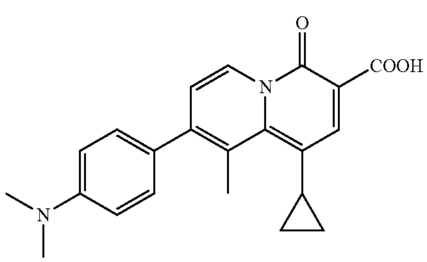 [SMILES: Cc1c(-c2ccc(N(C)C)cc2)ccn2c(=O)c(C(=O)O)cc(C3CC3)c12] | 8-(4-dimethylamino-phenyl)-1-cyclopropyl-9-methyl-4-oxo-quinolizine-3-carboxylic acid |
| Compound 38 | 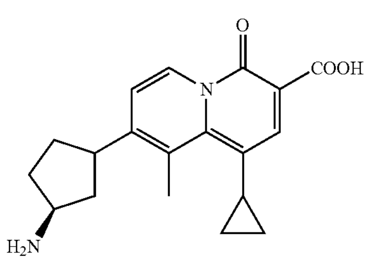 [SMILES: Cc1c(C2CC[C@H](N)C2)ccn2c(=O)c(C(=O)O)cc(C3CC3)c12] | 8-[(3S)-3-aminopyrrolidin-1-yl]-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 39 | 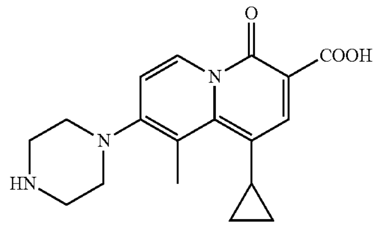 [SMILES: Cc1c(N2CCNCC2)ccn2c(=O)c(C(=O)O)cc(C3CC3)c12] | 8-(piperazin-1-yl)-1-cyclopropyl-9-methyl-4-oxo-quinolizine-3-carboxylic acid |
| Compound 40 | 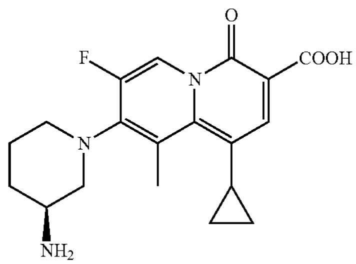 [SMILES: Cc1c(N2CCC[C@H](N)C2)c(F)cn2c(=O)c(C(=O)O)cc(C3CC3)c12] | 8-[(3S)-3-amino-1-piperidyl]-1-cyclopropyl-9-methyl-4-oxo-quinolizine-3-carboxylic acid |
| Compound 41 | 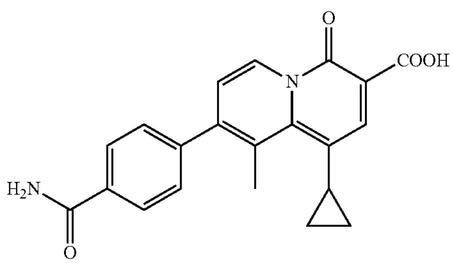 [SMILES: Cc1c(-c2ccc(C(N)=O)cc2)ccn2c(=O)c(C(=O)O)cc(C3CC3)c12] | 8-(4-carbamoyl-phenyl)-1-cyclopropyl-9-methyl-4-oxo-quinolizine-3-carboxylic acid |
| Compound 42 | 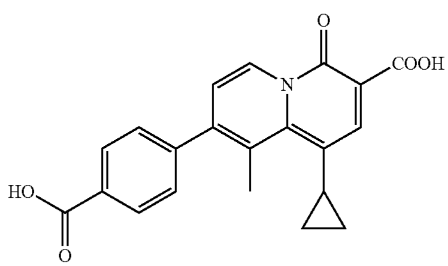 [SMILES: Cc1c(-c2ccc(C(=O)O)cc2)ccn2c(=O)c(C(=O)O)cc(C3CC3)c12] | 8-(4-carboxy-phenyl)-1-cyclopropyl-9-methyl-4-oxo-quinolizine-3-carboxylic acid |
| Compound 43 | 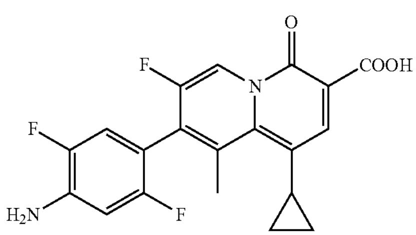 [SMILES: Cc1c(-c2cc(F)c(N)cc2F)c(F)cn2c(=O)c(C(=O)O)cc(C3CC3)c12] | 8-(2,5-difluoro-4-amino-phenyl)-1-cyclopropyl-7-fluoro-9-methyl-4-oxo-quinolizine-3-carboxylic acid |
| Compound 44 | 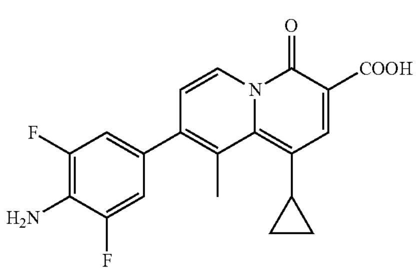 [SMILES: Cc1c(-c2cc(F)c(N)c(F)c2)ccn2c(=O)c(C(=O)O)cc(C3CC3)c12] | 8-(3,5-difluoro-4-amino-phenyl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 45 | 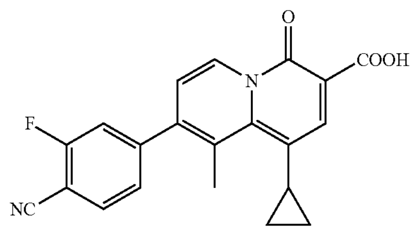 [SMILES: Cc1c(-c2ccc(C#N)c(F)c2)ccn2c(=O)c(C(=O)O)cc(C3CC3)c12] | 8-(3-fluoro-4-cyano-phenyl)-1-cyclopropyl-9-methyl-4-oxo-quinolizine-3-carboxylic acid |
| Compound 46 | 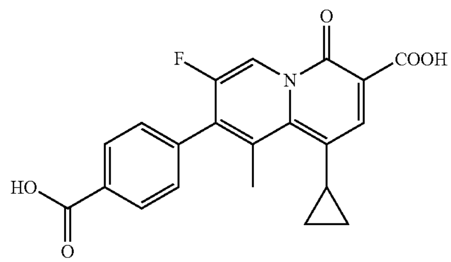 [SMILES: Cc1c(-c2ccc(C(=O)O)cc2)c(F)cn2c(=O)c(C(=O)O)cc(C3CC3)c12] | 8-(4-carboxy-phenyl)-1-cyclopropyl-7-fluoro-9-methyl-4-oxo-quinolizine-3-carboxylic acid |
| Compound 47 | 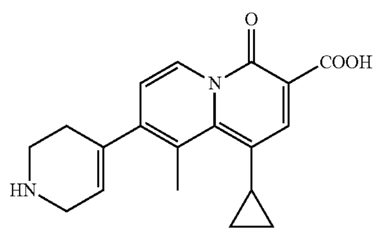 [SMILES: Cc1c(C2=CCNCC2)ccn2c(=O)c(C(=O)O)cc(C3CC3)c12] | 8-(1,2,3,6-tetrahydro-pyridin-4-yl)-1-cyclopropyl-9-methyl-4-oxo-quinolizine-3-carboxylic acid |
| Compound 48 | 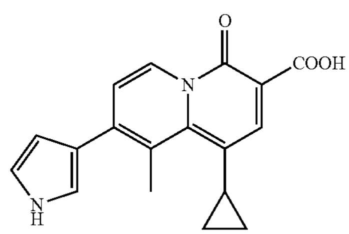 [SMILES: Cc1c(-c2cc[nH]c2)ccn2c(=O)c(C(=O)O)cc(C3CC3)c12] | 8-(1H-pyrrol-3-yl)-1-cyclopropyl-9-methyl-4-oxo-quinolizine-3-carboxylic acid |
| Compound 49 | 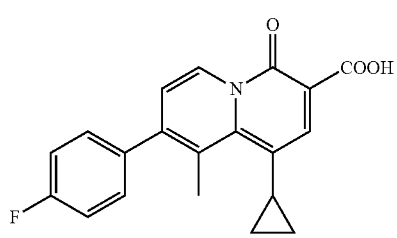 [SMILES: Cc1c(-c2ccc(F)cc2)ccn2c(=O)c(C(=O)O)cc(C3CC3)c12] | 8-(4-fluoro-phenyl)-1-cyclopropyl-9-methyl-4-oxo-quinolizine-3-carboxylic acid |
| Compound 50 | 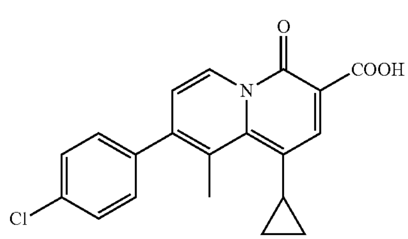 [SMILES: Cc1c(-c2ccc(Cl)cc2)ccn2c(=O)c(C(=O)O)cc(C3CC3)c12] | 8-(4-chloro-phenyl)-1-cyclopropyl-9-methyl-4-oxo-quinolizine-3-carboxylic acid |

TABLE 1-continued

Examples of 4-oxoquinolizines compounds

| Compounds | Structure | Name |
| --- | --- | --- |
| Compound 51 | 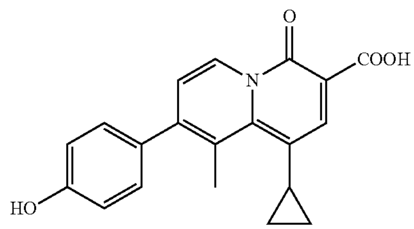 | 8-(4-hydroxy-phenyl)-1-cyclopropyl-9-methyl-4-oxo-quinolizine-3-carboxylic acid |
| Compound 52 | 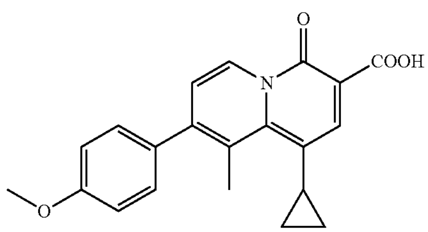 [SMILES: COc1ccc(-c2ccn3c(=O)c(C(=O)O)cc(C4CC4)c3c2C)cc1] | 8-(4-methoxy-phenyl)-1-cyclopropyl-9-methyl-4-oxo-quinolizine-3-carboxylic acid |
| Compound 53 | 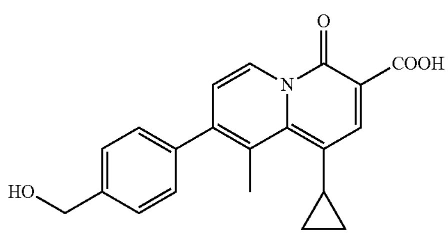 [SMILES: Cc1c(-c2ccc(CO)cc2)ccn2c(=O)c(C(=O)O)cc(C3CC3)c12] | 8-(4-hydroxymethyl-phenyl)-1-cyclopropyl-9-methyl-4-oxo-quinolizine-3-carboxylic acid |
| Compound 54 | 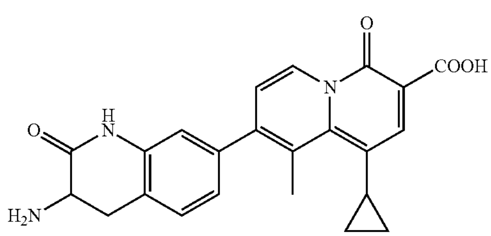 [SMILES: Cc1c(-c2ccc3c(c2)NC(=O)C(N)C3)ccn2c(=O)c(C(=O)O)cc(C3CC3)c12] | 8-(3-amino-2-oxo-3,4-dihydro-1H-quinolin-7-yl)-1-cyclopropyl-9-methyl-4-oxo-quinolizine-3-carboxylic acid |
| Compound 55 | 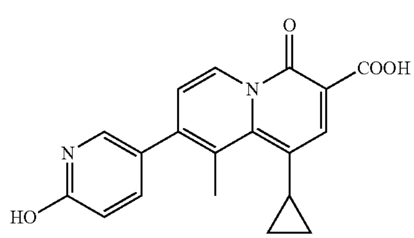 | 8-(6-hydroxy-3-pyridyl)-1-cyclopropyl-9-methyl-4-oxo-quinolizine-3-carboxylic acid |
| Compound 56 | 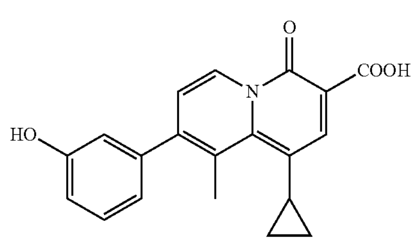 [SMILES: Cc1c(-c2cccc(O)c2)ccn2c(=O)c(C(=O)O)cc(C3CC3)c12] | 8-(4-hydroxyphenyl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 57 | 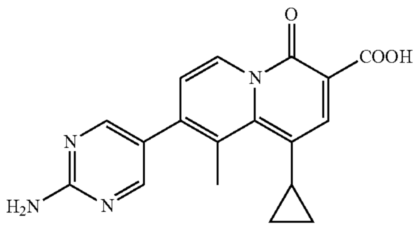 [SMILES: Cc1c(-c2cnc(N)nc2)ccn2c(=O)c(C(=O)O)cc(C3CC3)c12] | 8-(2-aminopyrimidin-5-yl)-1-cyclopropyl-9-methyl-4-oxo-quinolizine-3-carboxylic acid |
| Compound 58 | 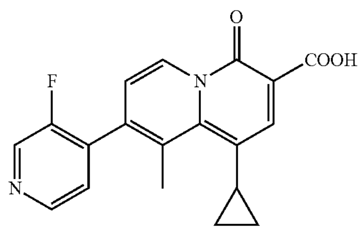 [SMILES: Cc1c(-c2ccncc2F)ccn2c(=O)c(C(=O)O)cc(C3CC3)c12] | 8-(3-fluoro-4-pyridyl)-1-cyclopropyl-9-methyl-4-oxo-quinolizine-3-carboxylic acid |
| Compound 59 | 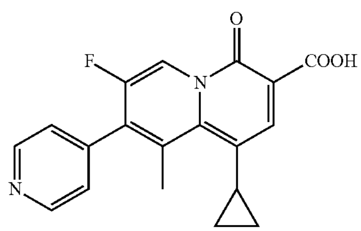 [SMILES: Cc1c(-c2ccncc2)c(F)cn2c(=O)c(C(=O)O)cc(C3CC3)c12] | 8-(4-pyridyl)-1-cyclopropyl-7-fluoro-9-methyl-4-oxo-quinolizine-3-carboxylic acid |
| Compound 60 | 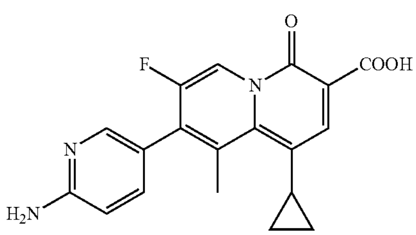 [SMILES: Cc1c(-c2ccc(N)nc2)c(F)cn2c(=O)c(C(=O)O)cc(C3CC3)c12] | 8-(6-amino-3-pyridyl)-1-cyclopropyl-7-fluoro-9-methyl-4-oxo-quinolizine-3-carboxylic acid |
| Compound 61 | 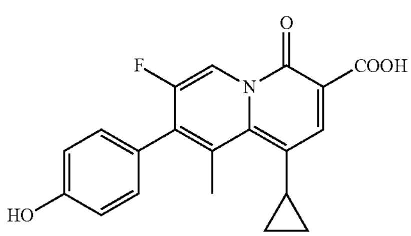 [SMILES: Cc1c(-c2ccc(O)cc2)c(F)cn2c(=O)c(C(=O)O)cc(C3CC3)c12] | 8-(4-hydroxyphenyl)-1-cyclopropyl-7-fluoro-9-methyl-4-oxo-quinolizine-3-carboxylic acid |
| Compound 62 | 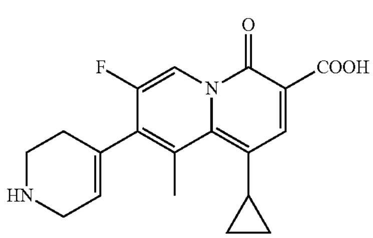 [SMILES: Cc1c(C2=CCNCC2)c(F)cn2c(=O)c(C(=O)O)cc(C3CC3)c12] | 8-(1,2,3,6-tetrahydro-pyridin-4-yl)-1-cyclopropyl-7-fluoro-9-methyl-4-oxo-quinolizine-3-carboxylic acid |

TABLE 1-continued

Examples of 4-oxoquinolizines compounds

| Compounds | Structure | Name |
|---|---|---|
| Compound 63 | 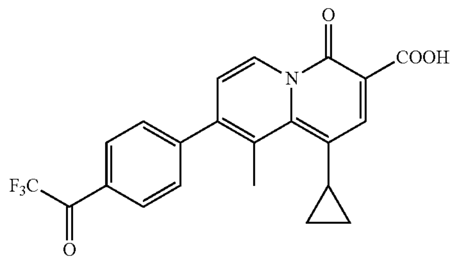 [SMILES: Cc1c(-c2ccc(C(=O)C(F)(F)F)cc2)ccn2c(=O)c(C(=O)O)cc(C3CC3)c12] | 8-[4-(2,2,2-trifluoroacetyl)phenyl]-1-cyclopropyl-9-methyl-4-oxo-quinolizine-3-carboxylic acid |
| Compound 64 | 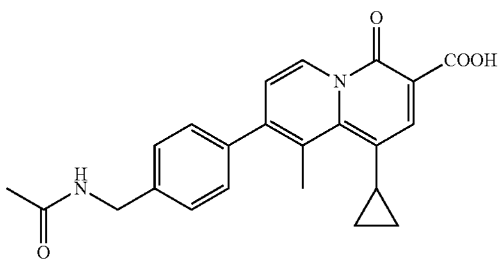 [SMILES: CC(=O)NCc1ccc(-c2ccn3c(=O)c(C(=O)O)cc(C4CC4)c3c2C)cc1] | 8-[4-(acetamidomethyl)phenyl]--1-cyclopropyl-9-methyl-4-oxo-quinolizine-3-carboxylic acid |
| Compound 65 | 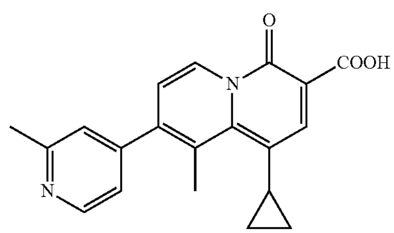 [SMILES: Cc1cc(-c2ccn3c(=O)c(C(=O)O)cc(C4CC4)c3c2C)ccn1] | 8-(3-methyl-4-pyridyl)-1-cyclopropyl-9-methyl-4-oxo-quinolizine-3-carboxylic acid |
| Compound 66 | 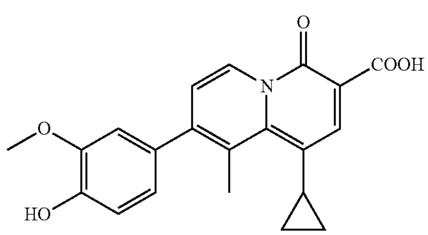 [SMILES: COc1cc(-c2ccn3c(=O)c(C(=O)O)cc(C4CC4)c3c2C)ccc1O] | 8-(3-methyl-4-hydroxyphenyl)-1-cyclopropyl-9-methyl-4-oxo-quinolizine-3-carboxylic acid |
| Compound 67 | 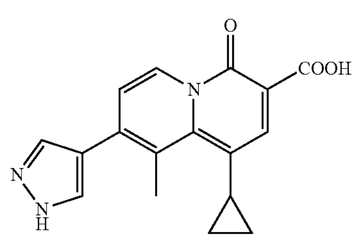 [SMILES: Cc1c(-c2cn[nH]c2)ccn2c(=O)c(C(=O)O)cc(C3CC3)c12] | 8-(1H-pyrazol-4-yl)-1-cyclopropyl-9-methyl-4-oxo-quinolizine-3-carboxylic acid |
| Compound 68 | 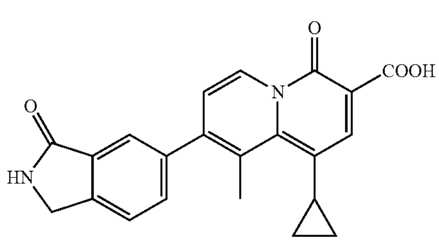 [SMILES: Cc1c(-c2ccc3c(c2)C(=O)NC3)ccn2c(=O)c(C(=O)O)cc(C3CC3)c12] | 8-(3-oxoisoindolin-5-yl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 69 | 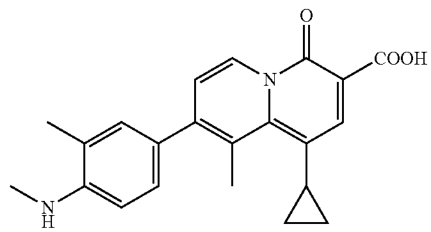 [SMILES: CNc1ccc(-c2ccn3c(=O)c(C(=O)O)cc(C4CC4)c3c2C)cc1C] | 8-[3-methyl-4-(methylamino)phenyl]-1-cyclopropyl-9-methyl-4-oxo-quinolizine-3-carboxylic acid |
| Compound 70 | 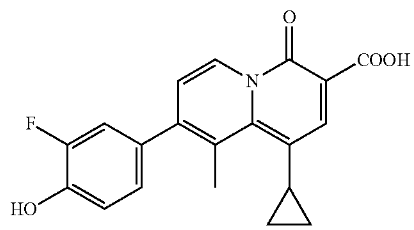 [SMILES: Cc1c(-c2ccc(O)c(F)c2)ccn2c(=O)c(C(=O)O)cc(C3CC3)c12] | 8-(3-fluoro-4-hydroxy-phenyl)-1-cyclopropyl-9-methyl-4-oxo-quinolizine-3-carboxylic acid |
| Compound 71 | 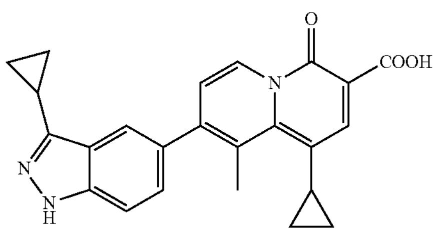 [SMILES: Cc1c(-c2ccc3[nH]nc(C4CC4)c3c2)ccn2c(=O)c(C(=O)O)cc(C3CC3)c12] | 8-(3-cyclopropyl-1H-indazol-5-yl)-1-cyclopropyl-9-methyl-4-oxo-quinolizine-3-carboxylic acid |
| Compound 72 | 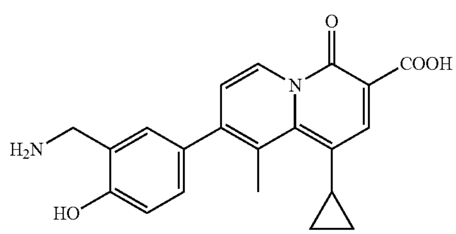 [SMILES: Cc1c(-c2ccc(O)c(CN)c2)ccn2c(=O)c(C(=O)O)cc(C3CC3)c12] | 8-[3-(aminomethyl)-4-hydroxy-phenyl]-1-cyclopropyl-9-methyl-4-oxo-quinolizine-3-carboxylic acid |
| Compound 73 | 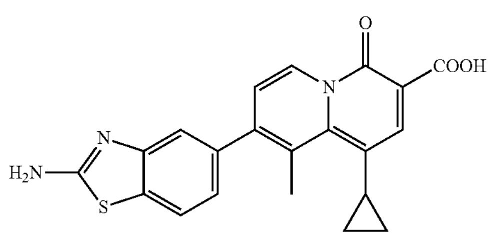 [SMILES: Cc1c(-c2ccc3sc(N)nc3c2)ccn2c(=O)c(C(=O)O)cc(C3CC3)c12] | 8-(2-amino-1,3-benzothiazol-5-yl)-1-cyclopropyl-9-methyl-4-oxo-quinolizine-3-carboxylic acid |
| Compound 74 | 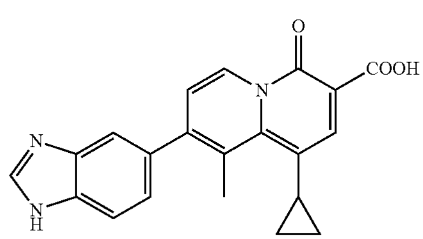 [SMILES: Cc1c(-c2ccc3[nH]cnc3c2)ccn2c(=O)c(C(=O)O)cc(C3CC3)c12] | 8-(1H-benzimidazol-5-yl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 75 | 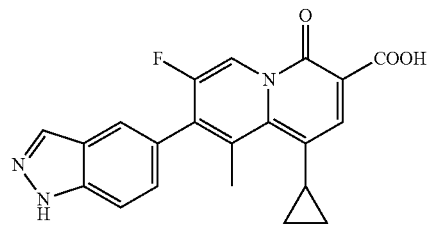 [SMILES: Cc1c(-c2ccc3[nH]ncc3c2)c(F)cn2c(=O)c(C(=O)O)cc(C3CC3)c12] | 8-(1H-indazol-5-yl)-1-cyclopropyl-7-fluoro-9-methyl-4-oxo-quinolizine-3-carboxylic acid |
| Compound 76 | 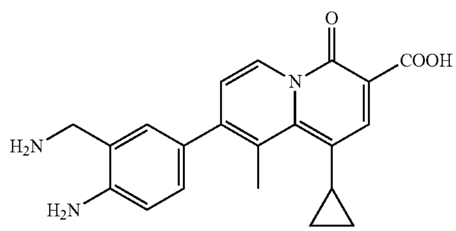 | 8-[3-(aminomethyl)-4-amino-phenyl]-1-cyclopropyl-9-methyl-4-oxo-quinolizine-3-carboxylic acid |
| Compound 77 | 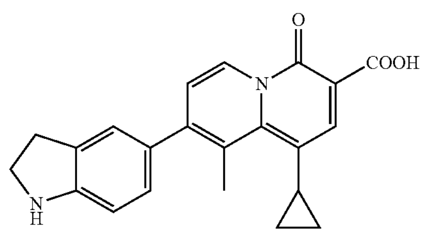 [SMILES: Cc1c(-c2ccc3c(c2)CCN3)ccn2c(=O)c(C(=O)O)cc(C3CC3)c12] | 8-(indolin-5-yl)-1-cyclopropyl-9-methyl-4-oxo-quinolizine-3-carboxylic acid |
| Compound 78 | 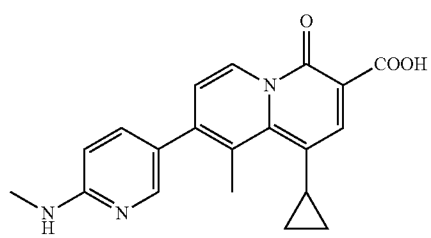 [SMILES: CNc1ccc(-c2ccn3c(=O)c(C(=O)O)cc(C4CC4)c3c2C)cn1] | 8-[6-(methylamino)-3-pyridyl]-1-cyclopropyl-9-methyl-4-oxo-quinolizine-3-carboxylic acid |
| Compound 79 | 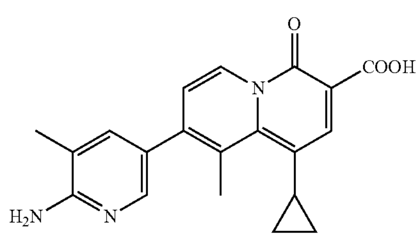 [SMILES: Cc1cc(-c2ccn3c(=O)c(C(=O)O)cc(C4CC4)c3c2C)cnc1N] | 8-(6-amino-5-methyl-3-pyridyl)-1-cyclopropyl-9-methyl-4-oxo-quinolizine-3-carboxylic acid |
| Compound 80 | 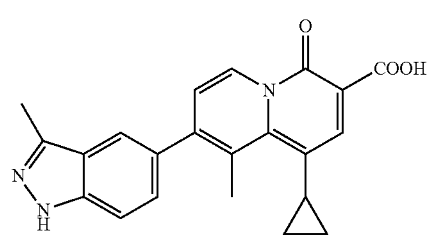 [SMILES: Cc1n[nH]c2ccc(-c3ccn4c(=O)c(C(=O)O)cc(C5CC5)c4c3C)cc12] | 8-(3-methyl-1H-indazol-5-yl)-1-cyclopropyl-9-methyl-4-oxo-quinolizine-3-carboxylic acid |

TABLE 1-continued

Examples of 4-oxoquinolizines compounds

| Compounds | Structure | Name |
| --- | --- | --- |
| Compound 81 | 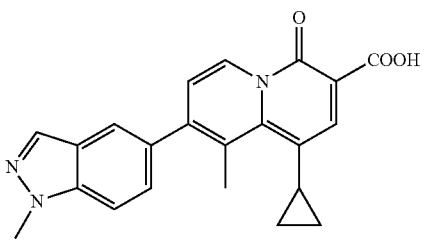 [SMILES: Cc1c(-c2ccc3c(cnn3C)c2)ccn2c(=O)c(C(=O)O)cc(C3CC3)c12] | 8-(1-methylindazol-5-yl)-1-cyclopropyl-9-methyl-4-oxo-quinolizine-3-carboxylic acid |
| Compound 82 | 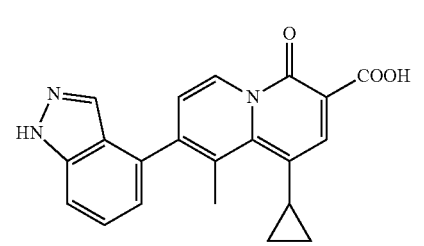 [SMILES: Cc1c(-c2cccc3[nH]ncc23)ccn2c(=O)c(C(=O)O)cc(C3CC3)c12] | 8-(1H-indazol-4-yl)-1-cyclopropyl-9-methyl-4-oxo-quinolizine-3-carboxylic acid |
| Compound 83 | 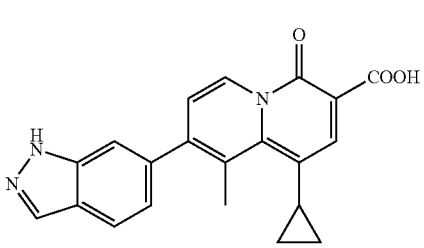 [SMILES: Cc1c(-c2ccc3cn[nH]c3c2)ccn2c(=O)c(C(=O)O)cc(C3CC3)c12] | 8-(1H-indazol-6-yl)-1-cyclopropyl-9-methyl-4-oxo-quinolizine-3-carboxylic acid |
| Compound 84 | 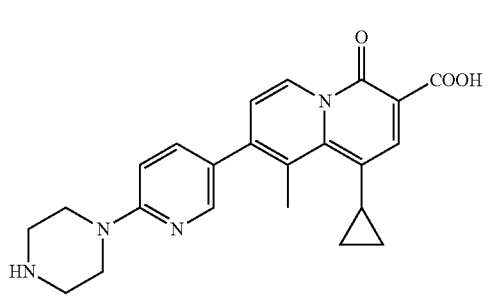 [SMILES: Cc1c(-c2ccc(N3CCNCC3)nc2)ccn2c(=O)c(C(=O)O)cc(C3CC3)c12] | 8-(6-piperazin-1-yl-3-pyridyl)-1-cyclopropyl-9-methyl-4-oxo-quinolizine-3-carboxylic acid |
| Compound 85 | 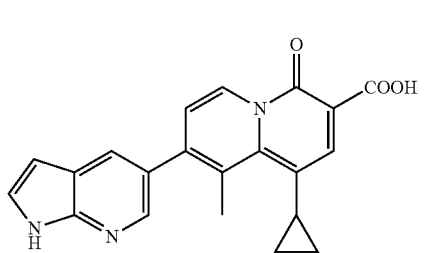 [SMILES: Cc1c(-c2cnc3[nH]ccc3c2)ccn2c(=O)c(C(=O)O)cc(C3CC3)c12] | 8-(1H-pyrrolo-[2,3-b]-pyridin-5-yl)-1-cyclopropyl-9-methyl-4-oxo-quinolizine-3-carboxylic acid |
| Compound 86 | 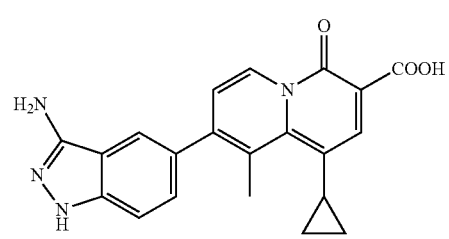 [SMILES: Cc1c(-c2ccc3[nH]nc(N)c3c2)ccn2c(=O)c(C(=O)O)cc(C3CC3)c12] | 8-(3-amino-1H-indazol-5-yl)-1-cyclopropyl-9-methyl-4-oxo-quinolizine-3-carboxylic acid |

TABLE 1-continued

Examples of 4-oxoquinolizines compounds

| Compounds | Structure | Name |
|---|---|---|
| Compound 87 | 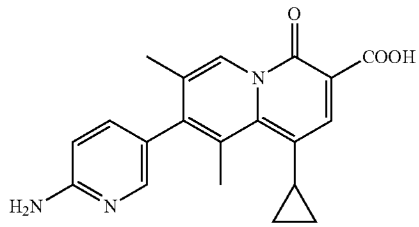 [SMILES: Cc1cn2c(=O)c(C(=O)O)cc(C3CC3)c2c(C)c1-c1ccc(N)nc1] | 8-(6-amino-3-pyridyl)-1-cyclopropyl-7,9-dimethyl-4-oxo-quinolizine-3-carboxylic acid |
| Compound 88 | 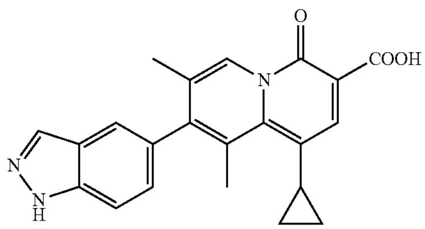 [SMILES: Cc1cn2c(=O)c(C(=O)O)cc(C3CC3)c2c(C)c1-c1ccc2[nH]ncc2c1] | 8-(1H-indazol-5-yl)-7,9-dimethyl-4-oxo-quinolizine-3-carboxylic acid |
| Compound 89 | 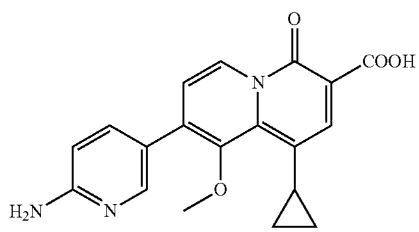 [SMILES: COc1c(-c2ccc(N)nc2)ccn2c(=O)c(C(=O)O)cc(C3CC3)c12] | 8-(6-amino-3-pyridyl)-1-cyclopropyl-9-methoxy-4-oxo-quinolizine-3-carboxylic acid |
| Compound 90 | 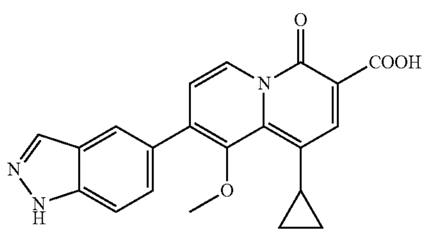 [SMILES: COc1c(-c2ccc3[nH]ncc3c2)ccn2c(=O)c(C(=O)O)cc(C3CC3)c12] | 8-(1H-indazol-5-yl)-9-methoxy-4-oxo-quinolizine-3-carboxylic acid |

Particular 4-Oxoquinolizines

It is one aspect of the present invention to provide pharmaceutical compositions comprising a 2-pyridone compound, preferably a 4-oxoquinolizine compound in combination with a Polymyxin, preferably Polymyxin B. Said 4-oxoquinolizine compound may be any of the 4-oxoquinolizine compounds described herein above in the section 4-oxoquinolizines, however it may also be any of the 4-oxoquinolizine compounds described in this section.

It is furthermore an aspect of the present invention to provide particularly useful 2-pyridines, i.e. such as particularly useful 4-oxoquinolizine compounds. Said particularly useful 4-oxoquinolizine compounds have a strong antibacterial effect, i.e. that they are useful in the treatment of bacterial infections.

The particular 4-oxoquinolizine compounds are preferably a compound having activity against a pathogen, having the structure of formula (I)

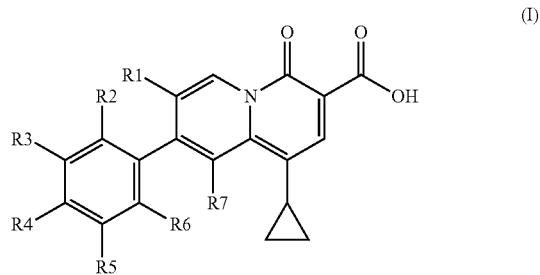

or a pharmaceutically acceptable salt thereof.

In one embodiment of the invention the compounds of formula (I) have R groups as follows: R1 and R2 are independently hydrogen or fluorine, R3 and R5 are independently hydrogen, fluorine or chlorine, R4 is —NH$_2$ or —CH$_2$NH$_2$, R6 is H or F, and R7 is H, CF$_3$, CONH$_2$, CH$_3$, OCH$_3$, or —CN.

In another embodiment of the invention the preferred 4-oxoquinolizine compounds are compounds of formula (I) or pharmaceutically acceptable salts thereof, wherein
R1 is hydrogen or fluorine; and
R3 is fluorine, —(CH$_2$)$_n$—NH$_2$ or C$_{1-3}$-alkyl, wherein n is an integer in the range of 0 to 2; and
R4 is —(CH$_2$)$_n$—NH$_2$, —NH—(CH2)$_n$—CH$_3$ or C$_{1-3}$-alkyl, wherein n is an integer in the range of 0 to 2; and
R5 is hydrogen or C$_{1-3}$ alkyl; and
R2 and R6 are hydrogen; and
R7 is C$_{1-3}$ alkyl or C$_{1-3}$ alkoxy.

In this embodiment it is preferred that
R1 is hydrogen or fluorine; and
R3 is fluorine, —NH$_2$, —CH$_2$—NH$_2$ or methyl; and
R4 is —NH$_2$, —(CH$_2$)—NH$_2$, —NH—CH$_3$ or methyl; and
R5 is hydrogen or ethyl; and
R2 and R6 are hydrogen; and
R7 is methyl.

It is furthermore preferred that when R3 is fluorine and R4 is amine, then R1 is fluorine.

Examples of useful 4-oxoquinolizine compounds according to this embodiment may for example be selected from the group consisting of compounds 4, 16, 17, 69 and 76 of Table 1.

In another embodiment of the present invention the preferred 4-oxoquinolizine compounds of the invention are compounds of formula (I) or a pharmaceutically acceptable salt thereof, wherein
R1 is as defined herein above in relation to compounds of formula (III); and
R2, R3, R4, R5 and R6 each independently are hydrogen, hydroxyl, —(CH$_2$)$_n$—NH—(C═O)—(CH$_2$)$_m$—CH$_3$, —(C═O)—C$_{1-8}$ alkyl, —(C═O)—C$_{1-8}$ haloalkyl, halogen, —(CH$_2$)$_n$—NH$_2$, —NH—(CH$_2$)$_n$—CH$_3$, C$_{1-8}$-alkyl or C$_{1-8}$ alkoxy, wherein n and m each independently is an integer in the range of 0 to 3 and wherein at least one of R2, R3, R4, R5 or R6 is hydroxyl, —(CH$_2$)$_n$—NH—(C═O)—(CH$_2$)$_n$—CH$_3$ or —(C═O)—C$_{1-8}$ haloalkyl; and
R7 is as defined herein above in relation to compounds of formula (III).

In this embodiment the 4-oxoquinolizine compounds are preferably compounds of formula (I) or a pharmaceutically acceptable salt thereof, wherein
R1 is hydrogen or fluorine; and
R2, R3, R4, R5 and R6 each independently are hydrogen, hydroxyl, flourine, —NH$_2$, —(CH$_2$)—NH$_2$, C$_{1-3}$-alkyl, —CH$_2$—NH—(C═O)—CH$_3$, —(C═O)—CF$_3$ or C$_{1-3}$ alkoxy, wherein at least one of R2, R3, R4, R5 or R6 is hydroxyl, —CH$_2$—NH—(C═O)—CH$_3$ or —(C═O)—CF$_3$; and
R7 is C$_{1-3}$ alkyl or C$_{1-3}$ alkoxy.

In this embodiment it is even more preferred that the 4-oxoquinolizine compounds are compounds of formula (I) or a pharmaceutically acceptable salt thereof, wherein
R1 is hydrogen or fluorine; and
R2, R3, R4, R5 and R6 each independently are hydrogen, hydroxyl, —CH$_2$—NH—(C═O)—CH$_3$, —(C═O)—CF$_3$, fluorine, —(CH$_2$)—NH$_2$, or methoxy, wherein at least one of R2, R3, R4, R5 or R6 is hydroxyl or —(C═O)—CF$_3$; and
R7 is methyl.

Examples of useful 4-oxoquinolizine compounds according to this embodiment may for example be selected from the group consisting of compounds 56, 61, 63, 64, 66, 70 and 72 of Table 1.

In another embodiment of the invention the preferred 4-oxoquinolizine compounds are compounds of formula (V) or a pharmaceutically acceptable salt thereof, wherein

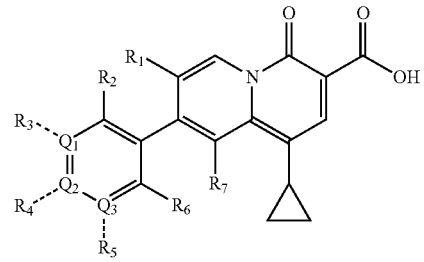

R$_1$ is hydrogen or fluorine; and
R$_2$, R$_3$, R$_4$ and R$_5$ each individually are selected from the group consisting of hydrogen, (CH$_2$)$_n$-hydroxyl, fluorine, C$_{1-3}$ alkyl, —(CH$_2$)$_n$—NH$_2$, —NH—(CH$_2$)$_n$—CH$_3$ and a 5 to 6 membered heterocyclic ring, wherein n is an integer in the range of 0 to 2; and
R$_6$ is hydrogen and
R$_7$ is C$_{1-3}$ alkyl or C$_{1-3}$ alkoxy; and
Q$_1$, Q$_2$ and Q$_3$ each individually are C or N, wherein at least one of Q$_1$, Q$_2$ and Q$_3$ is N and at least one of Q$_1$, Q$_2$ and Q$_3$ is C, and wherein if Q$_1$ is N, then R$_3$ is not present, and if Q$_2$ is N, then R$_4$ is not present and if Q$_3$ is N, then R$_5$ is not present.

Preferred compounds of formula (V) such compounds or pharmaceutically acceptable salts thereof in which
R$_1$ is hydrogen or fluorine; and
R$_2$, R$_3$, R$_4$ and R$_5$ each individually are selected from the group consisting of hydrogen, hydroxyl, fluorine, methyl, —NH$_2$, —NH—CH$_3$ and piperazinyl; and
R$_6$ is hydrogen and
R$_7$ is methyl or methoxy; and
Q$_1$, Q$_2$ and Q$_3$ each individually are C or N, wherein at least one of Q$_1$, Q$_2$ and Q$_3$ is N and at least one of Q$_1$, Q$_2$ and Q$_3$ is C, and wherein if Q$_1$ is N, then R$_3$ is not present, and if Q$_2$ is N, then R$_4$ is not present and if Q$_3$ is N, then R$_5$ is not present.

Even more preferred compounds of formula (V) such compounds or pharmaceutically acceptable salts thereof in which
R$_1$ is hydrogen or fluorine; and
R$_2$ is hydrogen or fluorine; and
R$_3$ is hydrogen or methyl; and
R$_5$ and R$_6$ are hydrogen and
R$_7$ is methyl; and
Q$_2$ is N, and Q$_2$ and Q$_3$ are C, and R$_4$ is not present.

Other very preferred compounds of formula (V) are such compounds or pharmaceutically acceptable salts thereof in which
R$_1$ is hydrogen or flourine;
R$_2$ and R$_6$ are hydrogen; and
R$_3$ is hydrogen or methyl; and
R$_4$ is (CH$_2$)$_n$-hydroxyl, —NH$_2$ or —NH—CH$_3$ or a 5 to 6 membered heterocyclic ring, wherein n is an integer in the range of 0 to 2; preferably R$_4$ is hydroxyl, —NH$_2$ or —NH—CH$_3$ or piperazinyl; and
R$_7$ is methyl or methoxy; and
Q$_3$ is N, and Q$_2$ and Q$_1$ are C, and R$_5$ is not present.

Other very preferred compounds of formula (V) are such compounds or pharmaceutically acceptable salts thereof in which R₁ is hydrogen or fluorine; and R₂ and R₄ each individually are selected from the group consisting of hydrogen, $(CH_2)_n$-hydroxyl, fluorine, $C_{1-3}$ alkyl, $-(CH_2)_n-NH_2$, $-NH-(CH_2)_n-CH_3$ and a 5 to 6 membered heterocyclic ring, wherein n is an integer in the range of 0 to 2; and R₆ is hydrogen; and Q₂ is C, and Q₁ and Q₃ are N, and R₃ and R₅ are not present.

In embodiments of the invention wherein the 4-oxoquinolizine compounds are compounds of formula (V), then it is preferred that if Q₁ is N and Q₂ and Q₃ are C, then at least one of R₂, R₄ and R₅ is not hydrogen. In this embodiment it is also preferred that if Q₁ is N and Q₂ and Q₃ are C and R₄ is $-NH_2$, then R₁ is fluorine and/or R₇ is methoxy. Similarly, it is also preferred that if Q₃ is N and Q₂ and Q₁ are C, then at least one of R₂, R₃ and R₄ is not hydrogen. In this embodiment it is also preferred that if Q₃ is N and Q₂ and Q₁ are C and R₄ is $-NH_2$, then R₁ is fluorine and/or R₇ is methoxy.

Preferred compounds of this embodiment may for example be selected from the group consisting of compounds 55, 57, 58, 59, 60, 65, 78, 79, 84, 87 and 89 of Table I.

In another embodiment of the invention the 4-oxoquinolizine compounds are compounds of formula (IIIa) or pharmaceutically acceptable salts thereof, wherein R₁ is as defined herein above in relation to compounds of formula (III); and Y is a heterobicyclic ring system optionally substituted with one or more substituents selected from the group consisting of oxo, $-(CH_2)_n-NH_2$, $-NH-(CH_2)_n-CH_3$, $-(CH_2)_n-OH$, $C_{1-8}$ alkyl, $C_{1-8}$ alkoxy, $C_{3-8}$-cycloalkyl and halogen, wherein n is an integer in the range of 0 to 3; and R₇ is as defined herein above in relation to compounds of formula (III).

In this embodiment it is preferred that the 4-oxoquinolizine compounds are compounds of formula (IIIa) or pharmaceutically acceptable salts thereof, wherein R₁ is as defined herein above in relation to compounds of formula (III); and Y is a 9 membered heterobicyclic ring system, preferably Y is a 9 membered heterobicyclic ring system selected from the group consisting of isoindolinyl, indazolyl, benzothiazolyl, benzimidazolyl, indolinyl and pyrrolopyridinyl optionally substituted with one or more substituents selected from the group consisting of oxo, $-(CH_2)_n-NH_2$, $-NH-(CH_2)_n-CH_3$, $-(CH_2)_n-OH$, $C_{1-8}$ alkyl, $C_{1-8}$ alkoxy, $C_{3-8}$-cycloalkyl and halogen, wherein n is an integer in the range of 0 to 3; and R₇ is as defined herein above in relation to compounds of formula (III).

In this embodiment it is preferred that the 4-oxoquinolizine compounds are compounds of formula (IIIa) or pharmaceutically acceptable salts thereof, wherein R₁ is hydrogen, methyl or fluorine; and Y is selected from the group consisting of isoindolinyl, indazolyl, benzothiazolyl, benzimidazolyl, indolinyl and pyrrolopyridinyl optionally substituted with one substituent selected from the group consisting of oxo, $-NH_2$, methyl and cyclopropyl; and R₇ methyl or methoxy.

Compounds according to this embodiment may for example be selected from the group consisting of compounds 68, 71, 73, 74, 75, 77, 80, 81, 82, 83, 85, 86, 88 and 90.

In yet another embodiment of the invention the 4-oxoquinolizine compounds are compounds of formula (IIIa) or pharmaceutically acceptable salts thereof, wherein R₁ is as defined herein above in relation to compounds of formula (III); and Y is selected from the group consisting of pyrazolyl and tetrahydropyrinidyl optionally substituted with one or more substituents selected from the group consisting of oxo, $-(CH_2)_n-NH_2$, $-NH-(CH_2)_n-CH_3$, $-(CH_2)_n-OH$, $C_{1-8}$ alkyl, $C_{1-8}$ alkoxy, $C_{3-8}$-cycloalkyl and halogen, wherein n is an integer in the range of 0 to 3; and R₇ is as defined herein above in relation to compounds of formula (III).

In this embodiment it is preferred that the 4-oxoquinolizine compounds are compounds of formula (IIIa) or pharmaceutically acceptable salts thereof, wherein R₁ is hydrogen or flourine; and Y is selected from the group consisting of unsubsituted pyrazolyl and tetrahydropyrinidyl; and R₇ is methyl or methoxy.

Compounds of this embodiment may preferably be selected from the group consisting of compounds 62 and 67 as mentioned in Table 1.

In specific embodiments, the invention provides the novel antimicrobial compounds, 1-6 and 17:

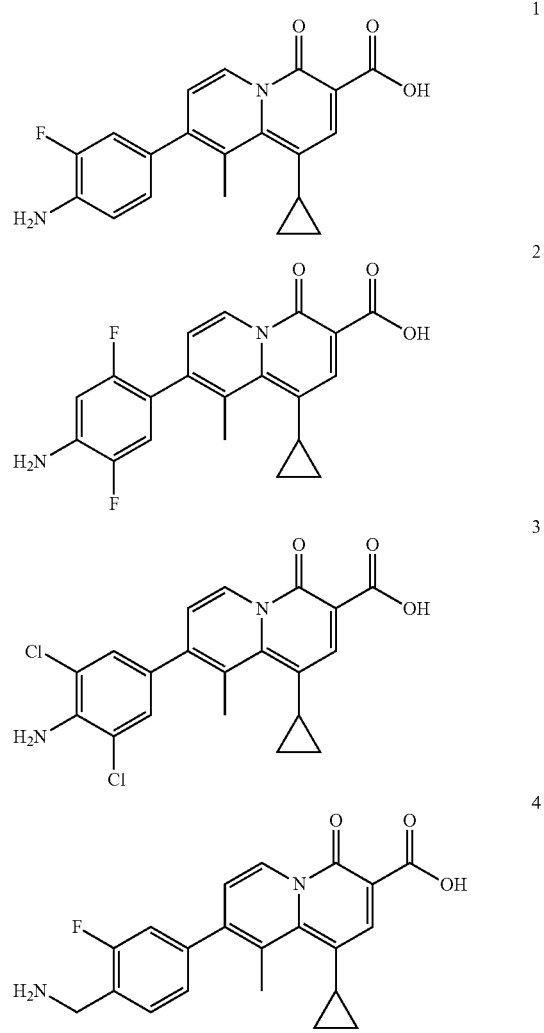

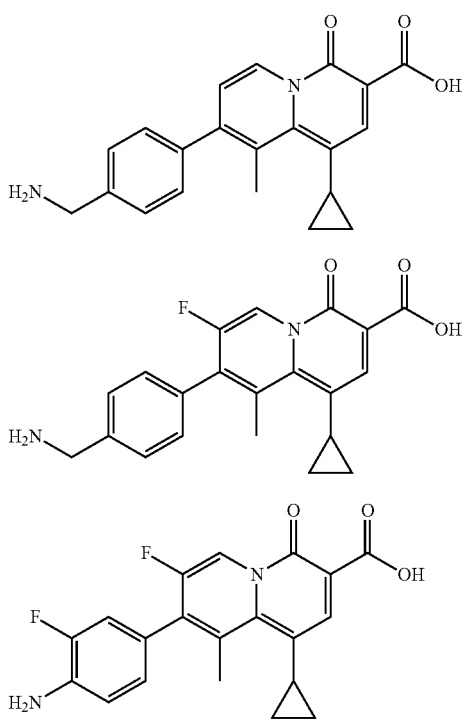

In embodiments of the invention relating to 4-oxoquinolizine compounds used in the absence of polymyxins it is preferred that said 4-oxoquinolizine compounds are not any of the compounds described in Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122 and 123 of US2004/0229903.

In embodiments of the invention relating to 4-oxoquinolizine compounds used in the absence of polymyxins it is preferred that said 4-oxoquinolizine compounds are not any of compounds 1, 2, 3, 5, 6, 7, 8, 9, 10, 11, 12, 13, 14, 15, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 or 54 of Table 1.

In embodiments of the invention relating to 4-oxoquinolizine compounds used in the absence of polymyxins it is preferred that said 4-oxoquinolizine compounds are not any of compounds named Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 of PCT application PCT/US2011/052003.

Salts of 4-Oxoquinolizines

Pharmaceutically acceptable salts of the 4-oxoquinolizine compounds of the invention may include acid or base addition salts. Acid and base addition salts refers to the relatively non-toxic, inorganic and organic addition salts of compounds of the present invention. These salts can be prepared in situ during the final isolation and purification of the compounds, or by subsequently reacting the purified compound in its free acid or base form with a suitable organic or inorganic compound and isolating the salt thus formed. In so far as the compounds of formula (I) of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt.

The pharmaceutically acceptable acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines. The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Salts may be prepared from inorganic acids or organic acids. One example of a salt of the 4-oxoquinolizines according to the invention may be hydrochloric salts.

Another example of a salt of the 4-oxoquinolizines according to the invention is potassium salts.

Methods of Preparing 4-Oxoquinolizines and Salts Thereof

The 4-oxoquinolizine compounds of the invention described herein in the sections "4-oxoquinolizines" and "Particular 4-oxoquinolizines" may be prepared using the methods outlined herein below in Example 8. In particular, useful scaffolds of the 4-oxoquinolizine compounds may be prepared as described in Example 8 and these may be further modified using methods known to the skilled person. Thus, suitable scaffolds may be prepared in 6 to 7 steps as described in Example 8. The suitable scaffolds may then be used to obtain the final 4-oxoquinolizine compounds in 2 to 5 steps.

The 4-oxoquinolizine compounds of the invention may also be prepared as described for specific 4-oxoquinolizine compounds in Example 8. These methods may optionally be modified with relevant modifications known to the skilled person.

Example 8 also described useful examples of preparing salts of 4-oxoquinolizine compounds. These methods may also be modified by the skilled person to prepare salts of other 4-oxoquinolizines.

The 2 pyridones to be used in pharmaceutical compositions comprising both a 4-oxoquinolizine compound and a Polymyxin may also be prepared as described in US patent application US2004/0229903.

Properties of Preferred 4-Oxoquinolizines

The preferred 4-oxoquinolizines according to the invention are preferably active antimicrobial compounds.

In particular the 2-pyridone compounds, such as the 4-oxoquinolizine compounds of the invention show potent activity against a pathogen that is resistant against one or more of quinolones, carbapenems, aminosides and glycopeptides antibiotics, and specifically, against a pathogen that is a CDC category A or category B pathogen. The 4-oxoquinolizine compounds may in particular have a MIC ≤10 μg/ml, such as ≤5 μg/ml, for example ≤1 μg/ml, such as ≤0.5 μg/ml against *B. thailandensis* when determined as described herein below in Example 1. *B. thailandensis* is a surrogate strain, which may be used experimentally instead of *B. pseudomallei*. Thus, the 4-oxoquinolizine compounds may have a MIC ≤10 μg/ml, such as ≤5 μg/ml, for example ≤1 μg/ml, such as ≤0.5 μg/ml against one or more of, preferably against all of *B. anthracis, F. tularensis, B. acortus* and *B. pseudomallei* when determined as described herein below in Example 1.

The 4-oxoquinolizine compounds of the invention may also have a MIC≤10 μg/ml, such as ≤5 μg/ml against one or more bacteria selected from the group consisting of *S. aureus, S. epidermis, E. faecalis* and *E. faecium* when determined as described herein below in Example 2.

The 4-oxoquinolizine compounds of the invention may also have a MIC≤50 μg/ml, such as ≤20 μg/ml against *A. baumanni*, wherein said *A. baumanni* is a drug resistant strain of *A. baumanni*, for example a multidrug resistant strain of *A. baumanni* when determined as described herein below in Example 3.

The 4-oxoquinolizine compounds of the invention preferably exhibit potent activities in presence of subinhibitory concentrations of polymyxin B against *A. baumannii* including quinolone and multiresistant strains of *A. baumannii*. The antimicrobial activity of the 4-oxoquinolizine compounds when combined with subinhibitory concentrations of polymyxin B against *Acinetobacter baumannii* including multiresistant clinical isolates may be determined as described herein below in Example 4. Thus the 4-oxoquinolizine compounds of the invention may have a MIC≤20 μg/ml, such as ≤15 μg/ml, for example ≤10 μg/ml, such as ≤5μ/ml against *A. baumannii* in the presence of 0.06 μg/ml Polymyxin B when determined as described in Example 4 herein below.

The particular 4-oxoquinolizine compounds of the invention may also have a MIC≤10 μg/ml, such as ≤5 μg/ml, for example ≤1 μg/ml, such as ≤0.5 μg/ml against at least one Gram negative bacterium and against at least one gram positive bacterium when determined as described herein below in Example 5.

The 4-oxoquinolizine compounds of the invention in general have at least partly synergistic antibacterial activity with Polymyxin, such as with Polymyxin B. This may for example be determined as described herein below in example 6. Thus, the 4-oxoquinolizine compounds of the invention may have a FICI<0.75, such as <0.5 in relation to Polymyxin B against *A. baumannii* and/or *K. pneumoniae*, when determined as described herein below in Example 6.

The 4-oxoquinolizine compounds of the invention preferably have a low cytotoxicity against human cells. Thus the 4-oxoquinolizine compounds of the invention may have an IC50 of at least 20 μM, such as at least 40 μM in respect of HEPG2 V1 cells when determined as described herein below in Example 7.

Polymyxin

It is an aspect of the present invention to provide pharmaceutical compositions comprising a 4-oxoquinolizine compound in combination with a Polymyxin. The Polymyxin to be used with the present invention may be any useful Polymyxin.

Polymyxins are antibiotics isolated from cultures of *Bacillus polymyxa*. In general Polymyxins are active as antibiotics against most Gram-negative bacteria. Polymyxins according to the present invention are preferably decapeptides containing five or six residues of L-2,4-diaminobutyric acid. Preferably, the sequence of seven residues at the C-terminal end of the decapeptide is formed into a peptide ring through an isopeptide link to one of the diaminobutyric acid residues, while the N-terminal residue preferably is acylated with a fatty acid. The fatty acid is preferably $-(CH_2)_m-COOH$, wherein m is an integer in the range of 6 to 15, preferably in the range of 7 to 10, more preferably in the range of 7 to 8, wherein said $-(CH_2)_m-COOH$ optionally may be substituted with one or more $C_{1-8}$ alkyl, preferably with one $C_{1-8}$ alkyl, more preferably with one $C_{1-5}$ alkyl, even more preferably with one $C_{1-2}$ alkyl, yet more preferably with one methyl.

Preferred Polymixins to be used with the present invention are Polymyxin B or Polymyxin E or pharmaceutically acceptable salts thereof.

Polymyxin B is a lipopeptide antibiotic originally isolated from *Bacillus polymyxa*. Polymyxin B according to the present invention preferably consists of a peptide ring of 7 amino acids and a tripeptide side chain with a fatty acid tail. Polymyxin B according to the invention preferably contains five primary amine groups and is thus a polycation at pH 7. Polymyxin B to be used with the present invention may be selected from the group consisting of Polymyxin B1 Polymyxin B2, Polymyxin B3 and Polymyxin B4. Polymyxin B to be used with the present invention may also be a mixture of 2 or more of the aforementioned, preferably Polymyxin B is a mixture containing at least Polymyxin B1 and Polymyxin B2, more preferably Polymyxin B to be used with the present invention is a mixture containing Polymyxin B1 Polymyxin B2, Polymyxin B3 and Polymyxin B4, Polymyxin B according to the present invention is preferably a compound of the formula (V)

(V)

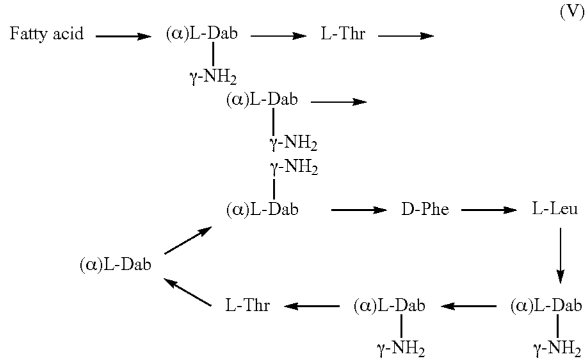

or a pharmaceutically acceptable salt thereof, wherein Dab is 2,4-diaminobutyric acid; and α and γ indicate which amino group is involved in the peptide linkage. The 3-letter code for amino acids is used.

In relation to formula (V) the fatty acid is preferably selected from the group consisting of heptanoic acid and octanoic acid, optionally substituted with methyl, Preferably Polymyxin B1 is a compound of formula (V) wherein the fatty acid is 6-methyloctanoic acid. Preferably Polymyxin B2 is a compound of formula (V) wherein the fatty acid is 6-methylheptanoic acid. Preferably Polymyxin B3 is a compound of formula (V) wherein the fatty acid is octanoic acid. Preferably Polymyxin B4 is a compound of formula (V) wherein the fatty acid is heptanoic acid.

Thus, Polymyxin B1 and B2 may preferably be compounds of the formula (VI)

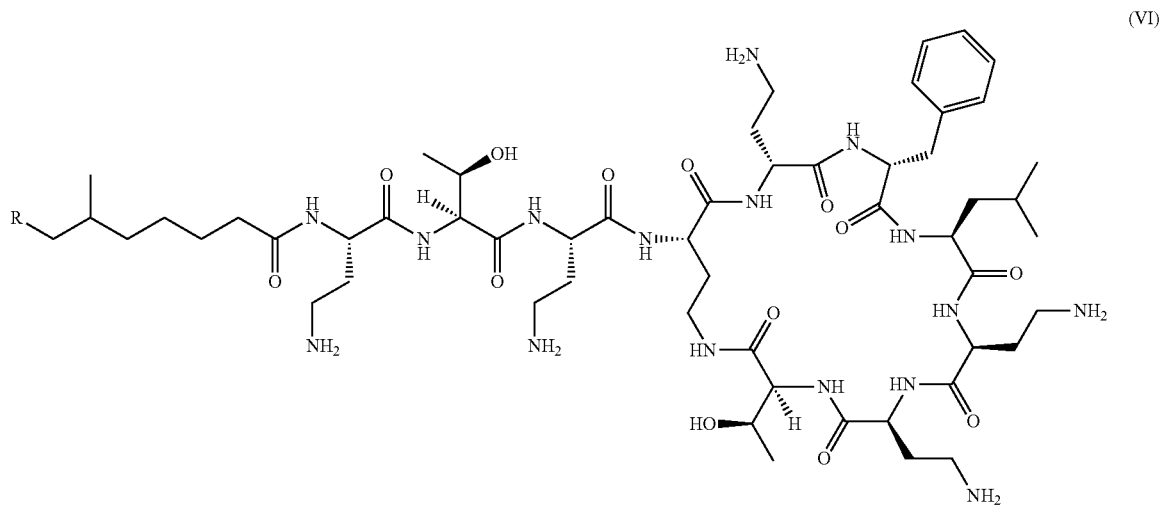

(VI)

wherein R is —H in Polymyxin B1, and R is —CH$_3$ in polymyxin B2.

The pharmaceutically acceptable salt of Polymyxin B may preferably be any of the salts prepared from an inorganic acid mentioned herein above in the section "Salts of 4-oxoquinolizines", a more preferably said salt is the sulfate salt.

The Polymyxin to be used with the present invention may in embodiment be Polymyxin E, which may also be referred to as colistin. Polymyxin E may preferably be a compound of the formula (VI):

or a pharmaceutically acceptable salt thereof. Polymyxin E may in one embodiment be available as a prodrug, more preferably as colistin methanesulphonate.

The pharmaceutically acceptable salt of Polymyxin E may for example be the sodium salt, such as the sodium salt of colistin methanesulphonate.

Dosage of Polymyxin

It is one aspect of the present invention to provide pharmaceutical compositions comprising a 4-oxoquinolizine compound in combination with Polymyxin, preferably Polymyxin B. In one embodiment of the invention said Polymyxin, e.g. Polymyxin B is present in a subinhibitory concentration.

Said subinhibitory concentration is in general dependent on the individual to receive treatment with the pharmaceutical composition. Preferably said subinhibitory concentration of Polymyxin is administration of a less than 2 mg

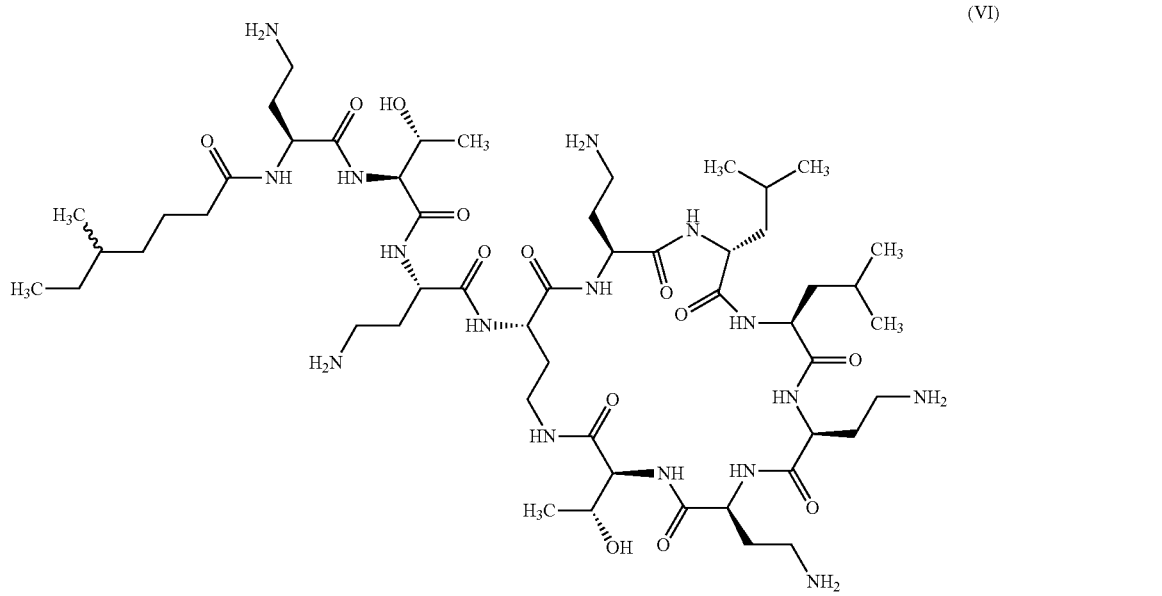 [SMILES: CCC(C)CCCC(=O)N[C@@H](CCN)C(=O)N[C@H](C(=O)N[C@@H](CCN)C(=O)N[C@H]1CCNC(=O)[C@H]([C@@H](C)O)NC(=O)[C@H](CCN)NC(=O)[C@H](CCN)NC(=O)[C@H](CC(C)C)NC(=O)[C@@H](CC(C)C)NC(=O)[C@H](CCN)NC1=O)[C@@H](C)O]

(VI)

Polymyxin per kg of said individual per day. Thus the subinhibitory concentration may be administration of less than 1.5 mg, such as less than 1 mg, for example less than 0.5 mg, such as less than 0.3 mg, for example less than 0.1 mg per kg of said individual per day. Preferably said subinhibitory concentration of Polymyxin B is administration of a less than 2 mg Polymyxin B per kg of said individual per day. Thus the subinhibitory concentration may be administration of less than 1.5 mg, such as less than 1 mg, for example less than 0.5 mg, such as less than 0.3 mg, for example less than 0.1 mg Polymyxin B per kg of said individual per day.

Thus, in embodiments of the invention where the pharmaceutical composition is prepared in daily unit dosages for administration to adult human being, then each dosage unit preferably comprises less than 150 mg Polymyxin, such as less than 130 mg Polymyxin, for example less than 110 mg Polymyxin, such as less than 90 mg Polymyxin, for example less than 70 mg Polymyxin, such as less than 50 mg Polymyxin, wherein the Polymyxin may be any of the Polymyxins described herein above in the section "Polymyxin", but preferably is Polymyxin B.

In one embodiment of the invention the subinhibitory concentration is less than 0.5 µg/ml, such as less than 0.4 µg/ml, for example less than 0.3 µg/ml, such as less than 0.2 µg/ml.

Polymyxin may however also be administered at regular concentrations, for example in the range of 2 to 5 mg Polymyxin, such as Polymyxin B per kg of said individual may be administered.

Compositions Comprising Polymyxin and a 4-Oxoquinolizine Compound

It is one aspect of the invention to provide pharmaceutical compositions comprising
 a) A Polymyxin, which may be any of the Polymyxins described herein above in the section "Polymyxin"; and
 b) A 4-oxoquinolizine compound, which may be any of the 4-oxoquinolizine compounds described herein above in the section "4-oxoquinolizine compound" or the section "Particular 4-oxoquinolizine compound".

Interestingly, the present invention discloses that the antibacterial effect of Polymyxin and 4-oxoquinolizines is synergistic. The synergistic effect may be determined according to any useful method, such as using a checkerboard technique, e.g. by using the method described in Example 6 herein below.

Thus, in one embodiment of the invention the compositions comprises a subinhibitory concentration of a polymyxin, for example Polymyxin B and a subinhibitory concentration of a 4-oxoquinolizine, wherein said composition is capable of inhibiting growth of at least one bacterium, more preferably the composition is capable of inhibiting growth of at least 2 different bacteria, for example of at least 5 different bacteria, such as of at least 10 different bacteria.

In one embodiment of the invention the pharmaceutical compositions comprises
 a) Polymyxin B; and
 b) a 4-oxoquinolizine compound, which may be any of the 4-oxoquinolizine compounds described herein above in the section "4-oxoquinolizine compound" or the section "Particular 4-oxoquinolizine compound", wherein the 4-oxoquinolizine compound has an antibacterial effect against at least one bacterium, such as against at least 2 different bacteria, for example against at least 5 different bacteria, such as against at least 10 different bacteria which is synergistic with the antibacterial effect of polymyxin B, wherein the synergistic effect preferably is determined as described herein below in Example 6.

In one aspect the invention relates to a method of treating a bacterial infection in an individual in need thereof, wherein the method comprises the steps of:
 i) administering Polymyxin B to a individual in need thereof; and
 ii) testing whether the bacterial infection is reduced or cured by said Polymyxin B; and
 iii) if the bacterial infection is not reduced or cured by said Polymyxin B, then administering to said individual a therapeutically effective amount of a 4-oxoquinolizine compound, which may be any of the 4-oxoquinolizine compounds described herein above in the section "4-oxoquinolizine compound" or the section "Particular 4-oxoquinolizine compound";

thereby treating said bacterial infection in said individual.

The Polyxin may be administered in any useful dosage, such as any of the dosages described herein above in the section "Dosage of Polymyxin". For example the polymyxin may be administered at in the range of 2 to 5 mg Polymyxin, such as Polymyxin B per kg of said individual, or the polymyxin may even be administered at subinhibitory concentrations.

The 4-oxoquinolizine compound may preferably be administered as described herein below in the section "Pharmaceutical formulations".

Bacterial Infection

It is an aspect of the present invention to provide pharmaceutical compositions comprising a 4-oxoquinolizine compound in combination with a Polymyxin. Said pharmaceutical compositions are in particular useful for treatment of a bacterial infection in an individual in need thereof, and preferably for treatment of any of the bacterial infections described herein in this section.

It is furthermore an aspect of the present invention to provide particularly useful 4-oxoquinolizine compounds as described herein above in the section "Particular 4-oxoquinolizines". Said 4-oxoquinolizine compounds are in particular useful for treatment of a bacterial infection in an individual in need thereof, and preferably for treatment of any of the bacterial infections described herein in this section.

In general the pharmaceutical compositions comprising a 4-oxoquinolizine compound in combination with a Polymyxin or the particular 4-oxoquinolizine compounds of invention are useful for treatment of a broad spectrum of different bacterial infections. Thus, they are typically useful for treatment infections by at least two different kinds of bacteria, such as at least 5 different kinds of bacteria, for example at least 10 different kinds of bacteria. In particular, said bacteria may be drug resistant bacteria, such as multidrug resistant bacteria.

The 4-oxoquinolizine compounds and the pharmaceutical compositions comprising 4-oxoquinolizine and Polymyxin are antibacterial agents usable for the treatment of local infectious diseases or general infectious diseases of human beings or animals caused by Gram-positive bacteria, Gram-negative bacteria, anaerobic bacteria, acid-fast bacteria or other bacteria.

This invention also provides methods of treating an infectious disorder in an individual in need thereof, wherein the individual for example may be a human or a mammal, by administering a safe and effective amount of a 4-oxoquinolizine compound to said subject optionally in combination with a Polymyxin. As used herein, an "infectious disorder" is any disorder characterized by the presence of a microbial infection. Exemplary methods of this invention are for the treatment of bacterial infections. Such infectious disorders include for example central nervous system infections, external ear infections, infections of the middle ear (such as acute otitis media), infections of the cranial sinuses, eye infections, infections of the oral cavity (such as infections of the teeth, gums and mucosa), upper respiratory tract infections, lower respiratory tract infections, including pneumonia, genitourinary infections, gastrointestinal infections, gynecological infections, septicemia, sepsis, peritonitis, bone and joint infections, skin and skin structure infections, bacterial endocarditis, burns, antibacterial prophylaxis of surgery, or antibacterial prophylaxis in post-operative patients or in immunosuppressed patients (such as patients receiving cancer chemotherapy, or organ transplant patients).

Thus the bacterial infection may be infection by one or more bacteria of for example the central nervous system, external ear, the middle ear (such as acute otitis media), the cranial sinuses, the eyes, the oral cavity (such as of the teeth, gums and mucosa), upper respiratory tract, lower respiratory tract, including lung, genitourinary tract, gastrointestinal tract, peritoneum, bone and joints, skin or burns. The bacterial infection may also be related to sepsis, surgery, or bacterial infections in post-operative patients or in immunosuppressed patients.

The bacterial infection may be infection by any bacteria; preferably the bacterium is pathogenic bacterium. The bacterial infection may be infection by a gram-negative or a gram-positive bacterium or it may be infection by a mixture of bacteria, which may be gram-positive or gram-negative. The present invention discloses that 4-oxoquinolizine compounds are effective in treatment of infections by both Gram-positive and Gram-negative bacteria.

In embodiments of the invention relating to pharmaceutical compositions comprising both 4-oxoquinolizine compounds and a Polymyxin, then it is preferred that the bacteria is a Gram-negative bacterium.

The bacterial infection to be treated with the pharmaceutical composition comprising a 4-oxoquinolizine compound and a Polymyxin or with the particular 4-oxoquinolizine compound according to the present invention is preferably infection by one or more bacteria of a genus selected from the group consisting of:

*Acinetobacter, Bacillus, Bordetella, Borrelia, Brucella, Camphylobacter, Chlamydia, Clostridium, Corynebacterium, Enterococcus, Escherichia, Fransisella, Haemophilus, Helicobacter, Legionella, Leptospira, Listeria, Mycobacterium, Mycoplasma, Neisseria, Propionibacterium, Pseudomonas, Rickettsia, Salmonella, Shigella, Staphylococcus, Streptococcus, Treponema, Vibrio* and *Yersinia.*

The bacterial infection to be treated with the pharmaceutical composition comprising a 4-oxoquinolizine compound and a Polymyxin or with the particular 4-oxoquinolizine compound according to the present invention is preferably infection by one or more bacteria of genus selected from the group consisting of:

*Acinetobacter, Bacillus, Brucella, Burkholderia, Citrobacter, Corynebacterium, Enterobacter, Enterococcus, Escherichia, Fransisella, Haemophilus, Klepsiella, Listeria, Moraxella, Morganella, Neisseria, Proteus, Providencia, Pseudomonas, Serratia, Shigella, Staphylococcus, Stenotrophomonas, Streptococcus* and *Yersinia.*

In one embodiment of the invention the bacterial infection to be treated with the pharmaceutical composition comprising a 4-oxoquinolizine compound and a Polymyxin or with the particular 4-oxoquinolizine compound according to the present invention is infection by one or more bacteria of a genus selected from the group consisting of *Acinetobacter, Bordetella, Borrelia, Brucella, Camphylobacter, Chlamydia, Clostridium, Corynebacterium, Fransisella, Helicobacter, Legionella, Leptospira, Listeria, Mycobacterium, Mycoplasma, Neisseria, Rickettsia, Salmonella, Shigella, Treponema, Vibrio* and *Yersinia.*

The bacterial infection to be treated with the pharmaceutical composition comprising a 4-oxoquinolizine compound and a Polymyxin or with the particular 4-oxoquinolizine compound according to the present invention is preferably infection by one or more bacteria of a genus selected from the group consisting of:

*Acinetobacter, Brucella, Burkholderia, Citrobacter, Corynebacterium, Enterobacter, Francisella, Listeria, Moraxella, Morganella, Neisseria, Proteus, Providencia, Serratia, Shigella, Stenotrophomonas,* and *Yersinia.*

The bacterial infection to be treated with the pharmaceutical composition comprising a 4-oxoquinolizine compound and a Polymyxin or with the particular 4-oxoquinolizine compound according to the present invention is preferably infection by one or more bacteria selected from the group consisting of:

*Acinetobacter* spp, *Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter* sp, *Enterobacter cloacae, Enterococcus faecalis, Enterococcus faecium, Enterococcus gallinarum, Escherichia coli, Francisella tularensis, Haemophilus influenza, Klepsiella* spp., *Klebsiella aerogenes, Klebsiella pneumoniae, Listeria monocytogenes, Moraxella catarrhalis, Morganella morganii, Neisseria meningitides, Proteus mirabilis, Providencia stuartii, Pseudomonas* spp., *Pseudomonas aeruginosa, Serratia marcescens, Shigella* sp, *Staphylococcus aureus, Staphylococcus epidermis, Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pneumoniae, Streptococcus pyogenes, Streptococcus oralis, Streptococcus sanguis*, Group C *Streptococcus, Yersinia pestis*, and drug-resistant strains thereof.

In an embodiment of any of the preceding embodiments, the bacteria can be selected from the group consisting of, (a) *Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter* sp, *Enterobacter cloacae, Enterococcus faecium, Enterococcus gallinarum, Francisella tularensis, Klebsiella aerogenes, Listeria monocytogenes, Moraxella catarrhalis, Morganella morganii, Neisseria meningitides, Proteus mirabilis, Providencia stuartii, Serratia marcescens, Shigella* sp, *Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pyogenes, Streptococcus oralis, Streptococcus sanguis*, Group C *Streptococcus*, and *Yersinia pestis*, (b) drug-resistant strains of any pathogen of part (a); and (c) and drug-resistant strains of *Staphylococcus aureus, Staphylococcus epidermis, Streptococcus pneumoniae, Enterococcus faecalis, Escherichia coli, Klebsiella pneumoniae, Pseudomonas aeruginosa*, and *Haemophilus influenza.*

By the term "drug-resistant strain" is meant a bacterial strain which is resistant to at least one antibiotic drug selected from the group consisting of quinolones, carbapenems, aminosides and glycopeptides antibiotics. Multidrug-resistant strains are bacterial strains resistant to at least two antibiotic drugs of different classes, wherein said classes are selected from the group consisting of quinolones, carbapenems, aminosides and glycopeptides antibiotics.

The bacterial infection to be treated with the 4-oxoquinolizine compounds described in the section "Particular 4-oxoquinolizines" are preferably bacteria selected from the group consisting of:

Acinetobacter spp, Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter sp, Enterobacter cloacae, Enterococcus gallinarum, Francisella tularensis, Klebsiella aerogenes, Listeria monocytogenes, Moraxella catarrhalis, Morganella morganii, Neisseria meningitides, Proteus mirabilis, Providencia stuartii, Serratia marcescens, Shigella sp, Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pyogenes, Streptococcus oralis, Streptococcus sanguis, Group C Streptococcus, Yersinia pestis, and drug-resistant strains thereof.

The bacterial infection to be treated with the pharmaceutical composition comprising a 4-oxoquinolizine compound and a Polymyxin or with the particular 4-oxoquinolizine compound according to the present invention may be selected from the group consisting of Burkholderia pseudomallei, Bacillus anthracis, Yersinia pestis, Francisella tularensis, and Brucella abortu, Klebsiella, Pseudomonas, Acinetobacter and Staphylococcus aureus, wherein said Staphylococcus aureus may be Methicillin-resistant Staphylococcus aureus (MRSA).

In one embodiment the bacterial infection to be treated with the pharmaceutical composition comprising a 4-oxoquinolizine compound and a Polymyxin or with the particular 4-oxoquinolizine compound according to the present invention the infection is infection by a Gram-positive bacterium. This may in particular be the case in embodiments of the invention relating to the particular 4-oxoquinolizine compounds described herein above in the section "Particular 4-oxoquinolizines". Said Gram-positive bacterium may for example be selected from the group consisting of B. anthracis, S. epidermidis, Staphylococcus aureus, Streptococcus aureus, Streptococcus pneumonia, Enterococcus faecalis and Enterococcus faecium.

The bacterial infection to be treated with pharmaceutical compositions comprising 4-oxoquinolizine compounds and Polymyxins may preferably be bacteria of a genus selected from the group consisting of:

Acinetobacter, Bordetella, Borrelia, Brucella, Camphylobacter, Escherichia, Fransisella, Haemophilus, Helicobacter, Legionella, Leptospira, Neisseria, Pseudomonas, Rickettsia, Salmonella, Shigella, Treponema, Vibrio and Yersinia.

The bacterial infection to be treated with pharmaceutical compositions comprising 4-oxoquinolizine compounds and Polymyxins may preferably be selected from bacteria of a genus selected from the group consisting of Acinetobacter, Brucella, Burkholderia, Citrobacter, Enterobacter, Escherichia, Francisella, Haemophilus, Klepsiella, Moraxella, Morganella, Neisseria, Proteus, Providencia, Pseudomonas, Serratia, Shigella, Stenotrophomonas and Yersinia.

In one embodiment the bacterial infection to be treated with the pharmaceutical composition comprising a 4-oxoquinolizine compound and a Polymyxin or with the particular 4-oxoquinolizine compound according to the present invention the infection is infection by a Gram-negative bacterium. Said Gram-negative bacterium may for example be selected from the group consisting of F. tularensis, B. abortus, B. pseudomallei, Pseudomonas aeruginosa, Burkholderia thailandensi, Acinetobacter baumannii, Acinetobacter Escherichia coli and Klebsiella.

In one embodiment the bacterial infection to be treated with the pharmaceutical composition comprising a 4-oxoquinolizine compound and a Polymyxin or with the particular 4-oxoquinolizine compound according to the present invention the infection is infection by an anaerobic bacterium. Said anaerobic bacterium may for example be Bacillus fragilis.

In particular the bacteria may be a bacterial strain that is resistant against one or more of quinolones, carbapenems, aminosides and glycopeptides antibiotics, and specifically, the bacterial infection may be infection by a pathogen that is a CDC category A or category B pathogen. CDC is the US Centers for Disease Control and Prevention, which have categorised pathogens according to risk to national security (Example 1 below describe examples of such bacteria).

Thus, the bacterial infection to be treated with the 4-oxoquinolizine compounds of the invention or with pharmaceutical compostions comprising 4-oxoquinolizine compounds and Polymyxin according to the present invention may in one embodiment be a Category A bacteria according to CDC's classification. Category A bacteria are defined as bacteria that can be easily disseminated or transmitted from person to person;

result in high mortality rates and have the potential for major public health impact;

might cause public panic and social disruption; and require special action for public health preparedness.

Category A bacteria may for example be selected from the group consisting of Bacillus anthracis, Clostridium botulinum, Yersinia pestis and Francisella tularensis.

Thus, the bacterial infection to be treated with the 4-oxoquinolizine compounds of the invention or with pharmaceutical compostions comprising 4-oxoquinolizine compounds and Polymyxin according to the present invention may in one embodiment be a Category B bacteria according to CDC's classification. Category B bacteria are defined as bacteria that are moderately easy to disseminate;

result in moderate morbidity rates and low mortality rates; and require specific enhancements of CDC's diagnostic capacity and enhanced disease surveillance.

Category B bacteria may for example be selected from the group consisting of Brucella species, Clostridium perfringens, Salmonella species, Escherichia coli O157:H7, Shigella, B. abortus, Burkholderia mallei, Burkholderia pseudomallei, Chlamydia psittaci, Coxiella burnetii, Staphylococcus spp. Rickettsia prowazekii, Vibrio cholerae and Cryptosporidium parvum.

The term "treatment" is used herein to mean that, at a minimum, administration of a compound of the present invention mitigates a disease associated an infectious disorder, e.g. a bacterial infection in a host, such as in a mammalian subject, such as in humans. Thus, the term "treatment" includes inhibiting the infectious disorder; and/or alleviating or reversing the infectious disorder. Insofar as the methods of the present invention are directed to preventing infectious disorders, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to infectious disorders, such that administration of the compounds of the present invention may occur prior to onset of infection. The term does not imply that the disease state be completely avoided.

Pharmaceutical Formulations

The present invention relates in one aspect to pharmaceutical compositions comprising 4-oxoquinolizine compounds and Polymyxin. The present invention also relates to pharmaceutical compositions comprising preferred 4-oxoquinolizine compounds with or without the presence of Polymyxins.

According to the present invention, the pharmaceutical compositions are preferably for treatment of an individual infected by the pathogen, such as an individual suffering from a bacterial infection. The compositions may however also be for administration to an individual at risk of acquiring such an infection. Generally, the individual is a vertebrate, preferably a mammal, and more preferably a human being. The treatment may be ameliorating or curative. By curative, it is intended to mean survival from the infection which otherwise in the absence of the treatment causes the subject suffering from the infection to show increasing pathology or even morbidity. Thus, the pharmaceutical compositions described herein may be prepared for prophylactic administration to an individual at risk of infection by the pathogen, preferably by the bacteria.

In one embodiment of the invention, the pharmaceutical composition is for reducing the risk of contagion caused by the infection or in an individual at risk of acquiring a bacterial infection. In relation to epidemic or even pandemic infections causing a high mortality rate, even slight reductions in risk of contagion may be of major importance.

In another embodiment, the pharmaceutical composition reduces the risk of contagion in a individual that has acquired a bacterial infection by at least 5%, preferably at least 10%, preferably at least 15%, more preferably at least 20%, or at least 30% or at least 40%, or at least 50%, or at least 60%, or at least 70% or at least 80%, or at least 90%, or more. The pharmaceutical compositions of the invention may also reduce the risk of contagion caused by a bacterial infection in an individual at risk of acquiring that infection by at least 5%, or at least 10%, or at least 15%, or at least 20%, or at least 30% or at least 40%, or at least 50%, or at least 60%, or at least 70% or at least 80%, or at least 90%, or more.

Administration of the anti-bacterial pharmaceutical compositions according to the invention may be only once or administration may be repeated for a number of times. For example, the pharmaceutical compositions comprising 4-oxoquinolizine compounds or the pharmaceutical compositions comprising both Polymyxins and 4-oxoquinolizine compounds may be given repeatedly with regular intervals, for example in the range of 1 to 5 times daily for in the range of 1 to 100 days, such as in the range of 1 to 50 days, for example in the range of 1 to 25 days, such as in the range of 10 to 16 days. The total daily dose of the compounds of this invention administered to a host in single or in divided doses can be in amounts, Single dose compositions may contain such amounts or submultiples thereof as make up the daily dose. Preferred dosages of Polymyxin to be contained in these compositions are described herein in the section "Dosage of Polymyxin" and preferred dosages of 4-oxoquinolizine compounds are described herein below.

The pharmaceutical compositions may be prepared for any suitable administration route, for example, topical, parenteral, oral, buccal, systemic, nasal, injection, transdermal, rectal, vaginal, etc., or a form suitable for administration by inhalation or insufflation. For example, the pharmaceutical compositions of the invention are prepared for oral administration or for intraperitoneal administration, such as for oral administration. Similarly, the pharmaceutical compositions of the invention may or may be used at the site of a wound on or in the body, for example as a result of surgery or injury. Equally, the pharmaceutical compositions of the invention may or may be used for an internal infection at the site of a prosthesis.

Formulations suitable for oral administration can consist of (a) liquid solutions, such as an effective amount of the active compound(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient(s) in a flavor, e.g., sucrose, as well as pastilles comprising the active ingredient in an inert base, such as gelatin and glycerin or sucrose and acacia emulsions, gels, and the like containing, in addition to the active ingredient(s), carriers known in the art.

The 4-oxoquinolizine compounds or the compositions comprising both Polymyxins and 4-oxoquinolizine compounds as described above, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged compound with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally.

In addition, dosages for injection of the pharmaceutical compositions of the invention may be prepared in dried or lyophilized form. Such forms can be reconstituted with water or saline solution, depending on the preparation of the dosage form. Such forms may be packaged as individual dosages or multiple dosages for easier handling. Where lyophilized or dried dosages are used, the reconstituted dosage form may be isotonic, and at a physiologically compatible pH.

Various oral dosage forms of the pharmaceutical compositions of the invention can be used, including such solid forms as tablets, capsules, granules and bulk powders. These oral forms comprise a safe and effective amount, usually at least about 5%, or from about 25% to about 50%, of the 4-oxoquinolizine compounds and optionally they may also comprise Polymyxins. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents, such are well known to the skilled artisan. Exemplary excipients for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions may comprise a safe and effective amount, usually at least about 0.1%, or from about 1% to about 5%, of the 4-oxoquinolizine compounds, and optionally also Polymyxins. Suitable excipients for topical administration may optionally remain in place on the skin as a continuous film, and resist being removed by perspiration or immersion in water. Generally, the excipient is organic in nature and capable of having dispersed or dissolved therein the 4-oxoquinolizine. The excipient may include pharmaceutically-acceptable emollients, emulsifiers, thickening agents, and solvents and the like; these are well known to the skilled artisan.

The 4-oxoquinolizine compounds and the pharmaceutical compositions of this invention can be administered topically or systemically. Systemic application includes any method of introducing the 4-oxoquinolizine compounds into the tissues of the body, e.g. by intrathecal, epidural, intramuscular, transdermal, intravenous, intraperitoneal, subcutaneous, sublingual, rectal or oral administration. The specific dosage of antimicrobial to be administered, as well as the duration of treatment, may be mutually dependent. The dosage and treatment regimen may also depend upon such factors as the specific 4-oxoquinolizine compound used, the resistance pattern of the infecting organism to the 4-oxoquinolizine compound used, the ability of the 4-oxoquinolizine compound to reach minimum inhibitory concentrations at the site of the infection, the nature and extent of other infections (if any), the personal attributes of the subject (such as weight), compliance with the treatment regimen, the age and health status of the patient, and the presence and severity of any side effects of the treatment.

As an illustration, for a human adult (weighing approximately 70 kilograms), from about 75 mg, or from about 200 mg, or from about 500 mg to about 30,000 mg, or to about 10,000 mg, or about 3,500 mg of a 4-oxoquinolizine compound is administered per day. Treatment regimens may extend from about 1 day to about 100 days, for example from about 3 to about 56 days, such as from 3 to 20 days, in duration. Prophylactic regimens (such as avoidance of opportunistic infections in immunocompromised patients) may extend 6 months, or longer, according to good medical practice.

One exemplary method of parenteral administration is through intravenous injection. As is known and practiced in the art, all formulations for parenteral administration must be sterile. For mammals, especially humans, (assuming an approximate body weight of 70 kilograms) individual doses of from 100 to 3500 mg, for example from 500 mg to 7,000 mg, more or to about 3,500 mg are typically acceptable.

In some cases, such as generalized, systemic infections or in immune-compromised patients, the invention may be dosed intravenously. The dosage form is generally isotonic and at physiological pH. The dosage amount will depend on the patient and severity of condition, as well as other commonly considered parameters. Determination of such doses is well within the scope of practice for the skilled practitioner using the guidance given in the specification.

An exemplary method of systemic administration is oral administration. Individual doses of from 20 to 500 mg, for example from 100 mg to 2,500 mg may typically be useful Topical administration can be used to deliver the 4-oxoquinolizine compounds systemically, or to treat a local infection. The amounts of 4-oxoquinolizine compounds to be topically administered may depend upon such factors as skin sensitivity, type and location of the tissue to be treated, the composition and excipient (if any) to be administered, the particular 4-oxoquinolizine compound to be administered, as well as the particular disorder to be treated and the extent to which systemic (as distinguished from local) effects are desired.

The pharmaceutical composition may be in unit dosage form. In such form the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below. In therapeutic use, the 4-oxoquinolizine compounds or the compositions comprising both Polymyxin and 4-oxoquinolizine compounds utilized in the methods of the invention may be administered to subjects at dosage levels suitable to achieve therapeutic benefit. By therapeutic benefit is meant that the administration of compound leads to a beneficial effect in the patient over time.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of the disease. For example, the dose may vary depending on the symptoms, age, body weight, etc. of the patient. Usually, the 4-oxoquinolizine compounds are administered to adults in a dose of 0.05 to 100 mg/kg/day, preferably 0.1 to 50 mg/kg/day, in the systemic administration. When 4-oxoquinolizine compounds are used for the local treatment, the concentration of the active ingredient is 0.01 to 5%, preferably 0.1 to 3%. Preferred dosages of Polymyxins are described herein elsewhere.

The 4-oxoquinolizine compounds and the Polymyxin may preferably be administered simultaneously, however it is also contemplated within the scope of the present invention that the 4-oxoquinolizine compounds and the Polymyxin is administered sequentially in any order.

The Examples that follow are illustrative of specific embodiments of the invention, and various uses thereof. They are set forth for explanatory purposes only, and are not to be taken as limiting the invention.

EXAMPLES

Example 1: Minimal Inhibitory Concentration (MIC) Determination for CDC Strains

This example shows that 4-oxoquinolizine compounds show potent activity against a pathogen that is a CDC category A or category B pathogen (Table 2) and for example *B. thailandensis* (Table 3).

The results for *B. anthracis, F. tularensis, B. abortus*, and *B. pseudomallei* are summarized in Table 2 below. The dilutions ranged from 32 μg/ml to 0.015 μg/ml (12 2-fold dilution range). The final DMSO concentration was 1.25% for *B. anthracis* and 2.5% for all other select agents. The assay was performed in duplicate in 96-well plates with a total assay volume of 100 μl. The bacteria were cultivated according to the CLSI guidelines. The MIC value was determined as the lowest concentration that resulted in no growth. The results for *B. thailandensis* are summarized in Table 3 below. A number of compounds showed a 2 to 4 dilutions improvement shift in MIC90 between pH7 and pH5. This property additionally makes the compounds therapeutically interesting, particularly for use in acidic infected tissues and tissues where cytosolic acidity rises as a result of infection.

TABLE 2 showing potent antimicrobial activity against a panel of CDC pathogens exhibited by 4-oxoquinolizine compounds.

| Compounds | Structures | MIC (ug/ml) | | | |
| --- | --- | --- | --- | --- | --- |
| | | *B. anthracis* | *F. tularensis* | *B. abortus* | *B. pseudomallei* |
| 1 | 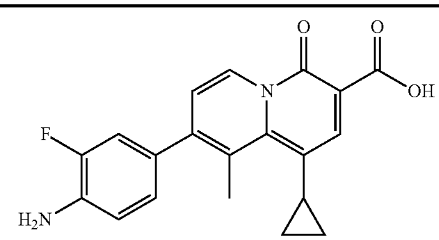 | <0.008 | <0.03 | 0.125 | 0.125 |
| 5 | 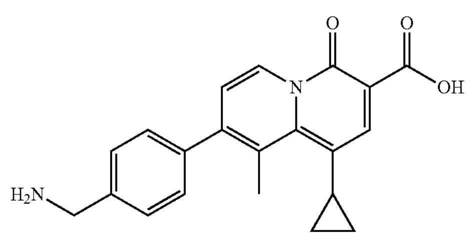 [SMILES: Cc1c(-c2ccc(CN)cc2)ccn2c(=O)c(C(=O)O)cc(C3CC3)c12] | 0.125 | 0.125 | 1 | 2 |
| 6 | 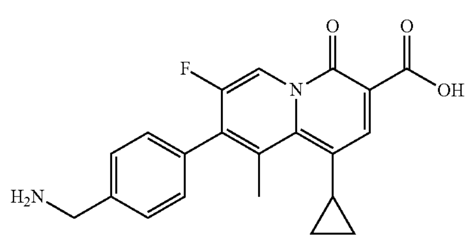 [SMILES: Cc1c(-c2ccc(CN)cc2)c(F)cn2c(=O)c(C(=O)O)cc(C3CC3)c12] | 0.125 | 0.125 | 0.5 | 2 |
| 9 | 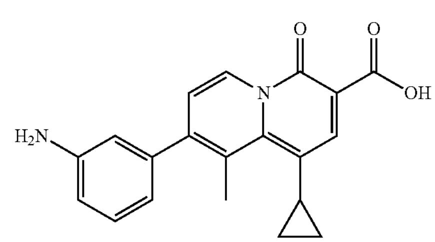 [SMILES: Cc1c(-c2cccc(N)c2)ccn2c(=O)c(C(=O)O)cc(C3CC3)c12] | 0.06 | 0.125 | 0.25 | 0.5 |

TABLE 3 showing the potent antimicrobial activity against *B. thailandensis* exhibited by 4-oxoquinolizine compounds and a 2 to 4 dilutions improvement shift in MIC90 between pH7 and pH5.

| Compounds | Structure | MIC90 *B. thailandensis* (ug/ml) | Dilutions improvement shift on *B. thailandensis* MIC90 (between pH 7 and pH 5) |
|---|---|---|---|
| 1 | 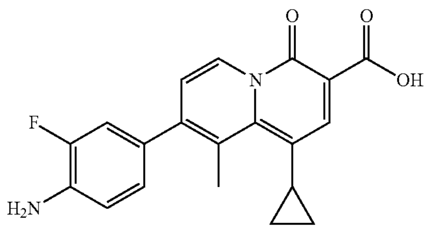 [SMILES: Cc1c(-c2ccc(N)c(F)c2)ccn2c(=O)c(C(=O)O)cc(C3CC3)c12]  | <0.048 | Yes, 4× |
| 2 | 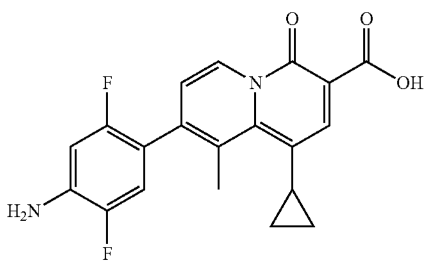 [SMILES: Cc1c(-c2cc(F)c(N)cc2F)ccn2c(=O)c(C(=O)O)cc(C3CC3)c12]  | <0.048 | |
| 3 | 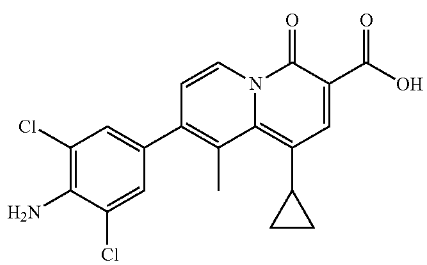 [SMILES: Cc1c(-c2cc(Cl)c(N)c(Cl)c2)ccn2c(=O)c(C(=O)O)cc(C3CC3)c12]  | <0.048 | |
| 5 | 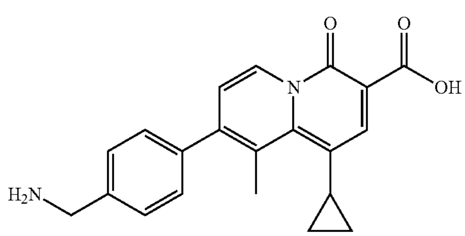 [SMILES: Cc1c(-c2ccc(CN)cc2)ccn2c(=O)c(C(=O)O)cc(C3CC3)c12]  | 0.390 | |
| 6 | 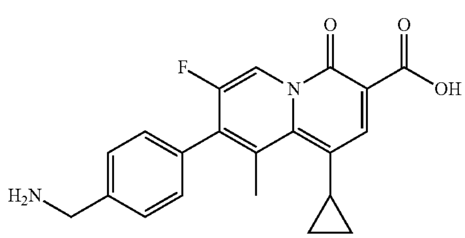 [SMILES: Cc1c(-c2ccc(CN)cc2)c(F)cn2c(=O)c(C(=O)O)cc(C3CC3)c12]  | 0.390 | No |
| 7 | 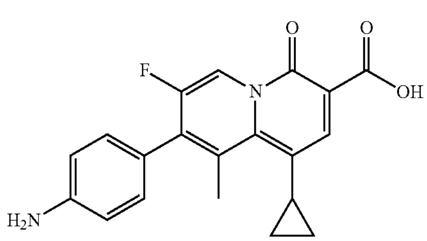 [SMILES: Cc1c(-c2ccc(N)cc2)c(F)cn2c(=O)c(C(=O)O)cc(C3CC3)c12]  | <0.048 | Yes, 4× |

TABLE 3-continued showing the potent antimicrobial activity against *B. thailandensis* exhibited by 4-oxoquinolizine compounds and a TABLE 3-continued showing the potent antimicrobial activity against *B. thailandensis* exhibited by 4-oxoquinolizine compounds and a 2 to 4 dilutions improvement shift in MIC90 between pH7 and pH5.

| Compounds | Structure | MIC90 *B. thailandensis* (ug/ml) | Dilutions improvement shift on *B. thailandensis* MIC90 (between pH 7 and pH 5) |
|---|---|---|---|
| 15 | 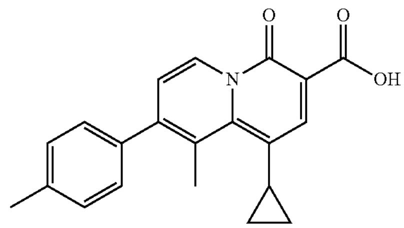 [SMILES: Cc1ccc(-c2ccn3c(=O)c(C(=O)O)cc(C4CC4)c3c2C)cc1] | <0.048 | |
| 16 | 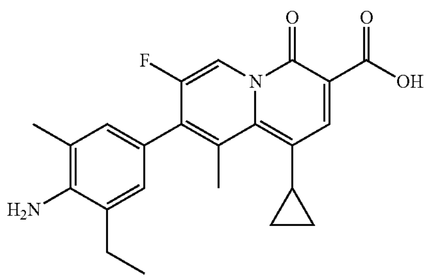 [SMILES: CCc1cc(-c2c(F)cn3c(=O)c(C(=O)O)cc(C4CC4)c3c2C)cc(C)c1N] | <0.048 | |

Example 2: Minimal Inhibitory Concentration (MIC) Determination for Gram-Positive and Gram-Negative Bacteria Example 2 shows the potent TABLE 4-continued showing the MIC values for a selection of 4-oxoquinolizines against standard panels of Gram-positive and Gram-negative bacteria in comparison to a well-known marketed quinolone (Ciprofloxacin) and glycopeptide (Vancomycin).

| | | | | | | | |
|---|---|---|---|---|---|---|---|
| Compound 3 | [structure: 3,5-dichloro-4-amino-phenyl substituted 4-oxoquinolizine with cyclopropyl and methyl] | <0.008 | 1 | 0, 06 | 0, 008 | 0, 016 | 0, 5 |
| Compound 4 | [structure: 3-fluoro-4-aminomethyl-phenyl substituted 4-oxoquinolizine with cyclopropyl and methyl] | 0, 06 | 0, 125 | 4 | 0, 06 | 0, 125 | 2 |
| Compound 5 | [structure: 4-aminomethyl-phenyl substituted 4-oxoquinolizine with cyclopropyl and methyl] | 0, 03 | 0, 125 | 4 | 0, 06 | 0, 125 | 2 |
| Compound 6 | [structure: fluoro-substituted 4-oxoquinolizine with 4-aminomethyl-phenyl, cyclopropyl and methyl] | 0, 03 | 0, 25 | 2 | 0, 03 | 0, 125 | 4 |
| Compound 7 | [structure: fluoro-substituted 4-oxoquinolizine with 4-aminophenyl, cyclopropyl and methyl] | <0.008 | 1 | 1 | <0.008 | 0, 06 | 2 |
| Compound 8 | [structure: 4-aminophenyl substituted 4-oxoquinolizine with cyclopropyl and methyl] | <0.008 | 0, 25 | 0, 5 | <0.008 | 0, 03 | 0, 5 |
| Vancomycin | Vancomycin | 2 | 2 | 2 | 2 | 2 | 1 |
| Ciprofloxacin | Ciprofloxacin | 1 | 1 | 128 | 0, 25 | 1 | 8 |

TABLE 4-continued showing the MIC values for a selection of 4-oxoquinolizines against standard panels of Gram-positive and Gram-negative bacteria in comparison to a well-known marketed quinolone (Ciprofloxacin) and glycopeptide (Vancomycin).

| Compounds | Structures | MIC (ug/ml) | | | | |
|---|---|---|---|---|---|---|
| | | E. coli 25922 | E. coli IMP | E. cloacae 13047 | P. aeruginosa 27853 | A. baumanii 19606 |
| Compound 2 | 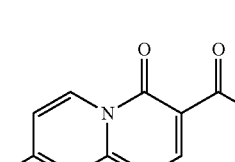 | <0.03 | <0.008 | 0, 25 | 2 | 0, 06 |
| Compound 3 | 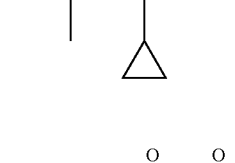 | <0.03 | 0, 06 | 0, 5 | 2 | 0, 25 |
| Compound 4 | 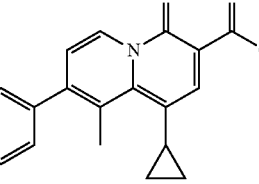 | <0.03 | <0.008 | 0, 06 | 0, 5 | 0, 25 |
| Compound 5 | 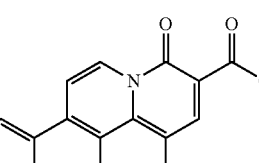 | <0.03 | <0.008 | 0, 06 | 0, 5 | 0, 25 |
| Compound 6 | 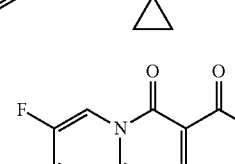 | <0.03 | 0, 03 | 0, 125 | 2 | 0, 5 |
| Compound 7 | 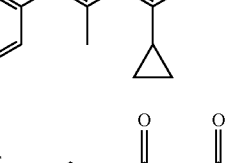 | 0, 03 | <0.008 | 1 | 4 | 0, 5 |

TABLE 4-continued showing the MIC values for a selection of 4-oxoquinolizines against standard panels of Gram-positive and Gram -negative bacteria in comparison to a well-known marketed quinolone (Ciprofloxacin) and glycopeptide (Vancomycin).

| Compound 8 | 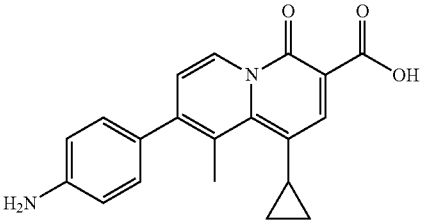 | 0, 03 | <0.008 | 0, 25 | 1 | 0, 125 |
|---|---|---|---|---|---|---|
| Vancomycin | Vancomycin | >128 | >128 | >128 | >128 | >128 |
| Ciprofloxacin | Ciprofloxacin | <0.125 | <0.125 | <0.125 | 0, 5 | 4 |

TABLE 5 listing the resistant strains used for the data displayed in Table 6

| Organism | Strain | Resistance Phenotype |
|---|---|---|
| *A. baumannii* | OXA-51 | CIP R, ESBL |
| *E. coli* | CTX-M-15 | CIP R, ESBL |
| *E. coli* | 2906 | CIP R |
| *Klebsiella* spp | KPC-3 | CIP R, ESBL |
| *Pseudomonas* spp | PER-1 | CIP R, ESBL |
| *P. aeruginosa* | 1388-3-02 | CIP R, POL R |
| *P. aeruginosa* | 143-3-03 | CIP I, POL R |
| *S. aureus* | SMITH | CIP R |
| *S. pneumoniae* | 49619 | LEV S |
| *S. pneumonia* | 1027 | LEV R |

CIP, ciprofloxacin;
POL, Polyoxin;
ESBL, extended spectrum beta-lactamases

TABLE 6 showing the activity of 4-o against a panel of quinolone-resistant strains

| | | MIC (ug/ml) | | | | |
|---|---|---|---|---|---|---|
| Compounds | Structures | *A. Baumanii* OXA-51 | *E. coli* CTX-M-15 | *E. coli* 2906 | *Klebsiella* ssp KPC-3 | *S. aureus* SMITH |
| Compound 2 | 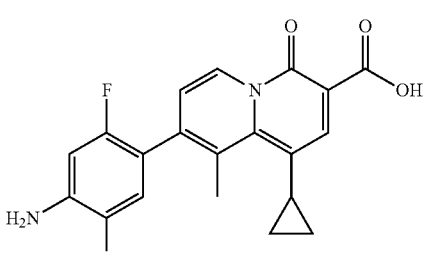 | 4 | >32 | 32 | 8 | <0.03 |
| Compound 3 | 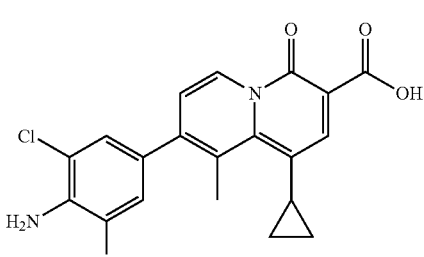 | 8 | >32 | >32 | 8 | 0, 5 |

TABLE 6-continued showing the activity of 4-o against a panel of quinolone-resistant strains

| Compound | Structure | | | | | |
|---|---|---|---|---|---|---|
| Compound 4 | (structure) | 16 | 16 | 8 | 4 | 0, 125 |
| Compound 5 | (structure) | 8 | 16 | 16 | 8 | 0, 125 |
| Compound 6 | (structure) | 8 | 16 | 16 | 16 | 0, 125 |
| Compound 7 | (structure) | 8 | 32 | 32 | 16 | 0, 25 |
| Compound 8 | (structure) | 4 | >32 | >32 | 16 | <0.03 |
| Ciprofloxacin | Ciprofloxacin | 128 | 128 | 128 | 128 | 32 |
| Levofloxacin | Levofloxacin | 16 | 16 | 32 | >128 | 8 |

| | | MIC (ug/ml) | | | | |
|---|---|---|---|---|---|---|
| Compounds | Structures | Pseudomonas ssp PER-1 | P. aeruginosa 1388-3-02 | P. aeruginosa 143-3-03 | S. pneumoniae 49619 | S. pneumoniae 1027 |
| Compound 2 | (structure) | 16 | 8 | 2 | <0.03 | 0, 5 |

TABLE 6-continued
showing the activity of 4-o against a panel of quinolone-resistant strains
| Compound 3 | 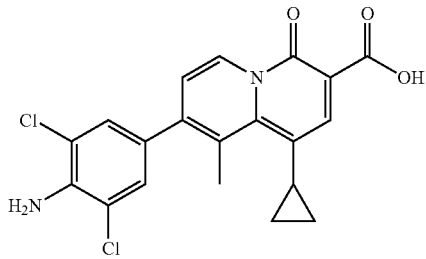 [SMILES: Cc1c(-c2cc(Cl)c(N)c(Cl)c2)ccn2c(=O)c(C(=O)O)cc(C3CC3)c12] | 32 | 8 | 4 | 0, 5 | 2 |
| --- | --- | --- | --- | --- | --- | --- |
| Compound 4 | 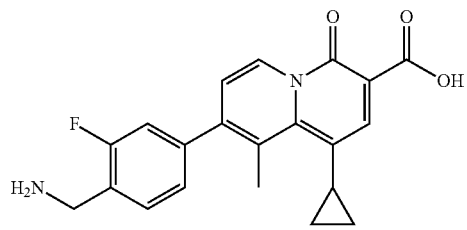 | 8 | 16 | 4 | 0, 125 | 1 |
| Compound 5 | 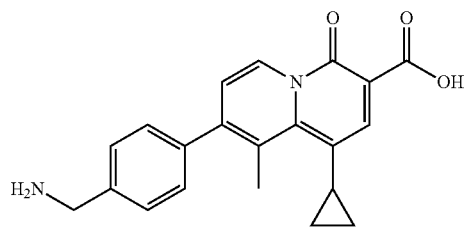 | 8 | 16 | 4 | 0, 125 | 2 |
| Compound 6 | 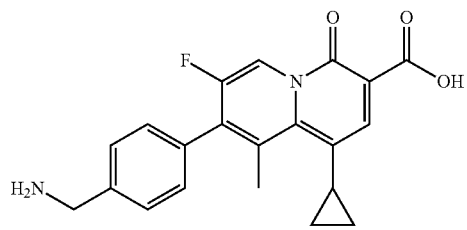 | 16 | 32 | 8 | 0, 125 | 2 |
| Compound 7 | 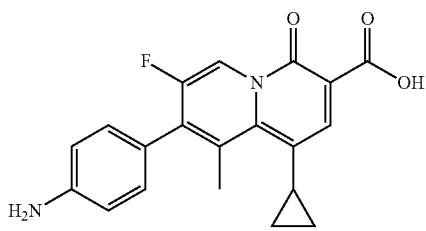 [SMILES: Cc1c(-c2ccc(N)cc2)c(F)cn2c(=O)c(C(=O)O)cc(C3CC3)c12] | 16 | 16 | 4 | 0, 25 | 4 |
| Compound 8 | 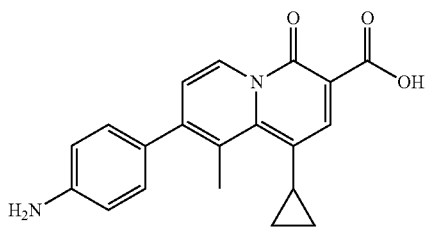 [SMILES: Cc1c(-c2ccc(N)cc2)ccn2c(=O)c(C(=O)O)cc(C3CC3)c12] | 16 | 8 | 2 | <0.03 | 2 |
| Ciprofloxacin | Ciprofloxacin | 16 | 16 | 2 | 0, 5 | 32 |
| Levofloxacin | Levofloxacin | 32 | 32 | 8 | 0, 5 | 16 |

Example 3: Minimal Inhibitory Concentration (MIC) Determination for *Acinetobacter* Strains Example 3 shows that 4-oxoquinolizine compounds show potent activity against a pathogen that is resistant against one or more of quinolones, carbapenems, aminosides and glycopeptides antibiotics. The antibacterial activity of the compounds was assessed against a variety of *A. bacter* strains consisting mostly of resistant clinical isolates (Table 7 and 8).

Bacterial Strains

Organisms used were one type strain and clinical isolates of *Acinetobacter baumannii* from commercial culture collections or from K. Towner, Nottingham, UK. One *Acinetobacter* sp. (H064200250) was obtained from D. Livermore, London, UK (see Table 7 below which lists the *Acinetobacter* strains referred to in Table 8 below).

Antimicrobial Agents

Ciprofloxacin, Levofloxacin, Vancomycin and Amikacin were purchased from Fluka and Aldrich (Sigma-Aldrich, Buchs, Switzerland); moxifloxacin, meropenem and imipenem/cilastatin were purchased from Apin Chemicals Ltd. (Abingdon, Oxon, UK).

Minimal Inhibitory Concentration (MIC) Determination

MICs were determined following the standard CLSI protocol as described herein below in Example 4 using doubling dilutions of compounds (0.03 to 32 µg/ml), Levofloxacin, Ciprofloxacin, Moxifloxacin, Amikacin, Vancomycin, Meropenem and Imipenem/Cilastatin (0.125 to 128 µg/ml) in cation adjusted Mueller Hinton broth (CAMHB, Oxoid). Additionally, MICs were run in CAMHB supplemented. CLSI breakpoints were used to classify resistance to carbapenems, quinolones, aminosides, and glycopeptides[1]. The *Acinetobacter* strains were grown in CAMHB for 20-24 hours at 37° C. in ambient air. The MIC was determined as the lowest concentration of an individual drug that lead to no visible growth. Referring to the following tables, Table 7 shows the *Acinetobacter* strains used and Table 8 below shows the activity of the present 4-oxoquinolizines against different *Acinetobacter* strains known to be resistant against a number of well-known marketed antibiotic drugs such as quinolones, carbapenems and aminoside antibiotics.

TABLE 7 showing the *Acinetobacter* strains used for the data displayed in Table 8 below.

| Organism | Strain | Source | Origin | Resistance Phenotype |
|---|---|---|---|---|
| *A. baumannii* | ATCC 19606 | DSMZ[1] | Reference strain | — |
| *A. baumannii* | J2 | Roche | unknown | LEV R, CIP R |
| *Acinetobacter* sp. | H064200250 (OXA51 upregulated) | D. Livermore[2] | unknown | LEV R, CIP R, MRP R, IMP I |
| *A. baumannii* | A329 | K. Towner[3] | Barcelona, ES | LEV R, CIP R, MRP R, IMP R, AMK R, TET R |
| *A. baumannii* | A387 | K. Towner | Ioannina, GR | LEV I, CIP R, IPM R, AMK R, TET R |
| *A. baumannii* | A390 | K. Towner | Pleven, Bulgaria | LEV R, CIP R, MRP R, IPM I, AMK R, TET I |
| *A. baumannii* | A401 | K. Towner | Taiwan | LEV R, CIP R, AMK R, TET R |
| *A. baumannii* | A472 | K. Towner | Warsaw, PL | LEV R, CIP R, MRP I, IMP I, AMK R, TET R |
| *A. baumannii* | A473 | K. Towner | Warsaw, PL | LEV R, CIP R, MRP R, IMP R, AMK R, TET R |
| *A. baumannii* | A489 | K. Towner | Nottingham, UK (patient repatriated from Crete) | LEV R, CIP R, MRP R, IMP R, AMK R, TET R |

LEV, Levofloxacin;

CIP, Ciprofloxacin;

MRP, Meropenem;

IPM, Imipenem;

AMK, Amikacin;

TET, tetracycline

[1]DSMZ, German Collection Strain of Microorganisms and Cell Cultures, Braunschweig, Germany.

[2]D. Livermore, Health Protection Agency, London, UK.

[3]K. Towner, Nottingham University Hospitals NHS Trust, Nottingham, UK.

TABLE 8
showing the MIC values for 4-oxoquinolizines against a panel of *Acinetobacter* resistant strains in comparison to the efficacy of known drugs Levofloxacin, Moxifloxacin, Meropenem, Imipenem and Amikacin.
| | | MIC (µg/ml) | | | | |
|---|---|---|---|---|---|---|
| Compound | Structure | *A. baumannii* ATCC 19606 | *A. baumannii* J2 | *Acinetobacter* spp. H064200250 | *A. baumannii* A329 | *A. baumannii* A489 |
| 1 | 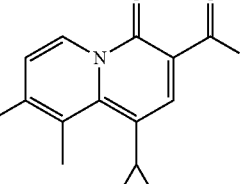 | 0.25 | 8 | 8 | 16 | 4 |
| 2 | 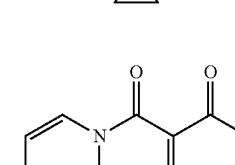 | ≤0.03 | 4 | 4 | 8 | 2 |
| 3 | 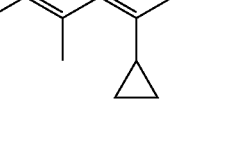 | 0.25 | 8 | 8 | 16 | 4 |
| 4 | 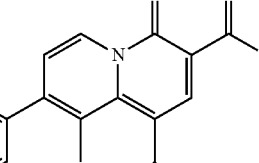 | 0.25 | 8 | 16 | 16 | 8 |
| 5 | 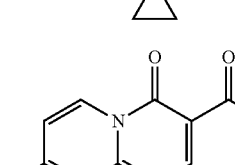 | 0.25 | 8 | 16 | 16 | 4 |
| 6 | 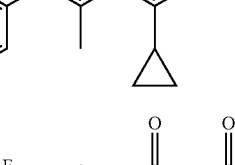 | 0.5 | 16 | 8 | 16 | 8 |

TABLE 8-continued showing the MIC values for 4-oxoquinolizines against a panel of *Acinetobacter* resistant strains in comparison to the efficacy of known drugs Levofloxacin, Moxifloxacin, Meropenem, Imipenem and Amikacin.

| Compound | Structure | | | | |
|---|---|---|---|---|---|
| 7 | (4-aminophenyl, F, methyl, cyclopropyl oxoquinolizine carboxylic acid) | 0.5 | 16 | 8 | 16 | 8 |
| 8 | (4-aminophenyl, methyl, cyclopropyl oxoquinolizine carboxylic acid) | 1 | 8 | 2 | 16 | 2 |
| Levofloxacin | Levofloxacin | 1 | 32 | 16 | 32 | 16 |
| Moxifloxacin | Moxifloxacin | 0.5 | 32 | 16 | 32 | 16 |
| Meropenem | Meropenem | 2 | 1 | 32 | 128 | 16 |
| Imipenem | Imipenem | 2 | 4 | 16 | 128 | 128 |
| Amikacin | Amikacin | 16 | 32 | 16 | >128 | >128 |

| | | MIC (ug/ml) | | | | |
|---|---|---|---|---|---|---|
| Compound | Structure | A. baumannii A387 | A. baumannii A390 | A. baumannii A 401 | A. baumannii A472 | A. baumannii A473 |
| 1 | (3-fluoro-4-aminophenyl oxoquinolizine) | 1 | 16 | 4 | 8 | 4 |
| 2 | (2,5-difluoro-4-aminophenyl oxoquinolizine) | 0.5 | 8 | 4 | 4 | 8 |
| 3 | (3,5-dichloro-4-aminophenyl oxoquinolizine) | 1 | >32 | 8 | 32 | 4 |

TABLE 8-continued showing the MIC values for 4-oxoquinolizines against a panel of *Acinetobacter* resistant strains in comparison to the efficacy of known drugs Levofloxacin, Moxifloxacin, Meropenem, Imipenem and Amikacin.

| # | Structure | | | | | |
|---|---|---|---|---|---|---|
| 4 | [4-oxoquinolizine with 3-fluoro-4-aminomethylphenyl, methyl, cyclopropyl] | 2 | 8 | 16 | 4 | 8 |
| 5 | [4-oxoquinolizine with 4-aminomethylphenyl, methyl, cyclopropyl] | 2 | 8 | 16 | 8 | 8 |
| 6 | [4-oxoquinolizine with F on ring, 4-aminomethylphenyl, methyl, cyclopropyl] | 4 | 8 | 16 | 8 | 8 |
| 7 | [4-oxoquinolizine with F on ring, 4-aminophenyl, methyl, cyclopropyl] | 2 | 8 | 4 | 4 | 4 |
| 8 | [4-oxoquinolizine with 4-aminophenyl, methyl, cyclopropyl] | 2 | 16 | 32 | 4 | 2 |
| Levofloxacin | Levofloxacin | 8 | 16 | 16 | 16 | 16 |
| Moxifloxacin | Moxifloxacin | 4 | 16 | 32 | 16 | 16 |
| Meropenem | Meropenem | 4 | 32 | 32 | 8 | 16 |
| Imipenem | Imipenem | 16 | 16 | 32 | 16 | 32 |
| Amikacin | Amikacin | >128 | >128 | >128 | >128 | >128 |

Example 4: Antimicrobial Activity of 4-Oxoquinolizines in Combination with Sub-Inhibitory Concentrations of Polymyxin B Against Clinical Isolates Including Those which are Resistant to Quinolones, Carbapenems and Other Antimicrobial Agents Example 4 describes the determination of antimicrobial activity of 4-oxoquinolizine compounds with 8-aniline and 8-aniline-like substitutions and shows that these exhibited potent activities in presence of sub-inhibitory concentrations of polymyxin B against *A. baumannii* which are resistant to quinolones, carbapenems and other antimicrobial agents. The inventive 4-oxoquinolizine compounds with aniline or aniline-like substitutions exhibited potent activities in presence of sub-inhibitory concentrations of polymyxin B against *A. baumannii* including quinolone and multi-resistant strains. The activities of non-aniline amines 8-substitutions compounds and compound 10 (ABT-719) were less potentiated by polymyxin B. The potent antimicrobial activity shown by the instant compounds when combined with sub-inhibitory concentrations of polymyxin B against *Acine-* tobacter baumannii including multi-resistant clinical isolates are shown in Table 9, 10 and 11 below. Additionally, the 4-oxoquinolizine compounds exhibit bactericidal activity in absence or presence of polymyxin B as determined using a preliminary MBC assay. MIC ranges without and with sub-inhibitory concentrations of polymyxin B against resistant strains of A. baumannii and one sensitive strain of Acinetobacter sp are shown in Table 12.

Bacterial Strains

Organisms used were one type strain and clinical isolates of Acinetobacter baumannii from commercial culture collections or from K. Towner, Nottingham, UK. One Acinetobacter sp. (H064200250) was obtained from D. Livermore, London, UK.

Antimicrobial Agents

The 4-oxoquinolizines with phenyl anilines and phenyl amines as 8-substitutions as well as reference compound 10 (ABT-719) (see Table 9 below) were synthesized. Polymyxin B sulfate, levofloxacin and amikacin were purchased from Fluka (Sigma-Aldrich, Buchs, Switzerland); moxifloxacin, meropenem and imipenem/cilastatin were purchased from Apin Chemicals Ltd. (Abingdon, Oxon, UK).

TABLE 9

Antimicrobial agents used and ranges tested

| Compounds | Structure | Range tested (µg/ml) |
|---|---|---|
| Compound 1 | 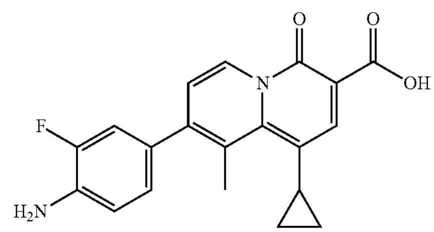 [SMILES: Cc1c(-c2ccc(N)c(F)c2)ccn2c(=O)c(C(=O)O)cc(C3CC3)c12] | 0.03-32 |
| Compound 17 | 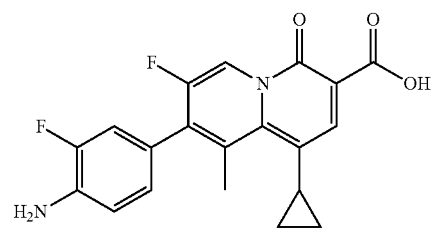 [SMILES: Cc1c(-c2ccc(N)c(F)c2)c(F)cn2c(=O)c(C(=O)O)cc(C3CC3)c12] | 0.03-32 |
| Compound 2 | 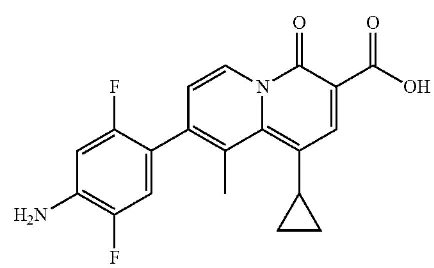 [SMILES: Cc1c(-c2cc(F)c(N)cc2F)ccn2c(=O)c(C(=O)O)cc(C3CC3)c12] | 0.03-32 |
| Compound 3 | 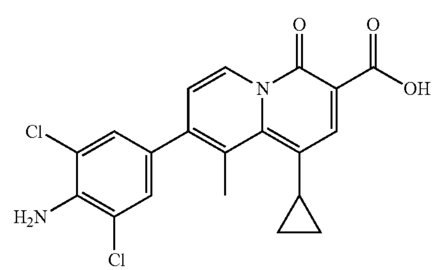 [SMILES: Cc1c(-c2cc(Cl)c(N)c(Cl)c2)ccn2c(=O)c(C(=O)O)cc(C3CC3)c12] | 0.03-32 |
| Compound 7 | 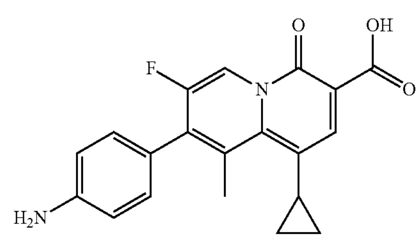 [SMILES: Cc1c(-c2ccc(N)cc2)c(F)cn2c(=O)c(C(=O)O)cc(C3CC3)c12] | 0.03-32 |

TABLE 9-continued

Antimicrobial agents used and ranges tested

| Compounds | Structure | Range tested (µg/ml) |
|---|---|---|
| Compound 8 | 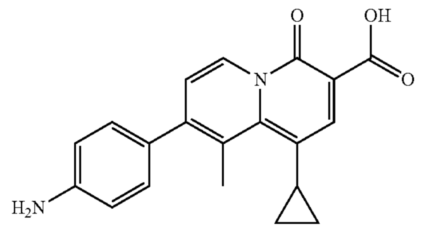 [SMILES: Cc1c(-c2ccc(N)cc2)ccn2c(=O)c(C(=O)O)cc(C3CC3)c12] | 0.03-32 |
| Compound 4 | 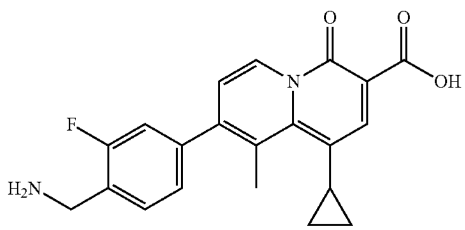 [SMILES: Cc1c(-c2ccc(CN)c(F)c2)ccn2c(=O)c(C(=O)O)cc(C3CC3)c12] | 0.03-32 |
| Compound 5 | 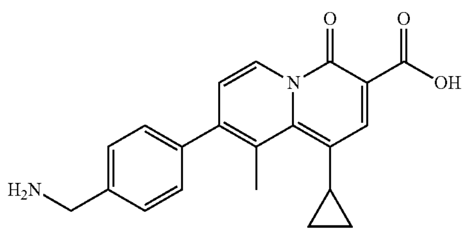 [SMILES: Cc1c(-c2ccc(CN)cc2)ccn2c(=O)c(C(=O)O)cc(C3CC3)c12] | 0.03-32 |
| Compound 6 | 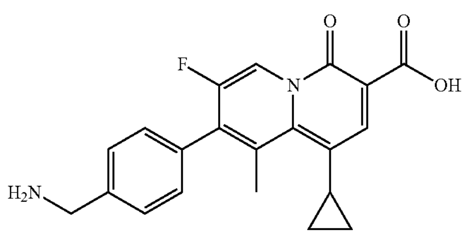 [SMILES: Cc1c(-c2ccc(CN)cc2)c(F)cn2c(=O)c(C(=O)O)cc(C3CC3)c12] | 0.03-32 |
| Compound 10 (ABT-719) | 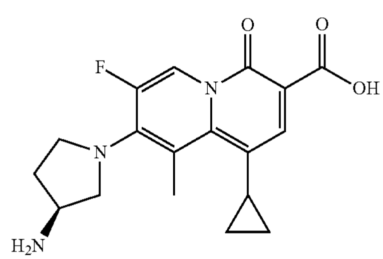 [SMILES: Cc1c(N2CC[C@H](N)C2)c(F)cn2c(=O)c(C(=O)O)cc(C3CC3)c12] | 0.008-8 |
| Levofloxacin | | 0.125-128 |
| Moxifloxacin | | 0.125-128 |
| Meropenem | | 0.125-128 |
| Imipenem/cilastatin | | 0.125-128 |
| Amikacin | | 0.125-128 |
| Polymyxin B | | 0.125-128 |

Minimal Inhibitory Concentration (MIC) Determination

MICs were determined following the standard CLSI protocol (Clinical and Laboratory Standards Institute. Methods for dilution antimicrobial susceptibility tests for bacteria that grow aerobically. Approved Standard-seventh edition M7-A7, Clinical and Laboratory Standards Institute, Wayne, Pa., USA, 2006) using doubling dilutions of the 8-phenyl anilines and 8-phenyl amines (0.03 to 32 µg/ml), reference compound 10 (ABT-719) (0.008 to 8 µg/ml), and polymyxin B, levofloxacin, moxifloxacin, amikacin, meropenem and imipenem/cilastatin (0.125 to 128 µg/ml) in cation adjusted Mueller Hinton broth (CAMHB, Oxoid). Additionally, MICs were run in CAMHB supplemented with sub-inhibitory concentrations (0.25×MIC) of polymyxin B sulfate. CLSI breakpoints were used to classify resistance to carbapenems, quinolones, aminoglycosides, and tetracyclines (DSMZ, German Collection Strain of Microorganisms and Cell Cultures, Braunschweig, Germany). The *Acinetobacter* strains were grown in CAMHB for 20-24 hours at 37° C. in ambient air. The MIC was determined as the lowest concentration of an individual drug that lead to no visible growth.

Since trailing was observed in the first experiment, MICs were confirmed by adding 10 µl alamarBlue (alamarBlue™ Assay, Biosource; Lucerna ChemAG) to each well in the 2nd experiment. The alamarBlue Assay incorporates a growth indicator based on detection of metabolic activity. Reduction related to growth causes the redox indicator to change from oxidized (blue) form to reduced (red) form. Following incubation at 37° C. for 1 hour, the MIC was read as lowest concentration of an individual drug that lead to no growth indicated by blue color.

Preliminary Minimal Bactericidal Concentration (MBC) Determination

After reading the MICs, microtiter plates were shaken (700 rpm, 5 minutes) and 5 µl culture from each well from the plates used for the MIC determination was spotted on Mueller-Hinton agar plates without antibiotic. The plates were incubated for 18-20 hours at 37° C. The MBC was read as the lowest concentration at which colony growth was ca. 90% less than the positive control (i.e. usually where single colonies or no colonies were observed).

MICs

MIC data are shown in Table 10 (1st experiment) and Table 11 (2nd experiment) and MIC ranges are summarized in Table 12 below. All *A. baumannii* strains except for the type strain ATCC 19606 and one *Acinetobacter* sp. were resistant to ciprofloxacin and levofloxacin (one strain, *A. baumannii* A387 exhibited intermediate susceptibility against levofloxacin and resistance to ciprofloxacin). Additionally, most of the strains were resistant to carbapenems, aminoglycosides, and tetracycline. MICs for polymyxin B were ranging from 0.25 to 2 µg/ml (1st experiment) and 0.25 to 0.5 µg/ml (2nd experiment).

TABLE 10

MICs and preliminary MBCs without and with sub-inhibitory concentrations of polymyxin B (PB) against 11 strains of *A. baumannii* and one strain of *Acinetobacter* sp. ($1^{st}$ experiment). Chemical names and structures of the compounds used are given in Table 1 herein above.

| | *A. baumannii* ATCC 19606 | | | | |
| --- | --- | --- | --- | --- | --- |
| | without PB | | +0.06 µg/ml PB | | MIC without |
| Compounds | MIC | MBC | MIC | MBC | PB/MIC + PB |
| Compound 1 | 0.25 | 0.25 | ≤0.03 | ≤0.03 | ≥8 |
| Compound 17 | 0.5 | 1 | ≤0.03 | ≤0.03 | ≥16 |
| Compound 2 | ≤0.03 | ≤0.03 | ≤0.03 | ≤0.03 | ≥1 |
| Compound 3 | 0.25 | 0.125 | ≤0.03 | ≤0.03 | ≥8 |
| Compound 7 | 0.5 | 0.5 | ≤0.03 | ≤0.03 | ≥16 |
| Compound 8 | 1 | 0.125 | ≤0.03 | ≤0.03 | ≥32 |
| Compound 4 | 0.25 | 0.125 | 0.125 | 0.06 | 2 |
| Compound 5 | 0.25 | 0.125 | 0.06 | 0.06 | 4 |
| Compound 6 | 0.5 | 0.25 | 0.06 | 0.06 | 8 |
| Compound 10 (ABT-719) | ND | ND | 0.03 | 0.03 | 256 |
| Levofloxacin | 1 | 0.5 | 1 | 1 | 1 |
| Moxifloxacin | 0.5 | 0.5 | 0.5 | 0.5 | 1 |
| Meropenem | 2 | 128 | 1 | 2 | 2 |
| Imipenem | 2 | 2 | 1 | 2 | 2 |
| Amikacin | 16 | 16 | 8 | 8 | 2 |
| Polymyxin B | 0.5 | 0.5 | 0.5 | 0.5 | 1 |

| | *A. baumannii* J2 | | | | |
| --- | --- | --- | --- | --- | --- |
| | without PB | | +0.125 µg/ml PB | | MIC without |
| Compounds | MIC | MBC | MIC | MBC | PB/MIC + PB |
| Compound 1 | 8 | 8 | ≤0.03 | ≤0.03 | ≥256 |
| Compound 17 | 4 | 4 | 0.06 | 0.06 | 64 |
| Compound 2 | 4 | 4 | ≤0.03 | ≤0.03 | ≥128 |
| Compound 3 | 8 | 8 | 0.125 | 0.125 | 64 |
| Compound 7 | 16 | 2 | ≤0.03 | ≤0.03 | ≥512 |
| Compound 8 | 8 | 8 | 0.125 | 0.125 | 64 |
| Compound 4 | 8 | 4 | 2 | 1 | 4 |
| Compound 5 | 8 | 8 | 0.5 | 0.5 | 16 |
| Compound 6 | 16 | 8 | 1 | 1 | 16 |
| Compound 10 (ABT-719) | 2 | 1 | 1 | 1 | 2 |
| Levofloxacin | 32 | 32 | 8 | 8 | 4 |
| Moxifloxacin | 32 | 32 | 8 | 8 | 4 |
| Meropenem | 1 | 2 | 1 | 1 | 1 |
| Imipenem | 4 | 4 | ≤0.125 | ≤0.125 | ≥32 |
| Amikacin | 32 | 32 | 4 | 4 | 8 |
| Polymyxin B | 0.5 | 0.5 | 0.5 | 0.5 | 1 |

TABLE 10-continued

MICs and preliminary MBCs without and with sub-inhibitory concentrations of
polymyxin B (PB) against 11 strains of *A. baumannii* and one strain of *Acinetobacter* sp.
(1$^{st}$ experiment). Chemical names and structures of the compounds used are given in Table 1
herein above.

| | *A. baumannii* NCTC 13301 | | | | |
|---|---|---|---|---|---|
| | without PB | | +0.125 µg/ml PB | | MIC without |
| Compounds | MIC | MBC | MIC | MBC | PB/MIC + PB |
| Compound 1 | 32 | 32 | ≤0.03 | 0.06 | ≥1024 |
| Compound 17 | 16 | 16 | ≤0.03 | ≤0.03 | ≥512 |
| Compound 2 | 16 | 8 | ≤0.03 | ≤0.03 | ≥512 |
| Compound 3 | >32 | >32 | 0.5 | 0.5 | ≥64 |
| Compound 7 | 16 | 16 | 0.06 | 0.06 | 256 |
| Compound 8 | 32 | 16 | 0.5 | 1 | 64 |
| Compound 4 | 8 | 8 | 1 | 0.5 | 8 |
| Compound 5 | 16 | 8 | 1 | 1 | 16 |
| Compound 6 | 32 | 16 | 1 | 4 (1)* | 32 |
| Compound 10 (ABT-719) | 8 | 2 | 1.00 | 1.00 | 8 |
| Levofloxacin | 32 | 32 | 16 | 16 | 2 |
| Moxifloxacin | 128 | 32 | 128 | 128 | 1 |
| Meropenem | 32 | 32 | 1 | 1 | 32 |
| Imipenem | 128 | 128 | 16 | 16 | 8 |
| Amikacin | >128 | >128 | >128 | >128 | ≥1 |
| Polymyxin B | 0.5 | 0.5 | 1 | 0.5 | 0.5 |

| | *Acinetobacter* spp. H064200250 | | | | |
|---|---|---|---|---|---|
| | without PB | | +0.125 µg/ml PB | | MIC without |
| Compounds | MIC | MBC | MIC | MBC | PB/MIC + PB |
| Compound 1 | 8 | 8 | ≤0.03 | 0.25 (0.06)* | ≥256 |
| Compound 17 | 8 | 8 | 0.06 | 0.06 | 128 |
| Compound 2 | 4 | 4 | ≤0.03 | ≤0.03 | ≥128 |
| Compound 3 | 8 | 8 | 0.5 | 0.5 | 16 |
| Compound 7 | 8 | 4 | 0.25 | 0.25 | 32 |
| Compound 8 | 2 | 4 | 0.06 | 0.5 (0.125)* | 32 |
| Compound 4 | 16 | 16 | 4 | 8 | 4 |
| Compound 5 | 16 | 8 | 1 | 1 | 16 |
| Compound 6 | 8 | 8 | 4 | 4 | 2 |
| Compound 10 (ABT-719) | 2 | 0.5 | 1 | 1 | 2 |
| Levofloxacin | 16 | 16 | 16 | 16 | 1 |
| Moxifloxacin | 16 | 16 | 16 | 16 | 1 |
| Meropenem | 32 | 16 | 1 | 1 | 32 |
| Imipenem | 16 | 16 | 0.5 | 2 (0.5)* | 32 |
| Amikacin | 16 | 16 | 16 | 64 (16)* | 1 |
| Polymyxin B | 0.5 | 0.5 | 0.25 | 0.5 | 2 |

| | *A. baumannii* A14 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 32 | 32 | 0.06 | 0.06 | 512 |
| Compound 17 | 16 | 16 | 1 | 1 | 16 |
| Compound 2 | 16 | 16 | ≤0.03 | ≤0.03 | ≥512 |
| Compound 3 | >32 | >32 | 1 | 1 | ≥32 |
| Compound 7 | 32 | 16 | 1 | 1 | 32 |
| Compound 8 | 32 | 16 | 1 | 1 | 32 |
| Compound 4 | 32 | 16 | 8 | 8 | 4 |
| Compound 5 | 32 | 16 | 4 | 8 | 8 |
| Compound 6 | 32 | 16 | 8 | 8 | 4 |
| Compound 10 (ABT-719) | 8 | 2 | 8.00 | 2.00 | 1 |
| Levofloxacin | 32 | 32 | 32 | 32 | 1 |
| Moxifloxacin | 32 | 32 | 32 | 32 | 1 |
| Meropenem | 1 | 2 | 0.5 | 0.5 | 2 |
| Imipenem | 1 | 2 | 1 | 1 | 1 |
| Amikacin | 32 | 32 | 16 | 16 | 2 |
| Polymyxin B | 0.5 | 0.5 | 0.5 | 0.5 | 1 |

TABLE 10-continued

MICs and preliminary MBCs without and with sub-inhibitory concentrations of
polymyxin B (PB) against 11 strains of *A. baumannii* and one strain of *Acinetobacter* sp.
(1st experiment). Chemical names and structures of the compounds used are given in Table 1
herein above.

| | *A. baumannii* A329 | | | | |
|---|---|---|---|---|---|
| | without PB | | +0.125 µg/ml PB | | MIC without |
| Compounds | MIC | MBC | MIC | MBC | PB/MIC + PB |
| Compound 1 | 16 | 16 | NR | NR | |
| Compound 17 | 8 | 8 | NR | NR | |
| Compound 2 | 8 | 8 | NR | NR | |
| Compound 3 | 16 | 16 | NR | NR | |
| Compound 7 | 16 | 16 | NR | NR | |
| Compound 8 | 16 | 16 | NR | NR | |
| Compound 4 | 16 | 16 | NR | NR | |
| Compound 5 | 16 | 16 | NR | NR | |
| Compound | 16 | 16 | NR | NR | |
| Compound 10 (ABT-719) | 8 | 2 | NR | NR | |
| Levofloxacin | 32 | 32 | NR | NR | |
| Moxifloxacin | 32 | 64 | NR | NR | |
| Meropenem | 128 | 128 | NR | NR | |
| Imipenem | 128 | 128 | NR | NR | |
| Amikacin | >128 | >128 | NR | NR | |
| Polymyxin B | 0.5 | 0.5 | NR | NR | |

| | *A. baumannii* A387 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 1 | 1 | ≤0.03 | ≤0.03 | ≥32 |
| Compound 17 | 1 | 2 | ≤0.03 | ≤0.03 | ≥32 |
| Compound 2 | 0.5 | 0.5 | ≤0.03 | ≤0.03 | ≥16 |
| Compound 3 | 1 | 1 | ≤0.03 | 0.25 (≤0.03)* | ≥32 |
| Compound 7 | 2 | 2 | ≤0.03 | ≤0.03 | ≥64 |
| Compound 8 | 2 | 2 | ≤0.03 | ≤0.03 | ≥64 |
| Compound 4 | 2 | 2 | 1 | 1 | 2 |
| Compound 5 | 2 | 1 | 0.25 | 0.25 | 8 |
| Compound 6 | 4 | 4 | 0.5 | 0.5 | 8 |
| Compound 10 (ABT-719) | 0.5 | 0.5 | 0.5 | 0.25 | 1 |
| Levofloxacin | 8 | 8 | 8 | 8 | 1 |
| Moxifloxacin | 4 | 4 | 4 | 4 | 1 |
| Meropenem | 4 | 4 | 1 | 1 | 4 |
| Imipenem | 16 | 16 | 8 | 8 | 2 |
| Amikacin | >128 | >128 | >128 | >128 | ≥1 |
| Polymyxin B | 0.25 | 0.25 | 0.25 | 0.25 | 1 |

| | *A. baumannii* A390 | | | | |
|---|---|---|---|---|---|
| | without PB | | +0.125 µg/ml PB | | MIC without |
| Compounds | MIC | MBC | MIC | MBC | PB/MIC + PB |
| Compound 1 | 16 | 16 | NR | NR | |
| Compound 17 | 16 | 16 | NR | NR | |
| Compound 2 | 8 | 8 | NR | NR | |
| Compound 3 | >32 | >32 | NR | NR | |
| Compound 7 | 8 | 4 | NR | NR | |
| Compound 8 | 16 | 8 | NR | NR | |
| Compound 4 | 8 | 8 | NR | NR | |
| Compound 5 | 8 | 8 | NR | NR | |
| Compound 6 | 8 | 8 | NR | NR | |
| Compound 10 (ABT-719) | 1 | 1 | NR | NR | |
| Levofloxacin | 16 | 8 | NR | NR | |
| Moxifloxacin | 16 | 16 | NR | NR | |
| Meropenem | 32 | 32 | NR | NR | |
| Imipenem | 16 | 16 | NR | NR | |
| Amikacin | >128 | >128 | NR | NR | |
| Polymyxin B | 0.25 | 0.25 | NR | NR | |

TABLE 10-continued

MICs and preliminary MBCs without and with sub-inhibitory concentrations of
polymyxin B (PB) against 11 strains of *A. baumannii* and one strain of *Acinetobacter* sp.
(1st experiment). Chemical names and structures of the compounds used are given in Table 1
herein above.

| | *A baumannii* A 401 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 4 | 16 (4)* | ≤0.03 | ≤0.03 | ≥128 |
| Compound 17 | 4 | 8 | 0.5 | 0.5 | 8 |
| Compound 2 | 4 | 2 | ≤0.03 | ≤0.03 | ≥128 |
| Compound 3 | 8 | 4 | 0.125 | 0.125 | 64 |
| Compound 7 | 4 | 4 | 0.5 | 0.5 | 8 |
| Compound 8 | 32 | 8 | ≤0.03 | ≤0.03 | ≥1024 |
| Compound 4 | 16 | 4 | 4 | 2 | 4 |
| Compound 5 | 16 | 8 | 2 | 2 | 8 |
| Compound 6 | 16 | 4 | 4 | 4 | 4 |
| Compound 10 (ABT-719) | 2 | 1 | 1.00 | 1.00 | 2 |
| Levofloxacin | 16 | 16 | 16 | 16 | 1 |
| Moxifloxacin | 32 | 16 | 16 | 8 | 2 |
| Meropenem | 32 | 16 | 4 | 4 | 8 |
| Imipenem | 32 | 32 | 8 | 8 | 4 |
| Amikacin | >128 | >128 | >128 | >128 | ≥1 |
| Polymyxin B | 1 | 1 | 0.5 | 0.5 | 2 |

| | *A. baumannii* A472 | | | | |
|---|---|---|---|---|---|
| | without PB | | +0.125 µg/ml PB | | MIC without |
| Compounds | MIC | MBC | MIC | MBC | PB/MIC + PB |
| Compound 1 | 8 | 8 | ≤0.03 | ≤0.03 | ≥256 |
| Compound 17 | 4 | 4 | ≤0.03 | 0.125 | ≥128 |
| Compound 2 | 4 | 4 | ≤0.03 | ≤0.03 | ≥128 |
| Compound 3 | 32 | >32 | 0.5 | 0.25 | 64 |
| Compound 7 | 4 | 4 | ≤0.03 | ≤0.03 | ≥128 |
| Compound 8 | 4 | 2 | ≤0.03 | ≤0.03 | ≥128 |
| Compound 4 | 4 | 2 | 1 | 1 | 4 |
| Compound 5 | 8 | 4 | 1 | 1 | 8 |
| Compound 6 | 8 | 4 | 0.5 | 0.5 | 16 |
| Compound 10 (ABT-719) | 1 | 1 | 0.5 | 0.25 | 2 |
| Levofloxacin | 16 | 8 | 4 | 4 | 4 |
| Moxifloxacin | 16 | 8 | 32 | 4 | 0.5 |
| Meropenem | 8 | 8 | ≤0.125 | ≤0.125 | ≥64 |
| Imipenem | 16 | 16 | 0.25 | 0.25 | 64 |
| Amikacin | >128 | >128 | 16 | 32 | ≥8 |
| Polymyxin B | 0.5 | 0.5 | ≤0.125 | ≤0.125 | ≥4 |

| | *A. baumannii* A473 | | | | |
|---|---|---|---|---|---|
| | without PB | | +0.125 µg/ml PB | | MIC without |
| Compounds | MIC | MBC | MIC | MBC | PB/MIC + PB |
| Compound 1 | 4 | 4 | NR | NR | |
| Compound 17 | 4 | 4 | NR | NR | |
| Compound 2 | 8 | 2 | NR | NR | |
| Compound 3 | 4 | 4 | NR | NR | |
| Compound 7 | 4 | 4 | NR | NR | |
| Compound 8 | 2 | 2 | NR | NR | |
| Compound 4 | 8 | 4 | NR | NR | |
| Compound 5 | 8 | 4 | NR | NR | |
| Compound 6 | 8 | 4 | NR | NR | |
| Compound 10 (ABT-719) | 1 | 0.5 | NR | NR | |
| Levofloxacin | 16 | 16 | NR | NR | |
| Moxifloxacin | 16 | 8 | NR | NR | |
| Meropenem | 16 | 64 (16)* | NR | NR | |
| Imipenem | 32 | 32 | NR | NR | |
| Amikacin | >128 | >128 | NR | NR | |
| Polymyxin B | 1 | 1 | NR | NR | |

TABLE 10-continued

MICs and preliminary MBCs without and with sub-inhibitory concentrations of polymyxin B (PB) against 11 strains of *A. baumannii* and one strain of *Acinetobacter* sp. (1$^{st}$ experiment). Chemical names and structures of the compounds used are given in Table 1 herein above.

| | *A. baumannii* A489 | | | | |
|---|---|---|---|---|---|
| | without PB | | +0.25 µg/ml PB | | MIC without |
| Compounds | MIC | MBC | MIC | MBC | PB/MIC + PB |
| Compound 1 | 4 | 8 | ≤0.03 | ≤0.03 | ≥128 |
| Compound 17 | 8 | 4 | ≤0.03 | ≤0.03 | ≥256 |
| Compound 2 | 2 | 2 | ≤0.03 | ≤0.03 | ≥64 |
| Compound 3 | 4 | 2 | 0.06 | 0.06 | 64 |
| Compound 7 | 8 | 4 | ≤0.03 | ≤0.03 | ≥256 |
| Compound 8 | 2 | 2 | ≤0.03 | ≤0.03 | ≥64 |
| Compound 4 | 8 | 4 | 1 | 1 | 8 |
| Compound 5 | 4 | 2 | 0.5 | 1 | 8 |
| Compound 6 | 8 | 8 | 0.5 | 1 | 16 |
| Compound 10 (ABT-719) | 1 | 1 | 1.00 | 1.00 | 1 |
| Levofloxacin | 16 | 32 | 8 | 8 | 2 |
| Moxifloxacin | 16 | 8 | 4 | 4 | 4 |
| Meropenem | 16 | 8 | 0.5 | 0.5 | 32 |
| Imipenem | 128 | 64 | 2 | 2 | 64 |
| Amikacin | >128 | >128 | 128 | 128 | ≥1 |
| Polymyxin B | 2 | 2 | 1 | 1 | 2 |

PB, polymyxin B
*skipped growth on MBC plate
ND, MIC value was higher than previous data, thus this value was not considered
NR, MIC was not readable due to inhomogeneous growth in the wells (i.e. skipped growth in many wells)

TABLE 11

MICs and preliminary MBCs without and with sub-inhibitory concentrations of polymyxin B (PB) against 11 strains of *A. baumannii* and one strain of *Acinetobacter* sp. (2$^{nd}$ experiment). Chemical names and structures of the compounds used are given in Table 1 herein above.

| | *A. baumannii* ATCC 19606 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 0.25 | 0.25 | ≤0.03 | ≤0.03 | ≥8 |
| Compound 2 | 0.125 *(0.06) | 0.125 | ≤0.03 | ≤0.03 | ≥4 |
| Compound 3 | 0.25 | 0.5 | ≤0.03 | ≤0.03 | ≥8 |
| Compound 7 | 0.25 | 0.25 | ≤0.03 | ≤0.03 | ≥8 |
| Compound 8 | 0.25 *(0.125) | 0.25 | ≤0.03 | ≤0.03 | ≥8 |
| Compound 4 | 0.5 | 0.5 | ≤0.03 (0.06)# | ≤0.03 | ≥16 |
| Compound 5 | 0.5 *(0.25) | 0.25 | 0.06 | 0.06 | 8 |
| Compound 6 | 0.25 | 0.25 | 0.06 | 0.06 | 4 |
| Compound 10 (ABT-719) | 0.125 *(0.06) | 0.125 | 0.06 | 0.03 | 2 |
| Levofloxacin | 1 | 1 | 1 (0.5)# | 1.00 | 1 |
| Moxifloxacin | 1 | 1 | 0.5 | 0.5 | 2 |
| Meropenem | 1 *(64) | 4 | 1 (2)# | 2 | 1 |
| Imipenem | 1 *(4) | 4 | 1 | 1 | 1 |
| Amikacin | 16 | 16 | 8 | 8 | 2 |
| Polymyxin B | 0.5 | 0.5 | 0.25 | 0.25 | 2 |

| | *A. baumannii* J2 | | | | |
|---|---|---|---|---|---|
| | without PB | | +0.125 µg/ml PB | | MIC without |
| Compounds | MIC | MBC | MIC | MBC | PB/MIC + PB |
| Compound 1 | 16 | 16 | ≤0.03 | ≤0.03 | ≥512 |
| Compound 2 | 4 | 8 | ≤0.03 | ≤0.03 | ≥128 |
| Compound 3 | 32 | 32 | ≤0.03 | ≤0.03 | ≥1024 |
| Compound 7 | 4 | 4 | ≤0.03 | ≤0.03 | ≥128 |
| Compound 8 | 4 | 4 | ≤0.03 | ≤0.03 | ≥128 |
| Compound 4 | 8 | 16 | 0.06 | 0.06 | 128 |
| Compound 5 | 4 | 4 | 0.5 | 0.5 | 8 |
| Compound 6 | 8 | 16 | 0.25 | 0.25 | 32 |
| Compound 10 (ABT-719) | 2 | 2 | 0.25 | 0.25 | 8 |
| Levofloxacin | 32 | 32 | 4 | 4 | 8 |

TABLE 11-continued

MICs and preliminary MBCs without and with sub-inhibitory concentrations of
polymyxin B (PB) against 11 strains of *A. baumannii* and one strain of *Acinetobacter* sp. ($2^{nd}$
experiment). Chemical names and structures of the compounds used are given in Table 1
herein above.

| | | | | | |
|---|---|---|---|---|---|
| Moxifloxacin | 32 | 32 | 8 | 8 | 4 |
| Meropenem | 2 | 2 | ≤0.125 | ≤0.125 | ≥16 |
| Imipenem | 8 (4)[#] | 8 | ≤0.125 | ≤0.125 | ≥64 |
| Amikacin | 8 | 8 | 0.5 | 0.5 | 16 |
| Polymyxin B | 0.5 | 0.5 | ≤0.125 | ≤0.125 | ≥4 |

*A. baumannii* NCTC 13301

| Compounds | without PB | | +0.125 µg/ml PB | | MIC without |
|---|---|---|---|---|---|
| | MIC | MBC | MIC | MBC | PB/MIC + PB |
| Compound 1 | 32 | 32 | ≤0.03 | ≤0.03 | ≥1024 |
| Compound 2 | 16 | 32 | ≤0.03 | ≤0.03 | ≥512 |
| Compound 3 | >32 | >32 | ≤0.03 | ≤0.03 | ≥1024 |
| Compound 7 | 16 | 16 | ≤0.03 | ≤0.03 | ≥512 |
| Compound 8 | 16 (8)[#] | 16 | 0.5 | 0.5 | 32 |
| Compound 4 | 32 | 32 | 0.25 | 0.25 | 128 |
| Compound 5 | 8 | 8 | 1 | 1 | 8 |
| Compound 6 | 16 | 8 | 1 | 2 | 16 |
| Compound 10 (ABT-719) | 2 | 2 | 0.5 | 0.5 | 4 |
| Levofloxacin | 32 | 16 | 8.00 | 4.00 | 4 |
| Moxifloxacin | 64 (32)[#] | 64 | 8 | 8 | 8 |
| Meropenem | 64 | 64 | 0.25 | ≤0.125 | 256 |
| Imipenem | 128 | 128 | 1 | 0.5 | 128 |
| Amikacin | >128 | >128 | 128 | 64 | ≥1 |
| Polymyxin B | 0.25 | 0.25 | ≤0.125 *(0.25) | ≤0.125 | ≥2 |

*Acinetobacter* spp. H064200250 (OXA51)

| Compounds | without PB | | +0.125 µg/ml PB | | MIC without |
|---|---|---|---|---|---|
| | MIC | MBC | MIC | MBC | PB/MIC + PB |
| Compound 1 | 16 | 32 | ≤0.03 | ≤0.03 | ≥512 |
| Compound 2 | 4 | 8 | ≤0.03 (0.06)[#] | 0.06 | ≥128 |
| Compound 3 | 16 | 16 | 0.06 | 0.06 | 256 |
| Compound 7 | 16 (8)[#] | 8 | ≤0.03 | ≤0.03 | ≥512 |
| Compound 8 | 4 (8)[#] | 4 | 0.125 | 0.125 | 32 |
| Compound 4 | 32 (16)[#] | 32 | 0.5 | 0.5 | 64 |
| Compound 5 | 16 | 16 | 4 | 4 | 4 |
| Compound 6 | 16 | >32 | 2 | 1 | 8 |
| Compound 10 (ABT-719) | 1 | 1 | 1 | 0.5 | 1 |
| Levofloxacin | 16 | 16 | 8 | 8 | 2 |
| Moxifloxacin | 16 | 16 | 16 | 16 | 1 |
| Meropenem | 16 | 16 | 0.25 | 0.25 | 64 |
| Imipenem | 8 | 8 | 0.5 | 0.5 | 16 |
| Amikacin | 8 | 8 | 1 | 1 | 8 |
| Polymyxin B | 0.25 | 0.25 | 0.25 | 0.25 | 1 |

*A. baumannii* A14

| Compounds | without PB | | +0.06 µg/ml PB | | MIC without |
|---|---|---|---|---|---|
| | MIC | MBC | MIC | MBC | PB/MIC + PB |
| Compound 1 | 32 | 32 | 0.06 | 0.06 | 512 |
| Compound 2 | 16 | 16 | 0.06 | 0.06 | 256 |
| Compound 3 | >32 | >32 | 0.125 | 0.125 | ≥256 |
| Compound 7 | 16 | 16 | 2 | 2 | 8 |
| Compound 8 | 8 | 16 | 0.5 | 0.5 | 16 |
| Compound 4 | 32 | >32 | 2 | 8 | 16 |
| Compound 5 | 16 | 16 | 4 | 4 | 4 |
| Compound 6 | 16 | 16 | 4 | 8 | 4 |
| Compound 10 (ABT-719) | 2 | 2 | 2 | 1 | 1 |
| Levofloxacin | 32 | 32 | 16.00 | 16.00 | 2 |
| Moxifloxacin | 32 | 32 | 16 | 16 | 2 |
| Meropenem | 1 (2)[#] | 2 | 1 | 1 | 1 |
| Imipenem | 1 | 1 | 1 | 0.5 | 1 |
| Amikacin | 16 | 16 | 8 | 8 | 2 |
| Polymyxin B | 0.25 | 0.25 | 0.25 | 0.25 | 1 |

TABLE 11-continued

MICs and preliminary MBCs without and with sub-inhibitory concentrations of polymyxin B (PB) against 11 strains of *A. baumannii* and one strain of *Acinetobacter* sp. (2$^{nd}$ experiment). Chemical names and structures of the compounds used are given in Table 1 herein above.

| | *A. baumannii* A329 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 16 | 32 | 2 | 2 | 8 |
| Compound 2 | 8 | 8 | 0.5 (1)$^{\#}$ | 0.5 | 16 |
| Compound 3 | 16 (>32)$^{\#}$ | 32 | 0.5 (1)$^{\#}$ | 0.25 | 32 |
| Compound 7 | 16 | 16 | 2 | 2 | 8 |
| Compound 8 | 8 | 8 | 2 | 2 | 4 |
| Compound 4 | 16 (32)$^{\#}$ | 32 | 8 | 8 | 2 |
| Compound 5 | 8 (16)$^{\#}$ | 16 | 8 | 8 | 1 |
| Compound 6 | 16 | 16 | 8 | 8 | 2 |
| Compound 10 (ABT-719) | 2 | 2 | 1 (2)$^{\#}$ | 2 | 2 |
| Levofloxacin | 16 | 32 | 32 | 16 | 0.5 |
| Moxifloxacin | 32 | 32 | 32 | 32 | 1 |
| Meropenem | 128 (>128)$^{\#}$ | >128 | 32 (64)$^{\#}$ | 32 | 4 |
| Imipenem | >128 | >128 | 128 | 128 | ≥1 |
| Amikacin | 128 (>128)$^{\#}$ | 128 | 128 | 128 | 1 |
| Polymyxin B | 0.25 | 0.25 | 0.25 | 0.25 | 1 |

| | *A. baumannii* A387 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 4 | 4 | ≤0.03 | ≤0.03 | ≥128 |
| Compound 2 | 1 | 1 | ≤0.03 | ≤0.03 | ≥32 |
| Compound 3 | 1 | 4 | ≤0.03 | ≤0.03 | ≥32 |
| Compound 7 | 2 | 2 | ≤0.03 | ≤0.03 | ≥64 |
| Compound 8 | 1 | 1 | 0.5 | 0.25 | 2 |
| Compound 4 | 2 | 2 | 0.25 (0.125)$^{\#}$ | 0.5 | 8 |
| Compound 5 | 4 | 4 | 1 | 1 | 4 |
| Compound 6 | 4 | 16 | 1 | 1 | 4 |
| Compound 10 (ABT-719) | 0.5 | 0.5 | 0.5 | 0.5 | 1 |
| Levofloxacin | 4 | 8 | 4.00 | 4.00 | 1 |
| Moxifloxacin | 8 | 8 | 8 | 8 | 1 |
| Meropenem | 8 | 8 | 4 (2)$^{\#}$ | 2 | 2 |
| Imipenem | 16 | 16 | 8 | 8 | 2 |
| Amikacin | >128 | >128 | 128 | 128 | ≥1 |
| Polymyxin B | 0.25 | 0.25 | ≤0.125 (0.25)$^{\#}$ | 0.25 | ≥2 |

| | *A. baumannii* A390 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 16 | 16 | ≤0.03 | ≤0.03 | ≥512 |
| Compound 2 | 16 | 16 | ≤0.03 (0.06)$^{\#}$ | 0.06 | ≥512 |
| Compound 3 | >32 | >32 | 0.125 | 0.125 | ≥256 |
| Compound 7 | 16 | 16 | 0.125 | 0.125 | 128 |
| Compound 8 | 16 | 16 | 0.5 | 0.5 | 32 |
| Compound 4 | 32 | 32 | 0.5 | 0.5 | 64 |
| Compound 5 | 8 (16)$^{\#}$ | 16 | 2 | 2 | 4 |
| Compound 6 | 16 (8)$^{\#}$ | 8 | 2 | 2 | 8 |
| Compound 10 (ABT-719) | 1 | 1 | 0.5 | 0.5 | 2 |
| Levofloxacin | 16 (8)$^{\#}$ | 8 | 8 | 8 | 2 |
| Moxifloxacin | 16 | 16 | 8 | 8 | 2 |
| Meropenem | 32 | 32 | 2 | 2 | 16 |
| Imipenem | 16 | 16 | 4 | 4 | 4 |
| Amikacin | >128 | >128 | 64 | 64 | ≥2 |
| Polymyxin B | 0.25 | 0.25 | ≤0.125 | ≤0.125 | ≥2 |

| | *A. baumannii* A 401 | | | | |
|---|---|---|---|---|---|
| | without PB | | +0.06 µg/ml PB | | |
| Compounds | MIC | MBC | MIC | MBC | MIC without |
| Compound 1 | 16 | 8 | ≤0.03 | ≤0.03 | ≥512 |
| Compound 2 | 4 | 4 | ≤0.03 | ≤0.03 | ≥128 |
| Compound 3 | 16 | 16 | 0.125 | 0.125 | 128 |

TABLE 11-continued

MICs and preliminary MBCs without and with sub-inhibitory concentrations of polymyxin B (PB) against 11 strains of *A. baumannii* and one strain of *Acinetobacter* sp. (2$^{nd}$ experiment). Chemical names and structures of the compounds used are given in Table 1 herein above.

| | | | | | |
|---|---|---|---|---|---|
| Compound 7 | 8 | 8 | 1 | 0.5 | 8 |
| Compound 8 | 8 | 8 | 0.25 | 0.25 | 32 |
| Compound 4 | 16 | 32 | 0.5 | 0.5 | 32 |
| Compound 5 | 8 | 8 | 4 | 4 | 2 |
| Compound 6 | 16 | 16 | 4 | 32 | 4 |
| Compound 10 (ABT-719) | 1 | 1 | 1 | 1 | 1 |
| Levofloxacin | 16 | 16 | 16.00 | 8.00 | 1 |
| Moxifloxacin | 16 | 16 | 16 | 8 | 1 |
| Meropenem | 16 | 32 | 4 | 4 | 4 |
| Imipenem | 32 | 32 | 4 | 4 | 8 |
| Amikacin | >128 | >128 | >128 | >128 | ≥1 |
| Polymyxin B | 0.5 | 0.5 | 0.25 | 0.25 | 2 |

| | *A. baumannii* A472 | | | | |
|---|---|---|---|---|---|
| | without PB | | +0.125 µg/ml PB | | |
| Compounds | MIC | MBC | MIC | MBC | MIC without |
| Compound 1 | 8 | 32 | ≤0.03 | ≤0.03 | ≥256 |
| Compound 2 | 4 | 8 | ≤0.03 | ≤0.03 | ≥128 |
| Compound 3 | >32 | >32 | ≤0.03 | ≤0.03 | ≥1024 |
| Compound 7 | 8 | 8 | ≤0.03 | ≤0.03 | ≥256 |
| Compound 8 | 4 | 4 | 0.06 | 0.06 | 64 |
| Compound 4 | 16 | 16 | 0.125 | 0.125 | 128 |
| Compound 5 | 4 | 4 | 1 | 1 | 4 |
| Compound 6 | 4 | 8 | 1 | 1 | 4 |
| Compound 10 (ABT-719) | 1 | 1 | 0.5 | 0.5 | 2 |
| Levofloxacin | 8 | 8 | 4 | 4 | 2 |
| Moxifloxacin | 16 | 16 | 4 | 4 | 4 |
| Meropenem | 8 | 8 | ≤0.125 | ≤0.125 | ≥64 |
| Imipenem | 8 | 8 | 0.25 | 0.25 | 32 |
| Amikacin | >128 | >128 | 32 | 32 | ≥4 |
| Polymyxin B | 0.5 | 0.5 | 0.25 | 0.25 | 2 |

| | *A. baumannii* A473 | | | | |
|---|---|---|---|---|---|
| | without PB | | +0.06 µg/ml PB | | MIC without |
| Compounds | MIC | MBC | MIC | MBC | PB/MIC + PB |
| Compound 1 | 8 | 8 | 1 | 1 | 8 |
| Compound 2 | 4 | 4 | 0.06 (0.125)[#] | 0.125 | 64 |
| Compound 3 | 8 | 8 | ≤0.03 (0.06)[#] | 0.06 | ≥256 |
| Compound 7 | 4 | 4 | 0.06 | 0.06 | 64 |
| Compound 8 | 4 | 4 | 0.5 | 0.5 | 8 |
| Compound 4 | 8 | 8 | 0.25 | 0.25 | 32 |
| Compound 5 | 8 | 8 | 1 | 1 | 8 |
| Compound 6 | 8 | 8 | 2 | 2 | 4 |
| Compound 10 (ABT-719) | 0 | 1 | 0.5 | 0.5 | 0 |
| Levofloxacin | 8 (16)[#] | 8 | 8.00 | 8.00 | 1 |
| Moxifloxacin | 8 | 8 | 8 | 8 | 1 |
| Meropenem | 16 (32)[#] | 16 | 2 | 2 | 8 |
| Imipenem | 32 | 32 | 4 | 4 | 8 |
| Amikacin | >128 | >128 | 128 | 128 | ≥1 |
| Polymyxin B | 0.25 (2)[#] | 0.25 | 0.25 | 0.25 | 1 |

| | *A. baumannii* A489 | | | | |
|---|---|---|---|---|---|
| | without PB | | +0.25 µg/ml PB | | MIC without |
| Compounds | MIC | MBC | MIC | MBC | PB/MIC + PB |
| Compound 1 | 16 | 16 | ≤0.03 | ≤0.03 | ≥512 |
| Compound 2 | 4 | 4 | ≤0.03 | ≤0.03 | ≥128 |
| Compound 3 | 4 | 4 | ≤0.03 | ≤0.03 | ≥128 |
| Compound 7 | 8 | 16 | ≤0.03 | ≤0.03 | ≥256 |
| Compound 8 | 8 | 8 | ≤0.03 | ≤0.03 | ≥256 |
| Compound 4 | 16 | 16 | ≤0.03 (0.06)[#] | 0.06 | ≥512 |
| Compound 5 | 8 (4)[#] | 8 | 0.5 | 0.5 | 16 |
| Compound 6 | 4 | 4 | 0.5 | 0.5 | 8 |
| Compound 10 (ABT-719) | 1 | 1 | 0.5 | 1 | 2 |
| Levofloxacin | 32 (16)[#] | 16 | 8 | 4 | 4 |
| Moxifloxacin | 16 | 16 | 4 | 4 | 4 |
| Meropenem | 16 (32)[#] | 16 | ≤0.125 | ≤0.125 | ≥128 |

TABLE 11-continued

MICs and preliminary MBCs without and with sub-inhibitory concentrations of polymyxin B (PB) against 11 strains of *A. baumannii* and one strain of *Acinetobacter* sp. (2$^{nd}$ experiment). Chemical names and structures of the compounds used are given in Table 1 herein above.

| | | | | | |
|---|---|---|---|---|---|
| Imipenem | 64 | 64 | 0.25 | 0.25 | 256 |
| Amikacin | >128 | >128 | 64 | 64 | ≥2 |
| Polymyxin B | 0.5 | 0.5 | 0.25 | 0.25 | 2 |

PB, polymyxin B
MIC read with alamar blue

TABLE 12

MIC ranges without and with sub-inhibitory concentrations of polymyxin B against resistant strains of *A. baumannii* and one strain of *Acinetobacter* sp.[1]

| Compounds | Structure | MIC range without PB 01-10-2008 n = 8[2] | MIC range without PB 14-10-2008 n = 11[3] | MIC range with PB (0.25 × MIC) 01-10-2008 n = 8 | MIC range with PB (0.25 × MIC) 14-10-2008 n = 11 | Range ratios MIC without PB/MIC with PB 01-10-2008 n = 8 | Range ratios MIC without PB/MIC with PB 14-10-2008 n = 11 |
|---|---|---|---|---|---|---|---|
| Compound 1 | *(structure)* | 1-32 | 4-32 | ≤0.03-0.06 | ≤0.03-2 | ≥32-≥1024 | 8-≥1024 |
| Compound 17 | *(structure)* | 1-16 | ND[4] | ≤0.03-1 | ND | 8-≥512 | ND |
| Compound 2 | *(structure)* | 0.5-16 | 1-16 | ≤0.03-1 | ≤0.03-0.5 | ≥16-≥512 | 16-≥512 |
| Compound 3 | *(structure)* | 1-≥32 | 1-≥32 | ≤0.03-1 | ≤0.03-0.5 | 16-≥64 | 32-≥1024 |
| Compound 7 | *(structure)* | 2-32 | 2-16 | ≤0.03-1 | ≤0.03-2 | 8-≥512 | 8-≥512 |
| Compound 8 | *(structure)* | 2-32 | 2-32 | ≤0.03-1 | ≤0.03-8 | 32-≥1024 | 2-≥512 |

TABLE 12-continued

MIC ranges without and with sub-inhibitory concentrations of polymyxin B against resistant strains of *A. baumannii* and one strain of *Acinetobacter* sp.[1]

| Compounds | Structure | MIC range without PB 01-10-2008 n = 8[2] | MIC range without PB 14-10-2008 n = 11[3] | MIC range with PB (0.25 × MIC) 01-10-2008 n = 8 | MIC range with PB (0.25 × MIC) 14-10-2008 n = 11 | Range ratios MIC without PB/MIC with PB 01-10-2008 n = 8 | Range ratios MIC without PB/MIC with PB 14-10-2008 n = 11 |
|---|---|---|---|---|---|---|---|
| Compound 4 | (structure) | 2-32 | 4-16 | 1-8 | 0.5-8 | 2-8 | 1-16 |
| Compound 5 | (structure) | 2-32 | 4-16 | 0.25-4 | 0.25-8 | 8-16 | 4-32 |
| Compound 6 | (structure) | 4-32 | ND | 0.5-8 | ND | 2-32 | ND |
| Compound 10 (ABT-719) | (structure) | 0.5-8 | 0.5-2 | 0.5-8 | 0.25-2 | 1-8 | 1-8 |
| Levofloxacin | | 8-32 | 4-32 | 4-32 | 4-32 | 1-4 | 0.5-8 |
| Moxifloxacin | | 4-128 | 8-64 | 4-128 | 4-32 | 0.5-4 | 1-8 |
| Meropenem | | 1-32 | 1-128 | <0.125-4 | ≤0.125-32 | 1-≥64 | 1-256 |
| Imipenem/cilastatin | | 1-128 | 1->128 | <0.125-16 | ≤0.125-128 | 1-64 | 1-256 |
| Amikacin | | 16->128 | 8->128 | 4->128 | 0.5->128 | 1-≥8 | 1-16 |

[1] *A. baumannii* ATCC 19606 was not taken for the calculation of MIC ranges since it was very susceptible against the 4-oxoquinolizine compounds.
[2] n = 8, three strains (*A. baumannii* A329, A390 and A473) were not taken for the calculation of MIC ranges since no homogenous growth (many skipped wells) was observed in presence of polymyxin B.
[3] n = 11, all strains except for the ATCC strain were taken for the calculation of MIC ranges
4ND, not determined The 8-phenyl anilines compounds 1-8 and reference compound 10 (ABT-719) exhibited potent activities against the *A. baumanii* ATCC 19606 strain with and without sub-inhibitory concentrations of polymyxin B. Since this strain was more susceptible compared to the clinical isolates, its MIC values were not taken into account for calculations for MIC ranges (Table 12).

Reference compound 10 (ABT-719) was more active against the quinolone resistant strains (MIC range: 0.5 to 8 μg/ml) than the 8-phenyl anilines (MIC ranges: 1 to >32 μg/ml) in the absence of polymyxin B.

Three *A. baumannii* strains did not grow homogenously in all wells of the microtiter plates containing 0.125 μg/ml polymyxin B in the first experiment (*A. baumannii* A329, A390, A473), thus these strains were not considered for the calculation of MIC ranges in Table 12. In the 2nd experiment, a lower polymyxin B concentration was used (0.06 μg/ml) and the growth was homogenous in all wells.

The activity of the 8-phenyl anilines compounds 1, 2, 3, 7, 8 and 17 was potentiated in the presence of polymyxin B. The compounds exhibited lower MICs ranging from 50.03 to 8 μg/ml in the presence of sub-inhibitory concentrations of polymyxin B compared to compound 10 (ABT-719) and the 8-phenyl amines (compounds 4, 5, and 6) for which MICs were ranging from 0.25 to 8 μg/ml. Thus, the activities of the 8-phenyl anilines were 2- to >1000-fold greater in presence of polymyxin B compared to activities without polymyxin B (Table 12). Overall, MICs of the 8-phenyl anilines were ≤0.03 to 0.5 μg/ml for the majority of strains except for 4-fold greater MICs against *A. baumannii* A-329

(MICs were 0.5 to 2 µg/ml). For this strain, MICs of the 8-phenyl anilines were less affected by the presence of polymyxin B (2- to 32-fold lower MICs in presence of polymyxin B) in contrast to the other strains (Table 11). Compound 2 and 3 were the most active 8-phenyl anilines in presence of polymyxin B against the quinolone resistant strains of A. baumannii with MICs ranging from ≤0.03 to 0.5 µg/ml (Table 12). However, compound 2 was more active against the quinolone resistant Acinetobacter strains than compound 3 in absence of polymyxin B (Table 10 and 11).

The activities of levofloxacin, moxifloxacin or amikacin were not significantly affected by polymyxin B, whereas MICs of meropenem and imipenem/cilastatin were 1- to 256-fold lower in presence of polymyxin B (Table 12).

Preliminary MBCs

MBCs were estimated by spotting 5 µl of cultures from the MIC plates on agar. Preliminary MBC data are shown in Table 10 (1st experiment) and Table 11 (2nd experiment). The 8-phenyl anilines, 8-phenyl amines and the reference compound 10 exhibited apparent bactericidal activities against A. baumannii with preliminary MBC/MIC ratios ranging from 1 to 4 except for a few compounds vs. a few strains with a MBC/MIC ratio of 8 (Table 10 and 11). There was no difference observed in MBC/MIC ratios in absence or presence of polymyxin B, although the absolute MBC (and MIC) values were lower in presence of polymyxin B especially for the 8-phenyl anilines.

Example 5: Antimicrobial Activity of 4-Oxoquinolizines Against a Selected Panel of Gram-Positive and Gram-Negative Strains and K. pneumonia Example 5 shows the antibacterial activity of particular 4-oxoquinolizines against a selection of Gram-positive and Gram-negative strains (Table 13) and of a selection of three 4-oxoquinolizines on K. pneumonia strains (Table 14).

MIC Values for all compounds were measured against a selection of bacterial strains. The MICs of 4-oxoquinolizines against a selection of Gram-negative and Gram-positive bacterial strains are shown in Table 13 in comparison with known antibiotics. Table 14 shows the activity of a selected number of 4-oxoquinolizines against strains of K. pneumonia, one sensitive and one quinolone-resistant strain (NDM-1 BAA-2146).

TABLE 13 showing the MIC value of some 4-oxoquinolizines on a selected panel of bacterial strains. Chemical names and structures of the compounds are given in Table 1 herein above.

| | MICs (µg/mL) against Gram negative bacteria | | | | MICs (µg/mL) against Gram positive bacteria | | |
|---|---|---|---|---|---|---|---|
| Compounds | B. thailandensis E264 | E. coli ATCC 25922 | P. aeruginosa ATCC 27853 | A. baumannii ATCC 19606 | S. aureus ATCC 25923 | S. aureus ATCC 43300 (MRSA, FQ-S) | S. aureus BAA-1556 (USA300-Type MRSA, FQ-R) |
| Compound 4 | 1 | 0,016 | 1 | 0,25 | 0,064 | 0.032-0.064 | 0,5 |
| Compound 13K salt | 0,5 | 0,016 | 1 | 0, 125 | 0,016 | 0,016 | 0,5 |
| Compound 54 | 4 | 0,25 | >8 | 4 | 0.064-0.125 | 0,064 | 0,5 |
| Compound 6K salt | 4 | 0.064-0.125 | 4-8 | 1 | 0, 125 | 0,064 | 1 |
| Compound 55K salt | 8 | 0,5 | >8 | 8 | 0,5 | 0.125-0.25 | 8 |
| Compound 56K salt | 0,25 | 0,032 | 2 | 0, 125 | 0,008 | 0,008 | 0, 125 |
| Compound 57 | >8 | 1 | >8 | 8 | 0.25-0.5 | 0,25 | 8 |
| Compound 58K salt | 1 | 0,25 | >8 | 1 | 0,064 | 0,064 | 1-2 |
| Compound 59K salt | 0,5 | 0,064 | 4 | 0,25 | 0,032 | 0,016 | 0,5 |
| Compound 60K salt | 0,5 | 0,032 | 2 | 0,064 | 0,008 | ≤0.004 | 0,125 |
| Compound 61K salt | 0,5 | 0,032 | 2 | 0, 125 | ≤0.004 | ≤0.004 | 0,064 |
| Compound 62K salt | 2 | 0,032 | 1 | 1 | 0,25 | 0, 125 | 4 |
| Compound 63 | 2 | 0,5 | >8 | 2 | 0,064 | 0,032 | 1 |
| Compound 64K salt | 2 | 0, 125 | 8 | 0,5 | 0,032 | 0,032 | 0,5 |
| Compound 65K salt | 0,5 | 0.032-0.064 | 4 | 0,25 | 0,016 | 0,008 | 0,25 |
| Compound 66K salt | 1 | 0, 125 | 4 | 0,5 | 0,008 | 0,008 | 0,25 |
| Compound 67K salt | 0,25 | 0,032 | 2 | 0,25 | 0,016 | 0,016 | 1 |
| Compound 68K salt | 1 | 0,064 | 2 | 0,25 | ≤0.004 | ≤0.004 | 0,25 |
| Compound 69K salt | 1 | 0, 125 | 4 | 0.25-0.5 | ≤0.004 | ≤0.004 | 0,25 |
| Compound 70K salt | 0,25 | 0,032 | 1 | 0, 125 | ≤0.004 | ≤0.004 | 0,064 |
| Compound 71K salt | 2 | 0, 125 | >8 | 0,5 | ≤0.004 | ≤0.004 | 0, 125 |
| Compound 72K salt | 2 | 0.008-0.016 | 0,5 | 0,25 | 0,008 | 0.008-0.016 | 0,25 |
| Compound 73K salt | 0,5 | 0,032 | 2 | 0, 125 | ≤0.004 | ≤0.004 | 0,064 |
| Compound 74K salt | 2 | 0.064-0.125 | 8 | 0,5 | 0,016 | 0,016 | 0,5 |
| Compound 75K salt | 0,25 | 0,032 | 1 | 0,064 | ≤0.004 | ≤0.004 | 0,032 |
| Compound 76K salt | 2 | 0,032 | 1 | 0,25 | 0,016 | 0.008-0.016 | 0,25 |
| Compound 77K salt | 1 | 0, 125 | 4 | 0,25 | 0,016 | 0,016 | 0,5 |
| Compound 78K salt | 0,5 | 0.064-0.125 | 2 | 0, 125 | 0,008 | 0,008 | 0, 125 |
| Compound 79K salt | 0,5 | 0,016 | 2 | 0,064 | ≤0.004 | ≤0.004 | 0, 125 |
| Compound 80K salt | 1 | 0,064 | 4 | 0,25 | ≤0.004 | ≤0.004 | 0, 125 |
| Compound 81K salt | 0,25 | 0,064 | 2 | 0, 125 | ≤0.004 | ≤0.004 | 0,064 |
| Compound 82K salt | 4 | 0.125-0.25 | 8 | 1 | 0,016 | 0,016 | 1 |
| Compound 83K salt | 0, 125 | 0,016 | 0,5 | 0,032 | ≤0.004 | ≤0.004 | 0,064 |
| Compound 84K salt | 8 | 0.125-0.25 | 8 | 2 | 0, 125 | 0, 125 | 2 |
| Compound 85K salt | 0,25 | 0,032 | 1 | 0,064 | ≤0.004 | ≤0.004 | 0.064-0.125 |
| Compound 86K salt | 2 | 0, 125 | 8 | 0.5-1 | 0.016-0.032 | 0,016 | 0,5 |
| Compound 87K salt | 4 | 0, 125 | 8 | 0,25 | 0,064 | 0,064 | 8 |
| Compound 88K salt | 1 | 0, 125 | 4 | 0,5 | 0,008 | 0,008 | 0,5 |

TABLE 13-continued showing the MIC value of some 4-oxoquinolizines on a selected panel of bacterial strains. Chemical names and structures of the compounds are given in Table 1 herein above.

| Compounds | MICs (μg/mL) against Gram negative bacteria | | | | MICs (μg/mL) against Gram positive bacteria | | |
|---|---|---|---|---|---|---|---|
| | B. thailandensis E264 | E. coli ATCC 25922 | P. aeruginosa ATCC 27853 | A. baumannii ATCC 19606 | S. aureus ATCC 25923 | S. aureus ATCC 43300 (MRSA, FQ-S) | S. aureus BAA-1556 (USA300-Type MRSA, FQ-R) |
| Compound 89K salt | 4 | 0, 125 | 8 | 0,5 | 0,032 | 0,032 | 2 |
| Compound 90K salt | 2 | 0, 125 | 4 | 0,5 | 0,008 | 0,008 | 0,25 |
| Ciprofloxacin | 4 | 0,008 | 0,25 | 1 | 0,25 | 0,5 | >8 |
| Levofloxacin | 4 | 0,016 | 1 | 0,5 | 0, 125 | 0,25 | 8 |
| Doxycycline | 2 | 1 | >8 | 0, 125 | 0, 125 | 0,25 | 4 |

In addition, specific MICs on *K. pneumoniae* for compound 2, compound 33 and compound 35 are shown in Table 14.

TABLE 14 showing MIC on *K. pneumoniae* for a selection of 4-oxoquinolizines.

| Compounds | Structure | MICs (μg/mL) | |
|---|---|---|---|
| | | K. pneumoniae ATCC 33495 | K. pneumoniae BAA-2146 (NDM-1, FQ-R) |
| Compound 33 K salt | 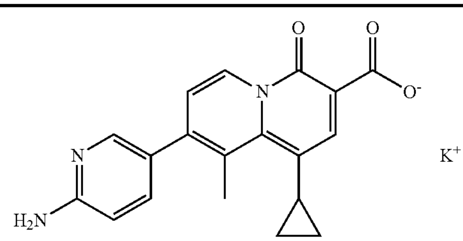 | 0, 064 | >8 |
| Compound 35 K salt | 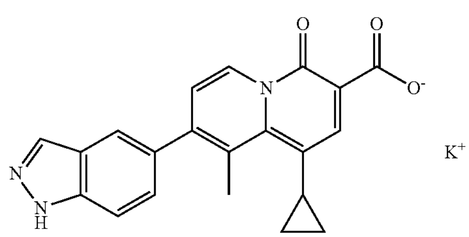 [SMILES: Cc1c(-c2ccc3[nH]ncc3c2)ccn2c(=O)c(C(=O)[O-])cc(C3CC3)c12 ; [K+]] | 0, 125 | >8 |
| Compound 2 K salt | 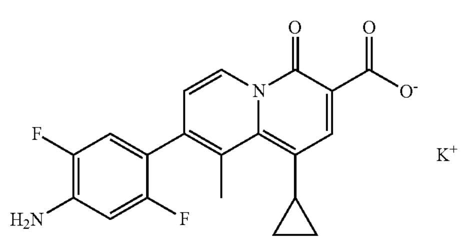 [SMILES: Cc1c(-c2cc(F)c(N)cc2F)ccn2c(=O)c(C(=O)[O-])cc(C3CC3)c12 ; [K+]] | 0, 25 | >8 |

Example 6: Synergy of Antimicrobial Activity of 4-Oxoquinolizines with Polymyxin B Against *Acinetobacter* and *K. pneumonia* Strains Example 6 shows that 4-oxoquinolizine compounds possess synergistic antibacterial activity with polymyxin B. A chequerboard technique was used to show synergistic interactions between three 4-oxoquinolizines compounds and polymyxin B (Table 15 and 16, FIGS. 1, 2 and 3). There is a strong indication that compounds 2, 33 and 35 in combination with polymyxin B are synergistic (or at least partially synergistic) against fluoroquinolone-resistant strains of *A. baumannii*. No interaction was seen between levofloxacin and polymyxin B.

A chequerboard technique was used to identify possible synergistic or antagonistic interactions between the 4-oxoquinolizines compounds, levofloxacin and polymyxin B.

Levofloxacin was included as a control. 10% Aqueous DMSO stock solutions were prepared for compound 2 (25.6 mg/mL), Compound 33 (12.8 mg/mL), and compound 35 (12.8/mL) as well as a levofloxacin stock solution of 1.28 mg/mL and a polymyxin B stock solution of 0.64 mg/mL. Final dilutions were made in Mueller-Hinton broth, the specific test medium used for MIC determinations according to CLSI guidelines (CLSI. Methods for Dilution Antimicrobial Susceptibility Tests for Bacteria That Grow Aerobically; Approved Standard-Eighth Edition (2009). CLSI Document M07-A8. CLSI, Wayne, Pa. 19087-1898, USA.). The test medium used was a cation-adjusted Mueller-Hinton Broth II (Becton Dickinson UK Ltd., Oxford Science Park, Oxford, UK, OX4 4DQ).

The compounds 2, 33 and 35, as well as levofloxacin were tested in combination with polymyxin B on the following isolates: GN31 *Acinetobacter baumannii*—antibiotic susceptible clinical isolate, GN52 *Acinetobacter baumannii*—levofloxacin resistant clinical isolate, GN56 *Acinetobacter baumannii*—levofloxacin resistant clinical isolate, GN48 *Klebsiella pneumoniae*—NCTC 13443—NDM-1-metallo-R-lactamase and GN10 *Pseudomonas aeruginosa*—ATCC 27853—antibiotic susceptible reference isolate. All isolates are from the collection maintained at Quotient Bioresearch Ltd., Cambridge, UK.

The MIC values for the compounds and polymyxin B and levofloxacin were determined by broth microdilution following CLSI guidelines, and the MICs of agents in combination were determined as described by Pillai et.al (Pillai S K, Moellering R C Jr, Eliopoulis G M; Antimicrobial Combinations in Antibiotics in Laboratory Medicine 5$^{th}$ Edition (V. Lorian Ed) (2005) p 365-440). Initial MIC results were used to determine the microtiter plate patterns for the chequerboards. A suitable doubling dilution concentration range was selected such that the combination antibiotic range was at least two concentrations above and four concentrations below the MIC for each isolate. A fixed range of 0.008 to 8 mg/L was tested for polymyxin B except in the case of *A. baumannii* GN31 where a range of 0.004 to 4 mg/L was tested when in combination with the compounds 2, 33 and 35 as well as levofloxacin.

From the raw data, fractional inhibitory concentration indices (FICI) were determined for the compounds of the invention and levofloxacin together with polymyxin B for each isolate as follows:

$FICI = FIC_X + FIC_Y$

Figure 2:
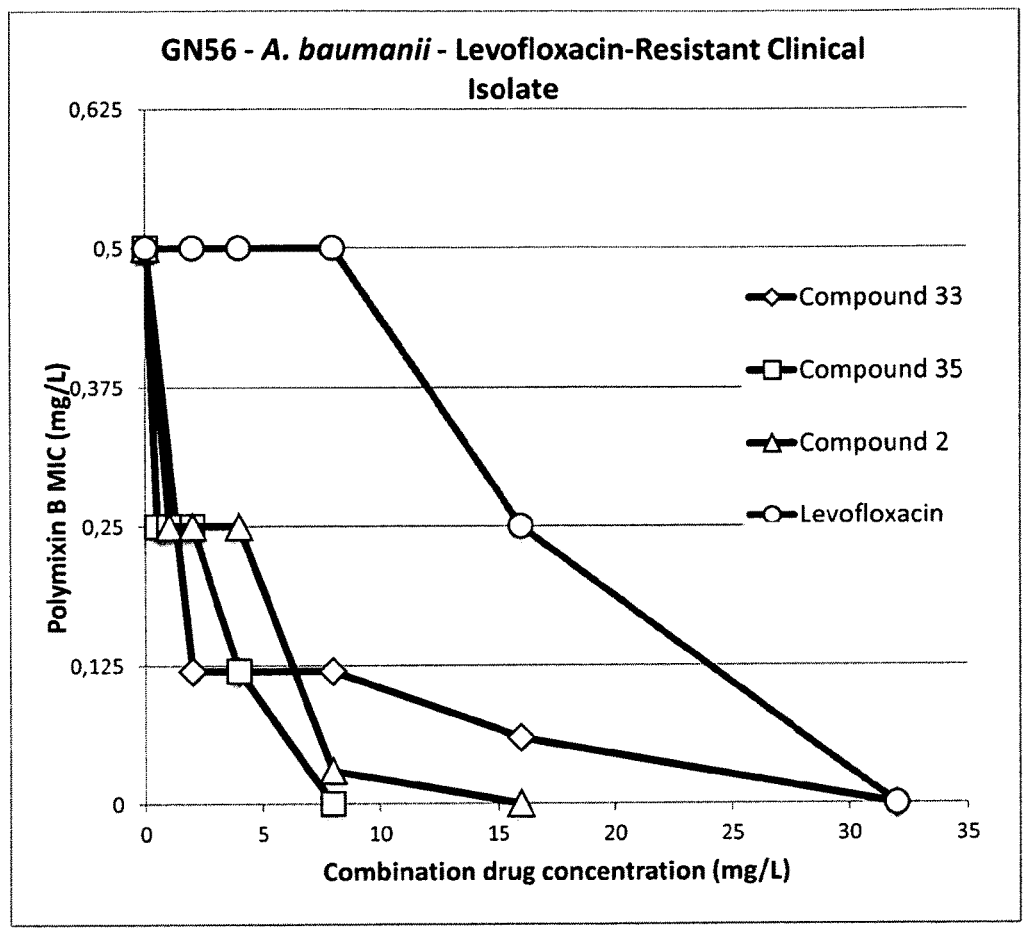
FIG. 2 shows the Isobologram related to the synergy of the antibacterial activity of compounds 2, 33 and 35 with Polymyxin B on the *Acinetobacter* GN56 strain.
Figure 3:
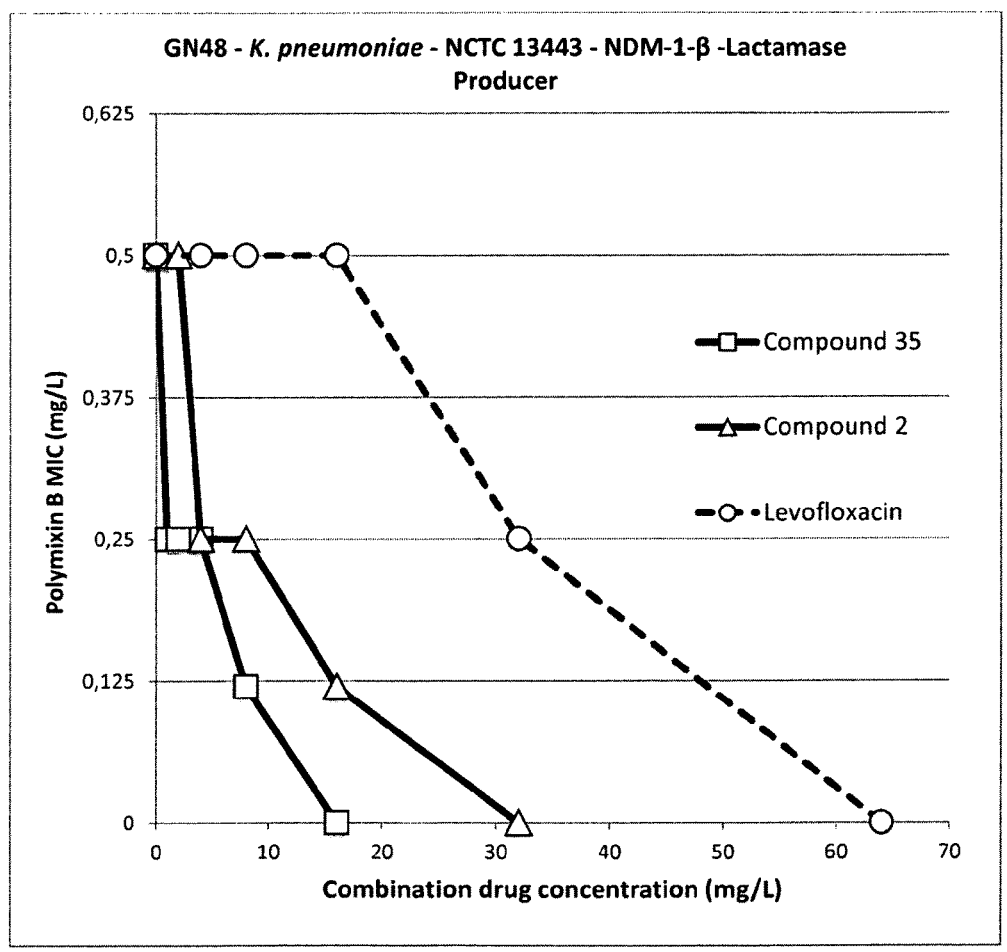
FIG. 3 shows the Isobologram related to the synergy of the antibacterial activity of compounds 2 and 35 with Polymyxin B on the *Klebsiella pneumonia*-NDM-1 strain.
Figure 4A:
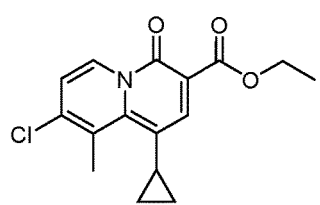
FIGS. 4A-4E show the structures of the 5 scaffolds used as intermediates towards the preparation of the 4-oxoquinolizines compounds
Figure 4B:
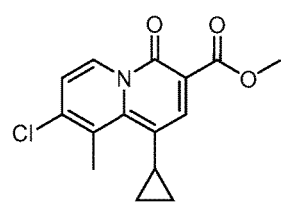
Figure 4C:
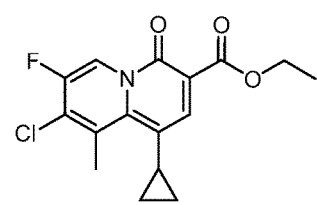
Figure 4D:
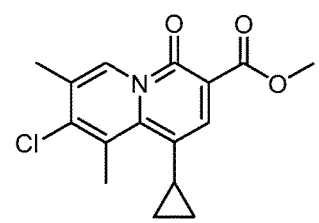
Figure 4E:
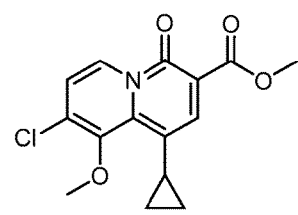
Figure 5A:
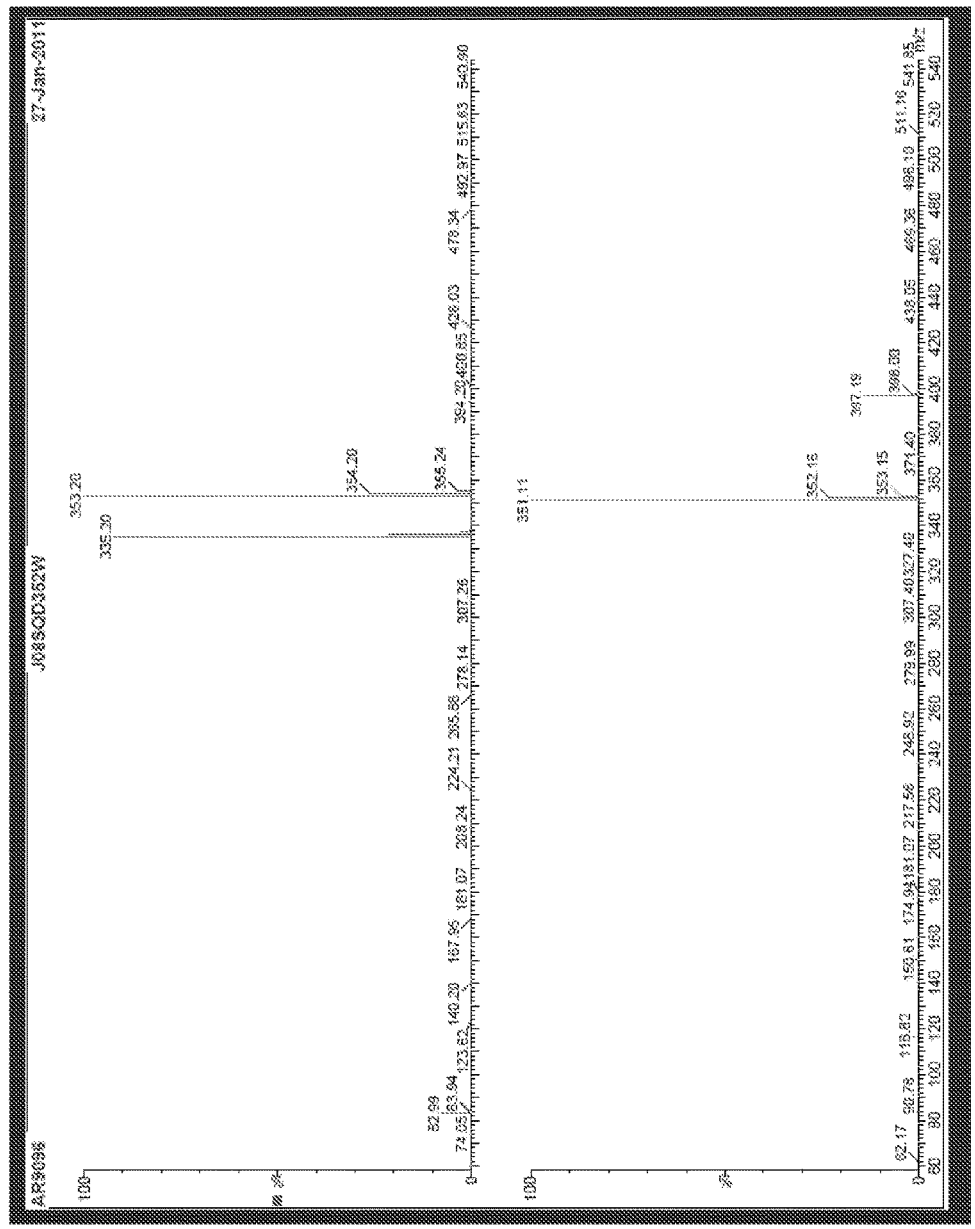
FIG. 5A is an LC-MS characterization of compound 1. The data was recorded on a Waters Acquity UPLC system, equipped with SQD, PDA and ELSD detectors, with an Acquity BEH C18 1.7 micron column.
Figure 5B:
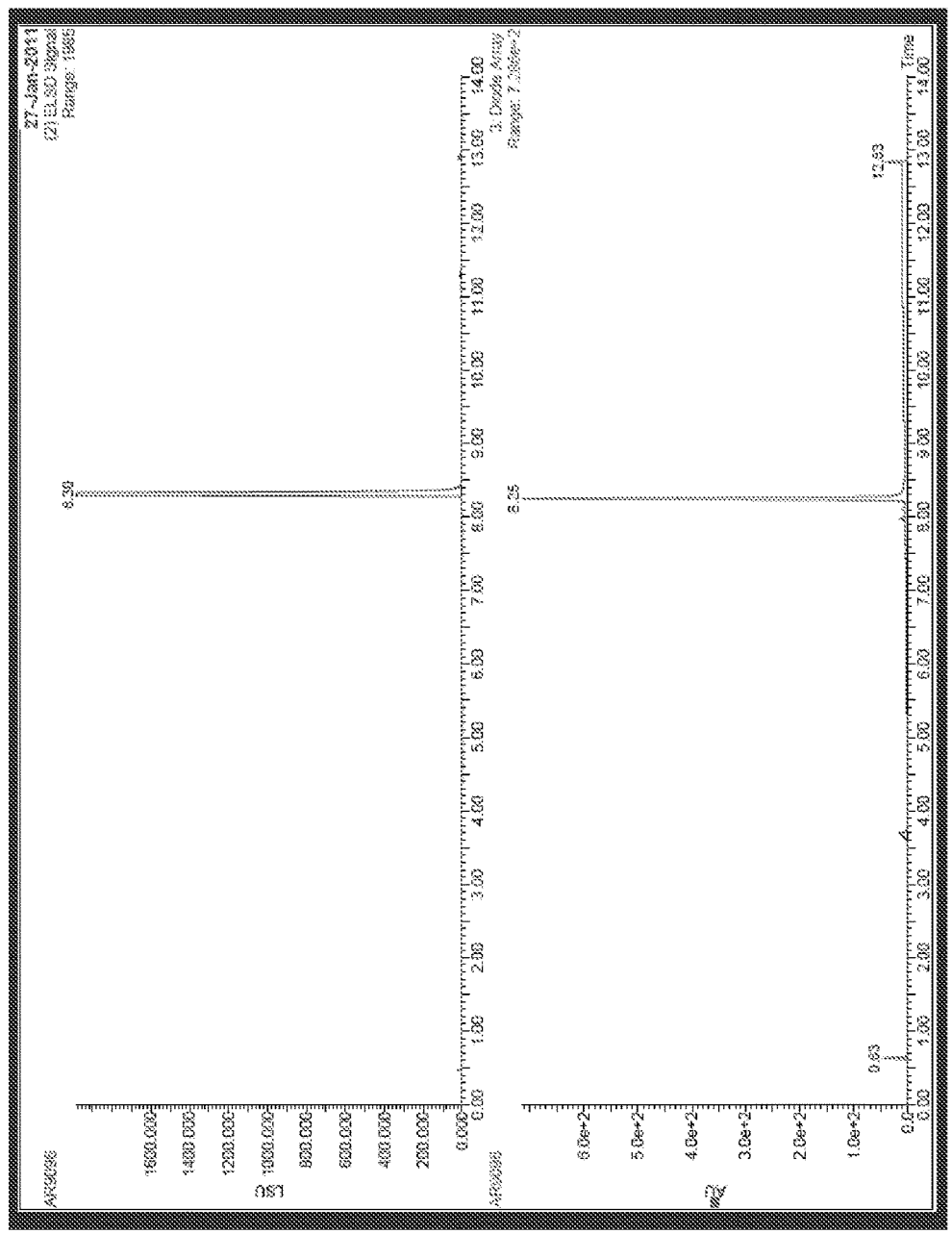
FIG. 5b is an LC characterization of compound 1. The LC was run with a 10 min gradient from 0 to 100% B (A: water with 0.1% formic acid, B: acetonitrile with 0.1% formic acid).
Figure 6A:
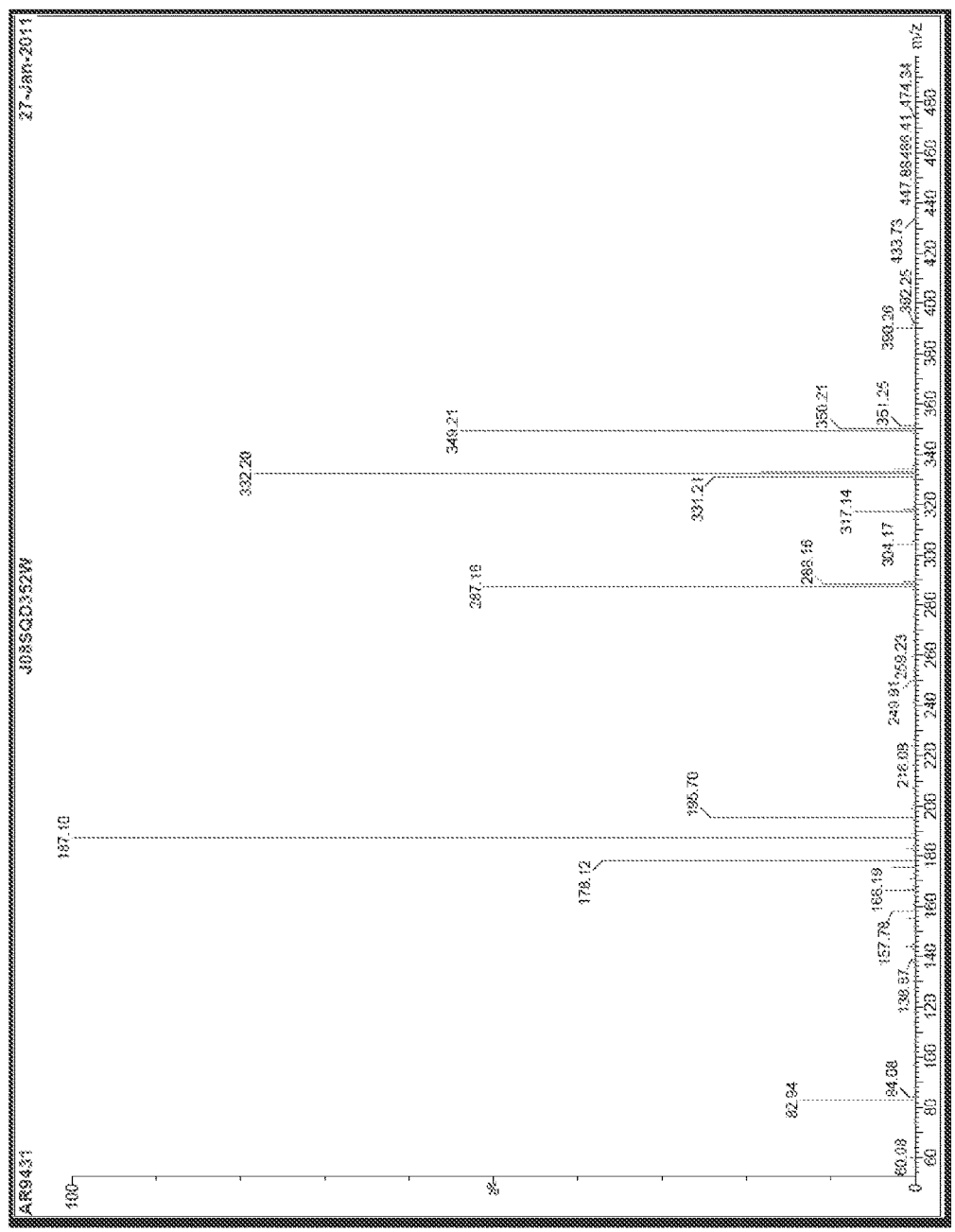
FIG. 6A is an LC-MS characterization of compound 5. The data was recorded on a Waters Acquity UPLC system, equipped with SQD, PDA and ELSD detectors, with an Acquity BEH C18 1.7 micron column.
Figure 6B:
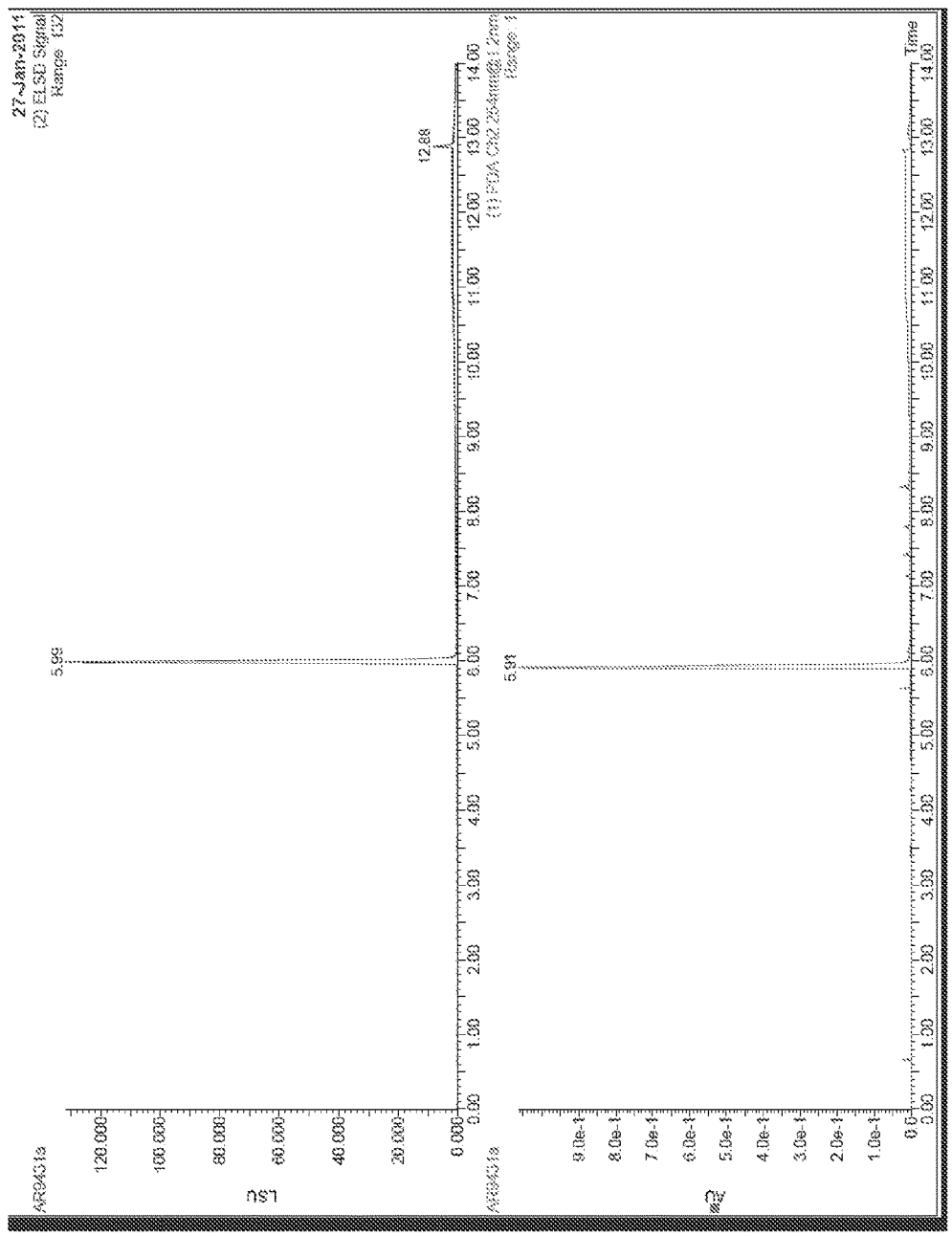
FIG. 6B is an LC characterization of compound 5. The LC was run with a 10 min gradient from 0 to 100% B (A: water with 0.1% formic acid, B: acetonitrile with 0.1% formic acid).
Figure 7A:
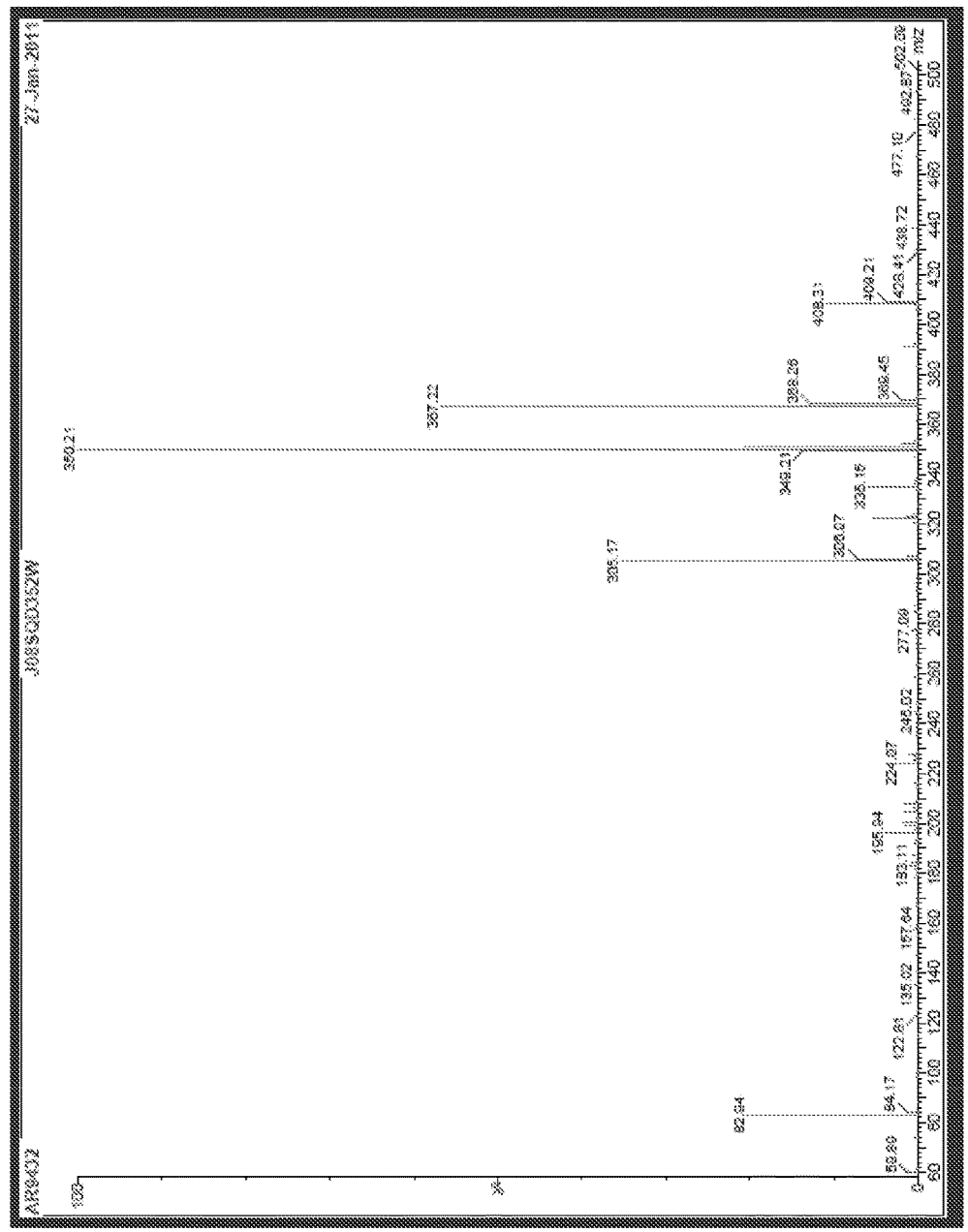
FIG. 7A is an LC-MS characterization of compound 6. The data was recorded on a Waters Acquity UPLC system, equipped with SQD, PDA and ELSD detectors, with an Acquity BEH C18 1.7 micron column.
Figure 7B:
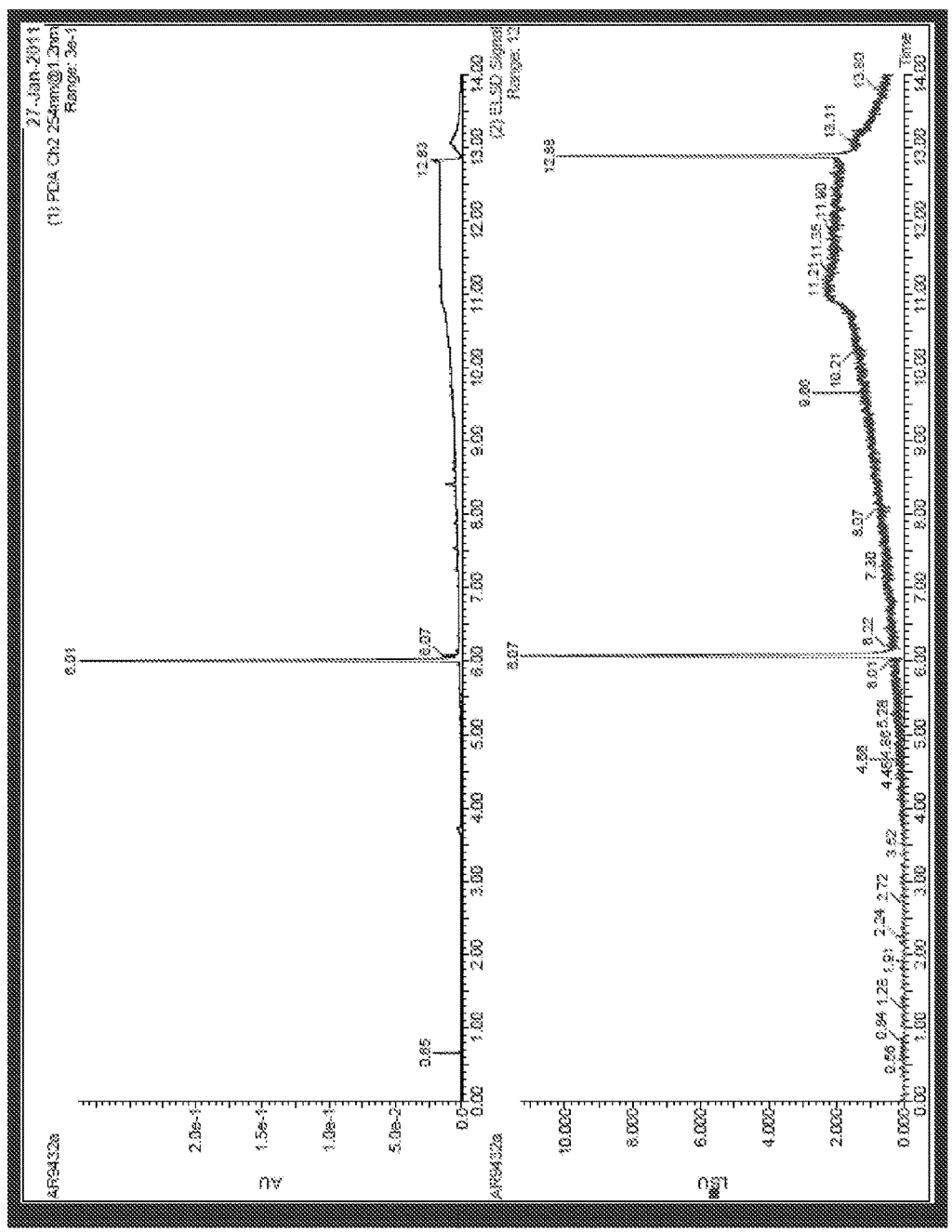
FIG. 7B is an LC characterization of compound 6. The LC was run with a 10 min gradient from 0 to 100% B (A: water with 0.1% formic acid, B: acetonitrile with 0.1% formic acid).

Where, $FIC_X$=concentration of the combination antibiotic in a particular row÷MIC of the combination drug alone $FIC_Y$=MIC of polymyxin B in combination÷MIC of the polymyxin B alone Data was interpreted according to the methodology of Pillai: Synergy (FICI <0.5), partial synergy/addition (FICI 0.51 to 0.75), indifference (FICI 0.76 to 2.75), antagonism (FICI >2.75). Additionally isobolograms were created to represent the same data visually. Here, the MIC of polymyxin B was plotted against every concentration of the combination antibiotic up to the MIC. Initial MIC results for all isolates are given in Table 15 and FICI data are given in Table 16 and Isobolograms are shown in FIGS. 1 to 3.

There is a strong indication that compounds 2, 33 and 35 in combination with polymyxin B are synergistic (or at least partially synergistic) against fluoroquinolone-resistant strains of *A. baumannii*. No interaction was seen between levofloxacin and polymyxin B in any of the chequerboard assays performed, all FICI values indicate indifference. No interaction was seen in any of the combinations tested for the antibiotic susceptible *P. aeruginosa* GN10. Surprisingly, also partial synergy was observed with compound 35 and compound 2 combined with polymyxin B against the NDM-1-beta-lactamase producing *Klebsiella pneumoniae* when combined with polymyxin B.

TABLE 15

Pre-chequerboard MIC of compounds for synergy study.

| | MIC mg/L | | | | |
|---|---|---|---|---|---|
| Antimicrobial agent | GN31 *Acinetobacter baumannii* | GN52 *Acinetobacter baumannii* | GN56 *Acinetobacter baumannii* | GN48 *Klebsiella pneumoniae* | GN10 *Pseudomonas aeruginosa* |
| Compound 33 | 0.03 | 2 | 16 | 16 | 0.5 |
| Compound 35 | 0.03 | 2 | 8 | 16 | 0.25 |
| Compound 2 | 0.06 | 8 | 16 | 32 | 1 |
| Levofloxacin | 0.12 | 8 | 32 | 64 | 1 |
| Polymyxin B | 0.5 | 0.5 | 0.5 | 1 | 1 |

TABLE 16

FICI data of combinations of Compound 33, 35 and 2 with polymyxin B

| Isolate | Antibiotic in combination with polymyxin B | Combination drug concentration in combination (mg/L) | Combination drug MIC alone (mg/L) | FICx | Polymyxin B MIC in combination (mg/L) | Polymyxin B MIC alone (mg/L) | FICy | FICI | Synergy |
|---|---|---|---|---|---|---|---|---|---|
| GN31 | Compound 35 | 0.004 | 0.03 | 0.13 | 0.12 | 0.25 | 0.48 | 0.61 | Partial synergy |
| | Compound 2 | 0.015 | 0.06 | 0.25 | 0.06 | 0.25 | 0.24 | 0.49 | Synergy |
| | Levofloxacin | 0.008 | 0.06 | 0.13 | 0.5 | 0.5 | 1.00 | 1.13 | Indifferent |
| GN52 | Compound 33 | 1 | 4 | 0.25 | 0.12 | 0.5 | 0.24 | 0.49 | Synergy |
| | Compound 35 | 0.5 | 2 | 0.25 | 0.12 | 0.5 | 0.24 | 0.49 | Synergy |
| | Compound 2 | 1 | 4 | 0.25 | 0.12 | 0.5 | 0.24 | 0.49 | Synergy |
| | Levofloxacin | 1 | 8 | 0.13 | 0.5 | 0.5 | 1.00 | 1.13 | Indifferent |

TABLE 16-continued

FICI data of combinations of Compound 33, 35 and 2 with polymyxin B

| Isolate | Antibiotic in combination with polymyxin B | Combination drug concentration in combination (mg/L) | Combination drug MIC alone (mg/L) | FICx | Polymyxin B MIC in combination (mg/L) | Polymyxin B MIC alone (mg/L) | FICy | FICI | Synergy |
|---|---|---|---|---|---|---|---|---|---|
| GN56 | Compound 33 | 2 | 32 | 0.06 | 0.12 | 0.5 | 0.24 | 0.30 | Synergy |
| | Compound 35 | 0.5 | 8 | 0.06 | 0.25 | 0.5 | 0.50 | 0.56 | Partial synergy |
| | Compound 2 | 1 | 16 | 0.06 | 0.25 | 0.5 | 0.50 | 0.56 | Partial synergy |
| | Levofloxacin | 4 | 32 | 0.13 | 0.5 | 0.5 | 1.00 | 1.13 | Indifferent |
| GN48 | Compound 35 | 1 | 16 | 0.06 | 0.25 | 0.5 | 0.50 | 0.56 | Partial synergy |
| | Compound 2 | 4 | 32 | 0.13 | 0.25 | 0.5 | 0.50 | 0.63 | Partial synergy |
| | Levofloxacin | 8 | 64 | 0.13 | 0.5 | 0.5 | 1.00 | 1.13 | Indifferent |

GN31-*Acinetobacter baumannii*—antibiotic susceptible isolate
GN52-*Acinetobacter baumannii*—levofloxacin resistant clinical isolate
GN56-*Acinetobacter baumannii*—levofloxacin resistant clinical isolate
GN48-*Klebsiella pneumoniae*—NCTC 13443-NDM-1-β-lactamase producing isolate Example 7

Cytotoxicity

Cytotoxicity was determined for the instant 4-oxoquinolizine compounds which show low cytotoxicity. (see Table 17 following). Thus, while the instant 4-oxoquinolizine compounds possess potent activity against both Gram-positive and Gram-negative resistant strains, including nosocomial strains as well as CDC pathogens, they have good drug profiles regarding safety and efficacy.

TABLE 17 showing cytotoxicity values for the instant 4-oxoquinolizines

| Compounds | Structures | Cytotoxicity $IC_{50}$ (μM) |
|---|---|---|
| 1 | | 500 |
| 2 | | 250 |
| 3 | 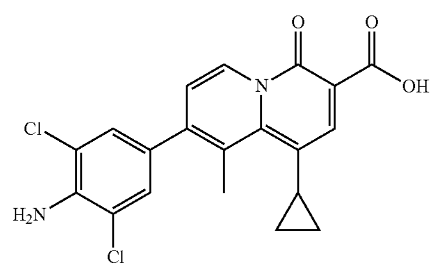 [SMILES: Cc1c(-c2cc(Cl)c(N)c(Cl)c2)ccn2c(=O)c(C(=O)O)cc(C3CC3)c12] | 50 |
| 4 | 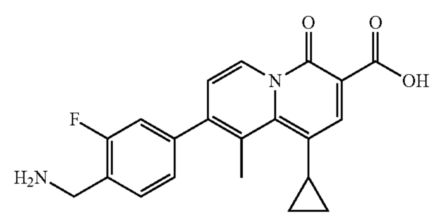 [SMILES: Cc1c(-c2ccc(CN)c(F)c2)ccn2c(=O)c(C(=O)O)cc(C3CC3)c12] | 60 |
| 7 | 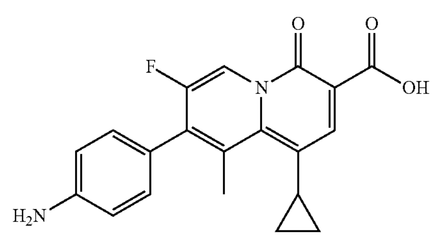 [SMILES: Cc1c(-c2ccc(N)cc2)c(F)cn2c(=O)c(C(=O)O)cc(C3CC3)c12] | 150 |
| 8 | 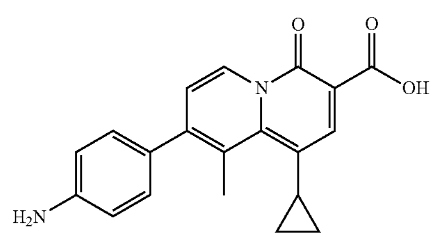 [SMILES: Cc1c(-c2ccc(N)cc2)ccn2c(=O)c(C(=O)O)cc(C3CC3)c12] | 90 |

Example 8: Preparation of 2-Pyridones Compounds

Analytical Methods

NMR spectra were recorded on a Bruker Avance-400 NMR or Bruker Avance-300 NMR or with samples in solution in deuterated chloroform (CDCl$_3$), deuterated MeOH (CD$_3$OD) or deuterated dimethyl sulfoxide (DMSO-d6). Chemical shifts and coupling constants are respectively expressed in part per million (ppm) and in Hertz (Hz). Mass spectrometry (MS) analyses were performed on an Agilent MSD G1946D or a Waters TQD with electrospray ionization (ESI). High resolution mass spectrometry (High-Res MS) analyses were recorded on a Shimadzu IT-TOF apparatus. HPLC analyses were performed on columns Waters XBridge (C18, 30×2.1 mm, 3.5 micron) at a column temperature of 35° C. with a flow rate of 1 mL/min of a mixture of eluent A (0.1% Formic acid in ACN) and eluent B (0.1% Formic acid in water); 3 methods of elution were used, method 1, method 2 and method 3 as described below.

HPLC Method 1

Lin. Gradient: t=0 min 2% A, t=1.6 min 98% A, t=3 min 98% A

Detection: DAD (220-320 nm)

Detection: MSD (ESI pos/neg) mass range: 100-800

Detection: ELSD (PL-ELS 2100) gas flow 1.1 mL/min; gas temp: 50° C.

HPLC Method 2

Lin. Gradient: t=0 min 2% A, t=3.5 min 98% A, t=6 min 98% A

Detection: DAD (220-320 nm)

Detection: MSD (ESI pos/neg) mass range: 100-800

Detection: ELSD (PL-ELS 2100) gas flow 1.1 mL/min; gas temp: 50° C.

HPLC Method 3

Lin. Gradient: t=0 min 2% A, t=10 min 98% A, t=14 min 98% A

Detection: DAD (220-320 nm)

Detection: MSD (ESI pos/neg) mass range: 100-800

Detection: ELSD (PL-ELS 2100) gas flow 1.1 mL/min; gas temp: 50° C.

The following acronyms and abbreviations are used:

| | |
|---|---|
| ACN | Acetonitrile |
| BOC | t-butoxycarbonyl |
| DCM | Dichloromethane |
| DMF | N,N-dimethylformamide |
| DMSO | Dimethylsulfoxide |
| ESI-MS | electrospray ionization mass spectrometry |
| HPLC | High-performance liquid chromatography |
| LCMS | Liquid chromatography-mass spectrometry |
| MeOH | methanol |
| nBuLi | n-butyl lithium |
| NMR | Nuclear magnetic resonance |
| TFA | Trifluoroacetic acid |
| THF | Tetrahydrofuran |

The 2-pyridones compounds were obtained in 2 steps from a suitable scaffold. Most of the compounds were prepared via a Palladium coupling between the ester-protected scaffold and a boronate reagent followed by hydrolysis of the ester moiety. Depending of the boronate reagents additional deprotection steps could be required. Some compounds were also made by substituting the scaffolds with an amine instead of a palladium coupling with a boronate hence forming an N—C bond instead of a C—C bond.

Scheme 1: Preparation of 2-pyridones from scaffolds in 2 or 3 steps.

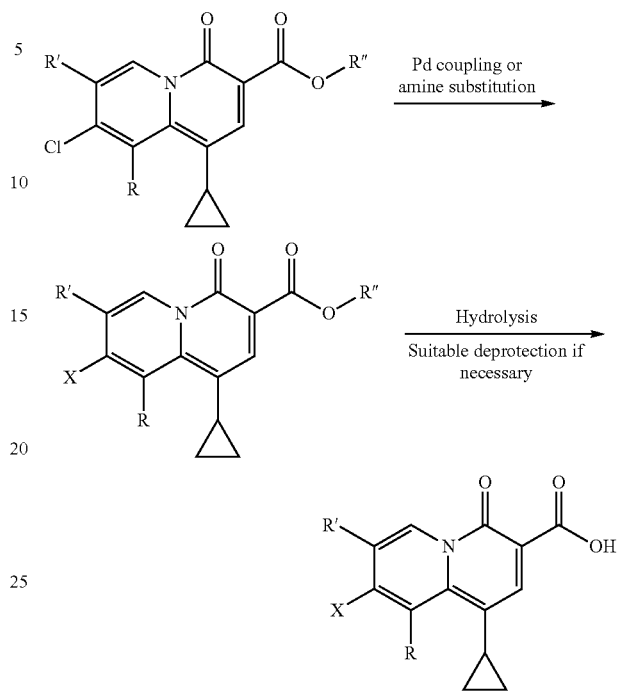

FIG. 4 shows the structure of 5 scaffolds.

Preparation of Scaffolds:

Scaffolds ethyl 8-chloro-1-cyclopropyl-9-methyl-4-oxo-quinolizine-3-carboxylate (Scaffold A), methyl 8-chloro-1-cyclopropyl-9-methyl-4-oxo-quinolizine-3-carboxylate (Scaffold B) and methyl 8-chloro-1-cyclopropyl-9-methoxy-4-oxo-quinolizine-3-carboxylate (Scaffold E) were prepared synthetically. Scaffolds ethyl 8-chloro-1-cyclopropyl-7,9-dimethyl-4-oxo-quinolizine-3-carboxylate (Scaffold D) was obtained as a side product of the synthesis of scaffold B. Scaffold methyl 8-chloro-1-cyclopropyl-7-fluoro-9-methyl-4-oxo-quinolizine-3-carboxylate (Scaffold C) was purchased from Beijing Louston Fine Chemical Co. Ltd., China.

Scaffolds A, B and E were prepared in 6-7 steps from commercial 2-bromo-3-methyl-4-chloro-pyridine.

Scheme 2: Synthesis of scaffolds A, B and E.

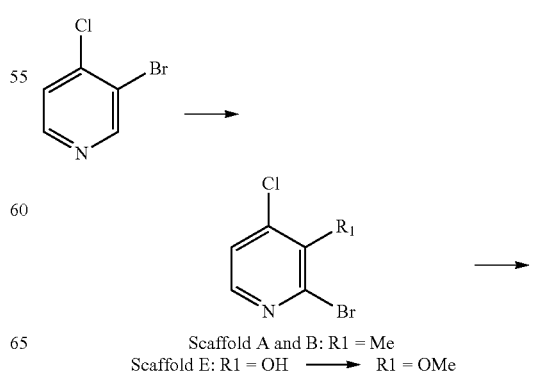

Scaffold A and B: R1 = Me
Scaffold E: R1 = OH ⟶ R1 = OMe

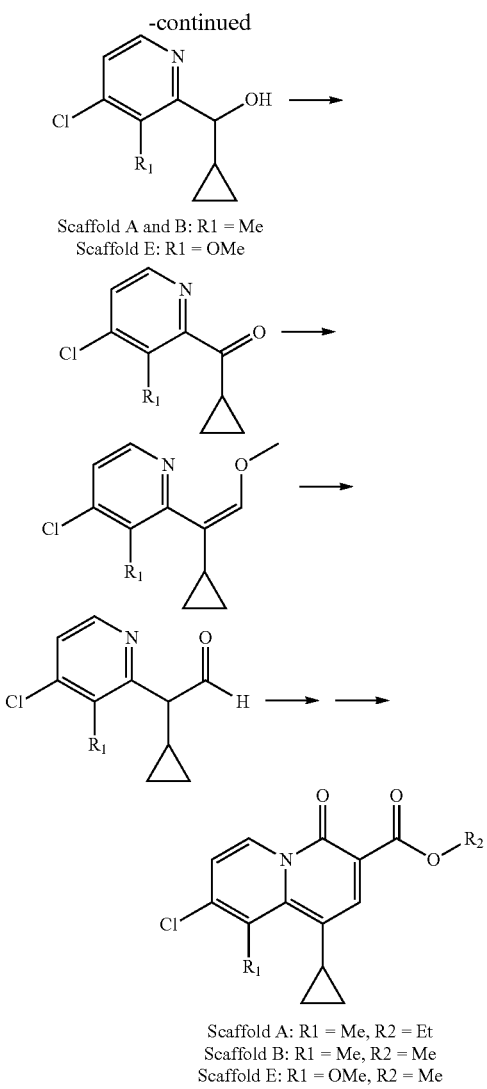

Scaffold A and B: R1 = Me
Scaffold E: R1 = OMe

Scaffold A: R1 = Me, R2 = Et
Scaffold B: R1 = Me, R2 = Me
Scaffold E: R1 = OMe, R2 = Me Preparation of scaffold A: ethyl 8-chloro-1-cyclopropyl-9-methyl-4-oxo-quinolizine-3-carboxylate Preparation of 2-bromo-3-methyl-4-chloro-pyridine To a solution of 2,2,6,6-tetramethyl-pyridine (21.1 mL, 125 mmol) in freshly distilled THF (120 mL) at −78° C. was added nBuLi (50 mL, 125 mmol) in 30 min. The resulting mixture was stirred at −78° C. for 30 min and was added through a cannula over 30 min to a solution of 3-bromo-4-chloro-pyridine (20.0 g, 104 mmol) in freshly distilled THF (60 mL) that had been cooled to −78° C. prior to the addition. The reaction mixture was stirred at −78° C. for 30 min before iodomethane (7.78 mL, 125 mmol) was added over a period of 10 min. The reaction was stirred at −78° C. for 30 min and was allowed to warm up to room temperature prior to be quenched with aqueous $NH_4Cl$ (65 mL). The aqueous phase was extracted with ethyl acetate (2×150 mL). The organic phases were separated, dried, and concentrated. The residue was purified by flash silica column chromatography (hexane:ethyl acetate, 5:1) to afford the title compound as a yellow solid (10.6 g, 49%).

$^1H$ NMR ($CDCl_3$, 300 MHz) δ ppm: 8.10 (d, J=5.1 Hz, 1H), 7.27 (d, J=5.1 Hz, 1H), 2.51 (s, 3H).

Preparation of (3-methyl-4-chloro-pyridin-2-yl)-cyclopropyl-methanol

A solution of 2-bromo-3-methyl-4-chloro-pyridine (10.6 g, 57.1 mmol) in freshly distilled THF (120 mL) was cooled down to 0° C. and treated with isopropyl magnesium chloride (45.7 mL, 2.0 M in THF, 91.5 mmol). The resulting mixture was stirred at room temperature for 3 h then cooled to −5° C. Cyclopropane carboxaldehyde (6.83 mL, 91.5 mmol) was added. The reaction mixture was stirred at room temperature for 1 h and quenched by adding water (100 mL), and extracted with ethyl acetate (2×150 mL). The organic phase was separated, dried, and concentrated. The residue was purified by flash silica column chromatography (hexane:ethyl acetate, 3:1) to afford the title compound as a yellow oil (7.01 g, 62%).

ESI-MS m/z: 198 $(M+H)^+$; $^1H$ NMR ($CDCl_3$, 300 MHz) δ ppm: 8.28 (d, J=5.4 Hz, 1H), 7.26 (d, J=5.4 Hz, 1H), 4.79 (d, J=5.4 Hz, 1H), 4.55 (br s, 1H), 2.39 (s, 3H), 1.10-1.28 (m, 1H), 0.41-0.58 (m, 4H).

Preparation of (3-methyl-4-chloro-pyridin-2-yl)-cyclopropyl-methanone

A solution of (3-methyl-4-chloro-pyridin-2-yl)-cyclopropyl-methanol (7.01 g, 35.5 mmol) in DCM (80 mL) was treated with $MnO_2$ (30.8 g, 355 mmol) at room temperature overnight.

The reaction mixture was filtered through a pad of Celite and the filtrate was concentrated to dryness, affording the title compound (6.82 g, 98%).

ESI-MS m/z: 196 $(M+H)^+$; $^1H$ NMR ($CDCl_3$, 300 MHz) δ ppm: 8.41 (d, J=5.4 Hz, 1H), 7.42 (d, J=5.4 Hz, 1H), 2.96-3.04 (m, 1H), 2.57 (s, 3H), 1.20-1.28 (m, 2H), 1.09-1.14 (m, 2H).

Preparation of 2-(1-cyclopropyl-2-methoxy-vinyl)-3-methyl-4-chloro-pyridine

A solution of methoxymethyl triphenylphosphonium chloride (17.9 g, 52.3 mmol) in dry THF (80 mL) was treated with NaH (2.79 g, 69.8 mmol) at 0° C. for 3 h. To this mixture was added a solution of (3-methyl-4-chloro-pyridin-2-yl)-cyclopropyl-methanone (6.82 g, 34.9 mmol) in dry THF (20 mL). The reaction mixture was heated at 40° C. overnight. The reaction mixture was cooled down to room temperature and filtered. The filtrate was concentrated to dryness. The residue was purified by flash silica column chromatography (hexane:ethyl acetate, 3:1) to afford the title compound (6.41 g, 82%).

ESI-MS m/z: 224 $(M+H)^+$; $^1H$ NMR ($CDCl_3$, 300 MHz) δ ppm: 8.31 (d, J=5.4 Hz, 0.5H), 8.23 (d, J=5.4 Hz, 0.5H), 7.17 (d, J=5.4 Hz, 1H), 6.13-6.16 (m, 1H), 3.70 (s, 1.5H), 3.56 (s, 1.5H), 2.38 (s, 1.5H), 2.31 (s, 1.5H), 1.91-1.94 (m, 0.5H), 1.63-1.65 (m, 0.5H), 0.66-0.72 (m, 1H), 0.56-0.62 (m, 1H), 0.35-0.38 (m, 1H), 0.26-0.33 (m, 1H).

Preparation of 2-(3-methyl-4-chloro-pyridin-2-yl)-2-cyclopropyl-acetaldehyde

A solution of 2-(1-cyclopropyl-2-methoxy-vinyl)-3-methyl-4-chloro-pyridine (6.41 g, 28.7 mmol) in acetic acid (50 mL) was treated with sulfuric acid (6.52 mL, 143 mmol) at room temperature overnight. The reaction mixture was neutralized with 2N NaOH to pH 8-9 extracted with ethyl acetate (2×100 mL). The organic phases were combined, dried, and concentrated. The residue was purified by flash silica column chromatography (hexane/ethyl acetate=2:1) to afford the title compound as a yellow solid (4.83 g, 80%).

ESI-MS m/z: 210 (M+H)+; 1H NMR (CDCl3, 300 MHz) δ ppm: 9.89 (d, J=2.4 Hz, 1H), 8.35 (d, J=5.1 Hz, 1H), 7.26 (d, J=5.4 Hz, 1H), 3.26-3.28 (m, 1H), 2.35 (s, 3H), 1.53-1.59 (m, 1H), 0.55-0.79 (m, 2H), 0.25-0.39 (m, 2H).

Preparation of 2-[2-(3-methyl-4-chloro-pyridin-2-yl)-2-cyclopropyl-ethylidene]-malonic acid diethyl ester A mixture of (3-methyl-4-chloro-pyridin-2-yl)-cyclopropyl-acetaldehyde (4.83 g, 23.0 mmol), diethyl malonate (7.02 g, 43.8 mmol), piperidine (3.62 mL, 36.6 mmol), and acetic acid (4.19 mL, 73.2 mmol) in ethanol (100 mL) was heated to reflux overnight. The reaction mixture was concentrated to dryness. The residue was purified by flash silica column chromatography (hexane:ethyl acetate, 4:1) to afford the title compound as a yellow oil (5.76 g, 71%).

ESI-MS m/z: 352 (M+H)+.

Preparation of ethyl 8-chloro-1-cyclopropyl-9-methyl-4-oxo-4H-quinolizine-3-carboxylate A solution of 2-[2-(3-methyl-4-chloro-pyridin-2-yl)-2-cyclopropyl-ethylidene]-malonic acid diethyl ester (5.76 g, 16.4 mmol) in Dowtherm A (80 mL) was heated in a preheated oil bath at 230° C. for 15 min. The reaction mixture was cooled to room temperature and purified by flash silica column chromatography (hexane:ethyl acetate, 2:1 to 1:2) to afford the title compound as a yellow solid (3.76 g, 75%).

ESI-MS m/z: 306 (M+H)+; 1H NMR (CDCl3, 300 MHz) δ ppm: 9.34 (d, J=7.8 Hz, 1H), 8.40 (s, 1H), 7.12 (d, J=7.8 Hz, 1H), 4.41 (q, 2H), 3.00 (s, 3H), 2.28-2.33 (m, 1H), 1.42 (t, 3H), 1.03-1.08 (m, 2H), 0.71-0.76 (m, 2H).

Preparation of scaffold B: methyl 8-chloro-1-cyclopropyl-9-methyl-4-oxo-quinolizine-3-carboxylate Preparation of 2-bromo-4-chloro-3-methyl-pyridine In a 250 mL 3-neck flask, 2,2,6,6-tetramethyl-pyridine (10.5 mL, 61.7 mmol) was added to dry THF (100 mL) under inert atmosphere and the resulting yellow solution was cooled down to −78° C. N-Butyl lithium 2.5 M solution in hexane (25 mL, 62.5 mmol) was added over 0.5 h and the reaction mixture was stirred at −78° C. for 0.5 h. The solution had turned from yellow to orange.

In a 500 mL 3-neck flask, 3-bromo-4-chloro-pyridine (9.6 g, 49.9 mmol) was added to dry THF (50 mL) under inert atmosphere. This reaction mixture was cooled down to −78 OC. The orange solution previously obtained was added via cannula over 0.75 h and stirred at −78° C. for 0.5 h. The solution/suspension turned black. Iodomethane (3.9 mL, 62.6 mmol) was added over 0.5 h and the reaction mixture was stirred at −78° C. for 0.5 h. The reaction mixture was left to warm to room temperature and was quenched by addition of an aqueous saturated ammonium chloride solution (65 mL). The reaction mixture was diluted with water (100 mL), ethanol (100 mL) and ethyl acetate (100 mL). The mixture was extracted with ethyl acetate (2×100 mL). The organic layers were combined and washed with 50% brine (1:1 water/brine, 100 mL total) and brine (100 mL). Combined water layers were extracted with ethyl acetate (100 mL). The combined organic layers were dried over sodium sulfate, filtered and evaporated to dryness to yield a brown oil.

The crude oil was dissolved again in ethyl acetate (50 mL), and ammonium salts precipitated and were filtered off. The filtrate was evaporated to dryness to yield a brown oily solid. A third of the obtained crude product was distilled with a Kigelrohr apparatus at 100° C. under a 0.1 mbar reduced pressure. The distillate crystallized out on cooling yielding the intended compound (1.68 g, 12.4%). The remaining crude product was purified by flash chromatography using a gradient of 10-75% ethyl acetate in heptane affording a second batch of the compound (3.53 g, 24.3). The combined batches yielded the intended product (5.21 g, 36.7%).

1H NMR (400 MHz, CDCl3) δ ppm 8.11 (d, J=5.2 Hz, 1H), 7.27 (d, J=6 Hz, 1H), 2.52 (s, 3H).

Preparation of (4-chloro-3-methyl-2-pyridyl)-cyclopropyl-methanol

A solution of 2-bromo-4-chloro-3-methylpyridine (7 g, 28.1 mmol) in dry THF (150 mL) was cooled down to 0° C. An isopropyl magnesium chloride—Lithium chloride complex (26 mL, 33.8 mmol) was added carefully so temperature would not rise above 5° C. during the addition. The mixture was allowed to warm up to room temperature and was stirred for 1 h. The reaction mixture was cooled down to 0° C. and cyclopropane carboxaldehyde (2.5 mL, 33.5 mmol) was added carefully so temperature would not rise above 5° C. during the addition. The mixture was allowed to warm up to room temperature and was stirred for 1 h. The reaction mixture was cooled to 0° C. and water (150 mL) was added carefully so temperature would not rise above 10° C. during the addition. The mixture was allowed to warm up to room temperature and was stirred for 1 h. The mixture was extracted with ethyl acetate (3×100 mL). The combined organic phases were washed with brine (100 mL), dried over sodium sulfate and evaporated. The residue was purified by flash chromatography over silica gel (0-30% ethyl acetate in heptane) yielding a yellow oil (3.47 g, 16.8%).

LC-MS: t=1.33 min (method 1); 198 (M+H)+; 1H NMR (400 MHz, CDCl3) δ ppm 8.28 (d, J=5.2 Hz, 1H), 7.25 (d, J=5.6 Hz, 1H), 4.80 (dd, J=7.8 and 5.3 Hz, 1H), 4.51 (d, J=5.6 Hz, 1H), 2.38 (s, 3H), 1.05-1.15 (m, 1H), 0.52-0.58 (m, 1H), 0.44-0.50 (m, 1H), 0.35-0.42 (m, 1H).

Preparation of (4-chloro-3-methyl-2-pyridyl)-cyclopropyl-methanone

Manganese dioxide (1126 mg, 12.95 mmol) was added to a solution of (4-chloro-3-methylpyridin-2-yl)-cyclopropyl-methanol (250 mg, 1.214 mmol) in DCM (10 mL). The reaction mixture was stirred at room temperature for 45 h. The mixture was filtered over a porosity 4 filter. The filtrate was concentrated to dryness to yield white crystals (245 mg, 98%).

LC-MS: t=1.92 min (method 1); 196 (M+H)+; 1H NMR (400 MHz, CDCl3) δ ppm 8.41 (d, J=5 Hz, 1H), 7.44 (d, J=5.3 Hz, 1H), 5.30 (s, 1H), 2.98-3.05 (1H, m), 2.52 (s, 3H), 1.24-1.29 (m, 2H), 1.08-1.14 (m, 2H).

Preparation of 4-chloro-2-[1-cyclopropyl-2-methoxy-vinyl]-3-methyl-pyridine

A yellow suspension of (4-chloro-3-methylpyridin-2-yl)(cyclopropyl) methanone (2.99 g, 15.28 mmol), (Methoxymethyl) triphenylphosphonium chloride (7.84 g, 22.87 mmol) and Potassium tert-butoxide (3.41 g, 30.4 mmol) in toluene (50 mL) was heated to 60° C. and stirred for 3.5 h. The reaction mixture was cooled down to room temperature and an aqueous solution of 4M Hydrochloric acid (50 mL) was added. The reaction mixture was washed with toluene (3×50 mL). The aqueous layer was diluted in ice, and solid sodium bicarbonate was added until pH reaches 7-8. The mixture was extracted with ethyl acetate (3×100 mL). The combined organic layers were washed with brine, dried over sodium sulfate, filtrated and evaporated to dryness. The oily residue was purified by flash column chromatography over silica gel using a gradient of ethyl acetate in heptane to yield a 1 to 1 mixture of the isomeric vinyl ethers as yellow oil (2.93 g, 82%).

LC-MS: t=1.68 min and 1.73 min (E and Z isomers) (method 1); 224 (M+H)$^+$.

Preparation of 2-(4-chloro-3-methyl-2-pyridyl)-2-cyclopropyl-acetaldehyde

To a solution of 4-chloro-2-(1-cyclopropyl-2-methoxyvinyl)-3-methylpyridine (1.7 g, 7.60 mmol) in THF (15 mL) a 2M aqueous solution of sulfuric acid (15.20 mL, 30.4 mmol) was added and the reaction mixture was stirred at 50° C. for a total of 2.5 h. The resulting mixture was poured into water and neutralized with a saturated sodium bicarbonate solution, and thereafter, extracted with chloroform (3×20 mL). The resulting organic layers were washed with saturated salt water (20 mL), dried over sodium sulfate and concentrated under reduced pressure. The resulting yellow solid was purified by silica gel column chromatography (hexane:ethyl acetate) (4:1) to obtain the aldehyde (1.08 g, 67.8%).

LC-MS: t=1.55 min (method 1); 210 (M+H)$^+$; 228 (M+H$_2$O+H)$^+$.

Preparation of methyl 8-chloro-1-cyclopropyl-9-methyl-4-oxo-quinolizine-3-carboxylate Piperidine (7 mL, 70.9 mmol) and acetic acid (5.5 mL, 95 mmol) were added to a solution of 2-(4-chloro-3-methyl-pyridin-2-yl)-2-cyclopropylacetaldehyde (4.98 g, 23.75 mmol) in absolute ethanol (200 mL). Dimethyl malonate (16.44 mL, 144 mmol) was added and the reaction mixture was stirred at 100° C. for 5 h (the reaction mixture turned into a red solution). The solvent was evaporated under reduced pressure. The resulting mixture was diluted with ether (100 mL) and washed with water (100 mL) and brine (50 mL). The organic layer was separated and dried over sodium sulfate. The mixture was evaporated to dryness. Dowtherm A (110 mL) was added. This reaction mixture was heated to 240° C. under microwave irradiation and stirred at this temperature for 0.5 h during which the reaction mixture turned into a black solution. The residue was purified by reversed phase flash chromatography using a 5%-100% ACN gradient in water with 1% TFA yielding the cyclized methyl ester (4 g, 51.4%).

LC-MS: t=1.88 min (method 1); 292 (M+H)$^+$.

Preparation of scaffold D: methyl 8-chloro-1-cyclopropyl-7,9-dimethyl-4-oxo-quinolizine-3-carboxylate During the first scale up preparation of methyl 8-chloro-1-cyclopropyl-9-methyl-4-oxo-quinolizine-3-carboxylate a side product was observed in the first step. Other scale-up preparations of the scaffold were optimized to avoid the side product. The side product was carried over till the last step. Reversed phase purification (40-80% ACN in 0.1% formic acid in water over $C_{18}$-silica) afforded methyl 8-chloro-1-cyclopropyl-7,9-dimethyl-4-oxo-4H-quinolizine-3-carboxylate as a yellow solid (0.4 g).

ESI-MS m/z: 306 (M+H)$^+$; 1H NMR (400 MHz DMSO-d6) δ ppm 9.33 (s, 1H), 8.36 (s, 1H), 3.93 (s, 3H), 3.04 (s, 3H), 2.48 (s, 3H), 2.27-2.37 (m, 1H), 1.01-1.09 (m, 2H), 0.70-0.77 (m, 2H); 13C NMR (100 MHz CDCl$_3$) δ ppm 166.7, 155.2, 147.1, 145.1, 144.0, 130.9, 127.5, 125.7, 115.7, 104.6, 52.1, 20.0, 18.5, 17.0, 9.76 (2 C).

Preparation of scaffold E: methyl 8-chloro-1-cyclopropyl-9-methoxy-4-oxo-quinolizine-3-carboxylate Preparation of 2-bromo-4-chloropyridin-3-ol A solution of 2.5 M n-BuLi in hexanes (180 mL, 450 mmol) was added dropwise to a solution of 2,2,6,6-Tetramethylpiperidine (75 mL, 441 mmol) in THF (800 mL) at −70° C. under inert atmosphere. The reaction mixture was agitated for 2 h and transferred to a solution of 3-bromo-4-chloropyridine (80.5 g, 418 mmol) in THF (500 mL) at −70° C. under inert atmosphere and stirred for 2 h. Trimethyl borate (100 mL, 881 mmol) was added dropwise and reacted for 2 h. 33% Peracetic acid in acetic acid (150 mL, 780 mmol) was added dropwise, the mixture was warmed to room temperature and stirred for 14 h. The mixture was cooled to 0° C. and sodium metabisulfite (200 g, 1.05 mol) in water (400 mL) was added over 2 h. Water (300 mL) and ethyl acetate (200 mL) were added. The layers were separated and the aqueous layer washed with ethyl acetate (3×1000 mL). The organic phase was dried over sodium sulfate, filtered and evaporated to dryness to obtain crude product which was purified over silica gel, using 0:1 to 3:2 ethyl acetate in heptane) to obtain 2-bromo-4-chloropyridin-3-ol as a white solid (46.3 g, 50%).

ESI-MS m/z: 210 (M+H)$^+$.

Preparation of 2-bromo-4-chloro-3-methoxy-pyridine 2-bromo-4-chloropyridin-3-ol (8.15 g, 39.1 mmol), potassium carbonate (10.5 g, 76 mmol) and iodomethane (3.65 ml, 58.6 mmol) were added to acetone (300 ml) and stirred for 18 h at room temperature under inert conditions. The reaction mixture was evaporated to dryness, dissolved in ethyl acetate (100 mL), filtered over silica gel and the filter washed with ethyl acetate (3×100 mL). The filtrate was evaporated to dryness to obtain crude product which was purified over silica gel using 0:1 to 1:0 ethyl acetate in heptane to obtain 2-bromo-4-chloro-3-methoxypyridine as a white crystalline solid (6.8 g, 78%).

ESI-MS m/z: 224 (M+H)$^+$; 1H NMR (400 MHz, CDCl$_3$) δ ppm 8.06 (d, J=3.6 Hz, 1H), 7.31 (d, J=5.0 Hz, 1H), 3.95 (s, 1H).

Preparation of (4-chloro-3-methoxy-2-pyridyl)-cyclopropyl-methanol 2-bromo-4-chloro-3-methoxy-pyridine (2.97 g, 13.4 mmol) was added to THF (dry) (100 ml) and cooled to 0° C. Isopropylmagnesium chloride—lithium chloride complex (13.5 ml, 17.6 mmol) was added and the reaction mixture stirred for 0.5 h at room temperature. The mixture was cooled to 0° C., cyclopropanecarboxaldehyde (1.297 ml, 17.4 mmol) was added and the reaction mixture stirred for 1 h at room temperature. The mixture was cooled to 0° C., water (72.3 ml, 4 mol) was added and the reaction mixture stirred overnight at room temperature. The reaction mixture was extracted with ethyl acetate (3×75 mL), the organic phase dried over sodium sulfate, filtered and evaporated to dryness to obtain crude product which was purified over silica gel using 0:1 to 1:0 ethyl acetate in heptane to obtain (4-chloro-3-methoxy-2-pyridyl)-cyclopropyl-methanol as a yellow oil (2.4 g, 70%)

ESI-MS m/z: 214 (M+H)$^+$; 1H NMR (400 MHz, CDCl$_3$) δ ppm 8.23 (d, J=5.0 Hz, 1H), 7.29 (d, J=5.0 Hz, 1H), 4.63 (t, J=7.8 Hz, 1H), 4.00 (d, J=8.1 Hz, 1H), 3.93 (s, 3H), 1.15-1.22 (m, 1H), 0.57-0.63 (m, 1H), 0.42-0.50 (m, 3H).

Preparation of (4-chloro-3-methoxy-2-pyridyl)-cyclopropyl-methanone

To a solution of (4-chloro-3-methoxy-2-pyridyl)-cyclopropyl-methanol (700 mg, 3.28 mmol) in DCM (20 ml), manganese (IV) oxide (4.6 g, 58 mmol) was added and stirred for 14 h at room temperature. The reaction mixture was filtered over Celite and the filtrate evaporated to dryness to obtain (4-chloro-3-methoxy-2-pyridyl)-cyclopropyl-methanone as a yellow oil (668 mg, 96%).

ESI-MS m/z: 212 (M+H)$^+$; 1H NMR (400 MHz, CDCl$_3$) δ ppm 8.35 (d, J=5.0 Hz, 1H), 7.49 (d, J=5.0 Hz, 1H), 3.95 (s, 3H), 2.96-2.89 (m, 1H), 1.28-1.33 (m, 2H), 1.08-1.16 (m, 2H).

Preparation of 4-chloro-2-(1-cyclopropyl-2-methoxyvinyl)-3-methoxypyridine (Methoxymethyl)triphenylphosphonium chloride (1.6 g, 4.7 mmol) was dissolved in THF (20 ml) and cooled to –30° C. 2.5 Molar n-BuLi in hexanes (1.89 ml, 4.7 mmol) was and the mixture stirred for 1 h. (4-chloro-3-methoxypyridin-2-yl)-(cyclopropyl)methanone (500 mg, 2.4 mmol) dissolved in THF (5 ml) was added slowly and stirred for 4 h. The reaction mixture was quenched with saturated ammonium chloride (20 mL) and stirred overnight. 25 mL ethyl acetate was added and the layers partitioned. The organic phase was dried over sodium sulfate, filtered and evaporated to dryness to obtain crude product which was purified over silica gel using 0:1 to 3:7 ethyl acetate in heptane to obtain 4-chloro-2-(1-cyclopropyl-2-methoxyvinyl)-3-methoxy-pyridine as a clear oil (361 mg, 63%).

ESI-MS m/z: 240 (M+H)$^+$; 1H NMR (400 MHz, CDCl$_3$) δ ppm 8.16 (d, J=5.3 Hz, 1H), 7.17 (d, J=5.0 Hz, 1H), 6.57 (s, 1H), 3.82 (s, 3H), 3.76 (s, 3H), 1.83-1.92 (m, 1H), 0.70-0.77 (m, 2H), 0.44-0.51 (m, 2H).

Preparation of 2-(4-chloro-3-methoxypyridin-2-yl)-2-cyclopropyl-acetaldehyde 4-chloro-2-(1-cyclopropyl-2-methoxyvinyl)-3-methoxypyridine (259 mg, 1.1 mmol) was dissolved in THF (10 ml) and cooled to 0° C. 4M sulfuric acid (2.7 ml, 10 mmol) was added and the reaction was performed at reduced pressure while heating at 50° C. for 2.5 h. The mixture was diluted in ice water (10 mL) and sodium bicarbonate added until neutralized. The mixture was washed with DCM (3×10 mL) and the organic phase dried, filtered and evaporated to dryness to obtain 2-(4-chloro-3-methoxy-pyridin-2-yl)-2-cyclopropyl-acetaldehyde as a yellow oil (233 mg) to be used without further purification.

ESI-MS m/z: 226 (M+H)$^+$.

Preparation of methyl 8-chloro-1-cyclopropyl-9-methoxy-4-oxo-4H-quinolizine-3-carboxylate 2-(4-chloro-3-methoxy-pyridin-2-yl)-2-cyclopropyl-acetaldehyde (4.13 g, 18.3 mmol) was dissolved (60 ml). Acetic acid (4.2 ml, 73 mmol), piperidine (3.6 ml, 37 mmol) and dimethyl malonate (12.5 ml, 110 mmol) were added and stirred at 100° C. for 5 h. The solvent was distilled off in vacuum, the resulting mixture diluted with diethyl ether (200 mL), washed with water (100 mL) and brine (100 mL). The organic phase was separated, dried over sodium sulfate, filtered and evaporated to dryness to obtain a red oil which was not purified. The mixture was dissolved in Dowtherm A (100 ml) and heated at 240° C. for 1 h. The reaction mixture was purified over silica gel, rinsing off the Dowtherm A with heptane. The product was purified using 0:1 to 1:0 ethyl acetate in heptane to obtain: methyl 8-chloro-1-cyclopropyl-9-methoxy-4-oxo-4H-quinolizine-3-carboxylate as an orange-yellow crystalline solid (2.83 g, 47%).

ESI-MS m/z: 308 (M+H)$^+$; 1H NMR (400 MHz, CDCl$_3$) δ ppm 9.27 (d, J=7.8 Hz, 1H), 8.28 (s, 1H), 7.13 (d, J=7.8 Hz, 1H), 3.98 (s, 3H), 3.94 (s, 3H), 2.47-2.56 (m, 1H), 0.97-1.04 (m, 2H), 0.73-0.78 (m, 2H).

Preparation of Compounds 1-17 from Scaffold B

The compounds were first prepared according to the following methods. The preparation of compounds 1, 2, 3, 4, 5, 6, and 17 is described below. The same methods were also used to prepare compounds 7-16. Chemical names and structures of the compounds are given in Table 1.

Preparation of Compound 2

Preparation of 2,5-difluoro-4-(4,4,5,5-tetramethyl-1,3,2-dioxaborolan-2-yl)aniline A 0.4 M solution of 4-Bromo-2,5-difluoroaniline (400 mg, 1.923 mmol) in dimethyl sulfoxide (4.8 mL) was added to sodium acetate (473 mg, 5.77 mmol) and bis-pinacolato diborane (537 mg, 2.115 mmol) in a flask under argon. The mixture was degassed with argon prior to the addition of bis-(triphenylphosphine) palladium(II) chloride (13.50 mg, 0.019 mmol).The reaction mixture was heated at 80° C. until complete consumption of starting material (16 h). After cooling the reaction mixture to room temperature ethyl acetate was added and the reaction mixture was partitioned between ethyl acetate and a saturated aqueous sodium bicarbonate solution. The organic layer was washed with brine (4 times) to remove the dimethyl sulfoxide. The material was dried with sodium sulfate and concentrated in vacuum. The crude product was purified by flash silica column chromatography (heptane/5% ethyl acetate) to give a white solid (220 mg, 44.9%).

$^1$H NMR (400 MHz, CDCl$_3$) δ ppm 7.26-7.30 (m, 1H), 6.38-6.43 (m, 1H), 4.02 (s, 2H), 1.33 (s, 12H).

Preparation of methyl 8-(4-amino-2,5-difluoro-phenyl)-1-cyclopropy-9-methyl-4-oxo-quinolizine-3-carboxylate The following Suzuki coupling method was used towards the preparation of compound 2 and is referred as the general Suzuki coupling method for the preparation of the other compounds.

General Suzuki Coupling Method:

Ethanol (96%) (129 µl), 2M aqueous sodium carbonate (175 µl, 0.350 mmol), 2,5-difluoro-4-(4,4,5,5-tetramethyl-1,3,2-dioxaborolan-2-yl)aniline (38.6 mg, 0.152 mmol) were added to a solution of methyl 8-chloro-1-cyclopropyl-9-methyl-4-oxo-4H-quinolizine-3-carboxylate (34 mg, 0.117 mmol) in toluene (250 µl). The mixture was degassed with argon. 1,1'-Bis-diphenylphosphine ferrocene palladium (II) dichloride (8.52 mg, 0.012 mmol) was added and the mixture was heated at 90° C. under an argon atmosphere for 4 h. The reaction mixture was cooled. The mixture was diluted with DCM (3 mL) and water was added (3 mL). The layers were separated using a phase separator and the aqueous layer was extracted with DCM (3×2 mL). The combined organic layers were concentrated in vacuum. Purification by with flash silica column chromatography using a gradient (heptane/ethyl acetate) (2:1 to 1:1) afforded a yellow solid (46 mg, 100%).

LC-MS: t=2.00 min (method 1); 385 (M+H)$^+$; 383 (M−H)$^-$.

Preparation of Compound 2 8-(4-amino-2,5-difluoro-phenyl)-1-cyclopropyl-9-methyl-4-oxo-quinolizine-3-carboxylic acid A solution of methyl 8-(4-amino-2,5-difluorophenyl)-1-cyclopropyl-9-methyl-4-oxo-4H-quinolizine-3-carboxylate (36 mg, 0.094 mmol) and sodium hydroxide 1N aqueous solution (0.5 mL, 0.5 mmol) in MeOH (2 mL) was stirred at 50° C. for 2 h. The reaction mixture was cooled down and the MeOH was removed in vacuum and the residue was taken-up in 5 mL water and then neutralized with 1N Hydrochloric acid (~0.5 mL). A precipitation was formed and the mixture was stirred at room temperature overnight. The yellow solid was collected by filtration and dried in a desiccator. The precipitate was triturated with toluene/isopropanol (1:1) (4 mL) and filtration afforded the product compound 2 (9 mg, 25.9%).

LC-MS: t=2.07 min (method 1); 371 (M+H)$^+$; 369 (M−H)$^-$; 1H NMR (400 MHz, CDCl$_3$) b ppm 9.45 (d, J=6 Hz, 1H), 8.43 (s, 1H), 7.05 (d, J=7.3 Hz, 1H), 7.05 (d, J=7.3 Hz. 1H), 6.97 (dd, J=11 and 6.3 Hz, 1H), 6.62 (dd, J=10.6 and 7.3 Hz, 1H), 5.30 (s, 2H), 2.30-2.40 (m, 1H), 2.05 (s, 3H), 1.00-1.10 (m, 2H), 0.75-0.82 (m, 2H).

Preparation of Compound 1

Preparation of Compound 1 8-(4-amino-3-fluoro-phenyl)-1-cyclopropyl-9-methyl-4-oxo-quinolizine-3-carboxylic acid The general Suzuki coupling method described above was used to couple methyl 8-chloro-1-cyclopropyl-9-methyl-4-oxo-4H-quinolizine-3-carboxylate with 3-fluoro-4-butyloxycarbonyl-aminophenyl boronic acid. Purification by flash silica column chromatography yielded methyl 8-[4-(tert-butoxycarbonylamino)-3-fluoro-phenyl]-1-cyclopropyl-9-methyl-4-oxo-quinolizine-3-carboxylate as a yellow solid. A solution of the obtained solid and TFA (0.2 mL) in DCM (1 mL) was stirred at room temperature for 2 h. The product was lyophilized and dissolved in a mixture of THF (0.5 mL). An aqueous 4N sodium hydroxide solution (0.33 mL) was added before being irradiated twice at 120° C. in a microwave oven for 10 min. The product was purified by preparative HPLC yielding compound 1 8-(4-amino-3-fluoro-phenyl)-1-cyclopropyl-9-methyl-4-oxo-quinolizine-3-carboxylic acid (19.2 mg, 16%).

LC-MS: t=8.30 min (method 3); 353 (M+H)$^+$; 351 (M−H)$^-$.

Preparation of Compound 3

Preparation of 3,5-dichloro-4-(4,4,5,5-tetramethyl-1,3,2-dioxaborolan-2-yl)-aniline A solution of 4-bromo-2,6-dichloroaniline (1 g, 4.15 mmol) in dimethyl sulfoxide (10 mL) (0.4 M) was added to sodium acetate (1.022 g, 12.45 mmol) and bis-pinacolato diborane (1.159 g, 4.57 mmol) in a flask under argon. The mixture was degassed with argon. 1,1'-Bis-diphenylphosphine ferrocene palladium(II) dichloride (0.328 g, 0.415 mmol) was added and the reaction mixture was heated at 80° C. for 16 h. After cooling to room temperature ethyl acetate (50 mL) was added and the reaction mixture was filtered and partitioned between ethyl acetate and a saturated aqueous sodium bicarbonate solution (50 mL). The organic layer was washed with brine (4×50 mL), dried sodium sulfate and concentrated in vacuum. The crude product was purified by flash silica column chromatography (heptane/5% ethyl acetate) to give a white solid (470 mg, 39.3%).

$^1$H NMR (400 MHz, CDCl$_3$) δ ppm 7.60 (s, 2H), 4.67 (s, 2H), 1.32 (s, 12H).

Preparation of methyl 8-(4-amino-3,5-dichloro-phenyl)-1-cyclopropyl-9-methyl-4-oxo-quinolizine-3-carboxylate The general Suzuki coupling method described above was used to couple methyl 8-chloro-1-cyclopropyl-9-methyl-4-oxo-4H-quinolizine-3-carboxylate with 3,5-dichloro-4-(4,4,5,5-tetramethyl-1,3,2-dioxaborolan-2-yl)aniline. Purification by flash silica column chromatography yielded methyl 8-(4-amino-3,5-dichloro-phenyl)-1-cyclopropyl-9-methyl-4-oxo-quinolizine-3-carboxylate as a yellow solid (41 mg, 78%).

LC-MS: t=2.14 min (method 1); 417 (M+H)$^+$ and isotopic 419 (M+H)$^+$.

Preparation of Compound 3 8-(4-amino-3,5-dichloro-phenyl)-1-cyclopropyl-9-methyl-4-oxo-quinolizine-3-carboxylic acid A solution of methyl 8-(4-amino-3,5-dichlorophenyl)-1-cyclopropyl-9-methyl-4-oxo-4H-quinolizine-3-carboxylate (29.2 mg, 0.052 mmol) and sodium hydroxide 1N aqueous solution (0.5 mL, 0.5 mmol) in MeOH (2 mL) was stirred at 50° C. for 2 h. The mixture was cooled and the MeOH was evaporated. The residue was taken-up in 5 mL water and neutralized with 1N hydrochloric acid ~0.5 mL. A yellow precipitation was formed and the precipitate was stirred at room temperature for 4 h. The yellow solid was collected by filtration and dried in a desiccator over potassium hydroxide. The crude product was purified with preparative HPLC and freeze-dried yielding compound 3 as a yellow solid (13 mg, 61.4%).

LC-MS: t=3.73 min (method 2); 403 (M+H)$^+$ and isotopic 405 (M+H)$^+$; 401 (M−H)$^-$ and isotopic 403 (M−H)$^-$.

Preparation of Compound 4

Preparation of tert-butyl N-[(4-bromo-2-fluoro-phenyl)methyl]-carbamate

Di-tert-butyl (4.01 g, 18.38 mmol) and triethylamine (2.56 mL, 18.38 mmol) were added to a solution of 4-bromo-2-fluorophenyl)-1-methylamine (2.5 g, 12.25 mmol) in DCM (50 mL) at 0° C. The mixture was allowed to warm up to room temperature and stirred for 2 h. Water was added (50 mL) and the layers were separated. The organic layer was washed with brine (3×50 mL), dried with sodium sulfate and concentrated in vacuum. The crude product was purified by flash silica column chromatography (heptane:ethyl) acetate (10:0 to 8:2) to yield a colorless oil (2.65 g, 71.1%).

$^1$H NMR (400 MHz, CDCl$_3$) δ ppm 7.20-7.30 (m, 3H), 4.90 (s, 1H), 4.30 (d, J=6 Hz, 2H), 1.44 (s, 9H).

Preparation of tert-butyl N-[[2-fluoro-4-(4,4,5,5-tetramethyl-1,3,2-dioxaborolan-2-yl)phenyl]methyl]carbamate A mixture of tert-butyl N-[(4-bromo-2-fluoro-phenyl)methyl]carbamate (1.3 g, 4.27 mmol), bis-pinacolato diborane (1.628 g, 6.41 mmol), and sodium acetate (1.052 g, 12.82 mmol) in dry dimethyl sulfoxide (4 mL) was degassed with argon. 1,1'-Bis-(diphenylphosphino)ferrocene palladium(II) dichloride (0.156 g, 0.214 mmol) was added and the mixture was heated at 90° C. for 3 h. After cooling down had taken place, the reaction mixture was partitioned between ethyl acetate (50 mL) and water (50 mL). The layers were separated and the organic layer was washed with water (50 mL), brine (50 mL), dried with sodium sulfate and concentrated to give a red/brown crude product. The material was purified by flash column chromatography (heptane:ethyl acetate) (10:0 to 8:2) affording a colorless oil (0.98 g, 65.3%).

$^1$H NMR (400 MHz, CDCl$_3$) δ ppm 5.53 (d, J=8 Hz, 1H), 5.44 (d, J=10 Hz, 1H), 5.53 (t, J=7.2 Hz, 1H), 4.90 (s 1H), 4.37 (d, J=5.8 Hz, 2H), 1.39 (s, 9H), 1.25 (s, 12H).

Preparation of methyl 8-[4-[(tert-butoxycarbonylamino)methyl]-3-fluoro-phenyl]-1-cyclopropyl-9-methyl-4-oxo-quinolizine-3-carboxylate The general Suzuki coupling method described above was used to couple methyl 8-chloro-1-cyclopropyl-9-methyl-4-oxo-4H-quinolizine-3-carboxylate with tert-butyl N-[[2-fluoro-4-(4,4,5,5-tetramethyl-1,3,2-dioxaborolan-2-yl)phenyl]methyl]carbamate. Purification by flash silica column chromatography yielded methyl 8-[4-[(tert-butoxycarbonylamino)methyl]-3-fluoro-phenyl]-1-cyclopropyl-9-methyl-4-oxo-quinolizine-3-carboxylate (24 mg, 31.7%).

LC-MS: t=2.22 min (method 1); 481 (M+H)$^+$.

Preparation of Compound 4

Preparation of 8-[4-[(tert-butoxycarbonylamino)methyl]-3-fluoro-phenyl]-1-cyclopropyl-9-methyl-4-oxo-quinolizine-3-carboxylic acid A solution of methyl 8-(4-((tert-butoxycarbonylamino)methyl)-3-fluorophenyl)-1-cyclopropyl-9-methyl-4-oxo-4H-quinolizine-3-carboxylate (24 mg, 0.050 mmol) and an aqueous 1N sodium hydroxide solution (0.500 mL, 0.500 mmol) in MeOH (2 mL) was stirred at 50° C. for 2 h. The reaction mixture was cooled. The MeOH was removed under reduced pressure, the residue was taken-up in water (5 mL) and then neutralized with a 1N hydrochloric acid solution (~0.5 mL). A precipitation was formed and the mixture was extracted with DCM (3×4 mL). The organic layer was concentrated to give the acid (20 mg, 86%).

LC-MS: t=2.17 min (method 1); 467 (M+H)$^+$; 465 (M−H)$^−$.

Preparation of Compound 4 8-[4-(aminomethyl)-3-fluoro-phenyl]-1-cyclopropyl-9-methyl-4-oxo-quinolizine-3-carboxylic acid A solution of 4M hydrochloric acid in dioxane (1 mL, 4 mmol) was added to a solution of 8-(4-((tert-butoxycarbonylamino)methyl)-3-fluorophenyl)-1-cyclopropyl-9-methyl-4-oxo-4H-quinolizine-3-carboxylic acid (24 mg, 0.051 mmol) in ACN (4 mL). The mixture was stirred for 4 h and a suspension was formed. The product compound 4 was collected by filtration (17.7 mg, 78%).

LC-MS: t=2.54 min (method 2); 367 (M+H)$^+$; 365 (M−H)$^−$.

Preparation of Compound 5

Preparation of Compound 5 8-(4-aminophenyl)-1-cyclopropyl-9-methyl-4-oxo-quinolizine-3-carboxylic acid The general Suzuki coupling method described above was used to couple methyl 8-chloro-1-cyclopropyl-9-methyl-4-oxo-4H-quinolizine-3-carboxylate with 4-butyloxycarbonyl-amino-phenyl boronic acid. Purification by flash silica column chromatography yielded methyl 8-[4-(tert-butoxycarbonylamino)-phenyl]-1-cyclopropyl-9-methyl-4-oxo-quinolizine-3-carboxylate as a yellow solid. A solution of the obtained solid in a mixture of THF (1.5 mL) and aqueous 4N sodium hydroxide solution (0.5 mL) was irradiated at 120° C. in a microwave oven for 10 min. The solvents were evaporated and the residue taken in DCM (10 mL). The organic phase was washed with water (10 mL), dried over sodium sulfate and concentrated to dryness. A solution of the residue and TFA (0.5 mL) in DCM (0.5 mL) was stirred at room temperature for 1.5 h. After evaporation of the solvents, the product was purified by preparative HPLC yielding compound 5 8-(4-aminophenyl)-1-cyclopropyl-9-methyl-4-oxo-quinolizine-3-carboxylic acid (28.9 mg, 43.7%).

LC-MS: t=5.99 min (method 3); 349 (M+H)$^+$; 332 (M−NH$_3$+H)$^+$.

Preparation of Compound 6

Preparation of 8-(4-aminophenyl)-1-cyclopropyl-7-fluoro-9-methyl-4-oxo-quinolizine-3-carboxylic acid The general Suzuki coupling method described above was used to couple ethyl 8-chloro-1-cyclopropyl-7-fluoro-9-methyl-4-oxo-4H-quinolizine-3-carboxylate with 4-butyloxy-carbonylamino-phenyl boronic acid. Purification by flash silica column chromatography yielded ethyl 8-[4-(tert-butoxycarbonylamino)-phenyl]-1-cyclopropyl-7-fluoro-9-methyl-4-oxo-quinolizine-3-carboxylate as a yellow solid.

A solution of the obtained yellow solid in a mixture of THF (1.5 mL) and of aqueous 4N sodium hydroxide solution (0.5 mL) was irradiated at 120° C. in a microwave oven for 10 min. The solvents were evaporated and the residue taken in DCM (10 mL). The organic phase was washed with water (10 mL), dried over sodium sulfate and concentrated to dryness. A solution of the residue and TFA (0.5 mL) in DCM (0.5 mL) was stirred at room temperature for 1.5 h. After evaporation of the solvents, the product was purified by preparative HPLC yielding compound 6 8-(4-aminophenyl)-

1-cyclopropyl-7-fluoro-9-methyl-4-oxo-quinolizine-3-carboxylic acid (16.4 mg, 52%).

LC-MS: t=6.01 min (method 3); 367 $(M+H)^+$; 350 $(M-NH_3+H)^+$; $^1H$ NMR (400 MHz, DMSO-d6) δ ppm 13.89 (s, 1H), 9.38 (d, J=5.6 Hz, 1H), 8.24 (s, 1H), 7.68 (d, J=8 Hz, 2H), 7.54 (d, J=8 Hz, 1H), 4.15 (s, 2H), 2.77 (s, 3H), 2.48-2.52 (m, 1H), 1.03-1.05 (m, 2H), 0.78-0.80 (m, 2H).

Preparation of Compound 17

Preparation of ethyl 8-[4-(tert-butoxycarbonylamino)-3-fluoro-phenyl]-1-cyclopropyl-7-fluoro-9-methyl-4-oxo-quinolizine-3-carboxylate The general Suzuki coupling method described above was used to couple ethyl 8-chloro-1-cyclopropyl-7-fluoro-9-methyl-4-oxo-4H-quinolizine-3-carboxylate with 3-fluoro-4-(tert-butyloxycarbonylamino-phenyl boronic acid. Purification by flash silica column chromatography yielded ethyl 8-[4-(tert-butoxycarbonylamino)-3-fluoro-phenyl]-1-cyclopropyl-7-fluoro-9-methyl-4-oxo-quinolizine-3-carboxylate as a yellow solid (280 mg, 61%).

LC-MS: t=2.85 min (method 1); 499 $(M+H)^+$.

Preparation of Compound 17 8-(4-amino-3-fluoro-phenyl)-1-cyclopropyl-7-fluoro-9-methyl-4-oxo-quinolizine-3-carboxylic acid A solution of ethyl 8-(4-(tert-butoxycarbonylamino)-3-fluoro-phenyl)-1-cyclopropyl-7-fluoro-9-methyl-4-oxo-4H-quinolizine-3-carboxylate (260 mg, 0.52 mmol) in a 4N hydrochloric acid solution (20 mL). The mixture was stirred for 20 min at 50° C. The product was lyophilized and dissolved in a mixture of THF (1 mL) and of an aqueous 4N sodium hydroxide solution (1.31 mL, 5.2 mmol) before being irradiated at 140° C. in a microwave oven for 10 min. The product was purified by preparative HPLC yielding compound 17 8-(4-amino-3-fluoro-phenyl)-1-cyclopropyl-7-fluoro-9-methyl-4-oxo-quinolizine-3-carboxylic acid (5.1 mg, 2.5%).

LC-MS: t=2.24 min (method 1); 371 $(M+H)^+$.

Preparation of the Compounds 1-11, 13, 15 and 17-89 from Scaffold A, B, C, D and E Chemical names and structures of the compounds are given in Table 1

The preparation of the compounds from scaffold A, C, D and E is described below. Compounds 1, 2, 3, 4, 5, 6, and 17 were also resynthesized according to this method. Preparation of the corresponding potassium salts is also described. Compounds are then referred as such with the letter K following their number. If a compound is obtained as another salt (for example hydrochloric salt), the compound is referred as such followed with the appropriate suffix (for example HCl).

Most of the examples were prepared according to the general procedures A-D described below. The preparation of the other examples is otherwise reported specifically in the experimental section. A number of boronates were specifically prepared to be reacted with the scaffolds by general procedures A or A'. These boronate were made from commercial bromo-nitriles with general procedures E, F and G described below.

General Procedure A:

The quinolizine scaffold (1 eq.), boronate (1.3 eq.) and cesium carbonate (3 eq.) were added to a 3:1 mixture of 1,2-dimethoxyethane and water (4 mL). The mixture was degassed with argon. 1,1'-Bis-diphenylphosphine ferrocene palladium(II) dichloride (0.1 eq.) was added and the mixture was heated at 90° C. under an argon atmosphere for 1 h. The reaction mixture was allowed to cool down.

The usual work up procedure was as follows. The mixture was diluted with DCM (3 mL) and water was added (3 mL). The layers were separated using a phase separator and the aqueous layer was extracted with DCM (2×5 mL). The combined organic layers were dried over sodium sulfate and concentrated in vacuum. An alternative work up procedure consisted in filtering the residue and rinsing it with DCM (5 mL) prior to concentration of the solvents.

The crude product was purified by flash silica column chromatography and dried in vacuum to afford the desired product.

General Procedure A' for Microwave Oven:

The quinolizine scaffold (1 eq.), boronate (1.3 eq.) and cesium carbonate (3 eq.) were added to a 3:1 mixture of 1,2-dimethoxyethane and water (4 mL). The mixture was degassed with argon. 1,1'-Bis-diphenylphosphine ferrocene palladium(II) dichloride (0.1 eq.) was added and the mixture was heated in a microwave oven at 150° C. under an argon atmosphere for 5 min. The reaction mixture was allowed to cool down.

The usual work up procedure was as follows. The mixture was diluted with DCM (3 mL) and water was added (3 mL). The layers were separated using a phase separator and the aqueous layer was extracted with DCM (2×5 mL). The combined organic layers were dried over sodium sulfate and concentrated in vacuum. An alternative work up procedure consisted in filtering the residue and rinsing it with DCM (5 mL) prior to concentration of the solvents.

The crude product was purified by flash silica column chromatography and dried in vacuum to afford the desired product.

General Procedure B:

The ester intermediate (1 eq.) was added to a solution of lithium hydroxide (2 eq.) in a 1:1 mixture of THF and water. The reaction mixture was stirred for 18 h at 30° C. The mixture was acidified using 1M HCl in water. The precipitate was filtered off and dried in vacuum to afford the desired product.

General Procedure C:

The BOC-protected amine intermediate (1 eq.) was suspended in DCM and 1 M HCl in diethyl ether (20 eq.) was added. The reaction mixture was stirred for 16 h. The precipitate was filtered off and dried in vacuum to afford the desired product.

General Procedure D:

The free acid (1 eq.) was added to a solution of potassium hydroxide (1.1 eq.) in water and stirred for 1 h. The solution was lyophilized to obtain the desired product General Procedure E:

A suspension of the bromo-nitrile (1 eq.) in dry (8 ml) was cooled in an ice bath under a $N_2$ atmosphere. Di-tert-butyl dicarbonate (2-3 eq.) was added followed by the careful addition of borane-THF complex (1M, 2.4 eq.). The mixture was stirred at room temperature for 2 hours. If needed, the borane-THF complex (1M, 2.4 eq.) was added again and the mixture was stirred at room temperature overnight.

The mixture was quenched at 0° C. with water (8 ml). The layers were separated. The water layer was extracted with DCM. The combined organic layers were dried over $Na_2SO_4$ and concentrated in vacuum to afford the crude BOC protected amine.

General Procedure F:

To a solution of the bromo-amine (1 eq.) in THF (8 ml) was added Et$_3$N (3 eq.), 4-dimethylaminopyridine (0.1 eq.) and di-tert-butyl dicarbonate (2.2 eq.). Gas evolution was observed. The mixture was stirred at room temperature overnight. Water was added. The mixture was extracted with DCM. The combined organic layers were dried over Na$_2$SO$_4$ and concentrated in vacuum to afford the crude BOC protected bromo-amine.

General Procedure G:

A mixture of the bromide (1 eq.), bis(pinacolato)diboron (1.5 eq.) and potassium acetate (3 eq.) in 1,4-dioxane (6 ml) and water (2 ml) was degassed with argon. 1,1'-bis-(diphenylphosphino)-ferrocene) palladium dichloride (0.1 eq.) was added, the reaction tube was capped and heated at 90° C. for 3 hours. Water was added and the mixture was extracted with DCM. The combined organic layers were dried over Na$_2$SO$_4$ and concentrated in vacuum to afford the crude pinacol ester.

Preparation and Characterization of Compounds 1-11, 13, 15 and 17-89

Preparation of Compound 1

Preparation of methyl 8-(4-amino-3-fluoro-phenyl)-1-cyclopropyl-9-methyl-4-oxo-4H-quinolizine-3-carboxylate Methyl 8-(4-amino-3-fluoro-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (200 mg, 0.68 mmol) and 2-fluoro-4-(4,4,5,5-tetramethyl-1,3,2-dioxaborolan-2-yl)aniline (195 mg, 0.82 mmol). Purification by flash silica column chromatography (DCM:MeOH) (1:0 to 9:1) afforded the title compound as a yellow solid (191 mg, 76%).

ESI-MS m/z: 367 (M+H)$^+$.

Preparation of Compound 1 8-(4-amino-3-fluoro-phenyl)-1-cyclopropyl-9-methyl-4-oxo-4H-quinolizine-3-carboxylic acid 8-(4-Amino-3-fluoro-phenyl)-1-cyclopropyl-9-methyl-4-oxo-4H-quinolizine-3-carboxylic acid was prepared according to General Procedure B from methyl 8-(4-amino-3-fluoro-phenyl)-1-cyclopropyl-9-methyl-4-oxo-4H-quinolizine-3-carboxylate (191 mg, 0.52 mmol) to afford the title compound 1 as a yellow solid (135 mg, 73%).

ESI-MS m/z: 353 (M+H)$^+$; 1H NMR (400 MHz, DMSO-d6) δ ppm: 14.05 (br s, 1H), 9.55 (d, J=7.3 Hz, 1H), 8.21 (s, 1H), 7.57 (d, J=7.3 Hz, 1H), 7.16-7.34 (m, 2H), 6.92 (t, J=8.8 Hz, 1H), 5.74 (s, 2H), 2.89 (s, 3H), 2.50-2.70 (m, 1H), 1.02-1.05 (m, 2H), 0.73-0.80 (m, 2H).

Preparation of Compound 1K, potassium salt of compound 1—potassium 8-(4-amino-3-fluoro-phenyl)-1-cyclopropyl-9-methyl-4-oxo-4H-quinolizine-3-carboxylate Potassium 8-(4-amino-3-fluoro-phenyl)-1-cyclopropyl-9-methyl-4-oxo-4H-quinolizine-3-carboxylate was prepared according to General Procedure D from 8-(4-amino-3-fluoro-phenyl)-1-cyclopropyl-9-methyl-4-oxo-4H-quinolizine-3-carboxylic acid (compound 1) (260 mg, 0.74 mmol) to afford the title compound K salt of compound 1 as a yellow solid (288 mg, 98%).

ESI-MS m/z: 353 (M-K+H)$^+$.

Preparation of Compound 2

Preparation of 2,5-difluoro-4-(4,4,5,5-tetramethyl-1,3,2-dioxaborolan-2-yl)-aniline Potassium acetate (7.08 g, 72 mmol), 4,4,4',4',5,5,5',5'-octamethyl-2,2'-bi(1,3,2-dioxaborolane) (7.94 g, 31 mmol) and 4-bromo-2,5-difluoro-aniline (5 g, 24 mmol) were dissolved in 1,2-dimethoxyethane (60 mL), followed by the addition of 1'-Bis-diphenylphosphine ferrocene palladium (II) dichloride (2.1 g, 2.6 mmol). The reaction mixture was heated at 90° C. for 16 h. The reaction mixture was evaporated to dryness in vacuum. The mixture was coated onto hydromatrix and purified by flash silica column chromatography (heptane:ethyl acetate, 3:1). The product was dried in vacuum and crystallized from DCM and heptane to give the title compound as a white solid (3.5 g, 57%).

ESI-MS m/z: 256.2 (M+H)$^+$; 1H NMR (400 MHz, CDCl$_3$) δ ppm: 7.30 (dd, J=5.0 Hz and J=11.1 Hz, 1H), 6.41 (q, J=6.8 Hz, 1H), 4.06 (br s, 1H), 1.33 (s, 12H).

Preparation of methyl 8-(4-amino-2,5-difluoro-phenyl)-1-cyclopropyl-9-methyl-4-oxo-4H-quinolizine-3-carboxylate Methyl 8-(4-amino-2,5-difluoro-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (500 mg, 1.71 mmol) and 2,5-difluoro-4-(4,4,5,5-tetramethyl-1,3,2-dioxaborolan-2-yl)-aniline (667 mg, 2.06 mmol). Purification by flash silica column chromatography (DCM:MeOH) (1:0 to 9:1) afforded the title compound as a yellow solid (500 mg, 75%).

ESI-MS m/z: 407 (M+Na)$^+$.

Preparation of Compound 2 8-(4-amino-2,5-difluoro-phenyl)-1-cyclopropyl-9-methyl-4-oxo-4H-quinolizine-3-carboxylic acid 8-(4-Amino-2,5-difluoro-phenyl)-1-cyclopropyl-9-methyl-4-oxo-4H-quinolizine-3-carboxylic acid was prepared according to General Procedure B from methyl 8-(4-amino-2,5-difluoro-phenyl)-1-cyclopropyl-9-methyl-4-oxo-4H-quinolizine-3-carboxylate (1 g, 2.6 mmol) to afford the title compound 2 as a yellow solid (639 mg, 66%).

ESI-MS m/z: 371 (M+H)$^+$; 1H NMR (400 MHz, DMSO-d6) δ ppm: 13.97 (s, 1H), 9.32 (d, J=5.5 Hz, 1H), 8.24 (s, 1H), 7.21 (d, J=12.1 Hz, 1H), 7.03 (d, J=8.1 Hz, 1H), 6.92 (t, J=8.7 Hz, 1H), 6.00 (s, 2H), 2.85 (s, 3H), 2.40-2.60 (m, 1H), 1.06-1.08 (m, 2H), 0.77-0.79 (m, 2H).

Preparation of Compound 2K (Potassium Salt of Compound 2) Potassium 8-(4-amino-2,5-difluoro-phenyl)-1-cyclopropyl-9-methyl-4-oxo-4H-quinolizine-3-carboxylate Compound 2K—potassium salt of compound 2—Potassium 8-(4-amino-2,5-difluoro-phenyl)-1-cyclopropyl-9-methyl-4-oxo-4H-quinolizine-3-carboxylate was prepared according to General Procedure D from 8-(4-amino-2,5-difluoro-phenyl)-1-cyclopropyl-9-methyl-4-oxo-4H-quinolizine-3-carboxylic acid (290 mg, 0.78 mmol) to afford the K salt of compound 2 as a yellow solid (287 mg, 90%).
ESI-MS m/z: 371 (M-K+H)$^+$.

Preparation of Compound 3

Preparation of ethyl 8-(4-amino-3,5-dichloro-phenyl)-1-cyclopropyl-9-methyl-4-oxo-4H-quinolizine-3-carboxylic acid A mixture of ethyl 8-chloro-1-cyclopropyl-9-methyl-4-oxo-4H-quinolizine-3-carboxylate (120 mg, 0.400 mmol), 2,6-dichloro-[4-(4,4,5,5-tetramethyl-[1,3,2]dioxa-borolan-2-yl)-aniline (138 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate (50 mL) and washed with water (2×20 mL). The organic phase was separated, dried, and concentrated. The residue was purified by flash silica column chromatography (hexane:ethyl acetate, 2:3) to afford the title compound as a yellow solid (140 mg, 81%).
ESI-MS m/z: 431 (M+H)$^+$.

Preparation of Compound 3 8-(4-amino-3,5-dichloro-phenyl)-1-cyclopropyl-9-methyl-4-oxo-4H-quinolizine-3-carboxylic acid A solution of ethyl 8-(4-amino-3,5-dichloro-phenyl)-1-cyclopropyl-9-methyl-4-oxo-4H-quinolizine-3-carboxylate (140 mg, 0.326 mmol) in THF (6 mL) and water (2 mL) was treated with LiOH (55 mg, 1.31 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound 3 as yellow solid (90 mg, 69%).
ESI-MS m/z: 403 (M+H)$^+$; $^1$H NMR (300 MHz, DMSO-d6) δ ppm: 9.30 (d, J=7.5 Hz, 1H), 8.25 (s, 1H), 7.64 (d, J=7.5 Hz, 1H), 7.57 (s, 2H), 6.12 (s, 2H), 2.92 (s, 3H), 2.54-2.51 (m, 1H), 1.13-1.10 (m, 2H), 0.84-0.83 (m, 2H).

Preparation of Compound 4

Preparation of tert-butyl 4-bromo-2-fluorobenzyl-carbamate

To a solution of (4-bromo-2-fluorophenyl) methanamine (2.5 g, 12 mmol) in DCM (50 mL) at 0° C. was added di-tert-butyl dicarbonate (4.01 g, 18 mmol) and triethylamine (2.6 mL, 18 mmol). The mixture was allowed to warm to room temperature and stirred for 2 h. Water was added (50 mL) and the layers were separated. The organic layer was washed with brine, dried over sodium sulfate and concentrated in vacuum. The crude product was purified by flash silica column chromatography (heptane:ethyl acetate) (1:0 to 4:1) to afford the title compound as a colorless oil. (2.7 g, 71%).
$^1$H NMR (400 MHz, DMSO-d6) δ ppm 7.21-7.26 (m, 3H), 4.90 (br s, H), 4.27-4.33 (m, 2H), 1.44 (s, 9H).

Preparation of tert-butyl 2-fluoro-4-(4,4,5,5-tetramethyl-1,3,2-dioxaborolan-2-yl)-benzylcarbamate A mixture of tert-butyl 4-bromo-2-fluorobenzyl-carbamate (1.3 g, 4.3 mmol), bis(pinacolato)-diboron (1.6 g, 6.4 mmol), and sodium acetate (1.1 g, 13 mmol) in DMSO (dry) (4 mL) was degassed with argon. 1,1'-Bis(diphenylphosphino)-ferrocene palladium(II) dichloride (0.156 g, 0.214 mmol) was added and the mixture was heated at 90° C. for 3 h. After cooling, the reaction mixture was partitioned between ethyl acetate (50 mL) and water (50 mL). The layers were separated and the organic layer was washed with water (50 mL), brine, dried over sodium sulfate and concentrated to give a red/brown crude product. The material was purified by flash silica column chromatography (heptane:ethyl acetate) (1:0 to 4:1) to afford the title compound as a colorless oil (980 mg, 65%).
$^1$H NMR (400 MHz, DMSO-d6) δ ppm 7.53 (d, J=7.6 Hz, 1H), 7.45 (d, J=10.4 Hz, 1H), 7.31-7.35 (m, 1H), 4.91 (br s, H), 4.36-4.40 (m, 2H), 1.44 (s, 9H), 1.34 (s, 12H).

Preparation of methyl 8-(4-((tert-butoxycarbonylamino)-methyl)-3-fluorophenyl)-1-cyclopropyl-9-methyl-4-oxo-4H-quinolizine-3-carboxylate Methyl 8-chloro-1-cyclopropyl-9-methyl-4-oxo-4H-quinolizine-3-carboxylate (46 mg, 0.158 mmol) was dissolved in toluene (500 μL), ethanol (96%) (237 μL) and aqueous sodium carbonate 2M (237 μL, 0.473 mmol). tert-Butyl 2-fluoro-4-(4,4,5,5-tetramethyl-1,3,2-dioxaborolan-2-yl) benzylcarbamate (97 mg, 0.21 mmol) was added. The mixture was degassed with argon and 1,1'-bis(diphenylphosphino)-ferrocene palladium(II) dichloride (11.5 mg, 0.016 mmol) was added. The mixture was heated at 90° C. for 4 h. After cooling, the mixture was diluted with DCM (3 mL) and water (3 mL). The layers were separated and the aqueous layer was extracted with DCM (3×2 mL). The organic layer was concentrated in vacuum. The crude product was purified with flash silica column chromatography (heptane:ethyl acetate) (1:1 to 1:2) to afford the title compound as a yellow solid (24 mg, 32%).
ESI-MS m/z: 481 (M+H)$^+$.

Preparation of 8-(4-((tert-butoxycarbonylamino) methyl)-3-fluorophenyl)-1-cyclopropyl-9-methyl-4-oxo-4H-quinolizine-3-carboxylic acid Methyl 8-(4-((tert-butoxycarbonylamino)methyl)-3-fluorophenyl)-1-cyclopropyl-9-methyl-4-oxo-4H-quinolizine-3-carboxylate (24 mg, 0.050 mmol) was dissolved in MeOH (2 mL) and 1M aqueous sodium hydroxide (0.5 mL, 0.5 mmol) was added. The mixture was stirred at 50° C. for 2 h. After cooling, the MeOH was removed in vacuum and the residue was dissolved in water (5 mL) and neutralized with 1M HCl (~0.5 mL).The precipitate formed was extracted with DCM (3×4 mL). The organic layer was concentrated to afford the title compound as a yellow solid (20 mg, 86%).
ESI-MS m/z: 467 (M+H)$^+$.

Preparation of Compound 4HCl—HCl salt of compound 4—8-(4-(aminomethyl)-3-fluorophenyl)-1-cyclopropyl-9-methyl-4-oxo-4H-quinolizine-3-carboxylic acid hydrochloride 8-(4-((tert-Butoxycarbonylamino) methyl)-3-fluorophenyl)-1-cyclopropyl-9-methyl-4-oxo-4H-quinolizine-3-carboxylic acid (24 mg, 0.051 mmol) was dissolved in ACN (4 mL). HCl 4M in dioxane (1 mL, 4 mmol) was added. The mixture was stirred for 4 h and a suspension was formed affording after filtration the title compound 4HCl as a yellow solid (17.7 mg, 86%).
ESI-MS m/z: 453 (M+H)$^+$.

Preparation of Compound 4K—potassium salt of compound 4—potassium 8-(4-(aminomethyl)-3-fluorophenyl)-1-cyclopropyl-9-methyl-4-oxo-4H-quinolizine-3-carboxylate Compound 4K Potassium 8-(4-(aminomethyl)-3-fluorophenyl)-1-cyclopropyl-9-methyl-4-oxo-4H-quinolizine-3-carboxylate was prepared according to General Procedure D from 8-(4-(aminomethyl)-3-fluorophenyl)-1-cyclopropyl-9-methyl-4-oxo-4H-quinolizine-3-carboxylic acid hydrochloride (65 mg, 0.16 mmol) to afford the K salt of compound 4 as a yellow solid (79 mg, 100%).
ESI-MS m/z: 367.0 (M-K+H)$^+$.

Preparation of Compound 5

Preparation of methyl 8-(4-(((tert-butoxycarbonyl)-amino)-methyl)-phenyl)-1-cyclopropyl-9-methyl-4-oxo-4H-quinolizine-3-carboxylate Methyl 8-(4-(((tert-butoxycarbonyl)-amino)-methyl)-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (500 mg, 1.71 mmol) and (4-(((tert-butoxycarbonyl)-amino)-methyl)-phenyl)-boronic acid (516 mg, 2.06 mmol).
Purification by flash silica column chromatography (DCM:MeOH) (1:0 to 9:1) afforded the title compound as a yellow solid (850 mg, 100%).
ESI-MS m/z: 485 (M+Na)$^+$, 463 (M+H)$^+$.

Preparation of 8-(4-(((tert-butoxycarbonyl)-amino)-methyl)-phenyl)-1-cyclopropyl-9-methyl-4-oxo-4H-quinolizine-3-carboxylic acid 8-(4-(((tert-Butoxycarbonyl)-amino)-methyl)-phenyl)-1-cyclopropyl-9-methyl-4-oxo-4H-quinolizine-3-carboxylic acid was prepared according to General Procedure B from methyl 8-(4-(((tert-butoxycarbonyl)-amino)-methyl)-phenyl)-1-cyclopropyl-9-methyl-4-oxo-4H-quinolizine-3-carboxylate (1050 mg, 2.3 mmol) to afford the title compound as a yellow solid (950 mg, 93%).
ESI-MS m/z: 449 (M+H)$^+$.

Preparation of Compound 5HCl—HCl salt of compound 5—8-(4-(aminomethyl)-phenyl)-1-cyclopropyl-9-methyl-4-oxo-4H-quinolizine-3-carboxylic acid hydrochloric salt 8-(4-(Aminomethyl)-phenyl)-1-cyclopropyl-9-methyl-4-oxo-4H-quinolizine-3-carboxylic acid was prepared according to General Procedure C from 8-(4-(((tert-butoxycarbonyl)-amino)-methyl)-phenyl)-1-cyclopropyl-9-methyl-4-oxo-4H-quinolizine-3-carboxylic acid (540 mg, 1.20 mmol) to afford the hydrochloric salt of the title compound 5 as a yellow solid (360 mg, 86%).
ESI-MS m/z: 349 (M+H)$^+$; 1H NMR (400 MHz, DMSO-d6) δ ppm: 14.07 (s, 1H), 9.35 (d, J=7.3 Hz, 1H), 8.64 (s, 2H), 8.27 (s, 1H), 7.73 (d, J=7.8 Hz, 2H), 7.56-7.63 (m, 3H), 4.13 (s, 2H), 2.86 (s, 3H), 2.40-2.60 (m, 1H), 1.07-1.09 (m, 2H), 0.78-0.80 (m, 2H).

Preparation of Compound 5K (Potassium Salt of Compound 5) potassium 8-(4-(amino-methyl)-phenyl)-1-cyclopropyl-9-methyl-4-oxo-4H-quinolizine-3-carboxylate Potassium 8-(4-(amino-methyl)-phenyl)-1-cyclopropyl-9-methyl-4-oxo-4H-quinolizine-3-carboxylate was prepared according to General Procedure D from 8-(4-(amino-methyl)-phenyl)-1-cyclopropyl-9-methyl-4-oxo-4H-quinolizine-3-carboxylic acid hydrochloric salt (200 mg, 0.52 mmol) to afford the K salt of compound 5 as a yellow solid (153 mg, 76%).
ESI-MS m/z: 349 (M-K+H)$^+$.

Preparation of Compound 6

Preparation of ethyl 8-(4-(((tert-butoxycarbonyl)-amino)-methyl)-phenyl)-1-cyclopropyl-7-fluoro-9-methyl-4-oxo-4H-quinolizine-3-carboxylate Ethyl 8-(4-(((tert-butoxycarbonyl)-amino)-methyl)-phenyl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (100 mg, 0.31 mmol) and (4-(((tert-butoxycarbonyl)-amino)-methyl)-phenyl)-boronic acid (101 mg, 0.40 mmol). Purification by flash silica column chromatography (DCM:MeOH) (1:0 to 9:1) afforded the title compound as a yellow solid (167 mg, 100%).
ESI-MS m/z: 495 (M+Na)$^+$.

Preparation of 8-(4-(((tert-butoxycarbonyl)-amino)-methyl)-phenyl)-1-cyclopropyl-7-fluoro-9-methyl-4-oxo-4H-quinolizine-3-carboxylic acid 8-(4-(((tert-Butoxycarbonyl)-amino)-methyl)-phenyl)-1-cyclopropyl-7-fluoro-9-methyl-4-oxo-4H-quinolizine-3-carboxylic acid was prepared according to General Procedure B from ethyl 8-(4-(((tert-butoxycarbonyl)-amino)-methyl)-phenyl)-1-cyclopropyl-7-fluoro-9-methyl-4-oxo-4H-quinolizine-3-carboxylate (167 mg, 0.34 mmol) to afford the title compound as a yellow solid (150 mg, 95%).
ESI-MS m/z: 467 (M+H)$^+$.

Preparation of Compound 6HCl (Hydrochloric Salt of Compound 6) 8-(4-amino-methyl-phenyl)-1-cyclopropyl-7-fluoro-9-methyl-4-oxo-4H-quinolizine-3-carboxylic acid hydrochloric salt 8-(4-Amino-methyl-phenyl)-1-cyclopropyl-7-fluoro-9-methyl-4-oxo-4H-quinolizine-3-carboxylic acid was prepared according to General Procedure C from 8-(4-(((tert-butoxycarbonyl)-amino)-methyl)-phenyl)-1-cyclopropyl-7-fluoro-9-methyl-4-oxo-4H-quinolizine-3-carboxylic acid (150 mg, 0.32 mmol) to afford the hydrochloric salt of the title compound 6 as a yellow solid (137 mg, 100%).
ESI-MS m/z: 367 (M+H)$^+$; 1H NMR (400 MHz, DMSO-d6) δ ppm: 13.9 (br s, 1H), 9.41 (d, J=7.3 Hz, 1H), 8.50 (br s, 2H), 8.28 (s, 1H), 7.72 (d, J=7.8 Hz, 2H), 7.56 (d, J=7.8 Hz 2H), 4.16 (s, 2H), 2.79 (s, 3H), 2.40-2.60 (m, 1H), 1.05-1.09 (m, 2H), 0.79-0.82 (m, 2H).

Preparation of Compound 6K (Potassium Salt of Compound 6) potassium 8-(4-amino-methyl)-phenyl)-1-cyclopropyl-7-fluoro-9-methyl-4-oxo-4H-quinolizine-3-carboxylate Potassium 8-(4-amino-methyl)-phenyl)-1-cyclopropyl-7-fluoro-9-methyl-4-oxo-4H-quinolizine-3-carboxylate was prepared according to General Procedure D from 8-(4-aminomethyl-phenyl)-1-cyclopropyl-7-fluoro-9-methyl-4-oxo-4H-quinolizine-3-carboxylic acid hydrochloric salt (65 mg, 0.16 mmol) to afford the K salt of compound 6 as a yellow solid (79 mg, 100%).

ESI-MS m/z: 367 (M−K+H))+; 1H NMR (400 MHz, DMSO-d6) δ ppm: 13.9 (br s, 1H), 9.40 (d, J=7.3 Hz, 1H), 8.43 (br s, 2H), 8.28 (s, 1H), 7.72 (d, J=7.8 Hz, 2H), 7.56 (d, J=7.8 Hz, 2H), 4.16 (s, 2H), 2.79 (s, 3H), 2.50-2.55 (m, 1H), 1.05-1.09 (m, 2H), 0.79-0.82 (m, 2H).

Preparation of Compound 7

Preparation of ethyl 8-(4-amino-phenyl)-1-cyclopropyl-7-fluoro-9-methyl-4-oxo-4H-quinolizine-3-carboxylate Ethyl 8-(4-amino-phenyl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (500 mg, 1.54 mmol) and 4-(4,4,5,5-tetramethyl-1,3,2-dioxaborolan-2-yl)-aniline (439 mg, 2.00 mmol). Purification by flash silica column chromatography (DCM:MeOH) (1:0 to 9:1) afforded the title compound as a yellow solid (550 mg, 93%).

ESI-MS m/z: 381 (M+H)+.

Preparation of Compound 7 8-(4-amino-phenyl)-1-cyclopropyl-7-fluoro-9-methyl-4-oxo-4H-quinolizine-3-carboxylic acid 8-(4-Amino-phenyl)-1-cyclopropyl-7-fluoro-9-methyl-4-oxo-4H-quinolizine-3-carboxylic acid was prepared according to General Procedure B from ethyl 8-(4-amino-phenyl)-1-cyclopropyl-7-fluoro-9-methyl-4-oxo-4H-quinolizine-3-carboxylate (550 mg, 1.45 mmol) to afford the title compound 7 as a yellow solid (435 mg, 85%).

ESI-MS m/z: 353 (M+H)+; 1H NMR (400 MHz, DMSO-d6) δ ppm: 13.95-14.02 (m, 1H), 9.32 (d, J=5.8 Hz, 1H), 8.21 (s, 1H), 7.21 (d, J=6.8 Hz, 2H), 6.79 (d, J=8.3 Hz, 2H), 2.85 (s, 3H), 2.50-2.60 (m, 1H), 1.05-1.07 (m, 2H), 0.76-0.78 (m, 2H).

Preparation of Compound 7K (Potassium Salt of Compound 7) potassium 8-(4-amino-phenyl)-1-cyclopropyl-7-fluoro-9-methyl-4-oxo-4H-quinolizine-3-carboxylate Potassium 8-(4-amino-phenyl)-1-cyclopropyl-7-fluoro-9-methyl-4-oxo-4H-quinolizine-3-carboxylate was prepared according to General Procedure D from 8-(4-amino-phenyl)-1-cyclopropyl-7-fluoro-9-methyl-4-oxo-4H-quinolizine-3-carboxylic acid (460 mg, 0.74 mmol) to afford the title compound K salt of compound 7 as a yellow solid (510 mg, 100%).

ESI-MS m/z: 353 (M−K+H)+.

Preparation of Compound 8

Preparation of methyl 8-(4-amino-phenyl)-1-cyclopropyl-9-methyl-4-oxo-4H-quinolizine-3-carboxylate Methyl 8-(4-amino-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (150 mg, 0.51 mmol) and 4-(4,4,5,5-tetramethyl-1,3,2-dioxaborolan-2-yl)-aniline (135 mg, 0.62 mmol). Purification by flash silica column chromatography (DCM:MeOH) (1:0 to 9:1) afforded the title compound as a yellow solid (25 mg, 14%).

ESI-MS m/z: 349 (M+H)+.

Preparation of Compound 8 8-(4-amino-phenyl)-1-cyclopropyl-9-methyl-4-oxo-4H-quinolizine-3-carboxylic acid 8-(4-Amino-phenyl)-1-cyclopropyl-9-methyl-4-oxo-4H-quinolizine-3-carboxylic acid was prepared according to General Procedure B from methyl 8-(4-amino-phenyl)-1-cyclopropyl-9-methyl-4-oxo-4H-quinolizine-3-carboxylate (25 mg, 0.07 mmol) to afford the title compound compound 8 as a yellow solid (18 mg, 77%).

ESI-MS m/z: 335 (M+H)+; 1H NMR (400 MHz, DMSO-d6) δ ppm: 14.11 (s, 1H), 9.24 (d, J=7.1 Hz, 1H), 8.22 (s, 1H), 7.53 (s, 1H), 7.30 (d, J=8.1 Hz, 2H), 6.72 (d, J=8.4 Hz, 2H), 5.67 (s, 2H), 2.89 (s, 3H), 2.40-2.50 (m, 1H), 1.05-1.07 (m, 2H), 0.73-0.75 (m, 2H).

Preparation of Compound 9

Preparation of methyl 8-(3-amino-phenyl)-1-cyclopropyl-9-methyl-4-oxo-4H-quinolizine-3-carboxylate Methyl 8-(3-amino-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (195 mg, 0.66 mmol) and (3-aminophenyl)-boronic acid (119 mg, 0.87 mmol). Purification by flash silica column chromatography (DCM:MeOH) (1:0 to 9:1) afforded the title compound as a yellow solid (91 mg, 39%).

ESI-MS m/z: 349 (M+H)+.

Preparation of Compound 9 8-(3-amino-phenyl)-1-cyclopropyl-9-methyl-4-oxo-4H-quinolizine-3-carboxylic acid 8-(3-Amino-phenyl)-1-cyclopropyl-9-methyl-4-oxo-4H-quinolizine-3-carboxylic acid was prepared according to General Procedure B from methyl 8-(3-amino-phenyl)-1-cyclopropyl-9-methyl-4-oxo-4H-quinolizine-3-carboxylate (91 mg, 0.26 mmol) to afford the title compound compound 9 as a yellow solid (62.4 mg, 72%).

ESI-MS m/z: 335 (M+H)+; 1H NMR (400 MHz, DMSO-d6) δ ppm: 14.20 (br s, 1H), 9.32 (d, J=7.3 Hz, 1H), 8.26 (s, 1H), 7.52 (d, J=7.3 Hz, 1H), 7.35-7.53 (m, 1H), 6.82-6.93 (m, 3H), 2.86 (s, 3H), 2.50-2.60 (m, 1H), 1.00-1.10 (m, 2H), 0.75-0.85 (m, 2H).

Preparation of Compound 10

Preparation of methyl 8-(3-S-((tert-butoxycarbonyl)-amino)-pyrrolidin-1-yl)-1-cyclopropyl-9-methyl-4-oxo-4H-quinolizine-3-carboxylate Methyl 8-chloro-1-cyclopropyl-9-methyl-4-oxo-4H-quinolizine-3-carboxylate (100 mg, 0.34 mmol), tert-butyl-pyrrolidin-3-S-yl-carbamate (313 mg, 1.68 mmol) and tri-ethylamine (0.5 mL, 3.6 mmol) were added to 2-propanol (20 mL). The reaction mixture was heated at 130° C. and stirred for 6 h. The reaction mixture was cooled and evaporated to dryness. The crude product was purified by flash silica column chromatography (DCM:MeOH) (1:0 to 9:1) and dried in vacuum to afford the title compound as a yellow foam (70 mg, 46%).

ESI-MS m/z: 442 (M+H)$^+$.

Preparation of Compound 10 8-(3-S-amino-pyrrolidin-1-yl)-1-cyclopropyl-9-methyl-4-oxo-4H-quinolizine-3-carboxylic acid 8-(3-S-amino-pyrrolidin-1-yl)-1-cyclopropyl-9-methyl-4-oxo-4H-quinolizine-3-carboxylic acid was prepared according to General Procedure B from methyl 8-(3-S-((tert-butoxycarbonyl)-amino)-pyrrolidin-1-yl)-1-cyclopropyl-9-methyl-4-oxo-4H-quinolizine-3-carboxylate (76 mg, 0.17 mmol) to afford a yellow residue. The residue was treated according to General Procedure C and purified using preparative LCMS to afford the title compound 10 as a yellow solid (5.5 mg, 10% over 2 steps).

ESI-MS m/z: 328 (M+H)$^+$; 1H NMR (400 MHz, DMSO-d6) δ ppm: 9.03 (d, J=10.8 Hz, 1H), 7.90 (s, 1H), 5.41 (s, 1H), 3.90-4.00 (m, 1H), 3.80-3.90 (m, 1H), 3.65-3.80 (m, 1H), 3.50-3.60 (m, 1H), 3.30-3.40 (m, 2H), 2.58 (s, 3H), 2.40-2.60 (m, 1H), 2.26-2.30 (m, 1H), 2.01-2.06 (m, 1H), 1.72-1.76 (m, 1H), 0.95-0.98 (m, 2H), 0.57-0.60 (m, 2H).

Preparation of Compound 11

Preparation of ethyl 8-(4-amino-2-chloro-5-methyl-phenyl)-1-cyclopropyl-9-methyl-4-oxo-4H-quinolizine-3-carboxylate A mixture of ethyl 8-chloro-1-cyclopropyl-9-methyl-4-oxo-4H-quinolizine-3-carboxylate (120 mg, 0.4 mmol), 3-chloro-6-methyl-[4-(4,4,5,5-tetramethyl-[1,3,2]dioxaborolan-2-yl)-aniline (128 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate (20 mL), and washed with water (20 mL). The organic phase was separated, dried, and concentrated. The residue was purified by flash silica column chromatography (hexane:ethyl acetate, 1:3) to afford the title compound as a yellow solid (70 mg, 43%).

ESI-MS m/z: 411 (M+H)$^+$.

Preparation of Compound 11 8-(4-amino-2-chloro-5-methyl-phenyl)-1-cyclopropyl-9-methyl-4-oxo-4H-quinolizine-3-carboxylic acid A solution of ethyl 8-(4-amino-2-chloro-5-methyl-phenyl)-1-cyclopropyl-9-methyl-4-oxo-4H-quinolizine-3-carboxylate (70 mg, 0.171 mmol) in THF (6 mL) and water (2 mL) was treated with LiOH (29 mg, 0.690 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound 11 as yellow solid (51 mg, 78%).

ESI-MS m/z: 383 (M+H)$^+$; 1H NMR (300 MHz, DMSO-d6) δ ppm: 9.28 (d, J=7.5 Hz, 1H), 8.24 (s, 1H), 7.43 (d, J=7.5 Hz, 1H), 6.99 (s, 1H), 6.81 (s, 1H), 5.55 (s, 2H), 2.75 (s, 3H), 2.52-2.54 (m, 1H), 2.07 (s, 3H), 1.01-1.03 (m, 2H), 0.70-0.74 (m, 2H).

Preparation of Compound 13

Preparation of methyl 8-(5-(((tert-butoxycarbonylamino)methyl)thiophen-2-yl)-1-cyclopropyl-9-methyl-4-oxo-4H-quinolizine-3-carboxylate Methyl 8-(5-(((tert-butoxycarbonylamino) methyl)thiophen-2-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 5-(BOC-aminomethyl)thiophene-2-boronic acid (106 mg, 0.41 mmol). Purification by flash silica column chromatography (DCM:MeOH) (1:0 to 9:1) afforded the title compound as a yellow solid (100.3 mg, 72%).

ESI-MS m/z: 469 (M+H)$^+$.

Preparation of 8-(5-((tert-butoxycarbonylamino) methyl)thiophen-2-yl)-1-cyclopropyl-9-methyl-4-oxo-4H-quinolizine-3-carboxylic acid The compound 8-(5-((tert-butoxycarbonylamino) methyl) thiophen-2-yl)-1-cyclopropyl-9-methyl-4-oxo-4H-quinolizine-3-carboxylic acid was prepared according to General Procedure B from methyl 8-(5-((tert-butoxycarbonylamino) methyl)thiophen-2-yl)-1-cyclopropyl-9-methyl-4-oxo-4H-quinolizine-3-carboxylate (76.2 mg, 0.19 mmol) to afford the compound as a yellow solid (54 mg, 68%).

ESI-MS m/z: 455 (M+H)$^+$, 453 (M–H)$^-$.

Preparation of Compound 13HCl (Hydrochloric Salt of Compound 13) 8-(5-(aminomethyl)thiophen-2-yl)-1-cyclopropyl-9-methyl-4-oxo-4H-quinolizine-3-carboxylic acid hydrochloride The compound 8-(5-(aminomethyl)thiophen-2-yl)-1-cyclopropyl-9-methyl-4-oxo-4H-quinolizine-3-carboxylic acid hydrochloride was prepared according to General Procedure C from 8-(5-((tert-butoxycarbonylamino)methyl) thiophen-2-yl)-1-cyclopropyl-9-methyl-4-oxo-4H-quinolizine-3-carboxylic acid (105.3 mg, 0.23 mmol) to afford compound 13HCl as an orange solid (77.2 mg, 85%).

ESI-MS m/z: 355 (M+H)$^+$; 1H NMR (400 MHz, DMSO-d6) δ ppm 9.27 (d, J=7.6 Hz, 1H), 8.80 (s, 2H), 8.26 (s, 1H), 7.63 (d, J=7.3 Hz, 1H), 7.61 (d, J=3.8 Hz, 1H), 7.45 (d, J=3.8 Hz, 1H), 4.35 (s, 2H), 3.03 (s, 3H), 2.50-2.57 (m, 1H), 1.06-1.11 (m, 2H), 0.73-0.77 (m, 2H).

Preparation of Compound 13K (Potassium Salt of Compound 13) potassium 8-(5-(aminomethyl)thiophen-2-yl)-1-cyclopropyl-9-methyl-4-oxo-4H-quinolizine-3-carboxylate The compound potassium 8-(5-(aminomethyl)thiophen-2-yl)-1-cyclopropyl-9-methyl-4-oxo-4H-quinolizine-3-carboxylate was prepared according to General Procedure D from 8-(5-(aminomethyl)thiophen-2-yl)-1-cyclopropyl-9-methyl-4-oxo-4H-quinolizine-3-carboxylic acid hydrochloride (77.2 mg, 0.20 mmol) to afford compound 13K as an orange solid (86.0 mg, 100%).

ESI-MS m/z: 355 (M–K+H)$^+$, 353 (M–K–H)$^-$.

Preparation of Compound 15

Preparation of ethyl 8-(4-methyl-phenyl)-1-cyclopropyl-9-methyl-4-oxo-4H-quinolizine-3-carboxylate A mixture of ethyl 8-chloro-1-cyclopropyl-9-methyl-4-oxo-4H-quinolizine-3-carboxylate (120 mg, 0.400 mmol), 4-methyl-phenyl boronic acid (65 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate (50 mL), and washed with water (2×20 mL). The organic phase was separated, dried, and concentrated. The residue was purified by flash silica column chromatography (hexane:ethyl acetate, 1:2) to afford the title compound as a yellow solid (90 mg, 62%).
ESI-MS m/z: 362 (M+H)$^+$.

Preparation of Compound 15 8-(4-methyl-phenyl)-1-cyclopropyl-9-methyl-4-oxo-4H-quinolizine-3-carboxylic acid A solution of ethyl 8-(4-methylphenyl)-1-cyclopropyl-9-methyl-4-oxo-4H-quinolizine-3-carboxylate (90 mg, 0.249 mmol) in THF (6 mL) and water (2 mL) was treated with LiOH (43 mg, 1.02 mmol). The reaction was heated to 60° C. for 2 h and acidified with 1N HCl to pH 4. The precipitate was dissolved with ethyl acetate (20 mL) and washed with brine (20 mL). The organic phase was separated, dried, and concentrated. The precipitate was filtered to afford the title compound 15 as a yellow solid (65 mg, 78%).
ESI-MS m/z: 334 (M+H)$^+$; $^1$H NMR (300 MHz, DMSO-d6) δ ppm: 9.31 (d, J=7.2 Hz, 1H), 8.24 (s, 1H), 7.54 (d, J=7.2 Hz, 1H), 7.44 (d, J=7.2 Hz, 2H), 7.38 (d, J=7.2 Hz, 2H), 2.84 (s, 3H), 2.52-2.54 (m, 1H), 2.39 (s, 3H), 1.03-1.06 (m, 2H), 0.75-0.77 (m, 2H).

Preparation of Compound 17

Preparation of ethyl 8-(4-amino-3-fluoro-phenyl)-1-cyclopropyl-7-fluoro-9-methyl-4-oxo-4H-quinolizine-3-carboxylate Ethyl 8-(4-amino-3-fluoro-phenyl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (149 mg, 0.46 mmol) and 2-fluoro-4-(4,4,5,5-tetramethyl-1,3,2-dioxaborolan-2-yl)-aniline (134 mg, 0.58 mmol). Purification by flash silica column chromatography (DCM:MeOH) (1:0 to 9:1) afforded the title compound as a yellow solid (18 mg, 10%).
ESI-MS m/z: 399 (M+H)$^+$.

Preparation of Compound 17 8-(4-amino-3-fluoro-phenyl)-1-cyclopropyl-7-fluoro-9-methyl-4-oxo-4H-quinolizine-3-carboxylic acid 8-(4-Amino-3-fluoro-phenyl)-1-cyclopropyl-7-fluoro-9-methyl-4-oxo-4H-quinolizine-3-carboxylic acid was prepared according to General Procedure B from ethyl 8-(4-amino-3-fluoro-phenyl)-1-cyclopropyl-7-fluoro-9-methyl-4-oxo-4H-quinolizine-3-carboxylate (24 mg, 0.06 mmol) to afford the title compound 17 as a yellow solid (19 mg, 85%).
ESI-MS m/z: 371 (M+H)$^+$; 1H NMR (400 MHz, DMSO-d6) δ ppm: 13.99 (br s, 1H), 9.32 (s, 1H), 8.22 (s, 1H), 6.80-7.30 (m, 3H), 5.73 (s, 2H), 2.84 (s, 3H), 2.50-2.60 (m, 1H), 1.04-1.08 (m, 2H), 0.76-0.80 (m, 2H).

Preparation of Compound 17K (Potassium Salt of Compound 17) potassium 8-(4-amino-3-fluoro-phenyl)-1-cyclopropyl-7-fluoro-9-methyl-4-oxo-4H-quinolizine-3-carboxylate Potassium 8-(4-amino-3-fluorop-phenyl)-1-cyclopropyl-7-fluoro-9-methyl-4-oxo-4H-quinolizine-3-carboxylate was prepared according to General Procedure D from 8-(4-amino-3-fluoro-phenyl)-1-cyclopropyl-7-fluoro-9-methyl-4-oxo-4H-quinolizine-3-carboxylic acid (250 mg, 0.68 mmol) and potassium hydroxide to afford the title compound K salt of compound 17 as a yellow solid (276 mg, 90%).
ESI-MS m/z: 371 (M−K+H)$^+$.

Preparation of Compound 18

Preparation of ethyl 8-(3-amino-phenyl)-1-cyclopropyl-7-fluoro-9-methyl-4-oxo-4H-quinolizine-3-carboxylate Ethyl 8-(3-amino-phenyl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (102.5 mg, 0.32 mmol) and (3-amino-phenyl)-boronic acid (54.8 mg, 0.40 mmol). Purification by flash silica column chromatography (DCM:MeOH) (1:0 to 9:1) afforded the title compound as a yellow solid (30 mg, 25%).
ESI-MS m/z: 381 (M+H)$^+$.

Preparation of Compound 18 8-(3-amino-phenyl)-1-cyclopropyl-7-fluoro-9-methyl-4-oxo-4H-quinolizine-3-carboxylic acid 8-(3-Amino-phenyl)-1-cyclopropyl-7-fluoro-9-methyl-4-oxo-4H-quinolizine-3-carboxylic acid was prepared according to General Procedure B from ethyl 8-(3-amino-phenyl)-1-cyclopropyl-7-fluoro-9-methyl-4-oxo-4H-quinolizine-3-carboxylate (140 mg, 0.37 mmol) to afford the title compound 18 as a yellow solid (30 mg, 25%).
ESI-MS m/z: 353 (M+H)$^+$; 1H NMR (400 MHz, DMSO-d6) δ ppm: 9.35 (d, J=5.8 Hz, 1H), 8.25 (s, 1H), 7.22 (t, J=7.6 Hz, 1H), 6.71 (dd, J=1.6 Hz and J=8.1 Hz, 1H), 6.57 (s, 1H), 6.51 (d, J=7.6 Hz, 1H), 5.40 (br s, 2H), 2.82 (s, 3H), 2.53-2.63 (m, 1H), 1.04-1.07 (m, 2H), 0.76-0.78 (m, 2H).

Preparation of Compound 19

Preparation of ethyl 8-(4-carbamoyl-phenyl)-1-cyclopropyl-7-fluoro-9-methyl-4-oxo-4H-quinolizine-3-carboxylate Ethyl 8-(4-carbamoyl-phenyl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (500 mg, 1.54 mmol) and (4-carbamoyl-phenyl)-boronic acid (305.7 mg, 1.85 mmol). Purification by flash silica column chromatography (DCM:MeOH) (1:0 to 9:1) afforded the title compound as a yellow solid (540 mg, 85%).
ESI-MS m/z: 409 (M+H)$^+$, 453 (M+HCOO)$^-$.

Preparation of Compound 19 8-(4-carbamoyl-phenyl)-1-cyclopropyl-7-fluoro-9-methyl-4-oxo-4H-quinolizine-3-carboxylic acid 8-(4-Carbamoyl-phenyl)-1-cyclopropyl-7-fluoro-9-methyl-4-oxo-4H-quinolizine-3-carboxylic acid was prepared according to General Procedure B from ethyl 8-(4-carbamoyl-phenyl)-1-cyclopropyl-7-fluoro-9-methyl-4-oxo-4H-quinolizine-3-carboxylate (540 mg, 1.32 mmol) and reacted for 10 days at 30° C. to afford the title compound 19 as a yellow solid: (360 mg, 71%).

ESI-MS m/z: 381 (M+H)+; 1H NMR (400 MHz, DMSO-d6) δ ppm: 13.94 (s, 1H), 9.42 (d, J=5.6 Hz, 1H), 8.28 (s, 1H), 8.16 (s, 1H), 8.08 (d, J=8.1 Hz, 2H), 7.57-7.60 (m, 3H), 2.80 (s, 3H), 2.50-2.60 (m, 1H), 1.06-1.08 (m, 2H), 0.76-0.80 (m, 2H).

Preparation of Compound 19K (Potassium Salt of Compound 19) potassium 8-(4-carbamoyl-phenyl)-1-cyclopropyl-7-fluoro-9-methyl-4-oxo-4H-quinolizine-3-carboxylate Potassium 8-(4-carbamoyl-phenyl)-1-cyclopropyl-7-fluoro-9-methyl-4-oxo-4H-quinolizine-3-carboxylate was prepared according to General Procedure D from 8-(4-carbamoyl-phenyl)-1-cyclopropyl-7-fluoro-9-methyl-4-oxo-4H-quinolizine-3-carboxylic acid (310 mg, 0.82 mmol) to afford the title compound K salt of compound 19 as a yellow solid (345 mg, 100%).
ESI-MS m/z: 381 (M−K+H)+.

Preparation of Compound 20

Preparation of methyl 8-(4-amino-2-fluoro-phenyl)-1-cyclopropyl-9-methyl-4-oxo-4H-quinolizine-3-carboxylate Methyl 8-(4-amino-2-fluoro-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 3-fluoro-4-(4,4,5,5-tetramethyl-1,3,2-dioxaborolan-2-yl)-aniline (122 mg, 0.51 mmol). Purification by flash silica column chromatography (DCM:MeOH) (1:0 to 94:6) afforded the title compound 20 as a yellow solid (87 mg, 64%).
ESI-MS m/z: 367 (M+H)+.

Preparation of Compound 20 8-(4-amino-2-fluoro-phenyl)-1-cyclopropyl-9-methyl-4-oxo-4H-quinolizine-3-carboxylic acid 8-(4-Amino-2-fluoro-phenyl)-1-cyclopropyl-9-methyl-4-oxo-4H-quinolizine-3-carboxylic acid was prepared according to General Procedure B from methyl 8-(4-amino-2-fluoro-phenyl)-1-cyclopropyl-9-methyl-4-oxo-4H-quinolizine-3-carboxylate (87 mg, 0.24 mmol) to afford the title compound 20 as a yellow solid (50 mg, 59%).
ESI-MS m/z: 353 (M+H)+; 1H NMR (400 MHz, DMSO-d6) δ ppm: 9.27 (d, J=7.3 Hz, 1H), 8.27 (s, 1H), 7.48 (s, 1H), 7.18 (t, J=8.6 Hz, 1H), 6.57 (dd, J=8.3 Hz, J=1.8 Hz, 1H), 6.49 (dd, J=13.4 Hz, J=1.8 Hz, 1H), 5.92 (s, 2H), 2.80 (s, 3H), 2.40-2.60 (m, 1H), 1.03-1.06 (m, 2H), 0.70-0.72 (m, 2H).

Preparation of Compound 21

Preparation of methyl 8-(3-amino-4-fluoro-phenyl)-1-cyclopropyl-9-methyl-4-oxo-4H-quinolizine-3-carboxylate Methyl 8-(3-amino-4-fluoro-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 2-fluoro-5-(4,4,5,5-tetramethyl-1,3,2-dioxaborolan-2-yl)-aniline (122 mg, 0.51 mmol). Purification by flash silica column chromatography (DCM:MeOH) (1:0 to 94:6) afforded the title compound as a yellow solid (128 mg, 98%).
ESI-MS m/z: 367 (M+H)+.

Preparation of Compound 21 8-(3-amino-4-fluoro-phenyl)-1-cyclopropyl-9-methyl-4-oxo-4H-quinolizine-3-carboxylic acid 8-(3-Amino-4-fluoro-phenyl)-1-cyclopropyl-9-methyl-4-oxo-4H-quinolizine-3-carboxylic acid was prepared according to General Procedure B from methyl 8-(3-amino-4-fluorophenyl)-1-cyclopropyl-9-methyl-4-oxo-4H-quinolizine-3-carboxylate (123 mg, 0.35 mmol) to afford the title compound 21 as a yellow solid (60 mg, 49%).
ESI-MS m/z: 353 (M+H)+; 1H NMR (400 MHz, DMSO-d6) δ ppm: 9.31 (d, J=7.3 Hz, 1H), 8.26 (s, 1H), 7.50 (d, J=7.3 Hz, 1H), 7.18 (dd, J=8.3 Hz, J=11.4 Hz, 1H), 6.89 (dd, J=2.0 Hz, J=8.6 Hz, 1H), 6.63-6.67 (m, 1H), 5.44 (s, 2H), 2.85 (s, 3H), 2.40-2.54 (m, 1H), 1.04-1.07 (m, 2H), 0.76-0.78 (m, 2H).

Preparation of Compound 22

Preparation of methyl 8-(3-amino-5-fluoro-phenyl)-1-cyclopropyl-9-methyl-4-oxo-4H-quinolizine-3-carboxylate Methyl 8-(3-amino-5-fluoro-phenyl)-1-cyclopropyl-9-methyl-4-oxo-4H-quinolizine-carboxylate was prepared according to General Procedure A from methyl 8-chloro-1-cyclopropyl-9-methyl-4-oxo-4H-quinolizine-3-carboxylate (100 mg, 0.34 mmol) and 3-amino-5-fluoro-phenyl-boronic acid (80 mg, 0.51 mmol). Purification by flash silica column chromatography (DCM:MeOH) (1:0 to 94:6) afforded the title compound as a yellow solid (108 mg, 81%).
ESI-MS m/z: 367 (M+H)+.

Preparation of Compound 22 8-(3-amino-5-fluoro-phenyl)-1-cyclopropyl-9-methyl-4-oxo-4H-quinolizine-3-carboxylic acid 8-(3-Amino-5-fluoro-phenyl)-1-cyclopropyl-9-methyl-4-oxo-4H-quinolizine-3-carboxylic acid was prepared according to General Procedure B from methyl 8-(3-amino-5-fluorophenyl)-1-cyclopropyl-9-methyl-4-oxo-4H-quinolizine-3-carboxylate (108 mg, 0.29 mmol) to afford the title compound 22 as a yellow solid (69 mg, 67%).
ESI-MS m/z: 353 (M+H)+; 1H NMR (400 MHz, DMSO-d6) δ ppm: 9.22 (d, J=7.3 Hz, 1H), 8.48 (s, 1H), 7.19 (d, J=7.6 Hz, 1H), 6.36-6.44 (m, 3H), 6.68 (s, 2H), 2.81 (s, 3H), 2.40-2.50 (m, 1H), 1.02-1.04 (m, 2H), 0.70-0.72 (m, 2H).

Preparation of Compound 23

Preparation of methyl 8-(3-fluoro-phenyl)-1-cyclopropyl-9-methyl-4-oxo-4H-quinolizine-3-carboxylate Methyl 8-(3-fluoro-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 3-fluoro-phenyl-boronic acid (71 mg, 0.51 mmol). Purification by flash silica column chromatography (DCM:MeOH) (1:0 to 94:6) afforded the title compound as a yellow solid (96 mg, 77%).
ESI-MS m/z: 352 (M+H)$^+$.

Preparation of Compound 23 8-(3-fluoro-phenyl)-1-cyclopropyl-9-methyl-4-oxo-4H-quinolizine-3-carboxylic acid 8-(3-Fluoro-phenyl)-1-cyclopropyl-9-methyl-4-oxo-4H-quinolizine-3-carboxylic acid was prepared according to General Procedure B from methyl 1-cyclopropyl-8-(3-fluoro-phenyl)-9-methyl-4-oxo-4H-quinolizine-3-carboxylate (96 mg, 0.27 mmol) to afford the title compound compound 23 as a yellow solid (21 mg, 23%).
ESI-MS m/z: 338 (M+H)$^+$; 1H NMR (400 MHz, DMSO-d6) δ ppm: 9.34 (d, J=7.3 Hz, 1H), 8.28 (s, 1H), 7.57-7.65 (m, 2H), 7.39-7.47 (m, 3H), 2.86 (s, 3H), 2.40-2.50 (m, 1H), 1.07-1.09 (m, 2H), 0.80-0.82 (m, 2H).

Preparation of Compound 24

Preparation of methyl 8-(4-amino-3-chloro-phenyl)-1-cyclopropyl-9-methyl-4-oxo-4H-quinolizine-3-carboxylate Methyl 8-(4-amino-3-chloro-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (76 mg, 0.26 mmol) and 2-chloro-4-(4,4,5,5-tetramethyl-1,3,2-dioxaborolan-2-yl)-aniline (78 mg, 0.31 mmol). Purification by flash silica column chromatography (DCM:MeOH) (1:0 to 94:6) afforded the title compound 24 as a yellow solid (63 mg, 62%).
ESI-MS m/z: 387 (M+H)$^+$.

Preparation of Compound 24 8-(4-amino-3-chloro-phenyl)-1-cyclopropyl-9-methyl-4-oxo-4H-quinolizine-3-carboxylic acid 8-(4-Amino-3-chloro-phenyl)-1-cyclopropyl-9-methyl-4-oxo-4H-quinolizine-3-carboxylic acid was prepared according to General Procedure B from methyl 8-(4-amino-3-chloro-phenyl)-1-cyclopropyl-9-methyl-4-oxo-4H-quinolizine-3-carboxylate (63 mg, 0.16 mmol) to afford the title compound 24 as a yellow solid (37 mg, 62%).
ESI-MS m/z: 369 (M+H)$^+$; 1H NMR (400 MHz, DMSO-d6) δ ppm: 9.21 (d, J=7.3 Hz, 1H), 8.38 (s, 1H), 7.43 (s, 1H), 7.30 (s, 1H), 7.26 (d, J=14.5 Hz, 1H), 6.94 (d, J=8.3 Hz, 1H), 5.82 (s, 2H), 2.85 (s, 3H), 2.40-2.50 (m, 1H), 1.04-1.06 (m, 2H), 0.72-0.74 (m, 2H).

Preparation of Compound 25

Preparation of methyl 8-(4-amino-3-methoxy-phenyl)-1-cyclopropyl-9-methyl-4-oxo-4H-quinolizine-3-carboxylate Methyl 8-(4-amino-3-methoxy-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (76 mg, 0.26 mmol) and 2-methoxy-4-(4,4,5,5-tetramethyl-1,3,2-dioxaborolan-2-yl)-aniline (78 mg, 0.31 mmol). Purification by flash silica column chromatography (DCM:MeOH) (1:0 to 94:6) afforded the title compound as a yellow solid (41 mg, 40%).
ESI-MS m/z: 379 (M+H)$^+$.

Preparation of Compound 25 8-(4-amino-3-methoxy-phenyl)-1-cyclopropyl-9-methyl-4-oxo-4H-quinolizine-3-carboxylic acid 8-(4-Amino-3-methoxy-phenyl)-1-cyclopropyl-9-methyl-4-oxo-4H-quinolizine-3-carboxylic acid was prepared according to General Procedure B from methyl 8-(4-amino-3-methoxy-phenyl)-1-cyclopropyl-9-methyl-4-oxo-4H-quinolizine-3-carboxylate (41 mg, 0.11 mmol) to afford the title compound 25 as a yellow solid (29 mg, 92%).
ESI-MS m/z: 365 (M+H)$^+$; 1H NMR (400 MHz, DMSO-d6) δ ppm: 9.27 (d, J=7.3 Hz, 1H), 8.19 (s, 1H), 7.43 (d, J=7.3 Hz, 1H), 7.03 (s, 1H), 6.99 (dd, J=1.8 Hz, J=8.1 Hz, 1H), 6.80 (d, J=8.1 Hz, 1H), 5.38 (s, 2H), 3.86 (s, 3H), 2.92 (s, 3H), 2.40-2.54 (m, 1H), 1.06-1.10 (m, 2H), 0.76-0.80 (m, 2H).

Preparation of Compound 26

Preparation of methyl 8-(4-acetamido-phenyl)-1-cyclopropyl-9-methyl-4-oxo-4H-quinolizine-3-carboxylate Methyl 8-(4-acetamido-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (77 mg, 0.26 mmol) and (4-acetamido-phenyl)-boronic acid (56 mg, 0.31 mmol). Purification by flash silica column chromatography (DCM:MeOH) (1:0 to 94:6) afforded the title compound 26 as a yellow solid (93 mg, 90%).
ESI-MS m/z: 391 (M+H)$^+$.

Preparation of Compound 26 8-(4-acetamido-phenyl)-1-cyclopropyl-9-methyl-4-oxo-4H-quinolizine-3-carboxylic acid 8-(4-Acetamido-phenyl)-1-cyclopropyl-9-methyl-4-oxo-4H-quinolizine-3-carboxylic acid was prepared according to General Procedure: using methyl 8-(4-acetamido-phenyl)-1-cyclopropyl-9-methyl-4-oxo-4H-quinolizine-3-carboxylate (93 mg, 0.24 mmol) to afford the title compound 26 as a yellow solid (45 mg, 50%).
ESI-MS m/z: 377 (M+H)$^+$; 1H NMR (400 MHz, DMSO-d6) δ ppm: 10.20 (s, 1H), 9.32 (d, J=7.3 Hz, 1H), 8.25 (s, 1H), 7.79 (d, J=8.4 Hz, 2H), 7.58 (d, J=7.3 Hz, 1H), 7.53 (d, J=8.1 Hz, 2H), 2.88 (s, 3H), 2.40-2.54 (m, 1H), 2.10 (s, 3H), 1.07-1.09 (m, 2H), 0.77-0.79 (m, 2H).

Preparation of Compound 27

Preparation of methyl 8-(4-(methylsulfonamido)-phenyl)-1-cyclopropyl-9-methyl-4-oxo-4H-quinolizine-3-carboxylate Methyl 8-(4-(methylsulfonamido)-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (74 mg, 0.25 mmol) and N-(4-(4,4,5,5-tetramethyl-1,3,2-dioxaborolan-2-yl)-phenyl)-methane-sulfonamide (96 mg, 0.32 mmol). Compound precipitated from solution and was filtered off and dried in vacuum to afford the title compound 27 as a yellow solid (83 mg, 77%).

ESI-MS m/z: 427 (M+H)+.

Preparation of Compound 27 8-(4-(methylsulfonamido)-phenyl)-1-cyclopropyl-9-methyl-4-oxo-4H-quinolizine-3-carboxylic acid 8-(4-(Methylsulfonamido)-phenyl)-1-cyclopropyl-9-methyl-4-oxo-4H-quinolizine-3-carboxylic acid was prepared according to General Procedure B from methyl 8-(4-(methylsulfonamido)-phenyl)-1-cyclopropyl-9-methyl-4-oxo-4H-quinolizine-3-carboxylate (83 mg, 0.20 mmol) to afford the title compound 27 as a yellow solid (53 mg, 64%).

ESI-MS m/z: 413 (M+H)+; 1H NMR (400 MHz, DMSO-d6) δ ppm: 10.1 (s, 1H), 9.33 (d, J=7.3 Hz, 1H), 8.26 (s, 1H), 7.55-7.58 (m, 3H), 7.39 (d, J=8.6 Hz, 2H), 3.11 (s, 3H), 2.88 (s, 3H), 2.40-2.55 (m, 1H), 1.06-1.09 (m, 2H), 0.78-0.80 (m, 2H).

Preparation of Compound 28

Preparation of methyl 8-(4-(methylamino)-phenyl)-1-cyclopropyl-9-methyl-4-oxo-4H-quinolizine-3-carboxylate Methyl 8-(4-(methylamino)-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (74 mg, 0.25 mmol) and N-methyl-4-(4,4,5,5-tetramethyl-1,3,2-dioxaborolan-2-yl)-aniline (71 mg, 0.31 mmol). Purification by flash silica column chromatography (DCM:MeOH) (1:0 to 94:6) afforded the title compound as a yellow solid (81 mg, 81%).

ESI-MS m/z: 363 (M+H)+.

Preparation of Compound 28 8-(4-(methylamino)-phenyl)-1-cyclopropyl-9-methyl-4-oxo-4H-quinolizine-3-carboxylic acid 8-(4-(Methylamino)-phenyl)-1-cyclopropyl-9-methyl-4-oxo-4H-quinolizine-3-carboxylic acid was prepared according to General Procedure B from methyl 8-(4-(methylamino)-phenyl)-1-cyclopropyl-9-methyl-4-oxo-4H-quinolizine-3-carboxylate (81 mg, 0.22 mmol) to afford the title compound 28 as a yellow solid (55 mg, 72%).

ESI-MS m/z: 349 (M+H)+; 1H NMR (400 MHz, DMSO-d6) δ ppm: 9.27 (d, J=7.3 Hz, 1H), 8.20 (s, 1H), 9.59 (d, J=7.3 Hz, 1H), 7.39 (d, J=8.6 Hz, 2H), 6.70 (d, J=8.6 Hz, 2H), 6.28 (d, J=5.1 Hz, 1H), 2.90 (s, 3H), 2.76 (d, J=4.8 Hz, 3H), 2.40-2.52 (m, 1H), 1.06-1.08 (m, 2H), 0.75-0.77 (m, 2H).

Preparation of Compound 29

Preparation of methyl 8-(pyridin-4-yl)-1-cyclopropyl-9-methyl-4-oxo-4H-quinolizine-3-carboxylate Methyl 8-(pyridin-4-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (500 mg, 1.71 mmol) and pyridin-4-yl-boronic acid (253 mg, 2.05 mmol). Purification by flash silica column chromatography (DCM:MeOH) (1:0 to 9:1) afforded the title compound as a yellow solid (400 mg, 69%).

ESI-MS m/z: 373 (M+K)+, 357 (M+Na)+, 335 (M+H)+.

Preparation of Compound 29 8-(pyridin-4-yl)-1-cyclopropyl-9-methyl-4-oxo-4H-quinolizine-3-carboxylic acid 8-(Pyridin-4-yl)-1-cyclopropyl-9-methyl-4-oxo-4H-quinolizine-3-carboxylic acid was prepared according to General Procedure B from methyl 1-cyclopropyl-9-methyl-4-oxo-8-(pyridin-4-yl)-4H-quinolizine-3-carboxylate (400 mg, 1.20 mmol) to afford the title compound 29 as a yellow solid (262 mg, 68%).

ESI-MS m/z: 321 (M+H)+; 1H NMR (400 MHz, DMSO-d6) δ ppm: 14.05 (s, 1H), 9.36 (d, J=7.3 Hz, 1H), 8.79 (d, J=5.8 Hz, 2H), 8.30 (s, 1H), 7.55-7.59 (m, 3H), 2.83 s, (3H), 2.50-2.60 (m, 1H), 1.05-1.10 (m, 2H), 0.79-0.84 (m, 2H).

Preparation of Compound 29K (Potassium Salt of Compound 29) potassium 8-(pyridin-4-yl)-1-cyclopropyl-9-methyl-4-oxo-4H-quinolizine-3-carboxylate Potassium 8-(pyridin-4-yl)-1-cyclopropyl-9-methyl-4-oxo-4H-quinolizine-3-carboxylate was prepared according to General Procedure D from 8-(pyridin-4-yl)-1-cyclopropyl-9-methyl-4-oxo-4H-quinolizine-3-carboxylic acid (compound 16) (250 mg, 0.78 mmol) to afford the K salt of title compound 29 as a yellow solid (290 mg, 100%).

ESI-MS m/z: 321 (M−K+H)+; 1H NMR (400 MHz, CD3OD) δ ppm: 9.43 (d, J=7.3 Hz, 1H), 8.72 (d, J=5.8 Hz, 2H), 8.62 (s, 1H), 7.58 (d, J=5.8 Hz, 2H), 7.20 (d, J=3.6 Hz, 2H), 2.87 (s, 3H), 2.46-2.53 (m, 1H), 0.80-1.10 (m, 2H), 0.84-0.86 (m, 2H).

Preparation of Compound 30

Preparation of methyl 8-(pyridin-3-yl)-1-cyclopropyl-9-methyl-4-oxo-4H-quinolizine-3-carboxylate Methyl 8-(pyridin-3-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and pyridin-3-ylboronic acid (63 mg, 0.51 mmol). Purification by flash silica column chromatography (DCM:MeOH) (1:0 to 94:6) afforded the title compound as a yellow solid (100 mg, 87%). ESI-MS m/z: 335 (M+H)+.

Preparation of Compound 30 8-(pyridin-3-yl)-1-cyclopropyl-9-methyl-4-oxo-4H-quinolizine-3-carboxylic acid 8-(Pyridin-3-yl)-1-cyclopropyl-9-methyl-4-oxo-4H-quinolizine-3-carboxylic acid was prepared according to General Procedure B from methyl 1-cyclopropyl-9-methyl-4-oxo-8-(pyridin-3-yl)-4H-quinolizine-3-carboxylate (100 mg, 0.30 mmol) to afford the title compound 30 as a yellow solid (84 mg, 87%).

ESI-MS m/z: 321 (M+H)+; 1H NMR (400 MHz, DMSO-d6) δ ppm: 9.35 (d, J=7.3 Hz, 1H), 8.73-8.78 (s, 2H), 8.28 (s, 1H), 8.02-8.05 (m, 1H), 7.61-7.65 (m, 2H), 2.86 (s, 3H), 2.40-2.54 (m, 1H), 1.06-1.10 (m, 2H), 0.80-0.83 (m, 2H).

Preparation of Compound 31

Preparation of 2-methyl-4-(4,4,5,5-tetramethyl-1,3,2-dioxaborolan-2-yl)-aniline

Potassium acetate (317 mg, 3.22 mmol), 4,4,4',4',5,5,5',5'-octamethyl-2,2'-bi(1,3,2-dioxaborolane) (300 mg, 1.18 mmol) and 4-bromo-2-methyl-aniline (200 mg, 1.08 mmol) were dissolved in DMSO (3 mL). The reaction mixture was degassed using argon. 1,1'-Bis-diphenylphosphine ferrocene palladium(II) dichloride (24 mg, 0.03 mmol) was added and the reaction mixture was heated at 80° C. for 5 h. The reaction mixture was cooled to room temperature and diluted with ethyl acetate (20 mL). The organic layer was washed with saturated sodium bicarbonate (20 mL) and brine (20 mL). The organic layer was dried with sodium sulfate, filtered and purified by flash silica column chromatography (heptane:ethyl acetate, 0-40%) to obtain a crude mixture of starting material and product. The mixture was purified using reversed phase column chromatography to obtain the title compound as a clear oil (50 mg, 21%).

ESI-MS m/z: 234 (M+H)$^+$.

Preparation of methyl 8-(4-amino-3-methyl-phenyl)-1-cyclopropyl-9-methyl-4-oxo-4H-quinolizine-3-carboxylate Methyl 8-(4-amino-3-methyl-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (50 mg, 0.17 mmol) and 4-(4,4,5,5-tetramethyl-1,3,2-dioxaborolan-2-yl)-aniline (52 mg, 0.22 mmol). Purification by flash silica column chromatography (DCM:MeOH) (1:0 to 9:1) afforded the title compound as a yellow solid (31 mg, 50%).

ESI-MS m/z: 363 (M+H)$^+$.

Preparation of Compound 31 8-(4-amino-3-methyl-phenyl)-1-cyclopropyl-9-methyl-4-oxo-4H-quinolizine-3-carboxylic acid 8-(4-Amino-3-methy-phenyl)-1-cyclopropyl-9-methyl-4-oxo-4H-quinolizine-3-carboxylic acid was prepared according to General Procedure B from methyl 8-(4-amino-3-methyl-phenyl)-1-cyclopropyl-9-methyl-4-oxo-4H-quinolizine-3-carboxylate (31 mg, 0.09 mmol) to afford the title compound 31 as a yellow solid (19 mg, 60%).

ESI-MS m/z: 349 (M+H)$^+$; 1H NMR (400 MHz, DMSO-d6) δ ppm: 13.99 (s, 1H), 9.16-9.25 (m, 1H), 8.21-8.34 (m, 1H), 7.52-7.54 (m, 2H), 7.16-7.20 (m, 1H), 6.76 (d, J=8.1 Hz, 1H), 5.43 (s, 2H), 2.99 (s, 3H), 2.89 (s, 3H), 2.40-2.50 (m, 1H), 1.03-1.07 (m, 2H), 0.70-0.75 (m, 2H).

Preparation of Compound 32

Preparation of methyl 8-(2-fluoro-pyridin-4-yl)-1-cyclopropyl-9-methyl-4-oxo-4H-quinolizine-3-carboxylate Methyl 8-(2-fluoro-pyridin-4-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 2-fluoro-pyridin-4-yl-boronic acid (72 mg, 0.51 mmol). Purification by flash silica column chromatography (DCM:MeOH) (1:0 to 94:6) afforded the title compound as a yellow solid (107 mg, 89%).

ESI-MS m/z: 353 (M+H)$^+$.

Preparation of Compound 32 8-(2-fluoro-pyridin-4-yl)-1-cyclopropyl-9-methyl-4-oxo-4H-quinolizine-3-carboxylic acid 8-(2-Fluoro-pyridin-4-yl)-1-cyclopropyl-9-methyl-4-oxo-4H-quinolizine-3-carboxylic acid was prepared according to General Procedure B from methyl 8-(2-fluoro-pyridin-4-yl)-1-cyclopropyl-9-methyl-4-oxo-4H-quinolizine-3-carboxylate (107 mg, 0.30 mmol) to afford the title compound 32 as a yellow solid (53 mg, 52%).

ESI-MS m/z: 339 (M+H)$^+$; 1H NMR (400 MHz, DMSO-d6) δ ppm: 9.21-9.31 (m, 1H), 8.52 (s, 1H), 8.39-8.47 (m, 1H,), 7.20-7.60 (m, 3H), 2.80 (s, 3H), 2.50-2.60 (m, 1H), 0.98-1.13 (m, 2H), 0.71-0.81 (m, 2H).

Preparation of Compound 33

Preparation of methyl 8-(6-amino-pyridin-3-yl)-1-cyclopropyl-9-methyl-4-oxo-4H-quinolizine-3-carboxylate Methyl 8-(6-amino-pyridin-3-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 5-(4,4,5,5-tetramethyl-1,3,2-dioxaborolan-2-yl)-pyridin-2-amine (113 mg, 0.51 mmol). Purification by flash silica column chromatography (DCM:MeOH) (1:0 to 94:6) afforded the title compound as a yellow solid (135 mg, 100%).

ESI-MS m/z: 350 (M+H)$^+$.

Preparation of Compound 33 8-(6-amino-pyridin-3-yl)-1-cyclopropyl-9-methyl-4-oxo-4H-quinolizine-3-carboxylic acid 8-(6-Amino-pyridin-3-yl)-1-cyclopropyl-9-methyl-4-oxo-4H-quinolizine-3-carboxylic acid was prepared according to General Procedure B from methyl 8-(6-amino-pyridin-3-yl)-1-cyclopropyl-9-methyl-4-oxo-4H-quinolizine-3-carboxylate (61 mg, 0.17 mmol) to afford the title compound 33 as a yellow solid (34 mg, 60%).

ESI-MS m/z: 336 (M+H)$^+$; 1H NMR (400 MHz, DMSO-d6) δ ppm: 9.20 (d, J=7.6 Hz, 1H), 8.47 (s, 1H), 8.33 (s, 1H), 8.12 (s, 1H), 7.60 (dd, J=2.3 Hz, J=8.6 Hz, 1H), 8.29 (d, J=6.6 Hz, 1H), 6.59 (d, J=8.8 Hz, 1H), 6.39 (s, 2H), 2.84 (s, 3H), 2.50-2.60 (m, 1H), 1.23 (s, 2H), 1.03-1.07 (m, 4H) 0.70-0.72 (m, 2H).

Preparation of Compound 33K (Potassium Salt of Compound 33) potassium 8-(6-amino-pyridin-3-yl)-1-cyclopropyl-9-methyl-4-oxo-4H-quinolizine-3-carboxylate Potassium 8-(6-amino-pyridin-3-yl)-1-cyclopropyl-9-methyl-4-oxo-4H-quinolizine-3-carboxylate was prepared according to General Procedure D from 8-(6-amino-pyridin-3-yl)-1-cyclopropyl-9-methyl-4-oxo-4H-quinolizine-3-carboxylic acid (510 mg, 1.52 mmol) to afford the K salt of compound 33 as a yellow solid (564 mg, 99%).

ESI-MS m/z: 336 (M−K+H)$^+$.

Preparation of Compound 34

Preparation of methyl 1-cyclopropyl-8-(1H-indol-5-yl)-9-methyl-4-oxo-4H-quinolizine-3-carboxylate Methyl 8-(1H-indol-5-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 1H-indol-5-yl-boronic acid (83 mg, 0.51 mmol) to afford the title compound as a yellow solid (60 mg, 47%).

ESI-MS m/z: 373 (M+H)$^+$.

Preparation of Compound 34 8-(1H-indol-5-yl)-1-cyclopropyl-9-methyl-4-oxo-4H-quinolizine-3-carboxylic acid 8-(1H-Indol-5-yl)-1-cyclopropyl-9-methyl-4-oxo-4H-quinolizine-3-carboxylic acid was prepared according to General Procedure B from methyl 8-(1H-indol-5-yl)-1-cyclopropyl-9-methyl-4-oxo-4H-quinolizine-3-carboxylate (60 mg, 0.16 mmol) to afford the title compound compound 34 as a yellow solid (20 mg, 35%).

ESI-MS m/z: 359 (M+H)$^+$; 1H NMR (400 MHz, DMSO-d6) δ ppm: 11.35 (s, 1H), 9.24 (d, J=7.0 Hz, 1H), 8.48 (s, 1H), 7.70 (s, 1H), 7.50-7.60 (m, 2H), 7.46 (s, 1H), 7.31 (d, J=7.6 Hz, 1H), 7.22 (d, J=7.8 Hz, 1H), 6.54 (s, 1H), 2.84 (s, 3H), 2.50-2.60 (m, 1H), 1.00-1.08 (m, 2H), 0.72-0.76 (m, 2H).

Preparation of Compound 35

Preparation of methyl 8-(1H-indazol-5-yl)-1-cyclopropyl-9-methyl-4-oxo-4H-quinolizine-3-carboxylate Methyl 8-chloro-1-cyclopropyl-9-methyl-4-oxo-4H-quinolizine-3-carboxylate (100 mg, 0.34 mmol), cesium carbonate (335 mg, 1.03 mmol) and 5-(4,4,5,5-tetramethyl-1,3,2-dioxaborolan-2-yl)-1H-indazole (92 mg, 0.38 mmol) were added to a mixture of 1,2-dimethoxyethane (3 mL) and water (1 mL). The mixture was degassed with argon. 1,1'-Bis-(diphenylphosphino)-ferrocene) palladium dichloride (28 mg, 0.03 mmol) was added. The reaction mixture was heated at 150° C. in a microwave oven under argon atmosphere for 0.25 h. The reaction mixture was cooled. The mixture was diluted with DCM (3 mL) and water was added (3 mL). The layers were separated using a phase separator and the aqueous layer was extracted with DCM (2×5 mL). The combined organic layers were concentrated in vacuum. The crude product was purified by flash silica column chromatography (DCM:MeOH) (1:0 to 9:1) and dried in vacuum to afford the title compound as a yellow solid (93 mg, 72%).

ESI-MS m/z: 374 (M+H)$^+$.

Preparation of Compound 35 8-(1H-indazol-5-yl)-1-cyclopropyl-9-methyl-4-oxo-4H-quinolizine-3-carboxylic acid 8-(1H-Indazol-5-yl)-1-cyclopropyl-9-methyl-4-oxo-4H-quinolizine-3-carboxylic acid was prepared according to General Procedure B from methyl 8-(1H-indazol-5-yl)-1-cyclopropyl-9-methyl-4-oxo-4H-quinolizine-3-carboxylate (555 mg, 1.49 mmol) to afford the title compound compound 35 as a yellow solid (200 mg, 37%).

ESI-MS m/z: 360 (M+H)$^+$; ([M–H]$^-$=358.2; 100%); 1H NMR (400 MHz, DMSO-d6) δ ppm: 14.13 (s, 1H), 13.35 (s, 1H), 9.36 (d, J=7.3 Hz, 1H), 8.25 (d, J=15.9 Hz, 2H), 8.01 (s, 1H), 7.74 (d, J=8.6 Hz, 1H), 7.67 (d, J=7.6 Hz, 1H), 7.54 (d, J=9.6 Hz, 1H), 2.90 (s, 3H), 2.40-2.60 (m, 1H), 1.07-1.11 (m, 2H), 0.79-0.82 (m, 2H).

Preparation of Compound 35K (Potassium Salt of Compound 35) potassium 8-(1H-indazol-5-yl)-1-cyclopropyl-9-methyl-4-oxo-4H-quinolizine-3-carboxylate Potassium 8-(1H-indazol-5-yl)-1-cyclopropyl-9-methyl-4-oxo-4H-quinolizine-3-carboxylate was prepared according to General Procedure D from 8-(1H-indazol-5-yl)-1-cyclopropyl-9-methyl-4-oxo-4H-quinolizine-3-carboxylic acid (180 mg, 0.50 mmol) to afford the K salt of compound 35 as a yellow solid (195 mg, 98%).

ESI-MS m/z: 360 (M–K+H)$^+$.

Preparation of Compound 36

Preparation of methyl 8-(4-ureido-phenyl)-1-cyclopropyl-9-methyl-4-oxo-4H-quinolizine-3-carboxylate Methyl 8-(4-ureido-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (75 mg, 0.26 mmol) and 1-(4-(4,4,5,5-tetramethyl-1,3,2-dioxaborolan-2-yl)-phenyl)-urea (84 mg, 0.32 mmol). Compound precipitated from solution and was filtered off and dried in vacuum to afford the title compound as a yellow solid (29 mg, 26%).

ESI-MS m/z: 392 (M+H)$^+$.

Preparation of Compound 36 8-(4-ureido-phenyl)-1-cyclopropyl-9-methyl-4-oxo-4H-quinolizine-3-carboxylic acid 8-(4-Ureido-phenyl)-1-cyclopropyl-9-methyl-4-oxo-4H-quinolizine-3-carboxylic acid was prepared according to General Procedure B from methyl 8-(4-ureido-phenyl)-1-cyclopropyl-9-methyl-4-oxo-4H-quinolizine-3-carboxylate (28 mg, 0.07 mmol) to afford the title compound compound 36 as a yellow solid (15 mg, 58%).

ESI-MS m/z: 378 (M+H)$^+$; 1H NMR (400 MHz, DMSO-d6) δ ppm: 14.10 (s, 1H), 9.30 (d, J=7.6 Hz, 1H), 9.09 (s, 1H), 8.23 (s, 1H), 7.57-7.63 (m, 3H), 7.46 (d, J=8.6 Hz, 2H), 6.04 (s, 2H), 2.89 (s, 3H), 2.40-2.55 (m, 1H), 1.06-1.08 (m, 2H,), 0.76-0.78 (m, 2H).

Preparation of Compound 37

Preparation of methyl 8-(4-(dimethylamino)-phenyl)-1-cyclopropyl-9-methyl-4-oxo-4H-quinolizine-3-carboxylate Methyl 8-(4-(dimethylamino)-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (77 mg, 0.26 mmol) and (4-(dimethylamino)-phenyl)-boronic acid (56 mg, 0.34 mmol). Purification by flash silica column chromatography (DCM:MeOH) (1:0 to 94:6) afforded the title compound as a yellow solid (39 mg, 31%).

ESI-MS m/z: 377 (M+H)$^+$.

Preparation of Compound 37 8-(4-(dimethylamino)-phenyl)-1-cyclopropyl-9-methyl-4-oxo-4H-quinolizine-3-carboxylic acid 8-(4-(Dimethylamino)-phenyl)-1-cyclopropyl-9-methyl-4-oxo-4H-quinolizine-3-carboxylic acid was prepared according to General Procedure B from methyl 8-(4-(dimethylamino)-phenyl)-1-cyclopropyl-9-methyl-4-oxo-4H-quinolizine-3-carboxylate (34 mg, 0.09 mmol) to afford the title compound 37 as a yellow solid (5.1 mg, 15%).

ESI-MS m/z: 363 (M+H)$^+$; 1H NMR (400 MHz, DMSO-d6) δ ppm: 9.10-9.20 (m, 1H), 8.44 (s, 1H), 7.20-7.40 (m, 3H), 6.80-6.85 (m, 2H), 2.88 (s, 6H), 2.82 (s, 3H), 2.50-2.60 (m, 1H), 0.98-1.05 (m, 1H), 0.65-0.70 (m, 1H).

Preparation of Compound 38

Preparation of methyl 8-(3-S-((tert-butoxycarbonyl)-amino)-pyrrolidin-1-yl)-1-cyclopropyl-9-methyl-4-oxo-4H-quinolizine-3-carboxylate Methyl 8-chloro-1-cyclopropyl-9-methyl-4-oxo-4H-quinolizine-3-carboxylate (100 mg, 0.34 mmol), tert-butyl-pyrrolidin-3-S-yl-carbamate (313 mg, 1.68 mmol) and triethylamine (0.5 mL, 3.6 mmol) were added to 2-propanol (20 mL). The reaction mixture was heated at 130° C. and stirred for 6 h. The reaction mixture was cooled and evaporated to dryness. The crude product was purified by flash silica column chromatography (DCM:MeOH) (1:0 to 9:1) and dried in vacuum to afford the title compound as a yellow foam (70 mg, 46%).

ESI-MS m/z: 442 (M+H)$^+$.

Preparation of Compound 38HCl (Hydrochloric Salt of Compound 38) 8-(3-S-amino-pyrrolidin-1-yl)-1-cyclopropyl-9-methyl-4-oxo-4H-quinolizine-3-carboxylic acid 8-(3-S-amino-pyrrolidin-1-yl)-1-cyclopropyl-9-methyl-4-oxo-4H-quinolizine-3-carboxylic acid was prepared according to General Procedure B from methyl 8-(3-S-((tert-butoxycarbonyl)-amino)-pyrrolidin-1-yl)-1-cyclopropyl-9-methyl-4-oxo-4H-quinolizine-3-carboxylate (76 mg, 0.17 mmol) to afford a yellow residue. The residue was treated according to General Procedure C and purified using preparative LCMS to afford the hydrochloric salt of the title compound 38 as a yellow solid (5.5 mg, 10% over 2 steps).

ESI-MS m/z: 328 (M+H)$^+$; 1H NMR (400 MHz, DMSO-d6) δ ppm: 9.03 (d, J=10.8 Hz, 1H), 7.90 (s, 1H), 5.41 (s, 1H), 3.90-4.00 (m, 1H), 3.80-3.90 (m, 1H), 3.65-3.80 (m, 1H), 3.50-3.60 (m, 1H), 3.30-3.40 (m, 2H), 2.58 (s, 3H), 2.40-2.60 (m, 1H), 2.26-2.30 (m, 1H), 2.01-2.06 (m, 1H), 1.72-1.76 (m, 1H), 0.95-0.98 (m, 2H), 0.57-0.60 (m, 2H).

Preparation of Compound 39

Preparation of Compound 39 8-piperazin-1-yl-1-cyclopropyl-9-methyl-4-oxo-quinolizine-3-carboxylic acid A mixture of methyl 8-chloro-1-cyclopropyl-9-methyl-4-oxo-4H-quinolizine-3-carboxylate (200 mg, 0.69 mmol), N-(tert-butoxycarbonyl)-piperazine (256 mg, 1.38 mmol) and NaHCO$_3$ (259 mg, 14.64 mmol) in ACN (8.6 mL) was heated in a microwave at 120° C. for 20 min. DMF (2 mL) was added to the mixture and the reaction was heated in a microwave at 120° C. for 20 min. Then the reaction was heated in a microwave at 130° C. for 30 min twice. The reaction mixture was diluted with ethyl acetate (30 mL), and washed with water (30 mL). After extraction of the aqueous phase with ethyl acetate (2×30 mL), the organic phases were combined washed with brine, dried with magnesium sulfate, filtrated, and concentrated. The residue was dissolved in TFA (1 mL) and agitated for 1 hour prior to evaporation of the solvent. The residue was dissolved in THF (1 mL) and an aqueous 4M NaOH solution (0.79 mL) and heated in a microwave at 120° C. for 10 min. More aqueous 4M NaOH solution (0.5 mL) was added and the reaction was heated in a microwave at 120° C. for 10 min. The mixture was evaporated and the residue purified by preparative HPLC. The title compound compound 39 was obtained after lyophilization (28 mg, 12.5%).

High-Res MS: calculated 328.1656 (M+H)$^+$, found 328.1642 (M+H)$^+$.

Preparation of Compound 40

Preparation of Compound 40 8-[(3S)-3-amino-1-piperidyl]-1-cyclopropyl-9-methyl-4-oxo-quinolizine-3-carboxylic acid A mixture of methyl 8-chloro-1-cyclopropyl-9-methyl-4-oxo-4H-quinolizine-3-carboxylate (300 mg, 1 mmol), 3-S—N-(tert-butoxycarbonyl)-amino)-piperidine (413 mg, 2 mmol) and NaHCO$_3$ (390 mg, 14.64 mmol) in ACN (13 mL) was heated in a microwave at 120° C. for 20 min, and twice at 130° C. for 30 min. The reaction mixture was diluted with ethyl acetate (30 mL), and washed with water (30 mL). After extraction of the aqueous phase with ethyl acetate (2×30 mL), the organic phases were combined washed with brine, dried with magnesium sulfate, filtrated, and concentrated. The residue was dissolved in TFA (1 mL) and agitated for 1 hour prior to evaporation of the solvent. The residue was dissolved in THF (1 mL) and an aqueous 4M NaOH solution (1.4 mL) and heated in a microwave at 100° C. for 10 min and at 120° C. for 10 min. The mixture was evaporated and the residue purified by preparative HPLC. The title compound 40 was obtained after lyophilization (65 mg, 19%).

High-Res MS: calculated m/z 342.1812 (M+H)$^+$, found m/z 342.1787 (M+H)$^+$.

Preparation of Compound 41

Preparation of methyl 8-(4-cyano-phenyl)-1-cyclopropyl-9-methyl-4-oxo-4H-quinolizine-3-carboxylate Methyl 8-(4-cyano-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (123 mg, 0.42 mmol) and 4-cyano-phenyl-boronic acid (132 mg, 0.90 mmol). Purification by flash silica column chromatography (DCM:MeOH) (1:0 to 9:1) afforded the title compound as a yellow solid (142 mg, 94%).

ESI-MS m/z: 359 (M+H)$^+$.

Preparation of Compound 41 8-(4-carbamoyl-phenyl)-1-cyclopropyl-9-methyl-4-oxo-4H-quinolizine-3-carboxylic acid 8-(4-Carbamoyl-phenyl)-1-cyclopropyl-9-methyl-4-oxo-4H-quinolizine-3-carboxylic acid was prepared according to General Procedure B from methyl 8-(4-cyano-phenyl)-1-cyclopropyl-9-methyl-4-oxo-4H-quinolizine-3-carboxylate (123 mg, 0.35 mmol) and purified by preparative LCMS to afford the title compound 41 as a yellow solid (9.1 mg, 7%).

ESI-MS m/z: 363 (M+H)$^+$; 1H NMR (400 MHz, DMSO-d6) δ ppm: 9.25 (d, J=7.3 Hz, 1H), 8.24 (s, 1H), 8.12 (s, 1H), 8.04 (d, J=8.1 Hz, 1H), 7.61 (d, J=8.1 Hz, 1H), 7.50 (s, 1H), 7.35 (d, J=7.1 Hz, 1H), 2.81 (s, 3H), 2.50-2.60 (m, 1H), 1.02-1.10 (m, 2H), 0.71-0.79 (m, 2H).

Preparation of Compound 42

Preparation of Compound 42 8-(4-carboxy-phenyl)-1-cyclopropyl-9-methyl-4-oxo-4H-quinolizine-3-carboxylic acid 8-(4-Carboxy-phenyl)-1-cyclopropyl-9-methyl-4-oxo-4H-quinolizine-3-carboxylic acid was prepared according to General Procedure B from methyl 8-(4-cyano-phenyl)-1-cyclopropyl-9-methyl-4-oxo-4H-quinolizine-3-carboxylate (123 mg, 0.35 mmol). Preparative LC-MS purification afforded the title compound 42 as a yellow solid (9.3 mg, 7%).

ESI-MS m/z: 364 (M+H)$^+$; 1H NMR (400 MHz, DMSO-d6) δ ppm: 9.36 (d, J=7.3 Hz, 1H), 8.50 (br s, 1H), 8.08 (d, J=8.1 Hz, 1H), 7.47 (d, J=8.1 Hz, 1H), 7.32 (br s, 1H), 2.86 (s, 3H), 2.46-2.55 (m, 1H), 1.02-1.12 (m, 1H), 0.78-0.82 (m, 1H).

Preparation of Compound 43

Preparation of ethyl 8-(4-amino-2,5-difluoro-phenyl)-1-cyclopropyl-7-fluoro-9-methyl-4-oxo-4H-quinolizine-3-carboxylate Ethyl 8-chloro-1-cyclopropyl-7-fluoro-9-methyl-4-oxo-4H-quinolizine-3-carboxylate (100 mg, 0.32 mmol), 2,5-difluoro-4-(4,4,5,5-tetramethyl-1,3,2-dioxaborolan-2-yl)-aniline (667 mg, 2.06 mmol), tricyclohexylphosphine (105 mg, 0.41 mmol) and cesium fluoride (482 mg, 3.2 mmol) were added to ACN (5 mL). The reaction mixture was degassed with argon. Palladium(II) acetate (24 mg, 0.11 mmol) was added. The reaction mixture was heated at 85° C. for 2 h. The reaction mixture was cooled and evaporated in vacuum. Purification by flash silica column chromatography (DCM:MeOH) (1:0 to 9:1) afforded the title compound as a yellow solid (100 mg, 35%).

ESI-MS m/z: 403 (M+H)$^+$.

Preparation of Compound 43 8-(4-amino-2,5-difluoro-phenyl)-1-cyclopropyl-7-fluoro-9-methyl-4-oxo-4H-quinolizine-3-carboxylic acid 8-(4-Amino-2,5-difluoro-phenyl)-1-cyclopropyl-7-fluoro-9-methyl-4-oxo-4H-quinolizine-3-carboxylic acid was prepared according to General Procedure B from ethyl 8-(4-amino-2,5-difluoro-phenyl)-1-cyclopropyl-7-fluoro-9-methyl-4-oxo-4H-quinolizine-3-carboxylate (100 mg, 0.24 mmol). The compound was purified using preparative LCMS and dried in vacuum to afford the title compound 43 as a yellow solid (11 mg, 12%).

ESI-MS m/z: 389 (M+H)$^+$; 1H NMR (400 MHz, DMSO-d6) δ ppm: 14.0 (br s, 1H), 9.30 (d, J=4.3 Hz, 1H), 8.26 (s, 1H), 7.25 (q, J=6.6 Hz, 1H), 6.72 (t, J=7.6 Hz, 1H), 6.02 (s, 2H), 2.84 (s, 3H), 2.50-2.60 (m, 1H), 0.98-1.12 (m, 2H), 0.63-0.83 (m, 2H).

Preparation of Compound 44

Preparation of 2,6-difluoro-4-(4,4,5,5-tetramethyl-1,3,2-dioxaborolan-2-yl)-aniline Potassium acetate (7.08 g, 72 mmol), 4,4,4',4',5,5,5',5'-octamethyl-2,2'-bi(1,3,2-dioxaborolane) (6.7 g, 26 mmol) and 4-bromo-2,6-difluoroaniline (5 g, 24 mmol) were dissolved in DMSO (30 mL), followed by the addition of 1'-Bis-diphenylphosphine ferrocene palladium(II) dichloride (0.53 g, 0.7 mmol). The reaction mixture was heated at 80° C. for 16 h. The reaction mixture was diluted in ethyl acetate (150 mL) and washed with saturated sodium bicarbonate and brine (2×100 mL). The organic layer was collected, dried over sodium sulfate and dried in vacuum. Purification by flash silica column chromatography (hexane: ethyl acetate, 3:2) afforded the title compound as a white solid (4.5 g, 73%).

ESI-MS m/z: 256 (M+H)$^+$; 1H NMR (400 MHz, CDCl$_3$) δ ppm: 7.20-7.30 (m, 2H), 3.93 (br s, 2H), 1.32 (s, 12H).

Preparation of methyl 8-(4-amino-3,5-difluoro-phenyl)-1-cyclopropyl-9-methyl-4-oxo-4H-quinolizine-3-carboxylate Methyl 8-(4-amino-3,5-difluoro-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (500 mg, 1.71 mmol) and 2,6-difluoro-4-(4,4,5,5-tetramethyl-1,3,2-dioxaborolan-2-yl)-aniline (667 mg, 2.06 mmol). Purification by flash silica column chromatography (DCM:MeOH) (1:0 to 9:1) afforded the title compound as a yellow solid (1140 mg, 86%).

ESI-MS m/z: 423 (M+K)$^+$, 407 (M+Na)$^+$, 385 (M+H)$^+$.

Preparation of Compound 44 8-(4-amino-3,5-difluoro-phenyl)-1-cyclopropyl-9-methyl-4-oxo-4H-quinolizine-3-carboxylic acid 8-(4-Amino-3,5-difluoro-phenyl)-1-cyclopropyl-9-methyl-4-oxo-4H-quinolizine-3-carboxylic acid was prepared according to General Procedure B from methyl 8-(4-amino-3,5-difluoro-phenyl)-1-cyclopropyl-9-methyl-4-oxo-4H-quinolizine-3-carboxylate (1140 mg, 3.0 mmol) to afford the title compound 44 as a yellow solid (916 mg, 97%).

ESI-MS m/z: 371 (M+H)$^+$; 1H NMR (400 MHz, DMSO-d6) δ ppm: 14.08 (s, 1H), 9.26 (d, J=7.3 Hz, 1H), 8.22 (s, 1H), 7.59 (d, J=7.6 Hz, 1H), 7.25 (d, J=7.3 Hz, 2H), 5.80 (s, 2H), 2.89-2.91 (m, 3H), 2.40-2.60 (m, 1H), 1.07-1.09 (m, 2H), 0.77-0.79 (m, 2H).

Preparation of Compound 44K (Potassium Salt of Compound 44) potassium 8-(4-amino-3,5-difluoro-phenyl)-1-cyclopropyl-9-methyl-4-oxo-4H-quinolizine-3-carboxylate Potassium 8-(4-amino-3,5-difluoro-phenyl)-1-cyclopropyl-9-methyl-4-oxo-4H-quinolizine-3-carboxylate was prepared according to General Procedure D from 8-(4-amino-3,5-difluoro-phenyl)-1-cyclopropyl-9-methyl-4-oxo-4H-quinolizine-3-carboxylic acid (300 mg, 0.81 mmol) to afford the K salt of compound 44 as a yellow solid (335 mg, 100%).

ESI-MS m/z: 371 (M−K+H)$^+$.

Preparation of Compound 45

Preparation of methyl 8-(4-cyano-3-fluoro-phenyl)-1-cyclopropyl-9-methyl-4-oxo-4H-quinolizine-3-carboxylate Methyl 8-(4-cyano-3-fluoro-phenyl)-1-cyclopropyl-9-methyl-4-oxo-4H-quinolizine-3-carboxylate was prepared according to General Procedure A from methyl 8-chloro-1- cyclopropyl-9-methyl-4-oxo-4H-quinolizine-3-carboxylate (100 mg, 0.34 mmol) and 4-cyano-3-fluoro-phenyl-boronic acid (85 mg, 0.51 mmol). Purification by flash silica column chromatography (DCM:MeOH) (1:0 to 94:6) afforded the title compound as a yellow solid (135 mg, 98%).

ESI-MS m/z: 377 (M+H)$^+$.

Preparation of Compound 45 8-(4-cyano-3-fluoro-phenyl)-1-cyclopropyl-9-methyl-4-oxo-4H-quinolizine-3-carboxylic acid 8-(4-Cyano-3-fluoro-phenyl)-1-cyclopropyl-9-methyl-4-oxo-4H-quinolizine-3-carboxylic acid was prepared according to General Procedure B from me methyl 8-(4-cyano-3-fluoro-phenyl)-1-cyclopropyl-9-methyl-4-oxo-4H-quinolizine-3-carboxylate (135 mg, 0.36 mmol) to afford the title compound 45 as a yellow solid (37 mg, 28%).

ESI-MS m/z: 363 (M+H)$^+$; 1H NMR (400 MHz, DMSO-d6) δ ppm: 14.0 (br s, 1H), 9.30 (d, J=7.3 Hz, 1H), 8.33 (s, 1H), 8.15 (t, J=7.6 Hz, 1H), 7.81 (d, J=7.6 Hz, 1H), 7.59-7.61 (m, 1H), 7.38-7.52 (m, 1H), 2.82 (s, 3H), 2.40-2.60 (m, 1H), 1.00-1.18 (m, 2H), 0.73-0.92 (m, 2H).

Preparation of Compound 46

Preparation of ethyl 8-(4-cyano-phenyl)-1-cyclopropyl-7-fluoro-9-methyl-4-oxo-4H-quinolizine-3-carboxylate Ethyl 8-(4-cyano-phenyl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (151 mg, 0.47 mmol) and 4-cyano-phenyl-boronic acid (82 mg, 0.56 mmol). Purification by flash silica column chromatography (DCM:MeOH, 1:0 to 9:1) afforded the title compound as a yellow solid (189 mg, 100%).

ESI-MS m/z: 391 (M+H)$^+$.

Preparation of Compound 46 8-(4-carboxy-phenyl)-1-cyclopropyl-7-fluoro-9-methyl-4-oxo-4H-quinolizine-3-carboxylic acid 8-(4-Carboxy-phenyl)-1-cyclopropyl-7-fluoro-9-methyl-4-oxo-4H-quinolizine-3-carboxylic acid was prepared according to General Procedure B from ethyl 8-(4-cyano-phenyl)-1-cyclopropyl-7-fluoro-9-methyl-4-oxo-4H-quinolizine-3-carboxylate (123 mg, 0.35 mmol). Preparative LC-MS purification afforded the title compound 46 as a yellow solid (12 mg, 7%).

ESI-MS m/z: 382 (M+H)$^+$; 1H NMR (400 MHz, CD$_3$OD) δ ppm 9.40 (br s, 1H), 8.50 (br s, 1H), 8.11 (d, J=8.1 Hz, 2H), 7.40 (d, J=8.1 Hz, 2H), 2.83 (s, 3H), 2.43-2.55 (m, 1H), 0.99-1.15 (m, 2H), 0.82-0.86 (m, 2H).

Preparation of Compound 47

Preparation of methyl 8-(1-(tert-butoxycarbonyl)-1,2,3,6-tetrahydropyridin-4-yl)-1-cyclopropyl-9-methyl-4-oxo-4H-quinolizine-3-carboxylate Methyl 8-(1-(tert-butoxycarbonyl)-1,2,3,6-tetrahydropyridin-4-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (500 mg, 1.71 mmol) and tert-butyl 4-(4,4,5,5-tetramethyl-1,3,2-dioxaborolan-2-yl)-5,6-dihydropyridine-1(2H)-carboxylate (467.0 mg, 1.51 mmol). Purification by flash silica column chromatography (DCM:MeOH) (1:0 to 9:1) afforded the title compound as a brown oil (830 mg, 100%).

ESI-MS m/z: 461 (M+Na)$^+$, 439 (M+H)$^+$.

Preparation of 8-(1-(tert-butoxycarbonyl)-1,2,3,6-tetrahydropyridin-4-yl)-1-cyclopropyl-9-methyl-4-oxo-4H-quinolizine-3-carboxylic acid 8-(1-(tert-Butoxycarbonyl)-1,2,3,6-tetrahydropyridin-4-yl)-1-cyclopropyl-9-methyl-4-oxo-4H-quinolizine-3-carboxylic acid was prepared according to General Procedure B using methyl 8-(1-(tert-butoxycarbonyl)-1,2,3,6-tetrahydropyridin-4-yl)-1-cyclopropyl-9-methyl-4-oxo-4H-quinolizine-3-carboxylate (830 mg, 1.89 mmol) to afford the title compound as a brown oil (628 mg, 78%).

ESI-MS m/z: 425 (M+H)$^+$.

Preparation of Compound 47 8-(1,2,3,6-tetrahydropyridin-4-yl)-1-cyclopropyl-9-methyl-4-oxo-4H-quinolizine-3-carboxylic acid 8-(1,2,3,6-Tetrahydropyridin-4-yl)-1-cyclopropyl-9-methyl-4-oxo-4H-quinolizine-3-carboxylic acid was prepared according to General Procedure C from 8-(1-(tert-butoxycarbonyl)-1,2,3,6-tetrahydropyridin-4-yl)-1-cyclopropyl-9-methyl-4-oxo-4H-quinolizine-3-carboxylic acid and purified by preparative LCMS to afford the title compound 47 as a yellow solid (164 mg, 47%).

ESI-MS m/z: 325 (M+H)$^+$; 1H NMR (400 MHz, DMSO-d6) δ ppm: 14.05 (s, 1H), 9.32 (d, J=7.3 Hz, 1H), 8.25 (s, 1H), 7.41 (d, J=7.3 Hz, 1H), 5.91 (s, 1H), 3.79 (s, 2H), 3.39-3.41 (m, 2H), 2.93 (s, 3H), 2.54-2.59 (s, 2H), 2.40-2.60 (m, 1H), 1.03-1.11 (m, 2H), 0.73-0.77 (m, 2H).

Preparation of Compound 48

Preparation of methyl 8-(1-(tert-butoxycarbonyl)-1H-pyrrol-3-yl)-1-cyclopropyl-9-methyl-4-oxo-4H-quinolizine-3-carboxylate Methyl 8-(1-(tert-butoxycarbonyl)-1H-pyrrol-3-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and tert-butyl 3-(4,4,5,5-tetramethyl-1,3,2-dioxaborolan-2-yl)-1H-pyrrole-1-carboxylate (151.0 mg, 0.51 mmol). Purification by flash silica column chromatography (DCM:MeOH) (1:0 to 94:6) afforded the title compound as a yellow solid (89 mg, 61%).

ESI-MS m/z: 423 (M+H)$^+$.

Preparation of Compound 48 8-(1H-pyrrol-3-yl)-1-cyclopropyl-9-methyl-4-oxo-4H-quinolizine-3-carboxylic acid 8-(1H-Pyrrol-3-yl)-1-cyclopropyl-9-methyl-4-oxo-4H-quinolizine-3-carboxylic acid was prepared according to General Procedure B from methyl 8-(1-(tert-butoxycarbonyl)-1H-pyrrol-3-yl)-1-cyclopropyl-9-methyl-4-oxo-4H-quinolizine-3-carboxylate (89 mg, 0.22 mmol) followed by BOC removal according to General Procedure C. Purification by preparative LCMS afforded the title compound 48 as a yellow solid (22 mg, 7% over 2 steps).

ESI-MS m/z: 309 (M+H)$^+$; 1H NMR (400 MHz, DMSO-d6) δ ppm: 14.14 (s, 1H), 11.58 (s, 1H), 9.18 (d, J=7.6 Hz, 1H), 8.14 (s, 1H), 7.78 (d, J=7.6 Hz, 1H), 7.53 (s, 1H), 7.01 (s, 1H), 6.64 (s, 1H), 3.04 (s, 3H), 2.50-2.60 (m, 1H), 1.03-1.12 (m, 2H), 0.68-0.72 (m, 2H).

Preparation of Compound 48K (Potassium Salt of Compound 48) potassium 8-(1H-pyrrol-3-yl)-1-cyclopropyl-9-methyl-4-oxo-4H-quinolizine-3-carboxylate The title compound potassium 8-(1H-pyrrol-3-yl)-1-cyclopropyl-9-methyl-4-oxo-4H-quinolizine-3-carboxylate was prepared according to General Procedure D from 8-(1H-pyrrol-3-yl)-1-cyclopropyl-9-methyl-4-oxo-4H-quinolizine-3-carboxylic acid (34.0 mg, 0.11 mmol) to afford the K salt compound 48 as a yellow solid (37.9 mg, 94%).
ESI-MS m/z: 309 (M−K+H)$^+$, 307 (M+H)$^+$. ([M−K−H]$^−$.

Preparation of Compound 49

Preparation of ethyl 8-(4-fluoro-phenyl)-1-cyclopropyl-9-methyl-4-oxo-4H-quinolizine-3-carboxylate A mixture of ethyl 8-chloro-1-cyclopropyl-9-methyl-4-oxo-4H-quinolizine-3-carboxylate (120 mg, 0.400 mmol), 4-fluoro-phenyl boronic acid (67 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate (50 mL), and washed with water (2×20 mL). The organic phase was separated, dried, and concentrated. The residue was purified by flash silica column chromatography (hexane:ethyl acetate, 1:2) to afford the title compound as a yellow solid (120 mg, 82%).
ESI-MS m/z: 366 (M+H)$^+$.

Preparation of Compound 49 8-(4-fluoro-phenyl)-1-cyclopropyl-9-methyl-4-oxo-4H-quinolizine-3-carboxylic acid A solution of ethyl 8-(4-fluoro-phenyl)-1-cyclopropyl-9-methyl-4-oxo-4H-quinolizine-3-carboxylate (120 mg, 0.329 mmol) in THF (6 mL) and water (2 mL) was treated with LiOH (55 mg, 1.31 mmol). The reaction was heated to 60° C. for 2 h and acidified with 1N HCl to pH 4. The precipitate was dissolved with ethyl acetate (50 mL) and washed with brine (2×20 mL). The organic phase was separated, dried, and concentrated. The precipitate was filtered to afford the title compound 49 as a yellow solid (110 mg, 99%).
ESI-MS m/z: 338 (M+H)$^+$; $^1$H NMR (300 MHz, DMSO-d6) δ ppm: 9.37 (d, J=7.5 Hz, 1H), 8.30 (s, 1H), 7.70-7.61 (m, 3H), 7.51-7.45 (m, 2H), 2.89 (s, 3H), 2.53-2.51 (m, 1H), 1.13-1.10 (m, 2H), 0.83-0.82 (m, 2H).

Preparation of Compound 50

Preparation of ethyl 8-(4-chloro-phenyl)-1-cyclopropyl-9-methyl-4-oxo-4H-quinolizine-3-carboxylate A mixture of ethyl 8-chloro-1-cyclopropyl-9-methyl-4-oxo-4H-quinolizine-3-carboxylate (120 mg, 0.400 mmol), 4-chloro-phenyl boronic acid (75 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate (50 mL), and washed with water (2×20 mL). The organic phase was separated, dried, and concentrated. The residue was purified by flash silica column chromatography (hexane:ethyl, acetate 2:3) to afford the title compound as a yellow solid (95 mg, 62%).
ESI-MS m/z: 382 (M+H)$^+$.

Preparation of Compound 50 8-(4-chloro-phenyl)-1-cyclopropyl-9-methyl-4-oxo-4H-quinolizine-3-carboxylic acid A solution of ethyl 8-(4-chloro-phenyl)-1-cyclopropyl-9-methyl-4-oxo-4H-quinolizine-3-carboxylate (95 mg, 0.249 mmol) in THF (6 mL) and water (2 mL) was treated with LiOH (43 mg, 1.02 mmol). The reaction was heated to 60° C. for 4 h and acidified with 1N HCl to pH 4. The precipitate was dissolved with ethyl acetate (50 mL) and washed with brine (2×20 mL). The organic phase was separated, dried, and concentrated. The precipitate was filtered to afford the title compound 50 as yellow solid (49 mg, 56%).
ESI-MS m/z: 354 (M+H)$^+$; $^1$H NMR (300 MHz, DMSO-d6) δ ppm: 9.34 (d, J=7.2 Hz, 1H), 8.27 (s, 1H), 7.56-7.68 (m, 5H), 2.84 (s, 3H), 2.52-2.55 (m, 1H), 2.39 (s, 3H), 1.05-1.08 (m, 2H), 0.78-0.80 (m, 2H).

Preparation of Compound 51

Preparation of methyl 8-(4-hydroxy-phenyl)-91-cyclopropyl-1-methyl-4-oxo-4H-quinolizine-3-carboxylate Methyl 8-(4-hydroxy-phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (500 mg, 1.71 mmol) and 4-hydroxy-phenyl-boronic acid (283 mg, 2.06 mmol). Purification by flash silica column chromatography (DCM:MeOH) (1:0 to 9:1) afforded the title compound as a yellow solid (610 mg, 100%).
ESI-MS m/z: 388 (M+K)$^+$, 372 (M+Na)$^+$, 350 (M+H)$^+$.

Preparation of Compound 51 8-(4-hydroxy-phenyl)-1-cyclopropyl-9-methyl-4-oxo-4H-quinolizine-3-carboxylic acid 8-(4-Hydroxy-phenyl)-1-cyclopropyl-9-methyl-4-oxo-4H-quinolizine-3-carboxylic acid was prepared according to General Procedure B from methyl 1-cyclopropyl-8-(4-hydroxy-phenyl)-9-methyl-4-oxo-4H-quinolizine-3-carboxylate (610 mg, 1.74 mmol) to afford the title compound 51 as a yellow solid (383 mg, 65%).
ESI-MS m/z: 336 (M+H)$^+$, 334.20 (M−H)$^−$; 1H NMR (400 MHz, DMSO-d6) δ ppm: 14.12 (s, 1H), 10.00 (s, 1H), 9.30 (d, J=7.3 Hz, 1H), 8.23 (s, 1H,), 7.57 (d, J=7.6 Hz, 1H), 7.43 (d, J=8.6 Hz, 2H), 6.96 (d, J=8.6 Hz, 2H), 2.88 (s, 3H), 2.40-2.60 (m, 1H), 1.05-1.08 (m, 2H), 0.76-0.78 (m, 2H).

Preparation of Compound 51K (Potassium Salt of Compound 51) potassium 8-(4-hydroxy-phenyl)-1-cyclopropyl-9-methyl-4-oxo-4H-quinolizine-3-carboxylate Potassium 8-(4-hydroxy-phenyl)-1-cyclopropyl-9-methyl-4-oxo-4H-quinolizine-3-carboxylate was prepared according to General Procedure D from 1-cyclopropyl-8-(4- hydroxy-phenyl)-9-methyl-4-oxo-4H-quinolizine-3-carboxylic acid (370 mg, 0.81 mmol) to afford the K salt of compound 51 as a yellow solid (429 mg, 100%).
ESI-MS m/z: 336 (M−K+H)$^+$, 334 (M−K−H)$^−$.

Preparation of Compound 52

Preparation of ethyl 8-(4-methoxy-phenyl)-1-cyclopropyl-9-methyl-4-oxo-4H-quinolizine-3-carboxylate A mixture of ethyl 8-chloro-1-cyclopropyl-9-methyl-4-oxo-4H-quinolizine-3-carboxylate (120 mg, 0.400 mmol), 4-methoxy-phenyl boronic acid (73 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate, and washed with water. The organic phase was separated, dried, and concentrated. The residue was purified by flash silica column chromatography (hexane:ethyl acetate, 1:2) to afford the title compound as a yellow solid (68 mg, 45%).
ESI-MS m/z: 378 (M+H)$^+$.

Preparation of Compound 52 8-(4-methoxy-phenyl)-1-cyclopropyl-9-methyl-4-oxo-4H-quinolizine-3-carboxylic acid A solution of ethyl 8-(4-methoxy-phenyl)-1-cyclopropyl-9-methyl-4-oxo-4H-quinolizine-3-carboxylate (68 mg, 0.180 mmol) in THF (6 mL) and water (2 mL) was treated with LiOH (33 mg, 0.78 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound 52 as yellow solid (22 mg, 35%).
ESI-MS m/z: 350 (M+H)$^+$; $^1$H NMR (300 MHz, DMSO-d6) δ ppm: 9.30 (d, J=7.5 Hz, 1H), 8.23 (s, 1H), 7.57 (d, J=7.5 Hz, 1H), 7.52 (d, J=8.4 Hz, 2H), 7.12 (d, J=7.5 Hz, 2H), 3.84 (s, 3H), 2.86 (s, 3H), 2.51-2.53 (m, 1H), 1.04-1.06 (m, 2H), 0.75-0.78 (m, 2H).

Preparation of Compound 53

Preparation of ethyl 8-(4-hydroxy-methyl-phenyl)-1-cyclopropyl-9-methyl-4-oxo-4H-quinolizine-3-carboxylate A mixture of ethyl 8-chloro-1-cyclopropyl-9-methyl-4-oxo-4H-quinolizine-3-carboxylate (120 mg, 0.400 mmol), 4-hydroxy-methyl-phenyl boronic acid (73 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate (50 mL) and washed with water (2×20 mL). The organic phase was separated, dried, and concentrated. The residue was purified by flash silica column chromatography (hexane:ethyl acetate, 1:3 to pure ethyl acetate) to afford the title compound as a yellow solid (60 mg, 40%).
ESI-MS m/z: 378 (M+H)$^+$.

Preparation of Compound 53 8-(4-hydroxy-methyl-phenyl)-1-cyclopropyl-9-methyl-4-oxo-4H-quinolizine-3-carboxylic acid A solution of ethyl 8-(4-hydroxy-methyl-phenyl)-1-cyclopropyl-9-methyl-4-oxo-4H-quinolizine-3-carboxylate (60 mg, 0.159 mmol) in THF (6 mL) and water (2 mL) was treated with LiOH (27 mg, 0.642 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound 53 as yellow solid (21 mg, 38%).
ESI-MS m/z: 350 (M+H)$^+$; $^1$H NMR (300 MHz, DMSO-d6) δ ppm: 9.38 (d, J=7.2 Hz, 1H), 8.30 (s, 1H), 7.62 (d, J=7.5 Hz, 1H), 7.56-7.59 (m, 4H), 5.41 (t, 1H), 4.64 (d, J=5.7 Hz, 2H), 2.91 (s, 3H), 2.51-2.54 (m, 1H), 1.10-1.13 (m, 2H), 0.81-0.83 (m, 2H).

Preparation of Compound 54

Preparation of tert-butyl 7-bromo-1-hydroxy-2-oxo-1,2,3,4-tetrahydroquinolin-3-yl-carbamate To a suspension of 3-amino-7-bromo-1-hydroxy-3,4-dihydroquinolin-2(1H)-one hydrochloride (203 mg, 0.692 mmol) in DCM (10 mL) was added di-tert-butyl dicarbonate (226 mg, 1.04 mmol) and triethylamine (0.482 mL, 3.46 mmol). The suspension was stirred at room temperature for 16 h. Water (20 mL) was added to the clear solution and the layers were separated. The organic layer was washed with brine, dried over sodium sulfate and concentrated in vacuum. The crude product was purified by flash silica column chromatography (heptane:ethyl acetate) (1:0 to 7:3) to afford the title compound as a white solid (102 mg, 41%).
ESI-MS m/z: 303, 301 (M-tBu+H)$^+$.

Preparation of tert-butyl 2-oxo-7-(4,4,5,5-tetramethyl-1,3,2-dioxaborolan-2-yl)-1,2,3,4-tetrahydroquinolin-3-ylcarbamate Sodium acetate (20.7 mg, 0.252 mmol) and bis(pinacolato)diboron (32.0 mg, 0.126 mmol) were placed as solids in a flask under argon. tert-Butyl 7-bromo-1-hydroxy-2-oxo-1,2,3,4-tetrahydroquinolin-3-ylcarbamate (30 mg, 0.084 mmol) in DMSO (dry) (1 mL) was added and the mixture was degassed with argon. trans-Bis(triphenylphosphine)-palladium(II) dichloride (5.9 mg, 8.4 μmol) was added and the reaction mixture was heated at 40° C. for 2 h. After cooling the reaction mixture was concentrated and purified by flash silica column chromatography (heptane:ethyl acetate) (95:5 to 3:2) to afford the title compound as a white solid (13.5 mg, 41%).
$^1$H NMR (400 MHz, DMSO-d6) δ ppm 7.78 (s, 1H), 7.46 (d, J=7.6 Hz, 1H), 7.21 (d, J=7.6 Hz, 1H), 5.60 (br s, 1H), (4.34 (br s, 1H), 3.48-3.53 (m, 1H), 2.81-2.89 (m, 2H), 1.47 (s, 9H), 1.34 (s, 12H).

Preparation of methyl 8-(3-(tert-butoxycarbonylamino)-2-oxo-1,2,3,4-tetrahydroquinolin-7-yl)-1-cyclopropyl-9-methyl-4-oxo-4H-quinolizine-3-carboxylate Methyl 8-chloro-1-cyclopropyl-9-methyl-4-oxo-4H-quinolizine-3-carboxylate (45 mg, 0.15 mmol) was dissolved in toluene (330 μL), ethanol (96%) (243 μL) and 2M aqueous sodium carbonate solution (231 μL, 0.463 mmol). tert-Butyl 2-oxo-7-(4,4,5,5-tetramethyl-1,3,2-dioxaborolan-2-yl)-1,2,3,4-tetrahydroquinolin-3-ylcarbamate (78 mg, 0.20 mmol) was added and the mixture was degassed with argon. 1,1'-Bis(diphenylphosphino)-ferrocene palladium(II) dichloride (11.3 mg, 0.015 mmol) was added and the mixture was heated at 80° C. under an argon atmosphere for 16 h. After cooling, the mixture was diluted with DCM (3 mL) and water (3 mL) and the layers were separated. The aqueous layer was extracted with DCM (3×2 mL). The combined organic layers were concentrated and the yellow crude product was purified with flash silica column chromatography (heptane/ethyl acetate) (1:0 to 0:1) to afford the title compound as a yellow solid (43 mg, 53%).

ESI-MS m/z: 518 (M+H)$^+$.

Preparation of 8-(3-(tert-butoxycarbonylamino)-2-oxo-1,2,3,4-tetrahydroquinolin-7-yl)-1-cyclopropyl-9-methyl-4-oxo-4H-quinolizine-3-carboxylic acid Methyl 8-(3-(tert-butoxycarbonylamino)-2-oxo-1,2,3,4-tetrahydroquinolin-7-yl)-1-cyclopropyl-9-methyl-4-oxo-4H-quinolizine-3-carboxylate (43 mg, 0.083 mmol) was dissolved in MeOH (2 mL) and sodium hydroxide 1M solution in water (0.5 mL, 0.5 mmol) was added. The mixture was stirred at 50° C. for 2 h. After cooling, the MeOH was removed in vacuum. The residue was dissolved in water (5 mL) and then neutralized with 1M HCl (~0.5 mL). The precipitate formed was stirred at room temperature overnight. The mixture was extracted with DCM (3×4 mL). The organic layers were concentrated to afford the title compound as a yellow solid (29 mg, 69%).

ESI-MS m/z: 504 (M+H)$^+$.

Preparation of Compound 54HCl (Hydrochloric Salt of Compound 54) 8-(3-amino-2-oxo-1,2,3,4-tetrahydroquinolin-7-yl)-1-cyclopropyl-9-methyl-4-oxo-4H-quinolizine-3-carboxylic acid hydrochloride 8-(3-(tert-Butoxycarbonylamino)-2-oxo-1,2,3,4-tetrahydroquinolin-7-yl)-1-cyclopropyl-9-methyl-4-oxo-4H-quinolizine-3-carboxylic acid (29 mg, 0.046 mmol) was dissolved in ACN (4 mL). HCl 4M in dioxane (1 mL, 4 mmol) was added. The mixture was stirred for 4 h and a suspension was formed. The solvents were evaporated and the crude was triturated with diethyl ether (4 mL) to afford the hydrochloric salt of the title compound 54 as a yellow solid (20 mg, 98%).

ESI-MS m/z: 404 (M+H)$^+$.

Preparation of Compound 55

Preparation of methyl 8-(6-hydroxypyridin-3-yl)-1-cyclopropyl-9-methyl-4-oxo-4H-quinolizine-3-carboxylate Methyl 8-(6-hydroxypyridin-3-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 5-(4,4,5,5-tetramethyl-1,3,2-dioxaborolan-2-yl)pyridin-2-ol (90.8 mg, 0.41 mmol). The precipitate was rinsed with DCM and dried in a vacuum stove to afford quantitatively the title compound as a yellow solid.

ESI-MS m/z: 351 (M+H)$^+$.

Preparation of Compound 55 8-(6-hydroxypyridin-3-yl)-1-cyclopropyl-9-methyl-4-oxo-4H-quinolizine-3-carboxylic acid 8-(6-Hydroxypyridin-3-yl)-1-cyclopropyl-9-methyl-4-oxo-4H-quinolizine-3-carboxylic acid was prepared according to General Procedure B from methyl 8-(6-hydroxypyridin-3-yl)-1-cyclopropyl-9-methyl-4-oxo-4H-quinolizine-3-carboxylate (0.34 mmol) to afford compound 55 as a yellow solid (113 mg, 99% in two steps).

ESI-MS m/z: 337 (M+H)$^+$, 335 (M–H)$^-$; 1H NMR (400 MHz, DMSO-d6) δ ppm 14.08 (s, 1H), 12.19 (s, 1H), 9.26 (d, J=7.3 Hz, 1H), 8.25 (s, 1H), 7.77 (s, 1H), 7.71 (d, J=9.4 Hz, 1H), 7.57 (s, 1H), 6.51 (d, J=9.6 Hz, 1H), 2.88 (s, 3H), 2.40-2.60 (m, 1H), 1.05-1.07 (m, 2H), 0.76-0.77 (m, 2H).

Preparation of Compound 55K (Potassium Salt of Compound 55) potassium 8-(6-hydroxypyridin-3-yl)-1-cyclopropyl-9-methyl-4-oxo-4H-quinolizine-3-carboxylate Potassium 8-(6-hydroxypyridin-3-yl)-1-cyclopropyl-9-methyl-4-oxo-4H-quinolizine-3-carboxylate was prepared according to General Procedure D from 8-(6-hydroxypyridin-3-yl)-1-cyclopropyl-9-methyl-4-oxo-4H-quinolizine-3-carboxylic acid (113.0 mg, 0.34 mmol) to afford the K salt of compound 55 as a yellow solid (123.0 mg, 95%).

ESI-MS m/z: 337 (M–K+H)$^+$, 335 (M–K–H)$^-$.

Preparation of Compound 56

Preparation of methyl 8-(3-hydroxyphenyl)-1-cyclopropyl-9-methyl-4-oxo-4H-quinolizine-3-carboxylate Methyl 8-(3-hydroxyphenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and (3-hydroxyphenyl)-boronic acid (56.6 mg, 0.41 mmol). Purification by flash silica column chromatography (DCM:MeOH) (1:0 to 9:1) afforded quantitatively the title compound as a yellow solid.

ESI-MS m/z: 350 (M+H)$^+$; 348 (M–H)$^-$.

Preparation of Compound 56 8-(3-hydroxyphenyl)-1-cyclopropyl-9-methyl-4-oxo-4H-quinolizine-3-carboxylic acid 8-(3-Hydroxyphenyl)-1-cyclopropyl-9-methyl-4-oxo-4H-quinolizine-3-carboxylic acid was prepared according to General Procedure B from methyl 8-(3-hydroxyphenyl)-1-cyclopropyl-9-methyl-4-oxo-4H-quinolizine-3-carboxylate (0.34 mmol) to afford compound 56 as a yellow solid (81 mg, 71% in two steps).

ESI-MS m/z: 336 (M+H)$^+$; 334 (M–H)$^-$; 1H NMR (400 MHz, DMSO-d6) δ ppm 14.10 (s, 1H), 9.83 (s, 1H), 9.32 (d, J=7.3 Hz, 1H), 8.27 (s, 1H), 7.53 (d, J=7.3 Hz 1H), 7.38 (t, J=7.8 Hz, 1H), 6.89-6.94 (m, 3H), 2.86 (s, 3H), 2.40-2.60 (m, 1H), 1.04-1.10 (m, 2H), 0.77-0.78 (m, 2H).

Preparation of Compound 56K (Potassium Salt of Compound 56) potassium 1-cyclopropyl-8-(3-hydroxyphenyl)-9-methyl-4-oxo-4H-quinolizine-3-carboxylate Potassium 8-(3-hydroxyphenyl)-1-cyclopropyl-9-methyl-4-oxo-4H-quinolizine-3-carboxylate was prepared according to General Procedure D 8-(3-hydroxyphenyl)-1-cyclopropyl-9-methyl-4-oxo-4H-quinolizine-3-carboxylic acid (81.0 mg, 0.24 mmol) to afford the K salt of compound 56 as a yellow (94.0 mg, 100%).
ESI-MS m/z: 336 (M−K+H)⁺.

Preparation of Compound 57

Preparation of methyl 8-(2-aminopyrimidin-5-yl)-1-cyclopropyl-9-methyl-4-oxo-4H-quinolizine-3-carboxylate Methyl 8-(2-aminopyrimidin-5-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 5-(4,4,5,5-tetramethyl-1,3,2-dioxaborolan-2-yl)pyrimidin-2-amine (90.8 mg, 0.41 mmol). Purification by flash silica column chromatography (DCM:MeOH) (1:0 to 9:1) afforded the title compound as a yellow solid (96 mg, 80%).
ESI-MS m/z: 351 (M+H)⁺; 349 (M−H)⁻.

Preparation of Compound 57 8-(2-aminopyrimidin-5-yl)-1-cyclopropyl-9-methyl-4-oxo-4H-quinolizine-3-carboxylic acid 8-(2-Aminopyrimidin-5-yl)-1-cyclopropyl-9-methyl-4-oxo-4H-quinolizine-3-carboxylic acid was prepared according to General Procedure B from methyl 8-(2-aminopyrimidin-5-yl)-1-cyclopropyl-9-methyl-4-oxo-4H-quinolizine-3-carboxylate (96 mg, 0.27 mmol). Purification by preparative HPLC afforded compound 57 as a yellow solid (10.8 mg, 11%).
ESI-MS m/z: 337 (M+H)⁺; 335 (M−H)⁻; 1H NMR (400 MHz, DMSO-d6) δ ppm 9.29 (d, J=7.6 Hz, 1H), 8.54 (s, 2H), 8.50 (s, 1H), 8.23 (s, 1H), 7.64 (d, J=7.4 Hz, 1H), 7.22 (s, 2H), 2.91 (s, 3H), 2.40-2.60 (m, 1H), 1.07-1.09 (m, 2H), 0.76-0.78 (m, 2H).

Preparation of Compound 58

Preparation of methyl 8-(3-fluoropyridin-4-yl)-1-cyclopropyl-9-methyl-4-oxo-4H-quinolizine-3-carboxylate Methyl 8-(3-fluoropyridin-4-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and (3-fluoropyridin-4-yl)-boronic acid (65.3 mg, 0.41 mmol). Purification by flash silica column chromatography (DCM:MeOH) (1:0 to 9:1) afforded the title compound as a yellow solid (78 mg, 65%).
ESI-MS m/z: 353 (M+H)⁺; 351 (M−H)⁻.

Preparation of Compound 58 8-(3-fluoropyridin-4-yl)-1-cyclopropyl-9-methyl-4-oxo-4H-quinolizine-3-carboxylic acid 8-(3-Fluoropyridin-4-yl)-1-cyclopropyl-9-methyl-4-oxo-4H-quinolizine-3-carboxylic acid was prepared according to General Procedure B from methyl 8-(3-fluoropyridin-4-yl)-1-cyclopropyl-9-methyl-4-oxo-4H-quinolizine-3-carboxylate (78 mg, 0.22 mmol) to afford compound 58 as a yellow solid (55 mg, 73%).
ESI-MS m/z: 339 (M+H)⁺; 337 (M−H)⁻; 1H NMR (400 MHz, DMSO-d6) δ ppm 14.03 (s, 1H), 9.36 (d, J=7.1 Hz, 1H), 8.84 (s, 1H), 8.67 (d, J=4.3 Hz, 1H), 8.34 (s, 1H), 7.60-7.70 (m, 1H), 7.57 (d, J=5.8 Hz, 1H,), 2.81 (s, 3H), 2.50-2.60 (m, 1H), 1.06-1.08 (m, 2H), 0.78-0.80 (m, 2H).

Preparation of Compound 58K (Potassium Salt of Compound 58) potassium 8-(3-fluoropyridin-4-yl)-1-cyclopropyl-9-methyl-4-oxo-4H-quinolizine-3-carboxylate Potassium 8-(3-fluoropyridin-4-yl)-1-cyclopropyl-9-methyl-4-oxo-4H-quinolizine-3-carboxylate was prepared according to General Procedure D from 8-(3-fluoropyridin-4-yl)-1-cyclopropyl-9-methyl-4-oxo-4H-quinolizine-3-carboxylic acid (55.0 mg, 0.16 mmol) to afford the K salt of compound 58 as a yellow solid (38.0 mg, 58%).
ESI-MS m/z: 339 (M−K+H)⁺; 337 (M−K−H)⁻.

Preparation of Compound 59

Preparation of ethyl 8-(pyridin-4-yl)-1-cyclopropyl-7-fluoro-9-methyl-4-oxo-4H-quinolizine-3-carboxylate Ethyl 8-(pyridin-4-yl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (100 mg, 0.34 mmol) and pyridin-4-ylboronic acid (52.1 mg, 0.42 mmol). Purification by flash silica column chromatography (DCM:MeOH) (1:0 to 9:1) afforded quantitatively the title compound as a yellow solid.
ESI-MS m/z: 367 (M+H)⁺.

Preparation of Compound 59 1-cyclopropyl-7-fluoro-9-methyl-4-oxo-8-(pyridin-4-yl)-4H-quinolizine-3-carboxylic acid 8-(Pyridin-4-yl)-1-cyclopropyl-7-fluoro-9-methyl-4-oxo-8-(pyridin-4-yl)-4H-quinolizine-3-carboxylic acid was prepared according to General Procedure B from ethyl 8-(pyridin-4-yl)-1-cyclopropyl-7-fluoro-9-methyl-4-oxo-4H-quinolizine-3-carboxylate (0.34 mmol) to afford compound 59 as a yellow solid (75 mg, 72% in two steps).
ESI-MS m/z: 339 (M+H)⁺; 1H NMR (400 MHz, DMSO) δ ppm 13.67 (s, 1H), 9.36 (d, J=6.0 Hz, 1H), 8.81 (d, J=5.8 Hz, 2H), 8.31 (s, 1H), 7.50 (d, J=5.6 Hz, 2H), 2.79 (s, 3H), 2.40-2.60 (m, 1H), 1.06-1.09 (m, 2H), 0.80-0.82 (m, 2H).

Preparation of Compound 59K (Potassium Salt of Compound 59) potassium 8-(pyridin-4-yl)-1-cyclopropyl-7-fluoro-9-methyl-4-oxo-4H-quinolizine-3-carboxylate Potassium 8-(pyridin-4-yl)-1-cyclopropyl-7-fluoro-9-methyl-4-oxo-4H-quinolizine-3-carboxylate was prepared according to General Procedure D from 8-(pyridin-4-yl)-1-cyclopropyl-7-fluoro-9-methyl-4-oxo-4H-quinolizine-3-carboxylic acid (75.0 mg, 0.22 mmol) to afford the K salt of compound 59 as a yellow solid (49.8 mg, 58%).
ESI-MS m/z: 339 (M−K+H)⁺, 337 (M−K−H)⁻.

Preparation of Compound 60

Preparation of methyl 8-(6-aminopyridin-3-yl)-1-cyclopropyl-7-fluoro-9-methyl-4-oxo-4H-quinolizine-3-carboxylate Ethyl 8-(6-aminopyridin-3-yl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (100 mg, 0.34 mmol) and 5-(4,4,5,5-tetramethyl-1,3,2-dioxaborolan-2-yl)pyridin-2-amine (93.7 mg, 0.43 mmol). Purification by flash silica column chromatography (DCM:MeOH) (1:0 to 9:1) afforded quantitatively the title compound as a yellow solid.

ESI-MS m/z: 382 (M+H)$^+$.

Preparation of Compound 60 8-(6-aminopyridin-3-yl)-1-cyclopropyl-7-fluoro-9-methyl-4-oxo-4H-quinolizine-3-carboxylic acid 8-(6-Aminopyridin-3-yl)-1-cyclopropyl-7-fluoro-9-methyl-4-oxo-4H-quinolizine-3-carboxylic acid was prepared according to General Procedure B from ethyl 8-(6-aminopyridin-3-yl)-1-cyclopropyl-7-fluoro-9-methyl-4-oxo-4H-quinolizine-3-carboxylate (0.32 mmol) to afford compound 60 as a yellow solid (81 mg, 72% in two steps).

ESI-MS m/z: 354 (M+H)$^+$, 352 (M−H)$^-$; 1H NMR (400 MHz, DMSO) δ ppm 13.94 (s, 1H), 9.34 (d, J=5.8 Hz, 1H), 8.24 (s, 1H), 8.12 (s, 1H), 7.68 (d, J=8.8 Hz, 1H), 7.10 (s, 2H), 6.79 (d, J=8.8 Hz, 1H), 2.87 (s, 3H), 2.40-2.60 (m, 1H), 1.06-1.08 (m, 2H), 0.78-0.80 (m, 2H).

Preparation of compound 60K (potassium salt of compound 60) potassium 8-(6-aminopyridin-3-yl)-1-cyclopropyl-7-fluoro-9-methyl-4-oxo-4H-quinolizine-3-carboxylate potassium 8-(6-aminopyridin-3-yl)-1-cyclopropyl-7-fluoro-9-methyl-4-oxo-4H-quinolizine-3-carboxylate was prepared according to General Procedure D from 8-(6-aminopyridin-3-yl)-1-cyclopropyl-7-fluoro-9-methyl-4-oxo-4H-quinolizine-3-carboxylic acid (81.0 mg, 0.23 mmol) to afford the K salt of compound 60 as a yellow solid (70.4 mg, 73%).

ESI-MS m/z: 354 (M−K+H)$^+$, 352 (M−K−H)$^-$.

Preparation of Compound 61

Preparation of ethyl 8-(4-hydroxyphenyl)-1-cyclopropyl-7-fluoro-9-methyl-4-oxo-4H-quinolizine-3-carboxylate Ethyl 8-(4-hydroxyphenyl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (100 mg, 0.34 mmol) and (4-hydroxyphenyl) boronic acid (55.4 mg, 0.40 mmol). Purification by flash silica column chromatography (DCM:MeOH) (1:0 to 9:1) afforded the title compound as a yellow solid (80 mg, 68%).

ESI-MS m/z: 382 (M+H)$^+$.

Preparation of Compound 61 8-(4-hydroxyphenyl)-1-cyclopropyl-7-fluoro-9-methyl-4-oxo-4H-quinolizine-3-carboxylic acid 8-(4-Hydroxyphenyl)-1-cyclopropyl-7-fluoro-9-methyl-4-oxo-4H-quinolizine-3-carboxylic acid was prepared according to General Procedure B from ethyl 8-(4-hydroxyphenyl)-1-cyclopropyl-7-fluoro-9-methyl-4-oxo-4H-quinolizine-3-carboxylate (80 mg, 0.21 mmol) to afford compound 61 as a yellow solid (71 mg, 96%).

ESI-MS m/z: 354 (M+H)$^+$; 1H NMR (400 MHz, DMSO) δ ppm 13.96 (s, 1H), 10.04 (s, 1H), 9.34 (d, J=5.8 Hz, 1H), 8.23 (s, 1H), 7.31 (d, J=8.1 Hz, 2H), 6.97 (d, J=8.1 Hz, 2H), 2.81 (s, 3H), 2.40-2.60 (m, 1H), 1.04-1.06 (m, 2H), 0.77-0.79 (m, 2H).

Preparation of Compound 61K (Potassium Salt of Compound 61) potassium 8-(4-hydroxyphenyl)-1-cyclopropyl-7-fluoro-9-methyl-4-oxo-4H-quinolizine-3-carboxylate Potassium 18-(4-Hydroxyphenyl)-1-cyclopropyl-7-fluoro-9-methyl-4-oxo-4H-quinolizine-3-carboxylate was prepared according to General Procedure D from 8-(4-Hydroxyphenyl)-1-cyclopropyl-7-fluoro-9-methyl-4-oxo-4H-quinolizine-3-carboxylic acid (71 mg, 0.20 mmol) to afford the K salt of compound 61 as a yellow solid (56.4 mg, 67%).

ESI-MS m/z: 354 (M−K+H)$^+$, 352 (M−K−H)$^-$.

Preparation of Compound 62

Preparation of methyl 8-(1-(tert-butoxycarbonyl)-1,2,3,6-tetrahydropyridin-4-yl)-1-cyclopropyl-7-fluoro-9-methyl-4-oxo-4H-quinolizine-3-carboxylate Ethyl 8-(1-(tert-butoxycarbonyl)-1,2,3,6-tetrahydropyridin-4-yl)-1-cyclopropyl-7-fluoro-9-methyl-4-oxo-4H-quinolizine-3-carboxylate was prepared according to General Procedure A from ethyl 8-chloro-1-cyclopropyl-7-fluoro-9-methyl-4-oxo-4H-quinolizine-3-carboxylate (100 mg, 0.32 mmol) and tert-butyl-4-(4,4,5,5-tetramethyl-1,3,2-dioxaborolan-2-yl)-5,6-dihydropyridine-1(2H)-carboxylate (124.5 mg, 0.40 mmol). Purification by flash silica column chromatography (DCM:MeOH) (1:0 to 9:1) afforded quantitatively the title compound as a yellow solid.

ESI-MS m/z: 471 (M+H)$^+$.

Preparation of 8-(1-(tert-butoxycarbonyl)-1,2,3,6-tetrahydropyridin-4-yl)-1-cyclopropyl-7-fluoro-9-methyl-4-oxo-4H-quinolizine-3-carboxylic acid 8-(1-(tert-Butoxycarbonyl)-1,2,3,6-tetrahydropyridin-4-yl)-1-cyclopropyl-7-fluoro-9-methyl-4-oxo-4H-quinolizine-3-carboxylic acid was prepared according to General Procedure B from ethyl 8-(1-(tert-butoxycarbonyl)-1,2,3,6-tetrahydropyridin-4-yl)-1-cyclopropyl-7-fluoro-9-methyl-4-oxo-4H-quinolizine-3-carboxylate (0.32 mmol) to afford the title compound as a yellow solid (98 mg, 69% in two steps).

ESI-MS m/z: 443 (M+H)$^+$, 441 (M−H)$^-$.

Preparation of Compound 62HCl (Hydrochloric Salt of Compound 62) 8-(1,2,3,6-tetrahydropyridin-4-yl)-1-cyclopropyl-7-fluoro-9-methyl-4-oxo-4H-quinolizine-3-carboxylic acid hydrochloride The compound 8-(1,2,3,6-tetrahydropyridin-4-yl)-1-cyclopropyl-7-fluoro-9-methyl-4-oxo-4H-quinolizine-3-carboxylic acid hydrochloride was prepared according to General Procedure C from 8-(1-(tert-butoxycarbonyl)-1,2,3,6-tetrahydropyridin-4-yl)-1-cyclopropyl-7-fluoro-9-methyl-4-oxo-4H-quinolizine-3-carboxylic acid (98 mg, 0.22 mmol) to afford the HCl salt of compound 62 as a yellow solid (87 mg, 100%).

ESI-MS m/z: 343 (M+H)$^+$, 341 (M−H)$^-$; 1H NMR (400 MHz, DMSO) δ ppm 13.90 (s, 1H), 9.33 (d, J=5.8 Hz, 1H), 9.28 (s, 1H), 9.25 (s, 1H), 5.96 (s, 1H), 3.83 (s, 2H), 3.42 (s, 1H), 3.35-3.41 (m, 2H), 3.23 (s, 1H), 2.97 (s, 3H), 2.50-2.58 (m, 1H), 1.04-1.07 (m, 2H), 0.77-0.79 (m, 2H).

Preparation of Compound 62K (Potassium Salt of Compound 62) potassium 8-(1,2,3,6-tetrahydropyridin-4-yl)-1-cyclopropyl-7-fluoro-9-methyl-4-oxo-4H-quinolizine-3-carboxylate Potassium 8-(1,2,3,6-tetrahydropyridin-4-yl)-1-cyclopropyl-7-fluoro-9-methyl-4-oxo-4H-quinolizine-3-carboxylate was prepared according to General Procedure D from 8-(1,2,3,6-tetrahydropyridin-4-yl)-1-cyclopropyl-7-fluoro-9-methyl-4-oxo-4H-quinolizine-3-carboxylic acid hydrochloride (87 mg, 0.22 mmol) to afford the K salt of compound 62 as a yellow solid (78.5 mg, 89%).
ESI-MS m/z: 343(M−K+H)$^+$.

Preparation of Compound 63

Preparation of methyl 8-(4-(2,2,2-trifluoroacetyl)phenyl)-1-cyclopropyl-9-methyl-4-oxo-4H-quinolizine-3-carboxylate Methyl 8-(4-(2,2,2-trifluoroacetyl)phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 2,2,2-trifluoro-1-(4-(4,4,5,5-tetramethyl-1,3,2-dioxaborolan-2-yl)phenyl)ethanone (123.3 mg, 0.41 mmol). Purification by flash silica column chromatography (DCM:MeOH) (1:0 to 9:1) afforded the title compound as a yellow solid (93 mg, 63%).
ESI-MS m/z: 448(M+H$_3$O)$^+$, 428 (M−H)$^-$.

Preparation of Compound 63 8-(4-(2,2,2-trifluoroacetyl)phenyl)-1-cyclopropyl-9-methyl-4-oxo-4H-quinolizine-3-carboxylic acid 8-(4-(2,2,2-Trifluoroacetyl)phenyl)-1-cyclopropyl-9-methyl-4-oxo-4H-quinolizine-3-carboxylic acid was prepared according to General Procedure B from methyl 8-(4-(2,2,2-trifluoroacetyl)phenyl)-1-cyclopropyl-9-methyl-4-oxo-4H-quinolizine-3-carboxylate (93 mg, 0.22 mmol). Purification by preparative HPLC afforded compound 63 as a yellow solid (7.9 mg, 9%).
ESI-MS m/z: 434 (M+H$_2$O+H)$^+$; 414 (M−H)$^-$; 1H NMR (400 MHz, MeOD-d6) δ ppm 9.42 (s, 1H), 8.44 (d, J=13.9 Hz, 1H), 7.82 (s, 2H), 7.61 (s, 1H), 7.50 (s, 2H), 2.94 (s, 3H), 2.53 (s, 1H), 1.13 (s, 2H), 0.84 (s, 2H).

Preparation of Compound 64

Preparation of methyl 8-(4-(acetamidomethyl)phenyl)-1-cyclopropyl-9-methyl-4-oxo-4H-quinolizine-3-carboxylate Methyl 8-(4-(acetamidomethyl)phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and (4-(acetamidomethyl)phenyl)boronic acid (79.3 mg, 0.41 mmol). Purification by flash silica column chromatography (DCM:MeOH) (1:0 to 9:1) afforded the title compound as a yellow solid (137 mg, 99%).
ESI-MS m/z: 405 (M+H)$^+$.

Preparation of Compound 64 8-(4-(acetamidomethyl)phenyl)-1-cyclopropyl-9-methyl-4-oxo-4H-quinolizine-3-carboxylic acid 8-(4-(Acetamidomethyl)phenyl)-1-cyclopropyl-9-methyl-4-oxo-4H-quinolizine-3-carboxylic acid was prepared according to General Procedure B from methyl 8-(4-(acetamidomethyl)phenyl)-1-cyclopropyl-9-methyl-4-oxo-4H-quinolizine-3-carboxylate (137 mg, 0.34 mmol) to afford compound 64 as a yellow solid (111.5 mg, 84%).
ESI-MS m/z: 391 (M+H)$^+$; 1H NMR (400 MHz, DMSO-d6) δ ppm 9.33 (d, J=7.3 Hz, 1H), 8.48 (t, J=5.8 Hz, 1H), 8.27 (s, 1H), 7.56 (s, 1H) 7.53 (d, J=8.1 Hz, 2H), 7.45 (d, J=8.1 Hz, 2H), 7.36 (d, J=5.8 Hz, 2H), 2.86 (s, 3H), 2.40-2.60 (m, 1H), 1.91 (s, 3H), 1.06-1.08 (m, 2H), 0.78-0.80 (m, 2H).

Preparation of Compound 64K (Potassium Salt of Compound 64) potassium 8-(4-(Acetamidomethyl)phenyl)-1-cyclopropyl-9-methyl-4-oxo-4H-quinolizine-3-carboxylate Potassium 8-(4-(Acetamidomethyl)phenyl)-1-cyclopropyl-9-methyl-4-oxo-4H-quinolizine-3-carboxylate was prepared according to General Procedure D from 8-(4-(acetamidomethyl)phenyl)-1-cyclopropyl-9-methyl-4-oxo-4H-quinolizine-3-carboxylic acid (108.0 mg, 0.28 mmol) to afford the K salt of compound 64 as a yellow solid (111.5 mg, 93%).
ESI-MS m/z: 391 (M−K+H)$^+$.

Preparation of Compound 65

Preparation of methyl 8-(2-methylpyridin-4-yl)-1-cyclopropyl-9-methyl-4-oxo-4H-quinolizine-3-carboxylate Methyl 8-(2-methylpyridin-4-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and (2-methylpyridin-4-yl)boronic acid (56.3 mg, 0.41 mmol). Purification by flash silica column chromatography (DCM:MeOH) (1:0 to 9:1) afforded quantitatively the title compound as a yellow solid.
ESI-MS m/z: 349 (M+H)$^+$.

Preparation of Compound 65 8-(2-methylpyridin-4-yl)-1-cyclopropyl-9-methyl-4-oxo-4H-quinolizine-3-carboxylic acid 8-(2-Methylpyridin-4-yl)-1-cyclopropyl-9-methyl-4-oxo-4H-quinolizine-3-carboxylic acid was prepared according to General Procedure B from methyl 8-(2-methylpyridin-4-yl)-1-cyclopropyl-9-methyl-4-oxo-4H-quinolizine-3-carboxylate (0.34 mmol) to afford compound 65 as a yellow solid (71.7 mg, 63%).
ESI-MS m/z: 335 (M+H)$^+$, 333 (M−H)$^-$; 1H NMR (400 MHz, DMSO-d6) δ ppm 14.04 (s, 1H), 9.35 (d, J=7.3 Hz, 1H), 8.65 (d, J=5.0 Hz, 1H), 8.30 (s, 1H), 7.54 (d, J=7.3 Hz, 1H), 7.44 (s, 1H), 7.36 (d, J=4.8 Hz, 1H), 2.84 (s, 3H), 2.40-2.60 (m, 1H), 2.59 (s, 3H), 1.06-1.09 (m, 2H), 0.79-0.81 (m, 2H).

Preparation of Compound 65K (Potassium Salt of Compound 65) potassium 8-(2-methylpyridin-4-yl)-1-cyclopropyl-9-methyl-4-oxo-4H-quinolizine-3-carboxylate Potassium 8-(2-methylpyridin-4-yl)-1-cyclopropyl-9-methyl-4-oxo-4H-quinolizine-3-carboxylate was prepared according to General Procedure D from 1-cyclopropyl-9-methyl-8-(2-methylpyridin-4-yl)-4-oxo-4H-quinolizine-3- carboxylic acid (68.0 mg, 0.20 mmol) to afford the K salt of compound 65 as a yellow solid (71.7 mg, 94%).

ESI-MS m/z: 335 (M−K+H)$^+$, 333 (M−K−H)$^−$.

Preparation of Compound 66

Preparation of methyl 8-(4-hydroxy-3-methoxyphenyl)-1-cyclopropyl-9-methyl-4-oxo-4H-quinolizine-3-carboxylate Methyl 8-(4-hydroxy-3-methoxyphenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 2-methoxy-4-(4,4,5,5-tetramethyl-1,3,2-dioxaborolan-2-yl)phenol (102.7 mg, 0.41 mmol). Purification by flash silica column chromatography (DCM:MeOH) (1:0 to 9:1) afforded the title compound as a yellow solid (101 mg, 78%).

ESI-MS m/z: 380 (M+H)$^+$, 378 (M−H)$^−$.

Preparation of Compound 66 8-(4-hydroxy-3-methoxyphenyl)-1-cyclopropyl-9-methyl-4-oxo-4H-quinolizine-3-carboxylic acid 8-(4-Hydroxy-3-methoxyphenyl)-1-cyclopropyl-9-methyl-4-oxo-4H-quinolizine-3-carboxylic acid was prepared according to General Procedure B from methyl 8-(4-hydroxy-3-methoxyphenyl)-1-cyclopropyl-9-methyl-4-oxo-4H-quinolizine-3-carboxylate (101 mg, 0.27 mmol) to afford compound 66 as a yellow solid (73.2 mg, 75%).

ESI-MS m/z: 366 (M+H)$^+$, 364 (M−H)$^−$; 1H NMR (400 MHz, DMSO-d6) δ ppm 13.93 (s, 1H), 9.58 (s, 1H), 9.28 (d, J=7.0 Hz, 1H), 8.29 (s, 1H), 7.53 (s, 1H), 7.11 (s, 1H), 6.96-6.99 (m, 2H), 3.85 (s, 3H), 2.89 (s, 3H), 2.40-2.60 (m, 1H), 1.06-1.09 (m, 2H), 0.77-0.79 (m, 2H).

Preparation of Compound 66K (Potassium Salt of Compound 66) potassium 8-(4-hydroxy-3-methoxyphenyl)-1-cyclopropyl-9-methyl-4-oxo-4H-quinolizine-3-carboxylate Potassium 8-(4-hydroxy-3-methoxyphenyl)-1-cyclopropyl-9-methyl-4-oxo-4H-quinolizine-3-carboxylate was prepared according to General Procedure D from 8-(4-hydroxy-3-methoxyphenyl)-1-cyclopropyl-9-methyl-4-oxo-4H-quinolizine-3-carboxylic acid (117.9 mg, 0.32 mmol) to afford the K salt of compound 66 as a yellow solid (73.2 mg, 53%).

ESI-MS m/z: 366 (M−K+H)$^+$, 364 (M−K−H)$^−$.

Preparation of Compound 67

Preparation of methyl 8-(1H-pyrazol-4-yl)-1-cyclopropyl-9-methyl-4-oxo-4H-quinolizine-3-carboxylate Methyl 8-(1H-pyrazol-4-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and tert-butyl 4-(4,4,5,5-tetramethyl-1,3,2-dioxaborolan-2-yl)-1H-pyrazole-1-carboxylate (120.8 mg, 0.41 mmol). Purification by flash silica column chromatography (DCM:MeOH) (1:0 to 9:1) afforded the title compound as a yellow solid (54 mg, 49%).

ESI-MS m/z: 324 (M+H)$^+$, 322 (M−H)$^−$.

Preparation of Compound 67 8-(1H-pyrazol-4-yl)-1-cyclopropyl-9-methyl-4-oxo-4H-quinolizine-3-carboxylic acid 8-(1H-Pyrazol-4-yl)-1-cyclopropyl-9-methyl-4-oxo-4H-quinolizine-3-carboxylic acid was prepared according to General Procedure B from methyl 8-(1H-pyrazol-4-yl)-1-cyclopropyl-9-methyl-4-oxo-4H-quinolizine-3-carboxylate (54 mg, 0.17 mmol) to afford compound 67 as a yellow solid (28 mg, 54%).

ESI-MS m/z: 310 (M+H)$^+$, 308 (M−H)$^−$; 1H NMR (400 MHz, MeOD-d6) δ ppm 9.34 (d, J=7.6 Hz, 1H), 8.358 (s, 1H), 8.20 (s, 2H), 7.67 (d, J=7.3 Hz, 1H), 3.11 (s, 3H), 2.49-2.53 (m, 1H), 1.12-1.15 (m, 2H), 0.76-0.79 (m, 2H).

Preparation of Compound 67K (Potassium Salt of Compound 67) potassium 8-(1H-pyrazol-4-yl)-1-cyclopropyl-9-methyl-4-oxo-4H-quinolizine-3-carboxylate Potassium 8-(1H-pyrazol-4-yl)-1-cyclopropyl-9-methyl-4-oxo-4H-quinolizine-3-carboxylate was prepared according to General Procedure D from 8-(1H-pyrazol-4-yl)-1-cyclopropyl-9-methyl-4-oxo-4H-quinolizine-3-carboxylic acid (25.0 mg, 0.08 mmol) to afford the K salt of compound 67 as a yellow solid (27.2 mg, 88%).

ESI-MS m/z: 310 (M−K+H)$^+$, 308 (M−K−H)$^−$.

Preparation of Compound 68

Preparation of methyl 8-(3-oxoisoindolin-5-yl)-1-cyclopropyl-9-methyl-4-oxo-4H-quinolizine-3-carboxylate Methyl 8-(3-oxoisoindolin-5-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 6-(4,4,5,5-tetramethyl-1,3,2-dioxaborolan-2-yl)isoindolin-1-one (106.5 mg, 0.41 mmol). The precipitate was rinsed with DCM and dried in a vacuum stove to afford the title compound as a yellow solid (116 mg, 87%).

ESI-MS m/z: 389(M+H)$^+$.

Preparation of Compound 68 8-(3-oxoisoindolin-5-yl)-1-cyclopropyl-9-methyl-4-oxo-4H-quinolizine-3-carboxylic acid 8-(3-Oxoisoindolin-5-yl)-1-cyclopropyl-9-methyl-4-oxo-4H-quinolizine-3-carboxylic acid was prepared according to General Procedure B from methyl 8-(3-oxoisoindolin-5-yl)-1-cyclopropyl-9-methyl-4-oxo-4H-quinolizine-3-carboxylate (54 mg, 0.14 mmol) to afford compound 68 as a yellow solid (46 mg, 88%).

ESI-MS m/z: 375 (M+H)$^+$, 373 (M−H)$^−$; 1H NMR (400 MHz, DMSO-d6) δ ppm 14.04 (s, 1H), 9.36 (d, J=7.1 Hz, 1H,), 8.77 (s, 1H), 8.30 (s, 1H), 7.86 (d, J=7.8 Hz, 1H), 7.77 (s, 1H), 7.64 (d, J=7.6 Hz, 1H), 7.57 (d, J=6.6 Hz, 1H), 4.50 (s, 2H), 2.86 (s, 3H), 2.40-2.60 (m, 1H), 1.06-1.09 (m, 2H), 0.79-0.81 (m, 2H).

Preparation of Compound 68K (Potassium Salt of Compound 68) potassium 8-(3-oxoisoindolin-5-yl)-1-cyclopropyl-9-methyl-4-oxo-4H-quinolizine-3-carboxylate Potassium 8-(3-oxoisoindolin-5-yl)-1-cyclopropyl-9-methyl-4-oxo-4H-quinolizine-3-carboxylate was prepared according to General Procedure D 8-(3-oxoisoindolin-5-yl)-1-cyclopropyl-9-methyl-4-oxo-4H-quinolizine-3-carboxylic acid (44.0 mg, 0.12 mmol) to afford the K salt of compound 68 as a yellow solid (46.5 mg, 93%).
ESI-MS m/z: 375 (M−K+H)$^+$, 373 (M−K−H)$^-$.

Preparation of Compound 69

Preparation of N,2-dimethyl-4-(4,4,5,5-tetramethyl-1,3,2-dioxaborolan-2-yl)aniline N,2-dimethyl-4-(4,4,5,5-tetramethyl-1,3,2-dioxaborolan-2-yl)aniline was prepared according to General Procedure G with 4-bromo-N,2-dimethylaniline and bis(pinacolato)diboron. Purification by flash silica column chromatography (heptane: ethyl acetate) (1:0 to 1:1) followed by recrystallization in DCM and heptane afforded the title compound as an off-white solid (104 mg, 17%).
ESI-MS m/z: 248 (M+H)$^+$; 1H NMR (400 MHz, DMSO) δ ppm 7.63 (dd, J=8.1 Hz, J=1.0 Hz, 1H), 7.50 (s, 1H), 6.58 (d, J=8.1 Hz, 1H), 3.83 (br s, 1H), 2.91 (s, 3H), 2.12 (s, 3H), 1.32 (s, 12H).

Preparation of methyl 8-(3-methyl-4-(methylamino)phenyl)-1-cyclopropyl-9-methyl-4-oxo-4H-quinolizine-3-carboxylate Methyl 8-(3-methyl-4-(methylamino)phenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and N,2-dimethyl-4-(4,4,5,5-tetramethyl-1,3,2-dioxaborolan-2-yl)aniline (101.5 mg, 0.41 mmol). The residue was rinsed with DCM and dried in a vacuum stove to afford the title compound as a yellow solid (50 mg, 39%).
ESI-MS m/z: 377 (M+H)$^+$, 375 (M−H)$^-$.

Preparation of Compound 69 8-(3-methyl-4-(methylamino)phenyl)-1-cyclopropyl-9-methyl-4-oxo-4H-quinolizine-3-carboxylic acid 8-(3-Methyl-4-(methylamino)phenyl)-1-cyclopropyl-9-methyl-4-oxo-4H-quinolizine-3-carboxylic acid was prepared according to General Procedure B from methyl 8-(3-methyl-4-(methylamino)phenyl)-1-cyclopropyl-9-methyl-4-oxo-4H-quinolizine-3-carboxylate (50 mg, 0.13 mmol) to afford compound 69 as a yellow solid (44.3 mg, 92%).
ESI-MS m/z: 363 (M+H)$^+$, 361 (M−H)$^-$; 1H NMR (400 MHz, DMSO-d6) δ ppm 14.15 (s, 1H), 9.27 (d, J=7.3 Hz, 1H), 8.19 (s, 1H), 7.60 (d, J=7.3 Hz, 1H), 7.34 (d, J=7.8 Hz, 1H), 7.26 (s, 1H), 6.64 (d, J=8.3 Hz, 1H), 6.62-6.65 (m, 1H), 2.91 (s, 3H), 2.82 (d, J=4.8 Hz, 3H), 2.40-2.60 (m, 1H), 2.17 (s, 3H), 1.05-1.10 (m, 2H), 0.74-0.78 (m, 2H).

Preparation of Compound 69K (Potassium Salt of Compound 69) potassium 8-(3-methyl-4-(methylamino)phenyl)-1-cyclopropyl-9-methyl-4-oxo-4H-quinolizine-3-carboxylate Potassium 8-(3-methyl-4-(methylamino)phenyl)-1-cyclopropyl-9-methyl-4-oxo-4H-quinolizine-3-carboxylate was prepared according to General Procedure D from 8-(3-methyl-4-(methylamino)phenyl)-1-cyclopropyl-9-methyl-4-oxo-4H-quinolizine-3-carboxylic acid (41.0 mg, 0.11 mmol) to afford the K salt of compound 69 as a yellow solid (44.3 mg, 97%).
ESI-MS m/z: 363 (M−K+H)$^+$, 361 (M−K−H)$^-$.

Preparation of Compound 70

Preparation of methyl 8-(3-fluoro-4-hydroxyphenyl)-1-cyclopropyl-9-methyl-4-oxo-4H-quinolizine-3-carboxylate Methyl 8-(3-fluoro-4-hydroxyphenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and (3-fluoro-4-hydroxyphenyl)boronic acid (64.1 mg, 0.41 mmol). The residue was rinsed with DCM and dried in a vacuum stove to afford the title compound as a yellow solid (95 mg, 76%).
ESI-MS m/z: 368 (M+H)$^+$, 366 (M−H)$^-$.

Preparation of Compound 70 8-(3-fluoro-4-hydroxyphenyl)-1-cyclopropyl-9-methyl-4-oxo-4H-quinolizine-3-carboxylic acid 8-(3-Fluoro-4-hydroxyphenyl)-1-cyclopropyl-9-methyl-4-oxo-4H-quinolizine-3-carboxylic acid was prepared according to General Procedure B from methyl 8-(3-fluoro-4-hydroxyphenyl)-1-cyclopropyl-9-methyl-4-oxo-4H-quinolizine-3-carboxylate (95 mg, 0.26 mmol) to afford compound 70 as a yellow solid (87.8 mg, 96%).
ESI-MS m/z: 354 (M+H)$^+$, 352 (M−H)$^-$; 1H NMR (400 MHz, DMSO-d6) δ ppm 14.10 (s, 1H), 10.47 (s, 1H), 9.30 (d, J=7.3 Hz, 1H), 8.24 (s, 1H), 7.58 (d, J=7.1 Hz, 1H), 7.46 (d, J=12.4 Hz, 1H), 7.24 (d, J=7.6 Hz, 1H), 7.14 (t, J=8.7 Hz, 1H), 2.88 (s, 3H), 2.40-2.60 (m, 1H), 1.07-1.09 (m, 2H), 0.77-0.79 (m, 2H).

Preparation of Compound 70K (Potassium Salt of Compound 70) potassium 8-(3-fluoro-4-hydroxyphenyl)-1-cyclopropyl-9-methyl-4-oxo-4H-quinolizine-3-carboxylate Potassium 8-(3-fluoro-4-hydroxyphenyl)-1-cyclopropyl-9-methyl-4-oxo-4H-quinolizine-3-carboxylate was prepared according to General Procedure D from 8-(3-fluoro-4-hydroxyphenyl)-1-cyclopropyl-9-methyl-4-oxo-4H-quinolizine-3-carboxylic acid (84.0 mg, 0.23 mmol) to afford the K salt of compound 70 as a yellow solid (87.8 mg, 92%).
ESI-MS m/z: 354 (M−K+H)$^+$, 352 (M−K−H)$^-$.

Preparation of Compound 71

Preparation of tert-butyl 5-bromo-3-cyclopropyl-1H-indazole-1-carboxylate tert-Butyl 5-bromo-3-cyclopropyl-1H-indazole-1-carboxylate was prepared according to General Procedure F from 5-bromo-3-cyclopropyl-1H-indazole (500 mg, 2.11 mmol). tert-Butyl 5-bromo-3-cyclopropyl-1H-indazole-1-carboxylate was obtained as a colorless oil (760 mg, 89%).

ESI-MS m/z: isotopic 339 and 337 (M+H)+.

Preparation of tert-butyl 3-cyclopropyl-5-(4,4,5,5-tetramethyl-1,3,2-dioxaborolan-2-yl)-1H-indazole-1-carboxylate tert-Butyl 3-cyclopropyl-5-(4,4,5,5-tetramethyl-1,3,2-dioxaborolan-2-yl)-1H-indazole-1-carboxylate was prepared according to General Procedure G from tert-butyl 5-bromo-3-cyclopropyl-1H-indazole-1-carboxylate (760 mg, 1.87 mmol). Purification by flash silica column chromatography (heptane: ethyl acetate) (1:0 to 3:1) afforded the title compound as a white solid (750 mg, 100%).

ESI-MS m/z: 385 (M+H)+; 1H NMR (400 MHz, DMSO) δ ppm 8.23 (s, 1H), 8.04 (d, J=8.6 Hz, 1H), 7.92 (dd, J=8.6 Hz, J=1.0 Hz, 1H), 2.23-2.31 (m, 1H), 1.71 (s, 9H), 1.38 (s, 12H), 1.21-1.28 (m, 2H), 1.04-1.10 (m, 2H).

Preparation of methyl 8-(3-cyclopropyl-1H-indazol-5-yl)-1-cyclopropyl-9-methyl-4-oxo-4H-quinolizine-3-carboxylate Methyl 8-(3-cyclopropyl-1H-indazol-5-yl)-1-cyclopropyl-9-methyl-4-oxo-4H-quinolizine-3-carboxylate was prepared according to General Procedure A' from methyl 8-chloro-1-cyclopropyl-9-methyl-4-oxo-4H-quinolizine-3-carboxylate (75 mg, 0.26 mmol) and tert-butyl 3-cyclopropyl-5-(4,4,5,5-tetramethyl-1,3,2-dioxaborolan-2-yl)-1H-indazole-1-carboxylate (157.9 mg, 0.41 mmol). Purification by flash silica column chromatography (DCM:MeOH) (1:0 to 9:1) afforded the title compound as a yellow solid (84 mg, 60%).

ESI-MS m/z: 414 (M+H)+, 412 (M−H)−.

Preparation of Compound 71 8-(3-cyclopropyl-1H-indazol-5-yl)-1-cyclopropyl-9-methyl-4-oxo-4H-quinolizine-3-carboxylic acid 8-(3-Cyclopropyl-1H-indazol-5-yl)-1-cyclopropyl-9-methyl-4-oxo-4H-quinolizine-3-carboxylic acid was prepared according to General Procedure B from methyl 8-(3-cyclopropyl-1H-indazol-5-yl)-1-cyclopropyl-9-methyl-4-oxo-4H-quinolizine-3-carboxylate (84 mg, 0.20 mmol) to afford compound 71 as a yellow solid (57 mg, 80%).

ESI-MS m/z: 400 (M+H)+, 398 (M−H)−; 1H NMR (400 MHz, DMSO-d6) δ ppm 12.87 (s, 1H), 9.35 (d, J=7.3 Hz, 1H), 8.25 (s, 1H), 8.01 (s, 1H), 7.70 (d, J=7.3 Hz, 1H), 7.63 (d, J=8.6 Hz, 1H), 7.51 (dd, J=8.6 Hz, J=1.4 Hz, 1H), 2.91 (s, 3H), 2.53-2.60 (m, 1H), 2.35-2.42 (m, 1H), 1.05-1.12 (m, 3H), 0.97-1.04 (m, 4H), 0.79-0.84 (m, 2H).

Preparation of Compound 71K (Potassium Salt of Compound 71) potassium 8-(3-cyclopropyl-1H-indazol-5-yl)-1-cyclopropyl-9-methyl-4-oxo-4H-quinolizine-3-carboxylate Potassium 8-(3-cyclopropyl-1H-indazol-5-yl)-1-cyclopropyl-9-methyl-4-oxo-4H-quinolizine-3-carboxylate was prepared according to General Procedure D from 8-(3-cyclopropyl-1H-indazol-5-yl)-1-cyclopropyl-9-methyl-4-oxo-4H-quinolizine-3-carboxylic acid (54.8 mg, 0.14 mmol) to afford the K salt of compound 71 as a yellow solid (54.3 mg, 89%).

ESI-MS m/z: 400 (M−K+H)+.

Preparation of Compound 72

Preparation of tert-Butyl 5-bromo-2-hydroxybenzylcarbamate tert-Butyl 5-bromo-2-hydroxybenzylcarbamate was prepared according to General Procedure E from 5-bromo-2-hydroxybenzonitrile (1 g, 5.05 mmol). Purification by flash silica column chromatography (heptane: ethyl acetate) (1:0 to 4:1) afforded the title compound as a white solid (376 mg, 19%).

ESI-MS m/z: isotopic 302 and 300 (M+H)+.

Preparation of tert-butyl 2-hydroxy-5-(4,4,5,5-tetramethyl-1,3,2-dioxaborolan-2-yl)benzylcarbamate tert-Butyl 2-hydroxy-5-(4,4,5,5-tetramethyl-1,3,2-dioxaborolan-2-yl)benzylcarbamate was prepared according to General Procedure G from tert-Butyl 5-bromo-2-hydroxybenzylcarbamate (376 mg, 1.24 mmol). Purification by flash silica column chromatography (heptane: ethyl acetate) (1:0 to 9:1) afforded the title compound as a white solid (96 mg, 21%).

SI-MS m/z: 348 (M−H)−; 1H NMR (400 MHz, DMSO) δ ppm 9.30 (s, 1H), 7.67 (dd, J=8.1 Hz, J=1.3 Hz, 1H), 7.53 (d, J=1.5 Hz, 1H), 6.94 (d, J=8.1 Hz, 1H), 5.23-5.26 (m, 1H), 4.23 (d, J=6.8 Hz, 2H), 1.43 (s, 9H), 1.33 (s, 12H).

Preparation of methyl 8-(3-(((tert-butoxycarbonyl)amino)methyl)-4-hydroxyphenyl)-1-cyclopropyl-9-methyl-4-oxo-4H-quinolizine-3-carboxylate Methyl 8-(3-(((tert-butoxycarbonyl)amino) methyl)-4-hydroxyphenyl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (65 mg, 0.22 mmol) and tert-butyl 2-hydroxy-5-(4,4,5,5-tetramethyl-1,3,2-dioxaborolan-2-yl)benzylcarbamate (93.3 mg, 0.27 mmol). Purification by flash silica column chromatography (DCM:MeOH) (1:0 to 9:1) afforded the title compound as a yellow solid (85 mg, 100%).

ESI-MS m/z: 479 (M+H)+, 477 (M−H)−.

Preparation of 8-(3-((tert-butoxycarbonylamino)methyl)-4-hydroxyphenyl)-1-cyclopropyl-9-methyl-4-oxo-4H-quinolizine-3-carboxylic acid 8-(3-((tert-Butoxycarbonylamino)methyl)-4-hydroxyphenyl)-1-cyclopropyl-9-methyl-4-oxo-4H-quinolizine-3-carboxylic acid was prepared according to General Procedure B from methyl 8-(3-(((tert-butoxycarbonyl)amino) methyl)-4-hydroxyphenyl)-1-cyclopropyl-9-methyl-4-oxo-4H-quinolizine-3-carboxylate (85 mg, 0.22 mmol) to afford the title compound as a yellow solid (27 mg, 27%).

ESI-MS m/z: 465 (M+H)+, 463 (M−H)−.

Preparation of Compound 72HCl (Hydrochloric Salt of Compound 72) 8-(3-(aminomethyl)-4-hydroxyphenyl)-1-cyclopropyl-9-methyl-4-oxo-4H-quinolizine-3-carboxylic acid hydrochloride 8-(3-(Aminomethyl)-4-hydroxyphenyl)-1-cyclopropyl-9-methyl-4-oxo-4H-quinolizine-3-carboxylic acid hydrochloride was prepared according to General Procedure C from 8-(3-((tert-butoxycarbonylamino) methyl)-4-hydroxyphenyl)-1-cyclopropyl-9-methyl-4-oxo-4H-quinolizine-3-carboxylic acid (27.0 mg, 0.06 mmol) to afford the HCl salt of compound 72 as a yellow solid (23.4 mg, 97%).

ESI-MS m/z: 365 (M+H)$^+$, 363 (M−H)$^-$; 1H NMR (400 MHz, MeOD-d6) δ ppm 9.40 (s, 1H), 8.42 (s, 1H), 7.40-7.65 (m, 3H), 7.11 (d, J=7.8 Hz, 1H), 4.22 (s, 2H), 2.96 (s, 3H), 2.45-2.60 (m, 1H), 1.05-1.20 (m, 2H), 0.75-0.90 (m, 2H).

Preparation of Compound 72K (Potassium Salt of Compound 72) potassium 8-(3-(aminomethyl)-4-hydroxyphenyl)-1-cyclopropyl-9-methyl-4-oxo-4H-quinolizine-3-carboxylate Potassium 8-(3-(aminomethyl)-4-hydroxyphenyl)-1-cyclopropyl-9-methyl-4-oxo-4H-quinolizine-3-carboxylate was prepared according to General Procedure D from 8-(3-(aminomethyl)-4-hydroxyphenyl)-1-cyclopropyl-9-methyl-4-oxo-4H-quinolizine-3-carboxylic acid hydrochloride (23.4 mg, 0.06 mmol) to afford the K salt of compound 72 as a yellow solid (21.2 mg, 88%).

ESI-MS m/z: 365 (M−K+H)$^+$, 363 (M−K−H)$^-$.

Preparation of Compound 73

Preparation of a Mixture of tert-butyl (5-bromobenzo[d]thiazol-2-yl)carbamate and di-tert-butyl (5-bromobenzo[d]thiazol-2-yl)di-carbamate tert-Butyl (5-bromobenzo[d]thiazol-2-yl)carbamate and di-tert-butyl (5-bromobenzo[d]thiazol-2-yl)di-carbamate were prepared according to General Procedure F from 5-bromobenzo[d]thiazol-2-amine (500 mg, 2.18 mmol). The reaction yielded a 1:1 mixture of tert-butyl (5-bromobenzo[d]thiazol-2-yl)carbamate and di-tert-butyl (5-bromobenzo[d]thiazol-2-yl)di-carbamate as an off white solid (782 mg, 83%). The mixture was not separated.

ESI-MS m/z: isotopic 331 and 329 (M+H)$^+$ for mono-BOC component and isotopic 431 and 429 (M+H)$^+$ for di-BOC component.

Preparation of a Mixture of tert-butyl (5-(4,4,5,5-tetramethyl-1,3,2-dioxaborolan-2-yl)benzo[d]thiazol-2-yl)carbamate and di-tert-butyl 5-(4,4,5,5-tetramethyl-1,3,2-dioxaborolan-2-yl) benzo[d]thiazol-2-yl-di-carbamate The titles compounds were made according to General Procedure G from a mixture of tert-butyl (5-bromobenzo[d]thiazol-2-yl)carbamate and di-tert-butyl (5-bromobenzo[d]thiazol-2-yl)di-carbamate (782 mg, 1.82 mmol). Purification by flash silica column chromatography (heptane: ethyl acetate) (1:0 to 3:1) afforded a 1:1 mixture of tert-butyl (5-(4,4,5,5-tetramethyl-1,3,2-dioxaborolan-2-yl)benzo[d]thiazol-2-yl)carbamate and di-tert-butyl 5-(4,4,5,5-tetramethyl-1,3,2-dioxaborolan-2-yl) benzo[d]thiazol-2-yl-di-carbamate as white solid (774 mg, 97%).

ESI-MS m/z: 377 (M+H)$^+$, 477 377 (M+H)$^+$.

Preparation of methyl 8-(2-(tert-butoxycarbonyl) amino)benzo[d]thiazol-5-yl)-1-cyclopropyl-9-methyl-4-oxo-4H-quinolizine-3-carboxylate and methyl 8-(2-aminobenzo[d]thiazol-5-yl)-1-cyclopropyl-9-methyl-4-oxo-4H-quinolizine-3-carboxylate The title compounds were prepared according to General Procedure A' from methyl 8-chloro-1-cyclopropyl-9-methyl-4-oxo-4H-quinolizine-3-carboxylate (100 mg, 0.34 mmol) and a mixture of tert-butyl (5-(4,4,5,5-tetramethyl-1,3,2-dioxaborolan-2-yl)benzo[d]thiazol-2-yl)carbamate and di-tert-butyl 5-(4,4,5,5-tetramethyl-1,3,2-dioxaborolan-2-yl)benzo[d]thiazol-2-yl-di-carbamate (195.7 mg, 0.41 mmol). Purification by flash silica column chromatography (DCM:MeOH) (1:0 to 9:1) afforded methyl 8-(2-aminobenzo[d]thiazol-5-yl)-1-cyclopropyl-9-methyl-4-oxo-4H-quinolizine-3-carboxylate (58 mg, 38%) and yellow solid methyl 8-(2-(tert-butoxycarbonylamino)benzo[d]thiazol-5-yl)-1-cyclopropyl-9-methyl-4-oxo-4H-quinolizine-3-carboxylate (42 mg, 20%).

ESI-MS m/z: 406 (M+H)$^+$ and 404 (M−H)$^-$ for deprotected compound and 506 (M+H)$^+$ and 504 (M−H)$^-$ for the BOC-protected compound.

Preparation of Compound 73 8-(2-aminobenzo[d]thiazol-5-yl)-1-cyclopropyl-9-methyl-4-oxo-4H-quinolizine-3-carboxylic acid 8-(2-Aminobenzo[d]thiazol-5-yl)-1-cyclopropyl-9-methyl-4-oxo-4H-quinolizine-3-carboxylic acid was prepared according to General Procedure B from methyl 8-(2-amino)benzo[d]thiazol-5-yl)-1-cyclopropyl-9-methyl-4-oxo-4H-quinolizine-3-carboxylate (58 mg, 0.13 mmol) to afford compound 73 as a yellow solid (25.7 mg, 55%).

ESI-MS m/z: 392 (M+H)$^+$, 390 (M−H)$^-$; 1H NMR (400 MHz, DMSO-d6) δ ppm 9.34 (d, J=7.3 Hz, 1H), 8.87 (s, 2H), 8.27 (s, 1H), 7.98 (d, J=8.3 Hz, 1H), 7.60 (d, J=7.3 Hz, 1H), 7.58 (d, J=1.3 Hz, 1H), 7.32 (dd, J=8.1 Hz, J=1.5 Hz, 1H), 2.88 (s, 3H), 2.52-2.58 (m, 1H), 1.05-1.10 (m, 2H), 0.78-0.82 (m, 2H)

Preparation of Compound 73K (Potassium Salt of Compound 73) potassium 8-(2-aminobenzo[d]thiazol-5-yl)-1-cyclopropyl-9-methyl-4-oxo-4H-quinolizine-3-carboxylate Potassium 8-(2-aminobenzo[d]thiazol-5-yl)-1-cyclopropyl-9-methyl-4-oxo-4H-quinolizine-3-carboxylate was prepared according to General Procedure D from 8-(2-aminobenzo[d]thiazol-5-yl)-1-cyclopropyl-9-methyl-4-oxo-4H-quinolizine-3-carboxylic acid (23.8 mg, 0.06 mmol) to afford the K salt of compound 73 as a yellow solid (21.6 mg, 80%).

ESI-MS m/z: 392 (M−K+H)$^+$, 390 (M−K−H)$^-$.

Preparation of Compound 74

Preparation of a Mixture of tert-butyl 5-bromo-1H-benzo[d]imidazole-1-carboxylate and tert-butyl 6-bromo-1H-benzo[d]imidazole-1-carboxylate The title compounds were made according to General Procedure F from 5-bromo-1H-benzo[d]imidazole (500 mg, 2.54 mmol). Purification by flash silica column chromatography (heptane: ethyl acetate) (1:0 to 1:1) afforded a mixture of tert-butyl 5-bromo-1H-benzo[d]imidazole-1-carboxylate and tert-butyl 6-bromo-1H-benzo[d]imidazole-1-carboxylate as a colorless oil (537 mg, 70%).

ESI-MS m/z: isotopic 299 and 297 (M+H)$^+$.

Preparation of a Mixture of tert-butyl 5-(4,4,5,5-tetramethyl-1,3,2-dioxaborolan-2-yl)-1H-benzo[d]imidazole-1-carboxylate and tert-butyl 6-(4,4,5,5-tetramethyl-1,3,2-dioxaborolan-2-yl)-1H-benzo[d]imidazole-1-carboxylate The title compounds were made according to General Procedure G from a mixture of tert-butyl 5-bromo-1H-benzo

[d]imidazole-1-carboxylate and tert-butyl 6-bromo-1H-benzo[d]imidazole-1-carboxylate (537 mg, 1.81 mmol). Purification by flash silica column chromatography (heptane: ethyl acetate) (1:0 to 3:1) afforded a mixture of tert-butyl 5-(4,4,5,5-tetramethyl-1,3,2-dioxaborolan-2-yl)-1H-benzo[d]imidazole-1-carboxylate and tert-butyl 6-(4,4,5,5-tetramethyl-1,3,2-dioxaborolan-2-yl)-1H-benzo[d]imidazole-1-carboxylate as an orange oil: (937 mg, 98%).
ESI-MS m/z: 345 (M+H)$^+$.

Preparation of methyl 8-(1H-benzo[d]imidazol-5-yl)-1-cyclopropyl-9-methyl-4-oxo-4H-quinolizine-3-carboxylate Methyl 8-(1H-benzo[d]imidazol-5-yl)-1-cyclopropyl-9-methyl-4-oxo-4H-quinolizine-3-carboxylate was prepared according to General Procedure A' from methyl 8-chloro-1-cyclopropyl-9-methyl-4-oxo-4H-quinolizine-3-carboxylate (75 mg, 0.26 mmol) and a mixture of tert-butyl 5-(4,4,5,5-tetramethyl-1,3,2-dioxaborolan-2-yl)-1H-benzo[d]imidazole-1-carboxylate and tert-butyl 6-(4,4,5,5-tetramethyl-1,3,2-dioxaborolan-2-yl)-1H-benzo[d]imidazole-1-carboxylate (141.5 mg, 0.41 mmol). Purification by flash silica column chromatography (DCM:MeOH) (1:0 to 9:1) afforded the title BOC-deprotected compound as a yellow solid (69.9 mg, 65%).
ESI-MS m/z: 374 (M+H)$^+$, 372 (M−H)$^−$.

Preparation of Compound 74 8-(1H-benzo[d]imidazol-5-yl)-1-cyclopropyl-9-methyl-4-oxo-4H-quinolizine-3-carboxylic acid 8-(1H-Benzo[d]imidazol-5-yl)-1-cyclopropyl-9-methyl-4-oxo-4H-quinolizine-3-carboxylic acid was prepared according to General Procedure B from methyl 8-(1H-benzo[d]imidazol-5-yl)-1-cyclopropyl-9-methyl-4-oxo-4H-quinolizine-3-carboxylate (69.9 mg, 0.17 mmol) to afford compound 74 as a yellow solid (57.5 mg, 94%).
ESI-MS m/z: 360 (M+H)$^+$, 358 (M−H)$^−$; 1H NMR (400 MHz, DMSO-d6) δ ppm 14.14 (s, 1H), 9.36 (d, J=7.3 Hz, 1H), 8.76 (s, 1H), 8.27 (s, 1H), 7.85-7.87 (m, 2H), 7.67 (d, J=7.4 Hz, 1H), 7.46-7.49 (m, 1H), 2.89 (s, 3H), 2.50-2.60 (m, 1H), 1.06-1.11 (m, 2H), 0.79-0.83 (m, 2H).

Preparation of Compound 74K (Potassium Salt of Compound 74) potassium 8-(1H-benzo[d]imidazol-5-yl)-1-cyclopropyl-9-methyl-4-oxo-4H-quinolizine-3-carboxylate Potassium 8-(1H-benzo[d]imidazol-5-yl)-1-cyclopropyl-9-methyl-4-oxo-4H-quinolizine-3-carboxylate was prepared according to General Procedure D from 8-(1H-benzo[d]imidazol-5-yl)-1-cyclopropyl-9-methyl-4-oxo-4H-quinolizine-3-carboxylic acid (54.5 mg, 0.15 mmol) to afford the K salt of compound 74 as a yellow solid (47.3 mg, 76%).
ESI-MS m/z: 360 (M−K+H)$^+$, 358 (M−K−H)$^−$.

Preparation of Compound 75

Preparation of ethyl 8-(1H-indazol-5-yl)-1-cyclopropyl-7-fluoro-9-methyl-4-oxo-4H-quinolizine-3-carboxylate Ethyl 8-(1H-indazol-5-yl)-1-cyclopropyl-7-fluoro-9-methyl-4-oxo-4H-quinolizine-3-carboxylate was prepared according to General Procedure A' from ethyl 8-chloro-1-cyclopropyl-7-fluoro-9-methyl-4-oxo-4H-quinolizine-3-carboxylate (50 mg, 0.15 mmol) and 5-(4,4,5,5-tetramethyl-1,3,2-dioxaborolan-2-yl)-1H-indazole (45.2 mg, 0.19 mmol). Purification by flash silica column chromatography (DCM:MeOH) (1:0 to 9:1) afforded the title compound as a yellow solid (48 mg, 77%).
ESI-MS m/z: 406 (M+H)$^+$.

Preparation of Compound 75 8-(1H-indazol-5-yl)-1-cyclopropyl-7-fluoro-9-methyl-4-oxo-4H-quinolizine-3-carboxylic acid 8-(1H-Indazol-5-yl)-1-cyclopropyl-7-fluoro-9-methyl-4-oxo-4H-quinolizine-3-carboxylic acid was prepared according to General Procedure B from ethyl 1-cyclopropyl-7-fluoro-9-methyl-4-oxo-4H-quinolizine-3-carboxylate (48 mg, 0.12 mmol) to afford compound 75 as a yellow solid (36 mg, 78%).
ESI-MS m/z: 378 (M+H)$^+$, 376 (M−H)$^−$; 1H NMR (400 MHz, DMSO) δ ppm 13.37 (s, 1H), 9.40 (d, J=5.6 Hz, 1H), 8.27 (s, 1H), 8.23 (s, 1H), 7.94 (s, 1H), 5.96 (d, J=8.6 Hz, 1H), 3.83 (d, J=8.6 Hz, 1H), 2.83 (s, 3H), 2.50-2.59 (m, 1H), 1.05-1.11 (m, 2H), 0.79-0.83 (m, 2H).

Preparation of Compound 75K (Potassium Salt of Compound 75) potassium 8-(1H-indazol-5-yl)-1-cyclopropyl-7-fluoro-9-methyl-4-oxo-4H-quinolizine-3-carboxylate Potassium 8-(1H-indazol-5-yl)-1-cyclopropyl-7-fluoro-9-methyl-4-oxo-4H-quinolizine-3-carboxylate according to General Procedure D from 8-(1H-indazol-5-yl)-1-cyclopropyl-7-fluoro-9-methyl-4-oxo-4H-quinolizine-3-carboxylic acid (30.0 mg, 0.08 mmol) to afford the K salt of compound 75 as a yellow solid (30.7 mg, 89%).
ESI-MS m/z: 354 (M−K+H)$^+$, 352 (M−K−H)$^−$.

Preparation of Compound 76

Preparation of tert-butyl N-[4-bromo-2-[(tert-butoxycarbonylamino)-methyl]-phenyl]carbamate tert-Butyl N-[4-bromo-2-[(tert-butoxycarbonylamino)-methyl]-phenyl]-carbamate was prepared according to General Procedure E from 2-amino-5-bromo-benzonitrile (1.045 g, 5.30 mmol). Purification by flash silica column chromatography (heptane: ethyl acetate) (1:0 to 9:1) afforded the title compound as a colorless oil (1.834 g, 84%).
ESI-MS m/z: isotopic 401 and 399 (M+H)$^+$; 1H NMR (400 MHz, DMSO) δ ppm 8.21 (br s, 1H), 7.95 (d, J=7.8 Hz, 1H), 7.37 (dd, J=8.8 Hz, J=2.3 Hz, 1H), 7.26 (d, J=2.3 Hz, 1H), 5.00 (br s, 1H), 4.22 (d, J=6.6 Hz, 1H), 1.53 (s, 9H), 1.46 (s, 9H).

Preparation of tert-butyl N-[2-[(tert-butoxycarbonylamino)methyl]-4-(4,4,5,5-tetramethyl-1,3,2-dioxaborolan-2-yl)phenyl]carbamate tert-Butyl N-[2-[(tert-butoxycarbonylamino) methyl]-4-(4,4,5,5-tetramethyl-1,3,2-dioxaborolan-2-yl)phenyl]-carbamate was prepared according to General Procedure G from tert-butyl N-[4-bromo-2-[(tert-butoxycarbonylamino)-methyl]-phenyl]-carbamate (780 mg, 1.94 mmol). Purification by flash silica column chromatography (heptane: ethyl acetate) (1:0 to 9:1) afforded the title compound as a white solid (314 mg, 30%).
ESI-MS m/z: 449 (M+H)$^+$, 447 (M−H)$^−$; 1H NMR (400 MHz, DMSO) δ ppm 8.39 (br s, 1H), 8.16 (d, J=8.1 Hz, 1H), 7.72 (dd, J=8.3 Hz, J=1.2 Hz, 1H), 7.55 (s, 1H), 4.85-5.00 (m, 1H), 4.28 (d, J=6.3 Hz, 2H), 1.52 (s, 9H), 1.46 (s, 9H), 1.33 (s, 12H).

Preparation of methyl 8-(4-(tert-butoxycarbonyl) amino)-3-((tert-butoxycarbonyl)amino)-methyl)-phenyl)-1-cyclopropyl-9-methyl-4-oxo-4H-quinolizine-3-carboxylate Methyl 8-(4-(tert-butoxycarbonyl)amino)-3-((tert-butoxycarbonyl)amino)-methyl)-phenyl)-1-cyclopropyl-9-methyl-4-oxo-4H-quinolizine-3-carboxylate was prepared according to General Procedure A' from methyl 8-chloro-1-cyclopropyl-9-methyl-4-oxo-4H-quinolizine-3-carboxylate (95 mg, 0.33 mmol) and tert-butyl N-[2-[(tert-butoxycarbonylamino)methyl]-4-(4,4,5,5-tetramethyl-1,3,2-dioxaborolan-2-yl)phenyl]-carbamate (175 mg, 0.39 mmol). Purification by flash silica column chromatography (DCM:MeOH) (1:0 to 9:1) afforded the title compound as a yellow solid (176 mg, 94%).
ESI-MS m/z: 578 (M+H)$^+$.

Preparation of 8-(4-(tert-butoxycarbonylamino)-3-((tert-butoxycarbonylamino)-methyl)-phenyl)-1-cyclopropyl-9-methyl-4-oxo-4H-quinolizine-3-carboxylic acid 8-(4-(tert-Butoxycarbonylamino)-3-((tert-butoxycarbonylamino)-methyl)-phenyl)-1-cyclopropyl-9-methyl-4-oxo-4H-quinolizine-3-carboxylic acid was prepared according to General Procedure B from methyl 8-(4-((tert-butoxycarbonyl)amino)-3-((tert-butoxycarbonyl)-amino) methyl)-phenyl)-1-cyclopropyl-9-methyl-4-oxo-4H-quinolizine-3-carboxylate (176 mg, 0.30 mmol) to afford the title compound as a yellow solid (123 mg, 84%).
ESI-MS m/z: 564 (M+H)$^+$, 562 (M−H)$^−$.

Preparation of Compound 76HCl (Hydrochloric Salt of Compound 76) 8-(4-amino-3-(aminomethyl) phenyl)-1-cyclopropyl-9-methyl-4-oxo-4H-quinolizine-3-carboxylic acid hydrochloride 8-(4-Amino-3-(aminomethyl)phenyl)-1-cyclopropyl-9-methyl-4-oxo-4H-quinolizine-3-carboxylic acid hydrochloride was prepared according to General Procedure C from 8-(4-(tert-butoxycarbonylamino)-3-((tert-butoxycarbonylamino)methyl)-phenyl)-1-cyclopropyl-9-methyl-4-oxo-4H-quinolizine-3-carboxylic acid (123.0 mg, 0.22 mmol) to afford the HCl salt of compound 76 as a yellow solid (54.7 mg, 60%).
ESI-MS m/z: 364 (M+H)$^+$, 362 (M−H)$^−$; 1H NMR (400 MHz, DMSO-d6) δ ppm 9.31 (d, J=7.3 Hz, 1H), 8.31 (s, 3H), 8.22 (s, 1H), 7.60 (d, J=7.6 Hz, 1H), 7.53 (d, J=1.8 Hz, 1H), 7.41 (dd, J=8.3 Hz, J=1.8 Hz, 1H), 6.95 (d, J=8.3 Hz, 1H), 4.04 (s, 2H), 2.92 (s, 3H), 2.40-2.57 (m, 1H), 1.06-1.11 (m, 2H), 0.75-0.78 (m, 2H).

Preparation of Compound 76K (Potassium Salt of Compound 76) potassium 8-(4-amino-3-(aminomethyl) phenyl)-1-cyclopropyl-9-methyl-4-oxo-4H-quinolizine-3-carboxylate Potassium 8-(4-amino-3-(aminomethyl)phenyl)-1-cyclopropyl-9-methyl-4-oxo-4H-quinolizine-3-carboxylate was prepared according to General Procedure D from 8-(4-amino-3-(aminomethyl)phenyl)-1-cyclopropyl-9-methyl-4-oxo-4H-quinolizine-3-carboxylic acid hydrochloride (51.7 mg, 0.13 mmol) to afford the K salt of compound 76 as a yellow solid (47.9 mg, 86%).
ESI-MS m/z: 364 (M−K+H)$^+$, 362 (M−K−H)$^−$.

Preparation of Compound 77

Preparation of tert-butyl 5-bromoindoline-1-carboxylate tert-Butyl 5-bromoindoline-1-carboxylate was prepared according to General Procedure F using 5-bromoindoline (500 mg, 2.52 mmol) and was obtained as a brown solid; (769 mg, 63%).
ESI-MS m/z: isotopic 244 and 242 (M-tBu+H)$^+$.

Preparation of tert-butyl 5-(4,4,5,5-tetramethyl-1,3,2-dioxaborolan-2-yl)indoline-1-carboxylate tert-Butyl 5-(4,4,5,5-tetramethyl-1,3,2-dioxaborolan-2-yl)indoline-1-carboxylate was prepared according to General Procedure G from tert-butyl 5-bromoindoline-1-carboxylate (769 mg, 1.60 mmol). Purification by flash silica column chromatography (heptane: ethyl acetate) (1:0 to 3:1) afforded the title compound as a white solid (581 mg, 100%).
ESI-MS m/z: 290 (M-tBu+H)$^+$; 1H NMR (400 MHz, DMSO) δ ppm 7.84 (br s, 1H), 7.64 (d, J=7.8 Hz, 1H), 7.59 (s 1H), 3.97 (t, J=8.4 Hz, 2H), 3.07 (t, J=8.7 Hz, 2H), 1.56 (s, 9H), 1.33 (s, 12H).

Preparation of methyl 8-(1-(tert-butoxycarbonyl) indolin-5-yl)-1-cyclopropyl-9-methyl-4-oxo-4H-quinolizine-3-carboxylate Methyl 8-(1-(tert-butoxycarbonyl)indolin-5-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (75 mg, 0.26 mmol) and tert-butyl 5-(4,4,5,5-tetramethyl-1,3,2-dioxaborolan-2-yl)indoline-1-carboxylate (106.4 mg, 0.31 mmol). Purification by flash silica column chromatography (DCM:MeOH) (1:0 to 9:1) afforded the title compound as a yellow solid (121 mg, 99%).
ESI-MS m/z: 475 (M+H)$^+$.

Preparation of 8-(1-(tert-butoxycarbonyl)indolin-5-yl)-1-cyclopropyl-9-methyl-4-oxo-4H-quinolizine-3-carboxylic acid 8-(1-(tert-Butoxycarbonyl)indolin-5-yl)-1-cyclopropyl-9-methyl-4-oxo-4H-quinolizine-3-carboxylic acid was prepared according to General Procedure B from methyl 8-(1-(tert-butoxycarbonyl)indolin-5-yl)-1-cyclopropyl-9-methyl-4-oxo-4H-quinolizine-3-carboxylate (121 mg, 0.26 mmol) to afford compound 77 as a yellow solid (102.2 mg, 89%).
ESI-MS m/z: 461 (M+H)$^+$, 362 (M−H)$^−$.

Preparation of Compound 77HCl (Hydrochloric Salt of Compound 77) 8-(indolin-5-yl)-1-cyclopropyl-9-methyl-4-oxo-4H-quinolizine-3-carboxylic acid hydrochloride 8-(Indolin-5-yl)-1-cyclopropyl-9-methyl-4-oxo-4H-quinolizine-3-carboxylic acid hydrochloride was prepared according to General Procedure C from 8-(1-(tert-butoxycarbonyl)indolin-5-yl)-1-cyclopropyl-9-methyl-4-oxo-4H- quinolizine-3-carboxylic acid (102.2 mg, 0.22 mmol) to afford the HCl salt of compound 77 as a yellow solid (84.9 mg, 94%).

ESI-MS m/z: 361 (M+H)⁺, 359 (M−H)⁻; 1H NMR (400 MHz, DMSO-d6) δ ppm 9.30 (d, J=7.6 Hz, 1H), 8.24 (s, 1H), 7.57 (d, J=7.3 Hz, 1H), 7.49 (s, 1H), 7.38 (d, J=7.8 Hz, 1H), 7.16 (d, J=7.6 Hz, 1H), 3.69 (t, J=8.2 Hz, 2H), 3.18 (t, J=8.2 Hz, 2H), 2.88 (s, 3H), 2.40-2.57 (m, 1H), 1.05-1.09 (m, 2H), 0.76-0.79 (m, 2H).

Preparation of Compound 77K (Potassium Salt of Compound 77) potassium 8-(indolin-5-yl)-1-cyclopropyl-9-methyl-4-oxo-4H-quinolizine-3-carboxylate Potassium 8-(indolin-5-yl)-1-cyclopropyl-9-methyl-4-oxo-4H-quinolizine-3-carboxylate was prepared according to General Procedure D from 8-(indolin-5-yl)-1-cyclopropyl-9-methyl-4-oxo-4H-quinolizine-3-carboxylic acid hydrochloride (82.9 mg, 0.21 mmol) to afford the K salt of compound 77 as a yellow solid (99.9 mg, 100%).

ESI-MS m/z: 361 (M−K+H)⁺, 359 (M−K−H)⁻.

Preparation of Compound 78

Preparation of methyl 8-(6-(methylamino)pyridin-3-yl)-1-cyclopropyl-9-methyl-4-oxo-4H-quinolizine-3-carboxylate Methyl 8-(6-(methylamino)pyridin-3-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and N-methyl-5-(4,4,5,5-tetramethyl-1,3-dioxolan-2-yl)pyridin-2-amine (96.2 mg, 0.41 mmol). Purification by flash silica column chromatography (DCM:MeOH) (1:0 to 9:1) afforded the title compound as a yellow solid (131.6 mg, 96%).

ESI-MS m/z: 364 (M+H)⁺.

Preparation of Compound 78 8-(6-(methylamino)pyridin-3-yl)-1-cyclopropyl-9-methyl-4-oxo-4H-quinolizine-3-carboxylic acid 8-(6-(Methylamino)pyridin-3-yl)-1-cyclopropyl-9-methyl-4-oxo-4H-quinolizine-3-carboxylic acid was prepared according to General Procedure B from methyl 8-(6-(methylamino)pyridin-3-yl)-1-cyclopropyl-9-methyl-4-oxo-4H-quinolizine-3-carboxylate (131.6 mg, 0.33 mmol) to afford compound 78 as a yellow solid (39.5 mg, 31%).

ESI-MS m/z: 350 (M+H)⁺, 348 (M−H)⁻; 1H NMR (400 MHz, DMSO-d6) δ ppm 14.01 (s, 1H), 9.33 (d, J=7.3 Hz, 1H), 8.85 (s, 1H), 8.26 (s, 1H), 8.20 (s, 1H), 8.01 (d, J=9.3 Hz, 1H), 7.61 (d, J=7.3 Hz, 1H), 7.11 (d, J=9.1 Hz, 1H), 3.01 (s, 3H), 2.89 (s, 3H), 2.50-2.58 (m, 1H), 1.06-1.10 (m, 2H), 0.78-0.82 (m, 2H).

Preparation of Compound 78K (Potassium Salt of Compound 78) potassium 8-(6-(methylamino)pyridin-3-yl)-1-cyclopropyl-9-methyl-4-oxo-4H-quinolizine-3-carboxylate Potassium 8-(6-(methylamino)pyridin-3-yl)-1-cyclopropyl-9-methyl-4-oxo-4H-quinolizine-3-carboxylate was prepared according to General Procedure D from 8-(6-(methylamino)pyridin-3-yl)-1-cyclopropyl-9-methyl-4-oxo-4H-quinolizine-3-carboxylic acid (38.2 mg, 0.11 mmol) to afford the K salt of compound 78 as a yellow solid (37.9 mg, 89%).

ESI-MS m/z: 350 (M−K+H)⁺, 348 (M−K−H)⁻.

Preparation of Compound 79

Preparation of methyl 8-(6-amino-5-methylpyridin-3-yl)-1-cyclopropyl-9-methyl-4-oxo-4H-quinolizine-3-carboxylate Methyl 8-(6-amino-5-methylpyridin-3-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 3-methyl-5-(4,4,5,5-tetramethyl-1,3,2-dioxaborolan-2-yl)pyridin-2-amine (96.2 mg, 0.41 mmol). Purification by flash silica column chromatography (DCM:MeOH) (1:0 to 9:1) afforded quantitatively the title compound as a yellow solid.

ESI-MS m/z: 364 (M+H)⁺.

Preparation of Compound 79 8-(6-amino-5-methylpyridin-3-yl)-1-cyclopropyl-9-methyl-4-oxo-4H-quinolizine-3-carboxylic acid 8-(6-Amino-5-methylpyridin-3-yl)-1-cyclopropyl-9-methyl-4-oxo-4H-quinolizine-3-carboxylic acid was prepared according to General Procedure B from methyl 8-(6-amino-5-methylpyridin-3-yl)-1-cyclopropyl-9-methyl-4-oxo-4H-quinolizine-3-carboxylate (0.34 mmol) to afford compound 79 as a yellow solid (75 mg, 57% in two steps).

ESI-MS m/z: 350 (M+H)⁺, 348 (M−H)⁻; 1H NMR (400 MHz, DMSO-d6) δ ppm 14.13 (s, 1H), 9.28 (d, J=7.0 Hz, 1H), 8.21 (s, 1H), 8.07 (s, 1H), 7.60 (d, J=6.8 Hz, 1H), 7.54 (s, 1H), 6.33 (s, 2H), 2.91 (s, 3H), 2.40-2.60 (m, 1H), 2.14 (s, 3H), 1.06-1.09 (m, 2H), 0.72-0.80 (m, 2H).

Preparation of Compound 79K (Potassium Salt of Compound 79) potassium 8-(6-amino-5-methylpyridin-3-yl)-1-cyclopropyl-9-methyl-4-oxo-4H-quinolizine-3-carboxylate Potassium 8-(6-amino-5-methylpyridin-3-yl)-1-cyclopropyl-9-methyl-4-oxo-4H-quinolizine-3-carboxylate was prepared according to General Procedure D from 8-(6-amino-5-methylpyridin-3-yl)-1-cyclopropyl-9-methyl-4-oxo-4H-quinolizine-3-carboxylic acid (71.2 mg, 0.20 mmol) to afford the K salt of compound 79 as a yellow solid (81.1 mg, 100%).

ESI-MS m/z: 350 (M−K+H)⁺.

Preparation of Compound 80

Preparation of methyl 8-(3-methyl-1H-indazol-5-yl)-1-cyclopropyl-9-methyl-4-oxo-4H-quinolizine-3-carboxylate Methyl 8-(3-methyl-1H-indazol-5-yl)-1-cyclopropyl-9-methyl-4-oxo-4H-quinolizine-3-carboxylate was prepared according to General Procedure A' from methyl 8-chloro-1-cyclopropyl-9-methyl-4-oxo-4H-quinolizine-3-carboxylate (100 mg, 0.34 mmol) and (3-methyl-1H-indazol-5-yl)boronic acid (176.1 mg, 0.41 mmol). Purification by flash silica column chromatography (DCM:MeOH) (1:0 to 9:1) afforded the title compound as a yellow solid (120 mg, 88%).

ESI-MS m/z: 388 (M+H)$^+$.

Preparation of Compound 80 8-(3-methyl-1H-indazol-5-yl)-1-cyclopropyl-9-methyl-4-oxo-4H-quinolizine-3-carboxylic acid 8-(3-Methyl-1H-indazol-5-yl)-1-cyclopropyl-9-methyl-4-oxo-4H-quinolizine-3-carboxylic acid was prepared according to General Procedure B from methyl 8-(3-methyl-1H-indazol-5-yl)-1-cyclopropyl-9-methyl-4-oxo-4H-quinolizine-3-carboxylate (120 mg, 0.30 mmol) to afford compound 80 as a yellow solid (97 mg, 84%).

ESI-MS m/z: 374 (M+H)$^+$, 372 (M−H)$^-$; 1H NMR (400 MHz, DMSO-d6) δ ppm 9.35 (d, J=7.3 Hz, 1H), 8.25 (s, 1H), 7.96 (s, 1H), 7.68 (d, J=7.3 Hz, 1H), 7.64 (d, J=8.6 Hz, 1H), 7.51 (dd, J=1.5 Hz, J=8.6 Hz, 1H), 2.90 (s, 3H), 2.50-2.60 (m, 1H), 2.56 (s, 3H), 1.06-1.10 (m, 2H), 0.79-0.83 (m, 2H).

Preparation of Compound 80K (Potassium Salt of Compound 80) potassium 8-(3-methyl-1H-indazol-5-yl)-1-cyclopropyl-9-methyl-4-oxo-4H-quinolizine-3-carboxylate Potassium 8-(3-methyl-1H-indazol-5-yl)-1-cyclopropyl-9-methyl-4-oxo-4H-quinolizine-3-carboxylate was prepared according to General Procedure D from 8-(3-methyl-1H-indazol-5-yl)-1-cyclopropyl-9-methyl-4-oxo-4H-quinolizine-3-carboxylic acid (92.2 mg, 0.25 mmol) to afford the K salt of compound 80 as a yellow solid (103.3 mg, 100%).

ESI-MS m/z: 374 (M+H)$^+$, 372 (M−H)$^-$.

Preparation of Compound 81

Preparation of methyl 8-(1-methyl-1H-indazol-5-yl)-1-cyclopropyl-9-methyl-4-oxo-4H-quinolizine-3-carboxylate Methyl 8-(1-methyl-1H-indazol-5-yl)-1-cyclopropyl-9-methyl-4-oxo-4H-quinolizine-3-carboxylate was prepared according to General Procedure A' from methyl 8-chloro-1-cyclopropyl-9-methyl-4-oxo-4H-quinolizine-3-carboxylate (100 mg, 0.34 mmol) and (1-methyl-1H-indazol-5-yl)boronic acid (176.0 mg, 0.41 mmol). Purification by flash silica column chromatography (DCM:MeOH) (1:0 to 9:1) afforded the title compound as a yellow solid (129.8 mg, 95%).

ESI-MS m/z: 388 (M+H)$^+$.

Preparation of Compound 81 8-(1-methyl-1H-indazol-5-yl)-1-cyclopropyl-9-methyl-4-oxo-4H-quinolizine-3-carboxylic acid 8-(1-Methyl-1H-indazol-5-yl)-1-cyclopropyl-9-methyl-4-oxo-4H-quinolizine-3-carboxylic acid was prepared according to General Procedure B from methyl 1-cyclopropyl-9-methyl-8-(1-methyl-1H-indazol-5-yl)-4-oxo-4H-quinolizine-3-carboxylate (129.8 mg, 0.33 mmol) to afford compound 81 as a yellow solid (104.2 mg, 77%).

ESI-MS m/z: 374 (M+H)$^+$, 372 (M−H)$^-$; 1H NMR (400 MHz, DMSO-d6) δ ppm 14.12 (s, 1H), 9.34 (d, J=7.3 Hz, 1H), 8.26 (s, 1H), 8.20 (s, 1H), 8.00 (s, 1H), 7.85 (d, J=8.6 Hz, 1H), 7.66 (d, J=7.1 Hz, 1H), 7.59 (d, J=8.4 Hz, 1H), 4.13 (s, 3H), 2.89 (s, 3H), 2.50-2.60 (m, 1H), 1.06-1.10 (m, 2H), 0.79-0.81 (m, 2H).

Preparation of Compound 81K (Potassium Salt of Compound 81) potassium 8-(1-methyl-1H-indazol-5-yl)-1-cyclopropyl-9-methyl-4-oxo-4H-quinolizine-3-carboxylate Potassium 8-(1-methyl-1H-indazol-5-yl)-1-cyclopropyl-9-methyl-4-oxo-4H-quinolizine-3-carboxylate was prepared according to General Procedure D from 1-cyclopropyl-9-methyl-8-(1-methyl-1H-indazol-5-yl)-4-oxo-4H-quinolizine-3-carboxylic acid (97.2 mg, 0.26 mmol) to afford the K salt of compound 81 as a yellow solid (101.5.0 mg, 87%).

ESI-MS m/z: 374 (M−K+H)$^+$, 372 (M−K−H)$^-$.

Preparation of Compound 82

Preparation of methyl 8-(1H-indazol-4-yl)-1-cyclopropyl-9-methyl-4-oxo-4H-quinolizine-3-carboxylate Methyl 8-(1H-indazol-4-yl)-1-cyclopropyl-9-methyl-4-oxo-4H-quinolizine-3-carboxylate was prepared according to General Procedure A' from methyl 8-chloro-1-cyclopropyl-9-methyl-4-oxo-4H-quinolizine-3-carboxylate (100 mg, 0.34 mmol) and 1H-Indazole-4-boronic acid (67 mg, 0.41 mmol). Purification by flash silica column chromatography (DCM:MeOH) (1:0 to 9:1) afforded the title compound as a yellow solid (110.5 mg, 79%).

ESI-MS m/z: 374 (M+H)$^+$.

Preparation of Compound 82 8-(1H-indazol-4-yl)-1-cyclopropyl-9-methyl-4-oxo-4H-quinolizine-3-carboxylic acid 8-(1H-Indazol-4-yl)-1-cyclopropyl-9-methyl-4-oxo-4H-quinolizine-3-carboxylic acid was prepared according to General Procedure B from methyl 8-(1H-indazol-4-yl)-1-cyclopropyl-9-methyl-4-oxo-4H-quinolizine-3-carboxylate (110.5 mg, 0.27 mmol) to afford compound 82 as a yellow solid (85.2 mg, 73%).

ESI-MS m/z: 360 (M+H)$^+$, 358 (M−H)$^-$; 1H NMR (400 MHz, DMSO-d6) δ ppm 14.13 (s, 1H), 13.44 (s, 1H), 9.40 (d, J=7.4 Hz, 1H), 8.30 (s, 1H), 7.95 (s, 1H), 7.73 (d, J=8.3 Hz, 1H), 7.65 (d, J=7.4 Hz, 1H), 7.56 (t, J=7.7 Hz, 1H), 7.25 (d, J=6.8 Hz, 1H), 2.78 (s, 3H), 2.54-2.61 (m, 1H), 1.04-1.10 (m, 2H), 0.80-0.87 (m, 2H).

Preparation of Compound 82K (Potassium Salt of Compound 82) potassium 8-(1H-indazol-4-yl)-1-cyclopropyl-9-methyl-4-oxo-4H-quinolizine-3-carboxylate Potassium 8-(1H-indazol-4-yl)-1-cyclopropyl-9-methyl-4-oxo-4H-quinolizine-3-carboxylate was prepared according to General Procedure D from 8-(1H-indazol-4-yl)-1-cyclopropyl-9-methyl-4-oxo-4H-quinolizine-3-carboxylic acid (30.0 mg, 0.08 mmol) to afford the K salt of compound 82 as a yellow solid (30.5 mg, 92%).

ESI-MS m/z: 360 (M−K+H)$^+$, 358 (M−K−H)$^-$.

Preparation of Compound 83

Preparation of methyl 8-(1H-indazol-6-yl)-91-cyclopropyl-1-methyl-4-oxo-4H-quinolizine-3-carboxylate Methyl 8-(1H-indazol-6-yl)-91-cyclopropyl-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 1H-indazole-6-boronic acid pinacol ester (103 mg, 0.41 mmol). Purification by flash silica column chromatography (DCM:MeOH) (1:0 to 9:1) afforded the title compound as a yellow solid (121.2 mg, 86%).
ESI-MS m/z: 374 (M+H)$^+$.

Preparation of Compound 83 8-(1H-indazol-6-yl)-1-cyclopropyl-9-methyl-4-oxo-4H-quinolizine-3-carboxylic acid 8-(1H-Indazol-6-yl)-1-cyclopropyl-9-methyl-4-oxo-4H-quinolizine-3-carboxylic acid was prepared according to General Procedure B from methyl 8-(1H-indazol-6-yl)-1-cyclopropyl-9-methyl-4-oxo-4H-quinolizine-3-carboxylate (121.2 mg, 0.30 mmol) to afford compound 83 as a yellow solid (51.7 mg, 43%).
ESI-MS m/z: 360 (M+H)$^+$, 358 (M−H)$^-$; 1H NMR (400 MHz, DMSO-d6) δ ppm 14.11 (s, 1H), 13.35 (s, 1H), 9.36 (d, J=7.3 Hz, 1H), 8.28 (s, 1H), 8.21 (s, 1H), 7.96 (d, J=8.2 Hz, 1H), 7.70 (s, 1H), 7.66 (d, J=7.3 Hz, 1H), 7.26 (d, J=8.2 Hz, 1H), 2.88 (s, 3H), 2.50-2.59 (m, 1H), 1.05-1.10 (m, 2H), 0.79-0.83 (m, 2H).

Preparation of Compound 83K (Potassium Salt of Compound 83) potassium 8-(1H-indazol-6-yl)-1-cyclopropyl-9-methyl-4-oxo-4H-quinolizine-3-carboxylate Potassium 8-(1H-indazol-6-yl)-1-cyclopropyl-9-methyl-4-oxo-4H-quinolizine-3-carboxylate was prepared according to General Procedure D from 8-(1H-indazol-6-yl)-1-cyclopropyl-9-methyl-4-oxo-4H-quinolizine-3-carboxylic acid (45.1 mg, 0.13 mmol) to afford the K salt of compound 83 as a yellow solid (49.6 mg, 97%).
ESI-MS m/z: 360 (M+H)$^+$, 358 (M−H)$^-$.

Preparation of Compound 84

Preparation of methyl 8-(6-(4-(tert-butoxycarbonyl)piperazin-1-yl)pyridin-3-yl)-1-cyclopropyl-9-methyl-4-oxo-4H-quinolizine-3-carboxylate Methyl 8-(6-(4-(tert-butoxycarbonyl)piperazin-1-yl)pyridin-3-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and tert-butyl 4-(5-(4,4,5,5-tetramethyl-1,3,2-dioxaborolan-2-yl)pyridin-2-yl)piperazine-1-carboxylate (159.9 mg, 0.41 mmol). Purification by flash silica column chromatography (DCM:MeOH) (1:0 to 9:1) afforded quantitatively the title compound as a yellow solid.
ESI-MS m/z: 519 (M+H)$^+$.

Preparation of 8-(6-(4-(tert-butoxycarbonyl)piperazin-1-yl)pyridin-3-yl)-1-cyclopropyl-9-methyl-4-oxo-4H-quinolizine-3-carboxylic acid 8-(6-(4-(tert-Butoxycarbonyl)piperazin-1-yl)pyridin-3-yl)-1-cyclopropyl-9-methyl-4-oxo-4H-quinolizine-3-carboxylic acid was prepared according to General Procedure B from methyl 8-(6-(4-(tert-butoxycarbonyl)piperazin-1-yl)pyridin-3-yl)-1-cyclopropyl-9-methyl-4-oxo-4H-quinolizine-3-carboxylate (0.34 mmol) to afford the title compound 84 as a yellow solid (144.6 mg, 100%).
ESI-MS m/z: 505(M+H)$^+$.

Preparation of Compound 84HCl (Hydrochloric Salt of Compound 84) 8-(6-(piperazin-1-yl)pyridin-3-yl)-1-cyclopropyl-9-methyl-4-oxo-4H-quinolizine-3-carboxylic acid hydrochloride 8-(6-(Piperazin-1-yl)pyridin-3-yl)-1-cyclopropyl-9-methyl-4-oxo-4H-quinolizine-3-carboxylic acid hydrochloride was prepared according to General Procedure C from 8-(6-(4-(tert-butoxycarbonyl)piperazin-1-yl)pyridin-3-yl)-1-cyclopropyl-9-methyl-4-oxo-4H-quinolizine-3-carboxylic acid (144.6 mg, 0.29 mmol) to afford the hydrochloric salt of compound 84 as a yellow solid (122.7 mg, 97%).
ESI-MS m/z: 405 (M+H)$^+$, 403 (M−H)$^-$; 1H NMR (400 MHz, DMSO-d6) δ ppm 9.40 (s, 2H), 9.30 (d, J=7.3 Hz, 1H), 8.40 (d, J=2.2 Hz, 1H), 8.23 (s, 1H), 7.92 (d, J=9.1 Hz, J=2.5 Hz, 1H), 7.63 (d, J=7.6 Hz, 1H), 7.15 (d, J=8.8 Hz, 1H), 3.89-3.92 (m, 4H), 3.18-3.26 (m, 4H), 2.90 (s, 3H), 2.50-2.57 (m, 1H), 1.05-1.11 (m, 2H), 0.76-0.81 (m, 2H).

Preparation of Compound 84K (Potassium Salt of Compound 84) potassium 8-(6-(piperazin-1-yl)pyridin-3-yl)-1-cyclopropyl-9-methyl-4-oxo-4H-quinolizine-3-carboxylate Potassium 8-(6-(piperazin-1-yl)pyridin-3-yl)-1-cyclopropyl-9-methyl-4-oxo-4H-quinolizine-3-carboxylate was prepared according to General Procedure D from 8-(6-(piperazin-1-yl)pyridin-3-yl)-1-cyclopropyl-9-methyl-4-oxo-4H-quinolizine-3-carboxylic acid hydrochloride (122.7 mg, 0.28 mmol) to afford the K salt of compound 84 as a yellow solid (137.1 mg, 100%).
ESI-MS m/z: 405 (M−K+H)$^+$, 403 (M−K−H)$^-$.

Preparation of Compound 85

Preparation of methyl 8-(1H-pyrrolo[2,3-b]pyridin-5-yl)-1-cyclopropyl-9-methyl-4-oxo-4H-quinolizine-3-carboxylate Methyl 8-(1H-pyrrolo[2,3-b]pyridin-5-yl)-1-cyclopropyl-9-methyl-4-oxo-4H-quinolizine-3-carboxylate was prepared according to General Procedure A' from methyl 8-chloro-1-cyclopropyl-9-methyl-4-oxo-4H-quinolizine-3-carboxylate (100 mg, 0.34 mmol) and 5-(4,4,5,5-tetramethyl-1,3,2-dioxaborolan-2-yl)-1H-pyrrolo[2,3-b]pyridine (100.3 mg, 0.41 mmol). Purification by flash silica column chromatography (DCM:MeOH) (1:0 to 9:1) afforded the title compound as a yellow solid (124.8 mg, 90%).
ESI-MS m/z: 374 (M+H)$^+$.

Preparation of Compound 85 8-(1H-pyrrolo[2,3-b]pyridin-5-yl)-1-cyclopropyl-9-methyl-4-oxo-4H-quinolizine-3-carboxylic acid 8-(1H-Pyrrolo[2,3-b]pyridin-5-yl)-1-cyclopropyl-9-methyl-4-oxo-4H-quinolizine-3-carboxylic acid was prepared according to General Procedure B from methyl 8-(1H-pyrrolo[2,3-b]pyridin-5-yl)-1-cyclopropyl-9-methyl-4-oxo-4H-quinolizine-3-carboxylate (124.8 mg, 0.31 mmol) to afford compound 85 as a yellow solid (26 mg, 21%).

ESI-MS m/z: 360 (M+H)⁺, 358 (M−H)⁻; 1H NMR (400 MHz, MeOD-d6) δ ppm 9.43 (d, J=7.3 Hz, 1H), 8.64 (s, 1H), 8.58 (s, 1H), 8.43 (s, 1H), 7.73 (d, J=3.5 Hz, 1H), 7.58 (d, J=7.6 Hz, 1H), 6.88 (d, J=3.5 Hz, 1H), 2.98 (s, 3H), 2.50-2.58 (m, 1H), 1.13-1.18 (m, 2H), 0.86-0.90 (m, 2H).

Preparation of Compound 85K (Potassium Salt of Compound 85) potassium 8-(1H-pyrrolo[2,3-b]pyridin-5-yl)-1-cyclopropyl-9-methyl-4-oxo-4H-quinolizine-3-carboxylate Potassium 8-(1H-pyrrolo[2,3-b]pyridin-5-yl)-1-cyclopropyl-9-methyl-4-oxo-4H-quinolizine-3-carboxylate was prepared according to General Procedure D from 8-(1H-pyrrolo[2,3-b]pyridin-5-yl)-1-cyclopropyl-9-methyl-4-oxo-4H-quinolizine-3-carboxylic acid (26.0 mg, 0.07 mmol) to afford the K salt of compound 85 as a yellow solid (21.1 mg, 70%).

ESI-MS m/z: 360 (M−K+H)⁺.

Preparation of Compound 86

Preparation of 5-(4,4,5,5-tetramethyl-1,3,2-dioxaborolan-2-yl)-1H-indazol-3-amine Compound 5-(4,4,5,5-tetramethyl-1,3,2-dioxaborolan-2-yl)-1H-indazol-3-amine was prepared according to General Procedure G from 5-bromo-1H-indazol-3-amine (500 mg, 2.36 mmol). Purification by flash silica column chromatography (DCM: MeOH) (1:0 to 94:6) and recrystallization in DCM and heptane gave the title compound as a brown solid (230 mg, 25%).

ESI-MS m/z: 260 (M+H)⁺.

Preparation of methyl 8-(3-amino-1H-indazol-5-yl)-1-cyclopropyl-9-methyl-4-oxo-4H-quinolizine-3-carboxylate Methyl 8-(3-amino-1H-indazol-5-yl)-1-cyclopropyl-9-methyl-4-oxo-4H-quinolizine-3-carboxylate was prepared according to General Procedure A from methyl 8-chloro-1-cyclopropyl-9-methyl-4-oxo-4H-quinolizine-3-carboxylate (100 mg, 0.34 mmol) and 5-(4,4,5,5-tetramethyl-1,3,2-dioxaborolan-2-yl)-1H-indazol-3-amine (106.4 mg, 0.41 mmol). Purification by flash silica column chromatography (DCM:MeOH) (1:0 to 9:1) afforded the title compound as a yellow solid (32 mg, 42%).

ESI-MS m/z: 389 (M+H)⁺, 387 (M−H)⁻.

Preparation of Compound 86 8-(3-amino-1H-indazol-5-yl)-1-cyclopropyl-9-methyl-4-oxo-4H-quinolizine-3-carboxylic acid 8-(3-Amino-1H-indazol-5-yl)-1-cyclopropyl-9-methyl-4-oxo-4H-quinolizine-3-carboxylic acid was prepared according to General Procedure B from methyl 8-(3-amino-1H-indazol-5-yl)-1-cyclopropyl-9-methyl-4-oxo-4H-quinolizine-3-carboxylate (32 mg, 0.14 mmol). Purification by preparative HPLC afforded compound 86 as a yellow solid (0.7 mg, 1%).

ESI-MS m/z: 375 (M+H)⁺; 1H NMR (400 MHz, CD₃OD) δ ppm 9.41 (d, J=7.3 Hz, 1H), 8.42 (s, 1H), 7.92 (s, 1H), 7.43-7.52 (m, 3H), 2.97 (s, 3H), 2.49-2.58 (m, 1H), 1.09-1.15 (m, 2H), 0.81-0.86 (m, 2H).

Preparation of Compound 87

Preparation of methyl 8-(6-amino-pyridin-3-yl)-1-cyclopropyl-7,9-dimethyl-4-oxo-4H-quinolizine-3-carboxylate Methyl 8-(6-amino-pyridin-3-yl)-1-cyclopropyl-7,9-dimethyl-4-oxo-4H-quinolizine-3-carboxylate was prepared according to General Procedure A from methyl 8-chloro-1-cyclopropyl-7,9-dimethyl-4-oxo-4H-quinolizine-3-carboxylate (50 mg, 0.16 mmol) and 2-amino-pyridine-5-boronic acid pinacol ester (43 mg, 0.20 mmol). Purification by flash silica column chromatography (DCM:MeOH) (1:0 to 25:4) afforded the title compound as a yellow solid (44 mg, 69%).

ESI-MS m/z: 3864 (M+H)⁺.

Preparation of Compound 87 8-(6-amino-pyridin-3-yl)-1-cyclopropyl-7,9-dimethyl-4-oxo-4H-quinolizine-3-carboxylic acid 8-(6-Amino-pyridin-3-yl)-1-cyclopropyl-7,9-dimethyl-4-oxo-4H-quinolizine-3-carboxylic acid was prepared according to General Procedure B from 8-(6-amino-pyridin-3-yl)-1-cyclopropyl-7,9-dimethyl-4-oxo-4H-quinolizine-3-carboxylate (44 mg, 0.12 mmol) to afford compound 87 as a yellow solid (19 mg, 41%).

ESI-MS m/z: 350 (M+H)⁺; 1H NMR (400 MHz DMSO-d6) δ ppm 14.2 (br s, 1H), 9.26 (s, 1H), 8.19 (s, 1H), 7.95 (s, 1H), 7.45-7.67 (m, 2H), 7.20 (br s, 2H), 6.86 (d, J=8.4 Hz, 1H), 2.73 (s, 3H), 2.50-2.60 (m, 1H), 2.20 (s, 3H), 0.98-1.12 (m, 2H), 0.71-0.79 (m, 2H).

Preparation of Compound 87K (Potassium Salt of Compound 87) potassium 8-(6-amino-pyridin-3-yl)-1-cyclopropyl-7,9-dimethyl-4-oxo-4H-quinolizine-3-carboxylate Potassium 8-(6-amino-pyridin-3-yl)-1-cyclopropyl-7,9-dimethyl-4-oxo-4H-quinolizine-3-carboxylate was prepared according to General Procedure D from 8-(6-amino-pyridin-3-yl)-1-cyclopropyl-7,9-dimethyl-4-oxo-4H-quinolizine-3-carboxylic acid (29 mg, 0.08 mmol) to afford the K salt of compound 87 as a yellow solid (28 mg, 90%).

ESI-MS m/z: 350 (M−K+H)⁺.

Preparation of Compound 88

Preparation of methyl 8-(1H-indazol-5-yl)-1-cyclopropyl-7,9-dimethyl-4-oxo-4H-quinolizine-3-carboxylate Methyl 8-(1H-indazol-5-yl)-1-cyclopropyl-7,9-dimethyl-4-oxo-4H-quinolizine-3-carboxylate was prepared according to General Procedure A from methyl 8-chloro-1-cyclopropyl-7,9-dimethyl-4-oxo-4H-quinolizine-3-carboxylate (50 mg, 0.17 mmol), and 1H-Indazole-5-boronic acid pinacol ester (48 mg, 0.19 mmol). Purification by flash silica

Preparation of Compound 88 8-(1H-indazol-5-yl)-1-cyclopropyl-7,9-dimethyl-4-oxo-4H-quinolizine-3-carboxylic acid 8-(1H-Indazol-5-yl)-1-cyclopropyl-7,9-dimethyl-4-oxo-4H-quinolizine-3-carboxylic acid was prepared according to General Procedure B from methyl 8-(1H-indazol-5-yl)-1-cyclopropyl-7,9-dimethyl-4-oxo-4H-quinolizine-3-carboxylate (30 mg, 0.08 mmol) to afford compound 88 as a yellow solid (22 mg, 77%).

ESI-MS m/z: 374 (M+H)$^+$; 1H NMR (400 MHz, CDCl$_3$) δ ppm 14.25 (s, 1H), 10.20 (br s, 1H), 9.32 (s, 1H), 8.54 (s, 1H), 8.19 (s, 1H), 7.71 (d, J=8.6 Hz, 1H), 7.59 (s, 1H), 7.26 (s, 1H), 7.18 (d, J=8.5 Hz, 1H), 2.73 (s, 3H), 2.33-2.43 (m, 1H), 2.14 (s, 3H), 1.02-1.10 (m, 2H), 0.82-0.87 (m, 2H).

Preparation of Compound 88K (Potassium Salt of Compound 88) potassium 8-(1H-indazol-5-yl)-1-cyclopropyl-7,9-dimethyl-4-oxo-4H-quinolizine-3-carboxylate Potassium 8-(1H-indazol-5-yl)-1-cyclopropyl-7,9-dimethyl-4-oxo-4H-quinolizine-3-carboxylate was prepared according to General Procedure D from 8-(1H-indazol-5-yl)-1-cyclopropyl-7,9-dimethyl-4-oxo-4H-quinolizine-3-carboxylic acid (20 mg, 0.05 mmol) to afford the K salt of compound 88 as a yellow solid (19 mg, 82%).

ESI-MS m/z: 374 (M−K+H)$^+$.

Preparation of Compound 89

Preparation of methyl 8-(6-amino-pyridin-3-yl)-1-cyclopropyl-9-methoxy-4-oxo-4H-quinolizine-3-carboxylate Methyl 8-(6-amino-pyridin-3-yl)-1-cyclopropyl-9-methoxy-4-oxo-4H-quinolizine-3-carboxylate was prepared according to General Procedure A from methyl 8-chloro-1-cyclopropyl-9-methoxy-4-oxo-4H-quinolizine-3-carboxylate (50 mg, 0.16 mmol), and 2-aminopyridine-5-boronic acid pinacol ester (42.9 mg, 0.20 mmol). Purification by flash silica column chromatography (DCM:MeOH) (1:0 to 9:1) afforded the title compound as an orange solid (35 mg, 57%).

ESI-MS m/z: 366 (M+H)$^+$.

Preparation of Compound 89 8-(6-amino-pyridin-3-yl)-1-cyclopropyl-9-methoxy-4-oxo-4H-quinolizine-3-carboxylic acid 8-(6-Amino-pyridin-3-yl)-1-cyclopropyl-9-methoxy-4-oxo-4H-quinolizine-3-carboxylic acid was prepared according to General Procedure B from methyl 8-(6-amino-pyridin-3-yl)-1-cyclopropyl-9-methoxy-4-oxo-4H-quinolizine-3-carboxylate (34 mg, 0.09 mmol) to afford compound 89 as an orange solid (22.3 mg, 68%).

ESI-MS m/z: 352 (M+H)$^+$; 1H NMR (400 MHz, CDCl$_3$) δ ppm 14.09 (br s, 1H), 9.29 (d, J=7.6 Hz, 1H), 8.51 (d, J=2 Hz, 1H), 8.42 (s, 1H), 7.94 (dd, J=8.8 Hz, J=2.5 Hz 1H), 7.38 (d, J=7.3 Hz, 1H), 6.67 (d, J=8.8 Hz, 1H), 4.84 (br s, 2H), 3.58 (s, 3H), 2.62-2.70 (m, 1H), 1.01-1.06 (m, 2H), 0.81-0.90 (m, 2H).

Preparation of Compound 89K (Potassium Salt of Compound 89) potassium 8-(6-amino-pyridin-3-yl)-1-cyclopropyl-9-methoxy-4-oxo-4H-quinolizine-3-carboxylate Potassium 8-(6-amino-pyridin-3-yl)-1-cyclopropyl-9-methoxy-4-oxo-4H-quinolizine-3-carboxylate was prepared according to General Procedure D from 8-(6-amino-pyridin-3-yl)-1-cyclopropyl-9-methoxy-4-oxo-4H-quinolizine-3-carboxylic acid (21.6 mg, 0.06 mmol) to afford the K salt of compound 89 as a yellow solid (22.7 mg, 91%).

ESI-MS m/z: 352 (M−K+H)$^+$.

Preparation of Compound 90

Preparation of methyl 8-(1H-indazol-5-yl)-1-cyclopropyl-9-methoxy-4-oxo-4H-quinolizine-3-carboxylate Methyl 8-(1H-indazol-5-yl)-1-cyclopropyl-9-methoxy-4-oxo-4H-quinolizine-3-carboxylate was prepared according to General Procedure A from methyl 8-chloro-1-cyclopropyl-9-methoxy-4-oxo-4H-quinolizine-3-carboxylate (50 mg, 0.16 mmol), and 1H-Indazole-5-boronic acid pinacol ester (47.6 mg, 0.20 mmol). Purification by flash silica column chromatography (DCM:MeOH) (1:0 to 9:1) afforded the title compound as an orange foam (32 mg, 46%).

ESI-MS m/z: 390 (M+H)$^+$.

Preparation of Compound 90 8-(1H-indazol-5-yl)-1-cyclopropyl-9-methoxy-4-oxo-4H-quinolizine-3-carboxylic acid 8-(1H-Indazol-5-yl)-1-cyclopropyl-9-methoxy-4-oxo-4H-quinolizine-3-carboxylic acid was prepared according to General Procedure B from methyl 1-cyclopropyl-8-(1H-indazol-5-yl)-9-methoxy-4-oxo-4H-quinolizine-3-carboxylate (32 mg, 0.08 mmol) to afford compound 90 as a yellow solid (22.5 mg, 73%).

ESI-MS m/z: 376 (M+H)$^+$; 1H NMR (400 MHz, CDCl$_3$) δ ppm 14.12 (br s, 1H), 13.37(s, 1H), 9.27 (d, J=7.6 Hz, 1H), 8.25 (s, 2H), 8.13 (s, 1H), 7.73-7.83 (m, 3H), 3.46 (s, 3H), 2.63-2.67 (m, 1H), 0.98-1.03 (m, 2H), 0.74-0.78 (m, 2H).

Preparation of Compound 90K (Potassium Salt of Compound 90) potassium 8-(1H-indazol-5-yl)-1-cyclopropyl-9-methoxy-4-oxo-4H-quinolizine-3-carboxylate Potassium 8-(1H-indazol-5-yl)-1-cyclopropyl-9-methoxy-4-oxo-4H-quinolizine-3-carboxylate was prepared according to General Procedure D from 1-cyclopropyl-8-(1H-indazol-5-yl)-9-methoxy-4-oxo-4H-quinolizine-3-carboxylic acid (15.3 mg, 0.04 mmol) to afford the K salt of compound 90 as a yellow solid (14.3 mg, 77%).

ESI-MS m/z: 376 (M−K+H)$^+$.

What is claimed is:

1. A pharmaceutical composition comprising Polymyxin B and a 4-oxoquinolizine compound of formula IIIc:

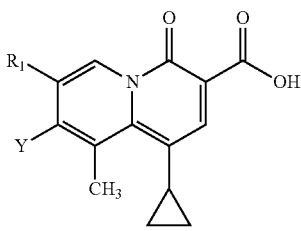

(IIIc)

or a pharmaceutically acceptable salt thereof, wherein
  $R_1$ is hydrogen, halogen, cyano, $C_{1-8}$ alkyl, $C_{1-8}$ haloalkyl, $-OR^X$, $-N(R^X)_2$, $-C(O)R^X$, $-C(O)OR^X$, or $-C(O)N(R^X)_2$, wherein each $R^X$ is independently hydrogen, $C_{1-8}$ alkyl, or $C_{1-8}$haloalkyl; and
  Y is aryl or heteroaryl, each of which is substituted with either $-N(R^{Y1})_2$ or $-C_1$-$C_8$ alkyl-$R^Y$ and further optionally substituted by one to four groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$) alkyl, heteroaryl($C_{1-8}$)alkyl, $-R^Y$, or $-C_{1-8}$ alkyl-$R^Y$,
  wherein $R^Y$ is nitro, cyano, $-OR^{Y1}$, $-SR^{Y1}$, $-N(R^{Y1})_2$, $-C(O)R^{Y1}$, $-C(O)OR^{Y1}$, $-C(O)N(R^{Y1})_2$, $-OC(O)R^{Y1}$, $-OC(O)OR^{Y1}$, $-OC(O)N(R^{Y1})_2$, $-N(R^{Y1})C(O)R^{Y1}$, $-N(R^{Y1})C(O)OR^{Y1}$, $-N(R^{Y1})C(O)N(R^{Y1})_2$, $-S(O)_2R^{Y1}$, $-S(O)_2OR^{Y1}$, $-S(O)_2N(R^{Y1})_2$, $-OS(O)_2R^{Y1}$, $-OS(O)_2OR^{Y1}$, $-OS(O)_2N(R^{Y1})_2$, $-N(R^{Y1})S(O)_2R^{Y1}$, $-N(R^{Y1})S(O)_2OR^{Y1}$, or $-N(R^{Y1})S(O)_2N(R^{Y1})_2$;
  wherein each $R^{Y1}$ is independently hydrogen, $C_{1-8}$ alkyl, or $C_{1-8}$ haloalkyl.

2. The pharmaceutical composition according to claim 1, wherein $R_1$ is hydrogen or halogen.

3. The pharmaceutical composition according to claim 1, wherein
  Y is phenyl substituted with one group which is $-N(R^{Y1})_2$ or $-C_{1-8}$ alkyl-$N(R^{Y1})_2$, and optionally substituted by one or two groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl ($C_{1-8}$) alkyl, heterocyclyl($C_{1-8}$)alkyl, aryl($C_{1-8}$)alkyl, heteroaryl($C_{1-8}$)alkyl, $-R^Y$, or $-C_{1-8}$ alkyl-$R^Y$;
  Y is a 5-membered or 6-membered heteroaryl each of which is substituted with either $-N(R^{Y1})_2$ or $-C_1$-$C_8$ alkyl-$R^Y$ and optionally substituted by one to four groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$) alkyl, aryl($C_{1-8}$)alkyl, heteroaryl($C_{1-8}$)alkyl, $-R^Y$, or $-C_{1-8}$ alkyl-$R^Y$; or
  Y is a bicyclic heteroaryl substituted with either $-N(R^{Y1})_2$ or $-C_1$-$C_8$ alkyl-$R^Y$ and optionally substituted by one to four groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, $-R^Y$, or $-C_{1-8}$ alkyl-$R^Y$.

4. A pharmaceutical composition according to claim 2, wherein
  Y is phenyl substituted with one group which is $-N(R^{Y1})_2$ or, $-C_{1-8}$ alkyl-$N(R^{Y1})_2$, and optionally substituted by one or two groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl ($C_{1-8}$) alkyl, heterocyclyl($C_{1-8}$)alkyl, aryl($C_{1-8}$)alkyl, heteroaryl($C_{1-8}$)alkyl, $-R^Y$, or $-C_{1-8}$ alkyl-$R^Y$;
  Y is a 5-membered or 6-membered heteroaryl each of which is substituted with either $-N(R^{Y1})_2$ or $-C_1$-$C_8$ alkyl-$R^Y$ and optionally substituted by one to four groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$) alkyl, aryl($C_{1-8}$)alkyl, heteroaryl($C_{1-8}$)alkyl, $-R^Y$, or $-C_{1-8}$ alkyl-$R^Y$; or
  Y is a bicyclic heteroaryl substituted with either $-N(R^{Y1})_2$ or $-C_1$-$C_8$ alkyl-$R^Y$ and optionally substituted by one to four groups that are each independently halogen, $C_{1-8}$ alkyl, $C_{1-8}$haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl ($C_{1-8}$)alkyl, $-R^Y$, or $-C_{1-8}$ alkyl-$R^Y$.

5. A pharmaceutical composition according to claim 1, wherein the 4-oxoquinolizine compound is selected from the group consisting of:

Compound 1

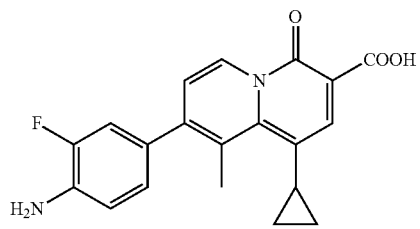 [SMILES: Cc1c(-c2ccc(N)c(F)c2)ccn2c(=O)c(C(=O)O)cc(C3CC3)c12]

8-(3-fluoro-4-amino-phenyl)-1-cyclopropyl-9-methyl-4-oxo-quinolizine-3-carboxylic acid Compound 4

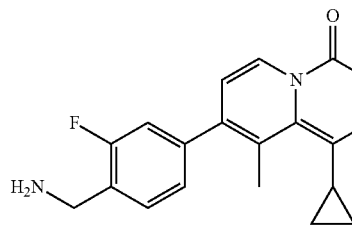

8-(3-fluoro-4-aminomethyl-phenyl)-1-cyclopropyl-9-methyl-4-oxo-quinolizine-3-carboxylic acid -continued

| | | |
|---|---|---|
| Compound 5 | 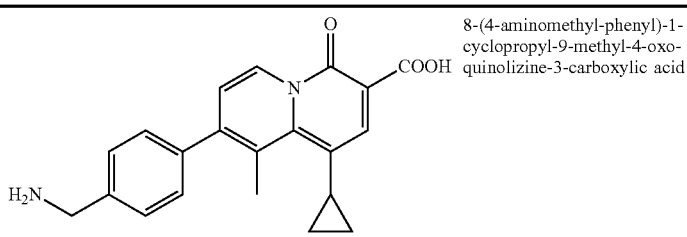 | 8-(4-aminomethyl-phenyl)-1-cyclopropyl-9-methyl-4-oxo-quinolizine-3-carboxylic acid |
| Compound 6 | 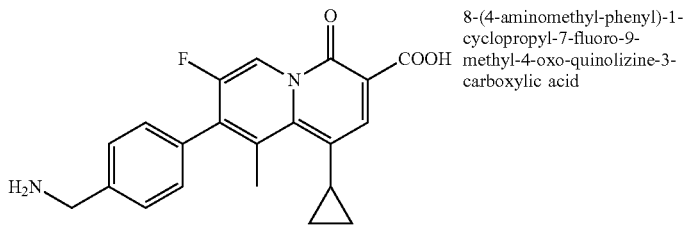 | 8-(4-aminomethyl-phenyl)-1-cyclopropyl-7-fluoro-9-methyl-4-oxo-quinolizine-3-carboxylic acid |
| Compound 7 | 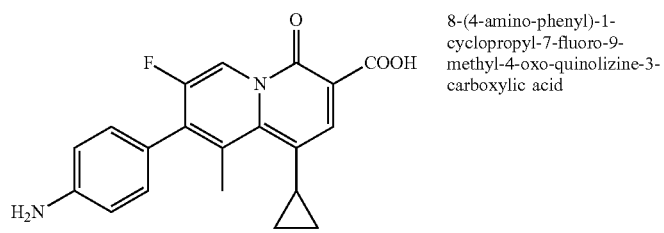 | 8-(4-amino-phenyl)-1-cyclopropyl-7-fluoro-9-methyl-4-oxo-quinolizine-3-carboxylic acid |
| Compound 8 | 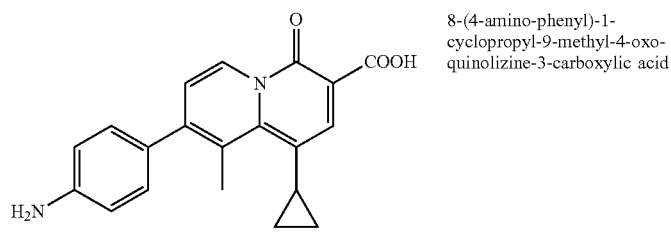 | 8-(4-amino-phenyl)-1-cyclopropyl-9-methyl-4-oxo-quinolizine-3-carboxylic acid |
| Compound 9 | 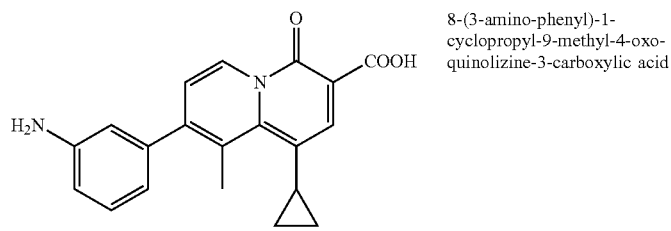 | 8-(3-amino-phenyl)-1-cyclopropyl-9-methyl-4-oxo-quinolizine-3-carboxylic acid |
| Compound 11 | 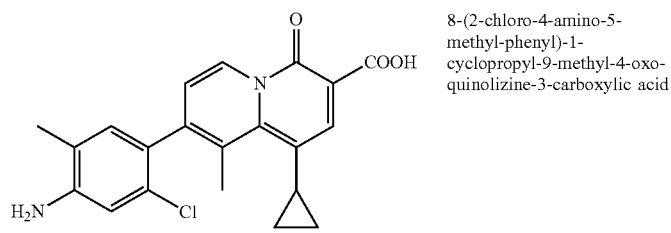 | 8-(2-chloro-4-amino-5-methyl-phenyl)-1-cyclopropyl-9-methyl-4-oxo-quinolizine-3-carboxylic acid |
| Compound 12 | 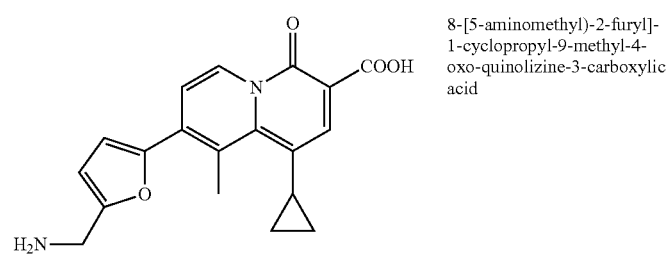 | 8-[5-aminomethyl)-2-furyl]-1-cyclopropyl-9-methyl-4-oxo-quinolizine-3-carboxylic acid |

-continued

Compound 13 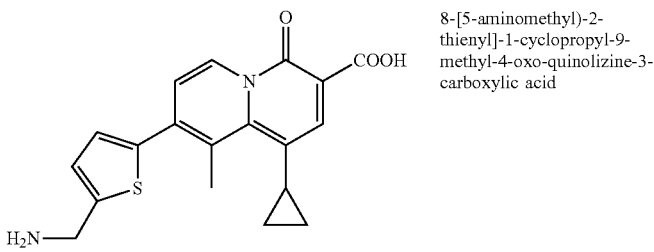 8-[5-aminomethyl)-2-thienyl]-1-cyclopropyl-9-methyl-4-oxo-quinolizine-3-carboxylic acid Compound 16 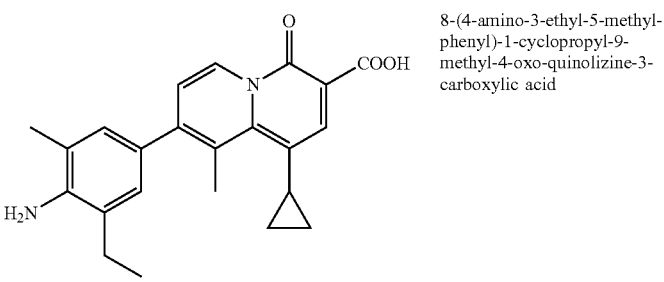 8-(4-amino-3-ethyl-5-methyl-phenyl)-1-cyclopropyl-9-methyl-4-oxo-quinolizine-3-carboxylic acid Compound 17 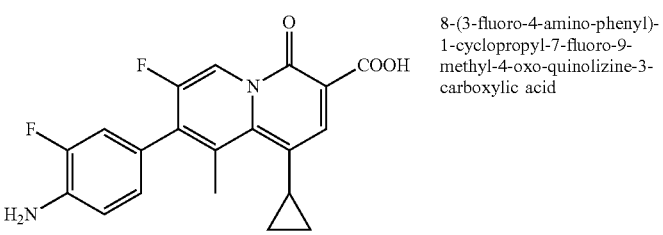 8-(3-fluoro-4-amino-phenyl)-1-cyclopropyl-7-fluoro-9-methyl-4-oxo-quinolizine-3-carboxylic acid Compound 18 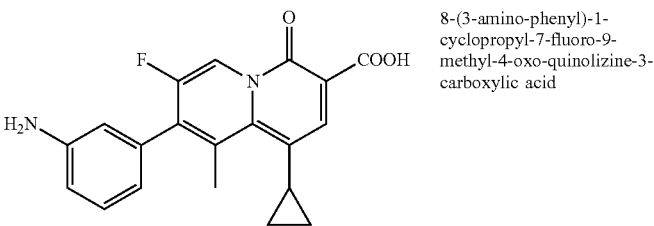 8-(3-amino-phenyl)-1-cyclopropyl-7-fluoro-9-methyl-4-oxo-quinolizine-3-carboxylic acid Compound 20 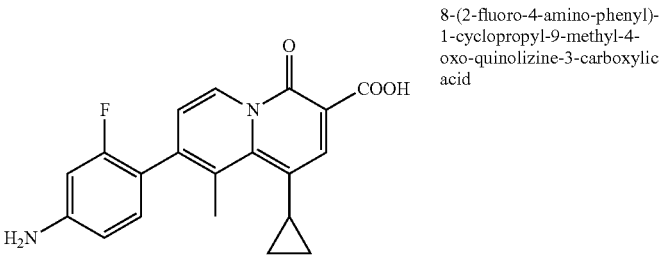 8-(2-fluoro-4-amino-phenyl)-1-cyclopropyl-9-methyl-4-oxo-quinolizine-3-carboxylic acid Compound 21 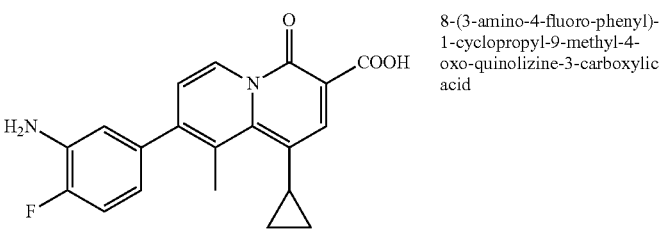 8-(3-amino-4-fluoro-phenyl)-1-cyclopropyl-9-methyl-4-oxo-quinolizine-3-carboxylic acid -continued

| | | |
|---|---|---|
| Compound 22 | 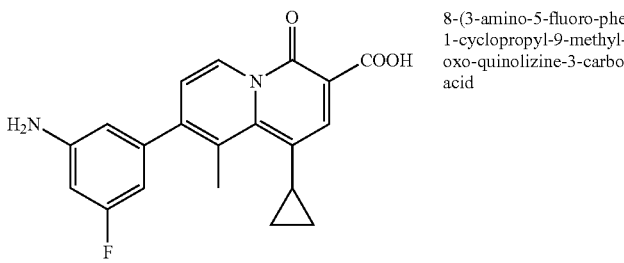 | 8-(3-amino-5-fluoro-phenyl)-1-cyclopropyl-9-methyl-4-oxo-quinolizine-3-carboxylic acid |
| Compound 24 | 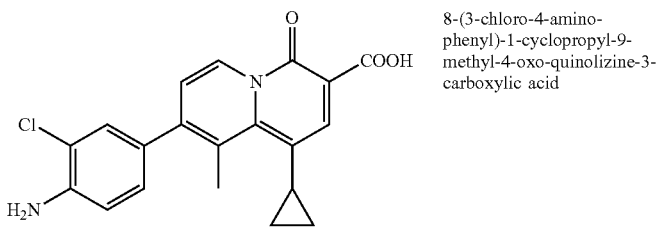 | 8-(3-chloro-4-amino-phenyl)-1-cyclopropyl-9-methyl-4-oxo-quinolizine-3-carboxylic acid |
| Compound 25 | 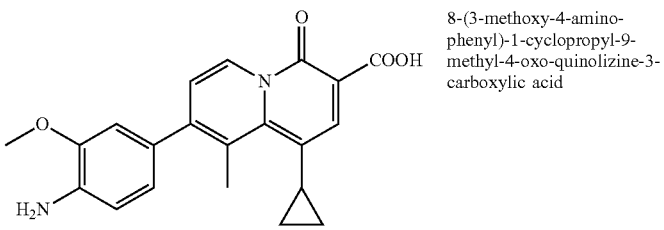 | 8-(3-methoxy-4-amino-phenyl)-1-cyclopropyl-9-methyl-4-oxo-quinolizine-3-carboxylic acid |
| Compound 28 | 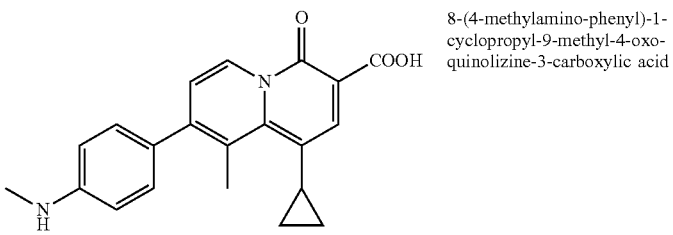 | 8-(4-methylamino-phenyl)-1-cyclopropyl-9-methyl-4-oxo-quinolizine-3-carboxylic acid |
| Compound 31 | 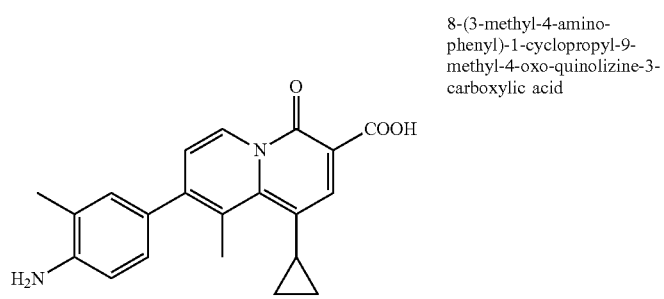 | 8-(3-methyl-4-amino-phenyl)-1-cyclopropyl-9-methyl-4-oxo-quinolizine-3-carboxylic acid |
| Compound 33 | 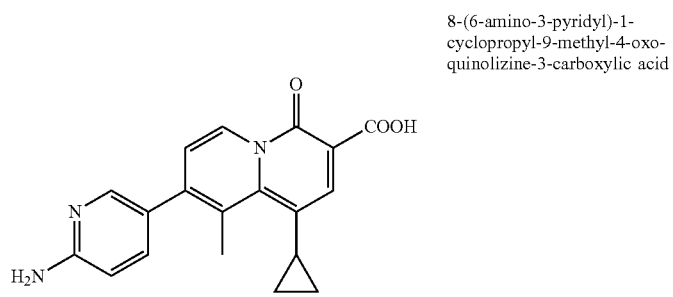 | 8-(6-amino-3-pyridyl)-1-cyclopropyl-9-methyl-4-oxo-quinolizine-3-carboxylic acid |

-continued

Compound 37 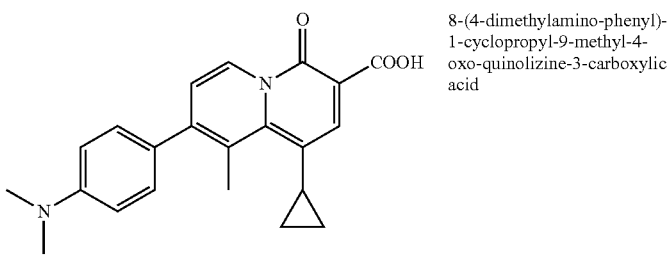 8-(4-dimethylamino-phenyl)-1-cyclopropyl-9-methyl-4-oxo-quinolizine-3-carboxylic acid Compound 57 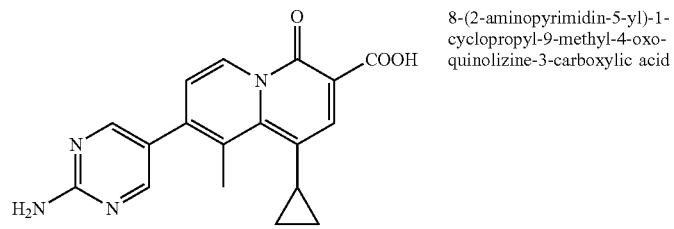 8-(2-aminopyrimidin-5-yl)-1-cyclopropyl-9-methyl-4-oxo-quinolizine-3-carboxylic acid Compound 60 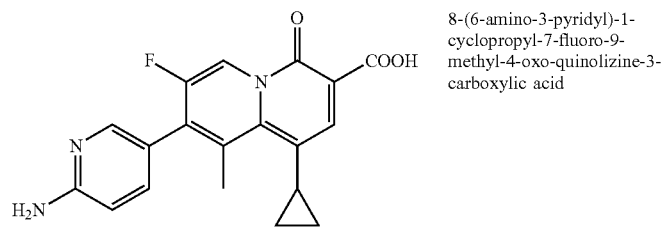 8-(6-amino-3-pyridyl)-1-cyclopropyl-7-fluoro-9-methyl-4-oxo-quinolizine-3-carboxylic acid Compound 69 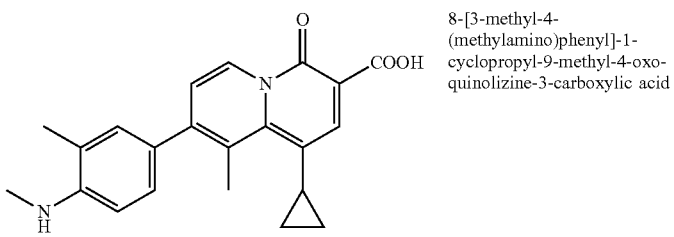 8-[3-methyl-4-(methylamino)phenyl]-1-cyclopropyl-9-methyl-4-oxo-quinolizine-3-carboxylic acid Compound 72 8-[3-(aminomethyl)-4-hydroxy-phenyl]-1-cyclopropyl-9-methyl-4-oxo-quinolizine-3-carboxylic acid
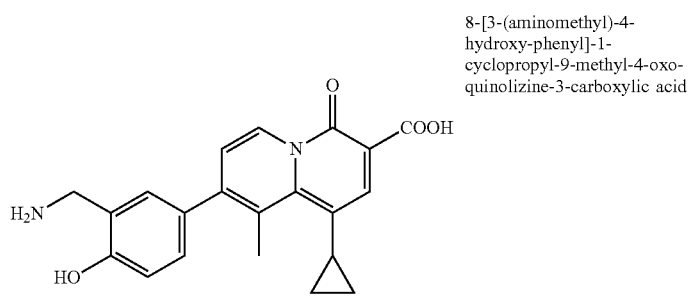

Compound 73 8-(2-amino-1,3-benzothiazol-5-yl)-1-cyclopropyl-9-methyl-4-oxo-quinolizine-3-carboxylic acid
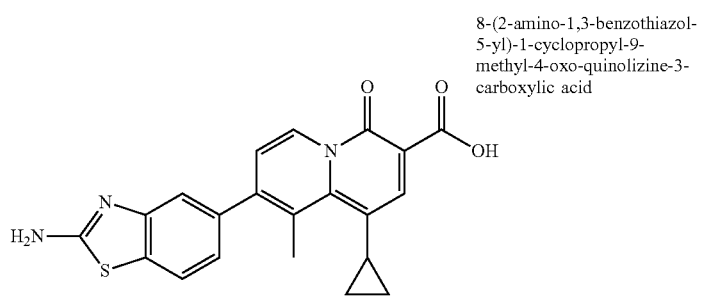

-continued

| | | |
|---|---|---|
| Compound 76 | [structure] | 8-[3-(aminomethyl)-4-amino-phenyl]-1-cyclopropyl-9-methyl-4-oxo-quinolizine-3-carboxylic acid |
| Compound 78 | [structure] | 8-[6-(methylamino)-3-pyridyl]-1-cyclopropyl-9-methyl-4-oxo-quinolizine-3-carboxylic acid |
| Compound 79 | [structure] | 8-(6-amino-5-methyl-3-pyridyl)-1-cyclopropyl-9-methyl-4-oxo-quinolizine-3-carboxylic acid |
| Compound 87 | [structure] | 8-(6-amino-3-pyridyl)-1-cyclopropyl-7,9-dimethyl-4-oxo-quinolizine-3-carboxylic acid |
| Compound 89 | [structure] | 8-(6-amino-3-pyridyl)-1-cyclopropyl-9-methoxy-4-oxo-quinolizine-3-carboxylic acid | or a pharmaceutically acceptable salt thereof.

6. A pharmaceutical composition according to claim 1, wherein the Polymyxin B is present in a subinhibitory concentration.

7. A method for treatment of a bacterial infection in an individual in need thereof comprising administering to the individual a pharmaceutical composition according to claim 1.

8. A method for treatment of a bacterial infection in an individual in need thereof, wherein the bacterial infection is infection by a multiresistant strain, comprising administering to the individual a pharmaceutical composition according to claim 1.

9. A method for treatment of a bacterial infection in an individual in need thereof, wherein the infection is infection by one or more bacteria of a genus selected from the group consisting of *Acinetobacter, Bacillus, Bordetella, Borrelia, Brucella, Camphylobacter, Chlamydia, Clostridium, Corynebacterium, Enterococcus, Escherichia, Fransisella, Haemophilus, Helicobacter, Legionella, Leptospira, Listeria, Mycobacterium, Mycoplasma, Neisseria, Propionibacterium, Pseudomonas, Rickettsia, Salmonella, Shigella, Staphylococcus, Streptococcus, Treponema, Vibrio* and *Yersinia*, comprising administering to the individual a pharmaceutical composition according to claim 1.

10. A compound which is 8-(6-amino-3-pyridyl)-1-cyclopropyl-7-fluoro-9-methyl-4-oxo-quinolizine-3-carboxylic acid, or a pharmaceutically acceptable salt thereof.

11. The compound according to claim 10, wherein the compound is a pharmaceutically acceptable salt, and the pharmaceutically acceptable salt is a hydrochloric acid salt.

12. A compound which is 8-[3-(aminomethyl)-4-hydroxyphenyl]-1-cyclopropyl-9-methyl-4-oxo-quinolizine-3-carboxylic acid, or a pharmaceutically acceptable salt thereof.

13. A compound which is 8-(2-amino-1,3-benzothiazol-5-yl)-1-cyclopropyl-9-methyl-4-oxo-quinolizine-3-carboxylic acid, or a pharmaceutically acceptable salt thereof.

14. A compound which is 8-(6-amino-5-methyl-3-pyridyl)-1-cyclopropyl-9-methyl-4-oxo-quinolizine-3-carboxylic acid, or a pharmaceutically acceptable salt thereof.

\* \* \* \* \*